(12) United States Patent
Koga et al.

(10) Patent No.: US 8,008,292 B2
(45) Date of Patent: Aug. 30, 2011

(54) CONDENSED BENZAMIDE COMPOUNDS AND INHIBITORS OF VANILLOID RECEPTOR SUBTYPE 1 (VR1) ACTIVITY

(75) Inventors: Yoshihisa Koga, Takatsuki (JP); Shinji Yata, Takatsuki (JP); Takashi Watanabe, Takatsuki (JP); Takuya Matsuo, Takatsuki (JP); Takayuki Yamasaki, Takatsuki (JP); Masahiro Sakata, Takatsuki (JP); Wataru Kondo, Takatsuki (JP); Hidekazu Ozeki, Takatsuki (JP); Yoshikazu Hori, Takatsuki (JP)

(73) Assignee: Japan Tobacco Inc., Tokyo (JP)

( * ) Notice: Subject to any disclaimer, the term of this patent is extended or adjusted under 35 U.S.C. 154(b) by 1232 days.

(21) Appl. No.: 11/183,265

(22) Filed: Jul. 15, 2005

(65) Prior Publication Data

US 2006/0035882 A1    Feb. 16, 2006

Related U.S. Application Data

(60) Provisional application No. 60/590,180, filed on Jul. 22, 2004, provisional application No. 60/641,874, filed on Jan. 6, 2005, provisional application No. 60/680,072, filed on May 12, 2005.

(30) Foreign Application Priority Data

| Jul. 15, 2004 | (JP) | 2004-208334 |
| Dec. 28, 2004 | (JP) | 2004-379551 |
| Apr. 28, 2005 | (JP) | 2005-133724 |

(51) Int. Cl.
- *A61K 31/535* (2006.01)
- *C07D 265/36* (2006.01)
- *C07D 498/02* (2006.01)

(52) U.S. Cl. ................ 514/230.5; 544/105

(58) Field of Classification Search .......... None
See application file for complete search history.

(56) References Cited

U.S. PATENT DOCUMENTS

| 1,893,091 | A | 1/1933 | Laska et al. |
| 3,678,094 | A | 7/1972 | Shen et al. |
| 3,773,936 | A | 11/1973 | Shen et al. |
| 4,640,916 | A | 2/1987 | Meguro et al. |
| 5,712,298 | A | 1/1998 | Amschler |
| 5,998,400 | A | 12/1999 | Brieaddy et al. |
| 6,239,267 | B1 | 5/2001 | Duckworth et al. |
| 6,268,387 | B1 | 7/2001 | Connor et al. |
| 6,495,555 | B1 | 12/2002 | Kennis et al. |
| 6,528,528 | B2 | 3/2003 | Connor et al. |
| 6,624,184 | B1 | 9/2003 | Gu et al. |
| 6,723,730 | B2 | 4/2004 | Bakthavatchalam et al. |
| 6,933,311 | B2 | 8/2005 | Lee et al. |
| 7,067,507 | B2 * | 6/2006 | Pulley et al. ........ 514/183 |
| 7,067,553 | B2 | 6/2006 | Suh et al. |
| 7,074,805 | B2 | 7/2006 | Lee et al. |
| 7,335,678 | B2 | 2/2008 | Lee et al. |
| 2001/0047090 | A1 | 11/2001 | Duckworth et al. |
| 2003/0153596 | A1 | 8/2003 | Suh et al. |
| 2003/0158188 | A1 | 8/2003 | Lee et al. |
| 2003/0158198 | A1 | 8/2003 | Lee et al. |
| 2003/0195201 | A1 | 10/2003 | Bo et al. |
| 2003/0212140 | A1 | 11/2003 | Suh et al. |
| 2003/0236280 | A1 | 12/2003 | Codd et al. |
| 2004/0038969 | A1 | 2/2004 | Doherty et al. |
| 2004/0044003 | A1 | 3/2004 | Kyle et al. |
| 2004/0082562 | A1 | 4/2004 | Gu et al. |
| 2004/0082780 | A1 | 4/2004 | Doherty et al. |
| 2004/0102497 | A1 | 5/2004 | Gu et al. |
| 2004/0122089 | A1 | 6/2004 | Martin et al. |
| 2004/0138252 | A1 | 7/2004 | Ikeda et al. |
| 2004/0142958 | A1 | 7/2004 | Herzberg et al. |
| 2004/0157849 | A1 | 8/2004 | Lee et al. |
| 2004/0176443 | A1 | 9/2004 | Bakthavatchalam et al. |
| 2004/0209884 | A1 | 10/2004 | Lee et al. |
| 2005/0004133 | A1 | 1/2005 | Makings et al. |
| 2005/0107388 | A1 | 5/2005 | Brown et al. |

(Continued)

FOREIGN PATENT DOCUMENTS

CA    2 571 133 A1    1/2006

(Continued)

OTHER PUBLICATIONS

Purandare et al. Tetrahedron Letters, 2002, 43 (31), 3903-3906.*
"Post-Operative Pain", http://www.painmd.com/types-of-pain/general-pain/post-operative-pain.html, accessed Jan. 4, 2010.*
Correll et al. Expert Opinion on Therapeutic Patents, 2006, 16(6), 783-95.*
Planells-Cases et al. Expert Opinion on Drug Discovery, 2007, 2(8), 1053-63.*

(Continued)

*Primary Examiner* — Noble Jarrell
(74) *Attorney, Agent, or Firm* — Leydig, Voit & Mayer, Ltd.

(57) ABSTRACT

To provide a compound having an excellent inhibitory effect on vanilloid receptor subtype 1 (VR1) activity which is effective in treating diseases to which the vanilloid receptor subtype 1 (VR1) activity is involved, such as pain, acute pain, chronic pain, neuropathic pain, rheumatoid arthritis pain, neuralgia, etc. and a pharmaceutical composition containing the compound. The object has been attained by a condensed benzamide compound represented by the following formula (the symbols in the formula have the same meanings defined in the specification) or its salt:

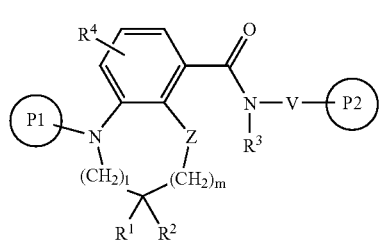

[1]

6 Claims, No Drawings

U.S. PATENT DOCUMENTS

| | | |
|---|---|---|
| 2005/0158827 A1 | 7/2005 | Curtis |
| 2005/0165046 A1 | 7/2005 | Hulme et al. |
| 2005/0165049 A1 | 7/2005 | Hulme et al. |
| 2005/0176726 A1 | 8/2005 | Wang et al. |
| 2005/0182067 A1 | 8/2005 | Balan et al. |
| 2005/0227986 A1 | 10/2005 | Bo et al. |
| 2005/0267163 A1 | 12/2005 | Doherty et al. |
| 2005/0272777 A1 | 12/2005 | Doherty et al. |
| 2005/0272931 A1 | 12/2005 | Bo et al. |
| 2005/0277631 A1 | 12/2005 | Doherty et al. |
| 2005/0277646 A1 | 12/2005 | Doherty et al. |
| 2006/0030618 A1 | 2/2006 | Bo et al. |
| 2006/0035939 A1 | 2/2006 | Koga et al. |
| 2006/0100202 A1 | 5/2006 | Raimi et al. |
| 2006/0142333 A1 | 6/2006 | MacDonald et al. |
| 2007/0149517 A1 | 6/2007 | Koga et al. |
| 2008/0064687 A1 | 3/2008 | Suh et al. |
| 2008/0214524 A1 | 9/2008 | Lee et al. |
| 2009/0105298 A1 | 4/2009 | Ikeda et al. |
| 2010/0022523 A1 | 1/2010 | Koga et al. |

FOREIGN PATENT DOCUMENTS

| | | | |
|---|---|---|---|
| CN | 1006382 | B | 1/1990 |
| CN | 1126468 | A | 7/1996 |
| CN | 1059674 | C | 12/2000 |
| CN | 1335845 | A | 2/2002 |
| JP | 57-141456 | A | 9/1982 |
| JP | 09-059236 | A | 3/1997 |
| JP | 2001-526255 | A | 12/2001 |
| JP | 2003-192673 | A | 7/2003 |
| JP | 2004-506714 | T2 | 3/2004 |
| JP | 2005-516951 | T | 6/2005 |
| JP | 2005-518371 | T | 6/2005 |
| WO | WO 97/48697 A1 | | 12/1997 |
| WO | WO 99/32433 A1 | | 7/1999 |
| WO | WO 0020421 | * | 4/2000 |
| WO | WO 00/26197 A1 | | 5/2000 |
| WO | WO 00/29577 A1 | | 5/2000 |
| WO | WO 00/32766 A1 | | 6/2000 |
| WO | WO 00-40580 A1 | | 7/2000 |
| WO | WO 00/63415 A1 | | 10/2000 |
| WO | WO 02/08221 A2 | | 1/2002 |
| WO | WO 02/16318 A1 | | 2/2002 |
| WO | WO 02/064545 A1 | | 8/2002 |
| WO | WO 02/074726 A2 | | 9/2002 |
| WO | WO 03/006019 A1 | | 1/2003 |
| WO | WO 03/049702 A2 | | 6/2003 |
| WO | WO 03/053945 A2 | | 7/2003 |
| WO | WO 03/066593 A2 | | 8/2003 |
| WO | WO 03/068749 A1 | | 8/2003 |
| WO | WO 03/070247 A1 | | 8/2003 |
| WO | WO 03/080578 A1 | | 10/2003 |
| WO | WO 03/097586 A1 | | 11/2003 |
| WO | WO 03/099284 A1 | | 12/2003 |
| WO | WO 2004/009552 A1 | | 1/2004 |
| WO | WO 2004/022002 A2 | | 3/2004 |
| WO | WO 2004-052846 A1 | | 6/2004 |
| WO | WO 2004/054582 A1 | | 7/2004 |
| WO | WO 2004/056394 A1 | | 7/2004 |
| WO | WO 2004-056774 A2 | | 7/2004 |
| WO | WO 2004/108133 A1 | | 12/2004 |
| WO | WO 2005/023807 A2 | | 3/2005 |
| WO | WO 2005/070885 A1 | | 8/2005 |
| WO | WO 2005/077938 A1 | | 8/2005 |
| WO | WO 2005/077944 A1 | | 8/2005 |
| WO | WO 2005/103018 A1 | | 11/2005 |

OTHER PUBLICATIONS

Bevan et al., *Trends Neurosci.*, 17(12): 509-512 (1994).
Birder et al., *Nature Neuroscience*, 5(9): 856-860 (Sep. 2002).
Carlton et al., *Neuroscience Letters*, 310: 53-56 (2001).
Caterina et al., *Nature*, 389: 816-824 (Oct. 23, 1997).
Caterina et al., *Science*, 288: 306-313 (Apr. 14, 2000).
Chuang et al., *Nature*, 411: 957-962 (Jun. 21, 2001).
Davis et al., *Nature*, 405: 183-187 (May 11, 2000).
Ikeda et al., *Life Sciences*, 69: 2911-2919 (2001).
Numazaki et al., *Journal of the Japanese Biochemical Society*, 75(5): 359-371 (2003).
Premkumar et al., *Journal of Physiology*, 545: 107-117 (2002).
Purandare et al., *Tetrahedron Letters*, 43: 3903-3906 (2002).
Shu et al., *Neuroscience Letters*, 274: 159-162 (1999).
Sugiura et al., *J. Neurophysiol.*, 88: 544-548 (Jul. 2002).
Szallasi et al., *Pharmacological Reviews*, 51(2): 159-211 (1999).
Tominaga et al., *Proc. Natl. Acad. Sci. USA*, 98(12): 6951-6956 (Jun. 5, 2001).
Yang et al., *J. Neurosci.*, 22(15): 6388-6393 (Aug. 1, 2002).
Yiangou et al., *Lancet*, 357: 1338-1339 (Apr. 28, 2001).
U.S. Appl. No. 11/181,235, Office Action dated Dec. 19, 2007.
U.S. Appl. No. 11/181,235, Reply to Office Action dated Jun. 13, 2008.
U.S. Appl. No. 11/181,235, Office Action dated Jun. 20, 2008.
U.S. Appl. No. 11/181,235, Reply to Office Action dated Sep. 9, 2008.
U.S. Appl. No. 11/181,235, Office Action dated Oct. 7, 2008.
U.S. Appl. No. 11/181,235, Reply to Office Action dated Jan. 7, 2009.
U.S. Appl. No. 11/616,962, Office Action dated Apr. 22, 2009.
U.S. Appl. No. 11/616,962, Reply to Office Action dated Jul. 22, 2009.
U.S. Appl. No. 11/616,962, Office Action dated Sep. 24, 2009.
U.S. Appl. No. 11/616,962, Reply to Office Action dated Dec. 23, 2009.
U.S. Appl. No. 11/616,962, Office Action dated Jan. 14, 2010.
U.S. Appl. No. 11/616,962, Office Action dated Apr. 6, 2010.
U.S. Appl. No. 12/430,268, Office Action dated Mar. 30, 2010.
Mashkovsky, M.D., *Medicaments*, vol. 1, p. 11 (2001).
U.S. Appl. No. 11/616,962, Reply to Office Action dated Jul. 6, 2010.
U.S. Appl. No. 12/430,268, Reply to Office Action dated Jun. 30, 2010.
U.S. Appl. No. 12/430,268, Office Action dated Aug. 19, 2010.
U.S. Appl. No. 12/430,268, Reply to Office Action dated Feb. 22, 2011.

* cited by examiner

CONDENSED BENZAMIDE COMPOUNDS AND INHIBITORS OF VANILLOID RECEPTOR SUBTYPE 1 (VR1) ACTIVITY

TECHNICAL FIELD

The present invention relates to a novel condensed benzamide compound having an inhibitory effect on vanilloid receptor subtype 1 (VR1) activity, and a pharmaceutical composition comprising the compound as an active ingredient, particularly a remedy of pain.

BACKGROUND ART

Capsaicin, which is the main ingredient of red pepper, is a pungency causing ingredient as well as a pain producing substance. It has been reported that many nociceptive nerves, particularly unmyelinated C fibers have capsaicin sensitivity and it is known that C fibers will selectively drop out when capsaicin is administered to an infant rodent. It has been also reported that there are many sites of action for capsaicin distributed in the skin, cornea, and oral mucosa, and the distribution thereof is also observed in the muscles, joints and internal organs, particularly in the cardiovascular system, respiratory system and bladder urinary tract system, and it is important for autonomic nerve reflex. In addition, capsaicin sensitivity is also observed in the nerves of the preoptic area of the thalamus, and involvement in the regulation of body temperature is presumed. Depolarization by inflow of $Na^+$ and $Ca^{2+}$ by capsaicin administration is observed in the nociceptive nerves and discharge of glutamic acid and neuropeptides (mainly Substance P and calcitonin gene-related peptide) from the center side end of the primary afferent fiber of the spinal dorsal horn is resulted. Now that specific binding activity of resiniferatoxin (RTX) which brings about similar effects to that of capsaicin has been observed, and that capsazepine has been revealed as a competitive inhibitor, liposoluble capsaicin is considered to act on receptor protein (see Szallasi A, Blumberg P M. (1999) Pharmacol. Rev. 51, 159-212).

The capsaicin receptor gene was cloned in 1997 (see, for example, Caterina M J, Schumacher M A Tominaga M, Posen T A, Levine J D, Julius D. (1997) Nature 389, 816-824). It was presumed from its amino acid sequence that it was an ion channel having a six-transmembrane domain. Since capsaicin has a vanillyl group in the structure, it is generically referred to as vanilloids along with its analogs such as RTX, and the cloned receptor was named vanilloid receptor subtype 1 (hereinafter referred to as VR 1; This VR1 may be also referred to as TRPV1 (transient receptor potential vanilloid receptor 1)). Then, electrophysiological functional analysis using the patch clamping method has been performed by making oocytes of *Xenopus laevis* and human derived cultured cells to express VR1, and it has been revealed that VR1 is directly activated by capsaicin, without mediated by an intracellular second messenger (see, for example, Caterina M J, Schumacher M A Tominaga M, Posen T A, Levine J D, Julius D. (1997) Nature 389, 816-824), and that VR1 is a non-selective cation ion channel having high $Ca^{2+}$ permeability with an outward rectification property (see, for example, Premkumar L S, Agarwal S, Steffen D. (2002) J. Physiol. 545, 107-117).

Although capsaicin is a pain causing substance, it is used as an analgesic agent to mitigate pain in diabetic neuropathy or rheumatic neurosis (see, for example, Szallasi A, Blumberg P M. (1999) Pharmacol. Rev. 51, 159-212). It is understood that such mitigation is resulted from a phenomenon that the sensory nerve end exposed to capsaicin stops answering to pain stimulus, that is, desensitization. Although it is considered that the desensitization mechanism of VR1 involves $Ca^{2+}$-mediated regulation, regulation depending on potential, activity control of VR1 by phosphorylation and dephosphorylation, etc., many points remain unclear.

As well as capsaicin, heat and acid also cause pain and it is known that the capsaicin sensitive nociceptive nerves respond to two or more types of stimulation. It was found that VR1 was directly activated by not only capsaicin but heat stimulation of 43° C. or more (see, for example, Yang D, Gereau R W 4th. (2002) J. Neurosci. 22, 6388-6393). The temperature of 43° C. is mostly in agreement with the temperature threshold which causes a pain in humans and animals, suggesting that VR1 participates in nociceptive heat stimulation receptance.

Acidification occurs in an organ in the case of inflammation or ischemia and it is known to cause or enhance pain (see, for example, Bevan S, Geppetti P. (1994) Trends Neurosci. 17, 509-512). It has turned out that when the pH outside cells is reduced within the limits of the acidification which takes place in the case of an organ lesion, VR1 can be directly activated by the acidification (proton) alone, and it is surmised that VR1 is the actual molecule which receives stimulation by acidification in an organ which takes place in the case of inflammation or ischemia (see, for example, Yang D, Gereau R W 4th. (2002) J. Neurosci. 22, 6388-6393).

Immunohistological analysis using a specific antibody has confirmed that the number of unmyelinated C fibers expressing VR1 increases in an inflamed region as compared in a normal region (see, for example, Carlton S M, Coggeshall R E. (2001) Neurosci. Lett. 310, 53-56). The enhancement of VR1 expression in submucosal plexus has been actually observed in human inflammatory bowel disease (see, for example, Yiangou Y, Facer P, Dyer N H, Chan C L, Knowles C, Williams N S, Anand P. (2001) Lancet 357, 1338-1339). Such an increase in the amount of VR1 expression causes peripheral sensitization in an inflamed organ and presumably contributes to duration of inflammatory hyperalgesia.

It has been also reported that extracellular ATP, bradykinin and a neuro growth factor which are inflammation related substances increase VR1 activity (see, for example, Tominaga M, Wada M, Masu M. (2001) Proc. Natl. Acad. Sci. USA 98, 6951-6956; Shu X, Mendell L M. (1999) Neurosci. Lett. 274, 159-162; Chuang H H, Prescott E D, Kong H, Shields S, Jordt S E, Basbaum A I, Chao, M V, Julius D. (2001) Nature 411, 957-962; and Sugiura T, Tominaga M, Katsuya H, Mizumura K. (2002) J. Neurophysiol. 88, 544-548) and it is said to be a fact without doubt that VR1 involves in pain and hypersensitivity of pain including those caused by inflammation (see, for example, Numazaki M, Tominaga M (2003) Biochemistry 75, 359-371).

The sensory nerve cells in a VR1-deficient mouse responded to none of capsaicin, proton and heat stimulation. It is also reported that in action analysis, VR1-deficient mouse does not show the pain reaction following capsaicin administration, and sensitivity to heat stimulation decreases and inflammatory hyperalgesia is not observed (see, for example, Caterina M J, Leffler A, Malmberg A B, Martin W J, Trafton J, Peterson-Zeitz K R, Koltzenburg M, Basbaum A I, Julius D. (2000) Science 288, 306-313 and Davis L B, Gray J, Gunthorpe M J et al. (2000) Nature 405, 183-187). Thus, it has been confirmed also on an individual level from the analysis of VR1-deficient mouse that VR1 functions as a wide range pain stimulation receptor.

Moreover, as for the relation between vanilloid receptor subtype 1 (VR1) and a disease, it has been reported already that a substance which inhibits VR1 activity is useful as a therapeutical agent of various diseases.

Particularly with regard to a therapeutical agent of pain, there is a report that capsazepine which is known as a VR1 antagonist has exhibited a significant analgesic effect in an animal model (see, for example, Ikeda Y, Ueno A, Naraba H, Oh-ishi S, (2001) Life Science 69, 2911-2919), and use is expected as a new therapeutical agent of pain having an inhibitory effect of VR1 activity.

It has been confirmed with regard to bladder hyperstrain type frequent urination and urinary incontinence that the bladder contraction function of VR1-deficient mouse decreases and there is a report that a compound having a capsaicin-like pharmacological mechanism or a compound having an inhibitory action on VR1, i.e., a compound inhibiting vanilloid receptor subtype 1 (VR1) activity is useful for improving bladder function, for example, as a therapeutical agent of frequent urination, urinary incontinence, etc (see, for example, (2002) Nat. Neurosci. 5, 856-860).

In addition, another reference reports that a substance having an inhibitory effect to the vanilloid receptor subtype 1 (VR1), particularly antagonist of VR1 receptor is useful for preventing and treating diseases related to VR1 activity, particularly urgent urinary incontinence, overactive bladder, chronic pain, neuropathic pain, postoperative pain, rheumatoid arthritis pain, neuralgia, neuropathy, hyperalgesia, nerve damage, ischemic symptom, neurodegenerative, cerebral apoplexy, incontinence, inflammatory disease, urgent urinary incontinence (UUI) and/or conditions and diseases including overactive bladder (see, for example, JP 2003-192673).

Furthermore, it is also known that diseases relevant to the vanilloid receptor activity may include pain, acute pain, chronic pain, neuropathic pain, postoperative pain, migraine, joint pain, neuropathy, nerve damage, diabetic nervous disease, neurodegenerative disease, neurogenic skin disorder, cerebral apoplexy, bladder hypersensitivity, irritable bowel syndrome, abnormalities in respiratory organs such as asthma and chronic obstructive pulmonary disease, stimulation of skin, eye or mucosa, fever, stomach or duodenal ulcer, inflammatory bowel disease, inflammatory disease, etc (see, for example, JP 2004-506714 T2).

Accordingly, it can be said that substances having vanilloid receptor subtype 1 (VR1) antagonistic activity is useful as a therapeutic agent for conditions in which C fibers participates, for example, not to mention pruritus, allergic and allergic rhinitis, overactive bladder type frequent urination and urinary incontinence, apoplexy, irritable bowel syndrome, respiratory ailment such as asthma and chronic obstructive pulmonary disease, dermatitis, mucositis, stomach and duodenal ulcer, inflammatory bowel disease, etc. but also pain, acute pain, chronic pain, neuropathic pain, postoperative pain, migraine, joint pain, neuropathy, nerve damage, diabetic nervous disease, neurodegenerative disease, rheumatoid arthritis pain, neuralgia, neuropathy, hyperalgesia, neurogenic skin disorder, apoplexy, overweight, urgent urinary incontinence, ischemic symptom and an inflammatory disease, etc.

Next, compounds considered to relatively resemble the known vanilloid receptor subtype 1 (VR1) antagonist and the compound of present invention are described.

The amide-type compounds represented by the following general formula [A], [B] and [C] are disclosed in WO03/068749 as compounds exhibiting antagonism to VR1.

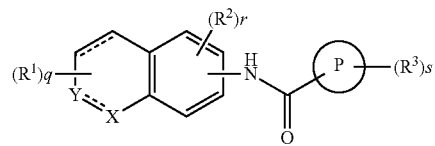

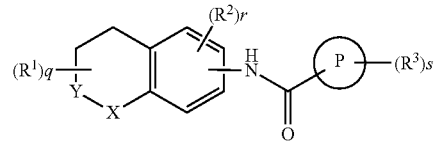

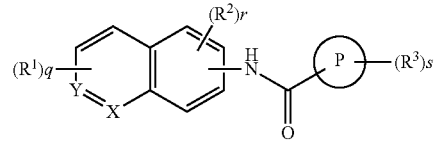

The urea-type compound represented by the following general formula [D] is disclosed in WO03/080578 as a compound exhibiting antagonism to VR1.

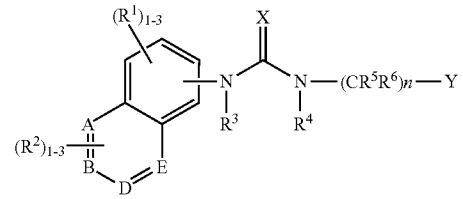

Quinuclidine-3'-yl 1-phenyl-1,2,3,4-tetrahydroisoquinoline-2-carboxylate is disclosed as a compound exhibiting an inhibitory effect against capsaicin-induced extravasation of a plasma protein in the bladder is disclosed in WO03/006019.

The urea-type compound represented by the following general formula [E] is disclosed in WO03/053945 as a compound exhibiting antagonism to VR1.

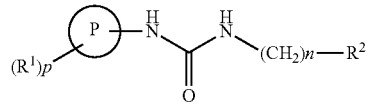

The compound represented by the following general formula [F] is disclosed as a compound in WO03/099284 as a compound exhibiting binding activity to VR1.

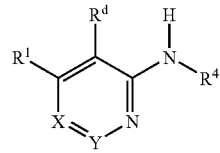

However, these compounds are different from the compound of the present invention in the structure, and there can be found no description which suggests the compound of the present invention.

DISCLOSURE OF THE INVENTION

As an analgesic agent, narcotic analgesics (morphine etc.), nonnarcotic analgesics (NSAID (nonsteroidal anti-inflammatory drug)), etc. are mainly used now. However, use of narcotic analgesics is severely restricted due to development of resistance/dependency and other serious side effects. It is known well other that an upper gastrointestinal tract disorder and a liver disorder frequently occur during long-term administration of nonnarcotic analgesics, and analgesic agent with a few side effects with higher analgesic effect is eagerly desired. Furthermore, as for diabetes-induced neuropathic pain, postherpetic neuralgia, and neuropathic pain such as trigeminal neuralgia, no effective analgesic agent has been found yet and development of an effective analgesic agent thereof is also expected.

Capsaicin-like compounds which act on VR1 are considered to develop the analgesic effect based on a pharmacological mechanism completely different from those of existing analgesic agents (desensitization of capsaicin-sensitive nerves), and the efficacy is greatly expected as a therapeutic agent for neuropathic pain and the pain which originates in various conditions such as rheumatic arthritis for which the existing analgesic agents are not effective.

The fact that the final target of various inflammation related substances is VR1 suggests possibility that an agent which acts on VR1 is effective for various inflammatory pains and interstitial cystitis and its efficacy is greatly expected as an analgesic agent which replaces the existing analgesic agents.

Therefore, the purpose of the present invention is to provide a new analgesic agent based on the pharmacological mechanism completely different from those of existing analgesic agents (desensitization of capsaicin-sensitive nerves), i.e., VR1 activity inhibitor.

As a result of intensive study for developing an analgesic agent based on new action mechanism which will replace conventional analgesic agents such as nonnarcotic analgesics, pyrazolone analgesics, non-pyrazolone analgesics and NSAIDs, the present inventors have found out a condensed benzamide compound which has excellent inhibitory effect on VR1, and completed the present invention. The present invention is described in more detail below.

1. A condensed benzamide compound represented by the following general formula [1] or a pharmaceutically acceptable salt thereof:

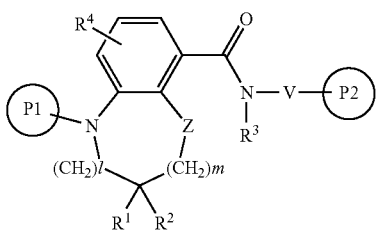

[1]

[wherein Z is
(1) —O—,
(2) —NR$^5$— (wherein R$^5$ is a hydrogen atom or a C1-6 alkyl group),
(3) —S—,
(4) —SO— or
(5) —SO$_2$—;
l is 0, 1 or 2;
m is 0, 1 or 2;
R$^1$ is
(1) a hydrogen atom or
(2) a C1-6 alkyl group which may be substituted with 1 to 5 substituents selected from the following Group A:
Group A:
(a) a halogen atom,
(b) a hydroxyl group,
(c) a C1-6 alkoxy group,
(d) a carboxyl group,
(e) a C1-6 alkoxycarbonyl group,
(f) —CONR$^6$R$^7$ (wherein R$^6$ and R$^7$ are the same or different and each represents a hydrogen atom, a C1-6 alkyl group or an acyl group and said alkyl group may be substituted with a hydroxyl group or an acyloxy group),
(g) —NR$^6$R$^7$ (wherein R$^6$ and R$^7$ are the same as above),
(h) —NR$^6$COR$^7$ (wherein R$^6$ and R$^7$ are the same as above),
(i) —NR$^8$CONR$^6$R$^7$ (wherein R$^6$ and R$^7$ are the same as above, and R$^8$ is a hydrogen atom or a C1-6 alkyl group); and
(j) —NR$^6$SO$_2$R$^9$ (wherein R$^6$ is the same as above, and R$^9$ is a C1-6 alkyl group);
R$^2$ is
(1) a hydrogen atom,
(2) a hydroxyl group,
(3) a C1-6 alkyl group which may be substituted with 1 to 5 substituents selected from the Group A (wherein the Group A is the same as above),
(4) a carboxyl group,
(5) a C1-6 alkoxycarbonyl group or
(6) —CONR$^{10}$R$^{11}$ (wherein R$^{10}$ and R$^{11}$ are the same or different and each represents a hydrogen atom or a C1-6 alkyl group); or R$^2$ together with R$^1$ forms =O;
R$^3$
(1) a hydrogen atom, or
(2) a C1-6 alkyl group;
R$^4$ is
(1) a hydrogen atom,
(2) a halogen atom
(3) a C1-6 alkyl group which may be substituted with 1 to 5 substituents selected from the following Group B,
(4) a C1-6 alkoxy group which may be substituted with 1 to 5 substituents selected from the following Group B,
(5) a cycloalkyl group which may be substituted with 1 to 5 substituents selected from the following Group B,
(6) an aralkyl group which may be substituted with 1 to 5 substituents selected from the following Group B,
(7) an aralkoxy group which may be substituted with 1 to 5 substituents selected from the following Group B, or
(8) a cycloalkylalkoxy group which may be substituted with 1 to 5 substituents selected from the following Group B,
Group B:
(a) a halogen atom,
(b) a halo C1-6 alkyl group,
(c) a hydroxyl group,
(d) a halo C1-6 alkoxy group,
(e) a C1-6 alkoxycarbonyl group,
(f) a C1-6 alkoxy group,
(g) a carboxyl group,
(h) —CONR$^{12}$R$^{13}$ (wherein R$^{12}$ and R$^{13}$ are the same or different and each represents a hydrogen atom or a C1-6 alkyl group);
(i) —NR$^{12}$R$^{13}$ (wherein R$^{12}$ and R$^{13}$ are the same as above), (j) —NR$^{12}$COR$^{13}$ (wherein R$^{12}$ and R$^{13}$ are the same as above),
(k) —NR$^{14}$CONR$^{12}$R$^{13}$ (wherein R$^{12}$ and R$^{13}$ are the same as above, and R$^{14}$ is a hydrogen atom or a C1-6 alkyl group),
(l) —SO$_2$R$^{15}$ (wherein R$^{15}$ is a C1-6 alkyl group), and
(m) —NR$^{12}$SO$_2$R$^{15}$ (wherein R$^{12}$ and R$^{15}$ are the same as above);
(9) a hydroxyl group,
(10) —NR$^{16}$R$^{17}$ (wherein R$^{16}$ and R$^{17}$ are the same or different and each represents a hydrogen atom or a C1-6 alkyl group),
(11) —COR$^{18}$ (wherein R$^{18}$ is a C1-6 alkyl group, a C1-6 alkoxy group, a cycloalkyl group, an aralkyl group, an aralkoxy group, a cycloalkylalkoxy group or a hydroxyl group),
(12) —CONR$^{16}$R$^{17}$ (wherein R$^{16}$ and R$^{17}$ are the same as above),
(13) —NR$^{19}$CONR$^{16}$R$^{17}$ (wherein R$^{16}$ and R$^{17}$ are the same as above, and R$^{19}$ is a hydrogen atom or a C1-6 alkyl group),
(14) —NR$^{16}$COOR$^{20}$ (wherein R$^{16}$ is the same as above, and R$^{20}$ is a C1-6 alkyl group or a cycloalkyl group),
(15) —SR$^{20}$ (wherein R$^{20}$ is the same as above),
(16) —SOR$^{20}$ (wherein R$^{20}$ is the same as above),
(17) —SO$_2$R$^{20}$ (wherein R$^{20}$ is the same as above),
(18) —SO$_2$NR$^{16}$R$^{17}$ (wherein R$^{16}$ and R$^{17}$ are the same as above) or
(19) —NR$^{16}$COR$^{18}$ (wherein R$^{16}$ and R$^{18}$ are the same as above);
V is
(1) a single bond or
(2) —(CR$^{21}$R$^{22}$)$_n$— (wherein R$^{21}$ and R$^{22}$ are the same or different and each represents a hydrogen atom or a C1-6 alkyl group, and n is 1 or 2);
P1 and P2 rings are the same or different and each represents
(1) a carbocyclic group which may be substituted with 1 to 5 substituents selected from the following group C or
(2) a heterocyclic group which may be substituted with 1 to 5 substituents selected from the following group,
Group C:
(a) a halogen atom,
(b) a hydroxyl group,
(c) a C1-6 alkoxy group which may be substituted with 1 to 5 substituents selected from the Group A,
(d) an C1-6 alkylthio group,
(e) a C1-6 alkyl group which may be substituted with 1 to 5 substituents selected from the Group A,
(f) —CONR$^{23}$R$^{24}$ (wherein R$^{23}$ and R$^{24}$ are the same or different and each represents a hydrogen atom or a C1-6 alkyl group which may be substituted with 1 to 5 substituents selected from the Group A),
(g) —NR$^{123}$R$^{124}$ (wherein R$^{123}$ and R$^{124}$ are the same or different and each represents a hydrogen atom or a C1-6 alkyl group which may be substituted with 1 to 5 substituents selected from the Group A),
(h) —NR$^{223}$COR$^{224}$ (wherein R$^{223}$ and R$^{224}$ are the same or different and each represents a hydrogen atom or a C1-6 alkyl group which may be substituted with 1 to 5 substituents selected from the Group A),
(i) —NR$^{25}$CONR$^{323}$R$^{324}$ (wherein R$^{323}$ and R$^{324}$ are the same or different and each represents a hydrogen atom or a C1-6 alkyl group which may be substituted with 1 to 5 substituents selected from the Group A),
(j) —SR$^{26}$ (wherein R$^{26}$ is a C1-6 alkyl group),
(k) —SOR$^{126}$ (wherein R$^{126}$ is a C1-6 alkyl group),
(l) —SO$_2$R$^{226}$ (wherein R$^{226}$ is a C1-6 alkyl group),
(m) —NR$^{423}$SO$_2$R$^{326}$ (wherein R$^{423}$ is a hydrogen atom or a C1-6 alkyl group which may be substituted with 1 to 5 substituents selected from the Group A, and R$^{326}$ is a C1-6 alkyl group),
(n) —SO$_2$NR$^{523}$R$^{524}$ (wherein R$^{523}$ and R$^{524}$ are the same or different and each represents a hydrogen atom or a C1-6 alkyl group which may be substituted with 1 to 5 substituents selected from the Group A),
(o) —COR$^{27}$ (wherein R$^{27}$ is a C1-6 alkyl group, C1-6 alkoxy group, a cycloalkyl group, an aralkyl group, an aralkoxy group, a cycloalkylalkoxy group or a hydroxyl group),
(p) a carbocyclic group which may be substituted with 1 to 5 substituents selected from (a) to (o) of the Group C,
(q) a heterocyclic group which may be substituted with 1 to 5 substituents selected from (a) to (o) of the Group C,
(r) —O—R$^{28}$ (wherein R$^{28}$ is an acyl group, a carbocyclic group which may be substituted with 1 to 5 substituents selected from (a) to (o) of the Group C or a heterocyclic group which may be substituted with 1 to 5 substituents selected from (a) to (o) of the Group C),
(s) —O—(CR$^{21}$R$^{22}$)$_n$—R$^{28}$ (wherein R$^{21}$, R$^{22}$, n, and R$^{28}$ are the same as above),
(t) a nitro group, and
(u) a cyano group.

2. The condensed benzamide compound or pharmaceutically acceptable salt thereof according to above 1 wherein Z is —O—, —NR$^5$—, —S— or —SO—.

3. The condensed benzamide compound or pharmaceutically acceptable salt thereof according to above 1 or 2 wherein R$^3$ is a hydrogen atom or a C1-4 alkyl group.

4. The condensed benzamide compound or pharmaceutically acceptable salt thereof according to above 1 to 3 wherein the P1 ring is a saturated or unsaturated 5-membered or 6-membered heterocyclic ring having 1 to 4 hetero atoms selected from a nitrogen atom, an oxygen atom and a sulfur atom, or a condensed ring of these heterocyclic rings, or a condensed heterocyclic ring of said heterocyclic ring and a carbocyclic ring selected from benzene, cyclopentane and cyclohexane, or a phenyl group (wherein said heterocyclic ring may be substituted with a halogen atom, a hydroxyl group, a C1-6 alkyl group which may be substituted with 1 to 5 substituents selected from the Group A, and a C1-6 alkoxy group which may be substituted with 1 to 5 substituents selected from the Group A).

5. The condensed benzamide compound or pharmaceutically acceptable salt thereof according to above 4 wherein the P1 ring is a saturated or unsaturated 5-membered or 6-membered heterocyclic ring having at least 1 to 3 nitrogen atoms or a phenyl group (wherein said heterocyclic ring may be substituted with a C1-6 alkyl group which may be substituted with a hydroxyl group or a C1-6 alkyl group, a halogen atom, a hydroxyl group, and a C1-6 alkoxy group which may be substituted with 1 to 5 substituents selected from the Group A).

6. The condensed benzamide compound or a pharmaceutically acceptable salt thereof according to above 5 wherein the P1 ring is a heterocyclic group selected from a pyridyl group, a pyrazinyl group and a thiazolyl group or a phenyl group (wherein these heterocyclic groups may be substituted with a C1-6 alkyl group which may be substituted with a hydroxyl group, a halogen atom, a hydroxyl group, and a C1-6 alkoxy group which may be substituted with 1 to 5 substituents selected from the Group A).

7. The condensed benzamide compound or a pharmaceutically acceptable salt thereof according to above 1 to 3 wherein the P2 ring is a carbon cyclic group which may be substituted with a substituent group selected from

9 a halogen atom,
a hydroxyl group,
a C1-6 alkoxy group (wherein said alkoxy group may be substituted with a halogen atom, —CONR$^{623}$R$^{624}$ (wherein R$^{623}$ and R$^{624}$ are the same or different and each represents a hydrogen atom or a C1-6 alkyl group which may be substituted with 1 to 5 substituents selected from the Group A), a C3-8 cycloalkyl group, a C1-6 alkoxy group, a carboxyl group or a C1-6 alkoxycarbonyl group),
a C1-6 alkyl group (wherein said alkyl group may be substituted with a halogen atom, a hydroxyl group or a C1-6 alkoxy group),
—NR$^{123}$R$^{124}$ (wherein R$^{123}$ and R$^{124}$ are the same as above),
—NR$^{223}$COR$^{224}$ (wherein R$^{223}$ and R$^{224}$ are the same as above),
—COR$^{27}$ (wherein R$^{27}$ is a C1-6 alkyl group, C1-6 alkoxy group, a cycloalkyl group, an aralkyl group, an aralkoxy group, a cycloalkylalkoxy group or a hydroxyl group),
—CONR$^{23}$R$^{24}$ (wherein R$^{23}$ and R$^{24}$ are the same as above),
a heterocyclic group as a saturated or unsaturated substituent group which has 1 to 3 nitrogen atoms as hetero atoms (wherein said heterocyclic group may be substituted with a substituent group selected from a hydroxyl group, —CONR$^{723}$R$^{724}$ (wherein R$^{723}$ and R$^{724}$ are the same or different and each represents a hydrogen atom or a C1-6 alkyl group which may be substituted with 1 to 5 substituents selected from the Group A), a C1-6 alkoxy group, a carboxyl group, a C1-6 alkyl group which may be substituted with a C1-6 alkoxy group, a C1-6 alkoxycarbonyl group and an acyloxy group),
—O—R$^{28}$ (wherein R$^{28}$ is an acyl group, a carbocyclic group which may be substituted with 1 to 5 substituents selected from (a) to (i) of the Group C or a heterocyclic group which may be substituted with 1 to 5 substituents selected from (a) to (l) of the Group C),
—O—(CR$^{121}$R$^{122}$)$_n$—R$^{128}$ (wherein R$^{121}$ and R$^{122}$ are the same or different and each represents a hydrogen atom or a C1-6 alkyl group, n is 1 or 2, and R$^{28}$ is an acyl group, a carbocyclic group which may be substituted with 1 to 5 substituents selected from (a) to (i) of the Group C or a heterocyclic group which may be substituted with 1 to 5 substituents selected from (a) to (l) of the Group C),
a nitro group and
a cyano group, or
a heterocyclic group which may be substituted with a substituent as described for the carbocyclic group (wherein said heterocyclic group means a saturated or unsaturated 5-membered or 6-membered heterocyclic ring which has 1 to 4 hetero atoms selected from a nitrogen atom, an oxygen atom and a sulfur atom, or a condensed ring of these heterocyclic rings, or a condensed heterocyclic group of said heterocyclic ring and a carbocyclic ring selected from benzene, cyclopentane and cyclohexane).

8. The condensed benzamide compound or a pharmaceutically acceptable salt thereof according to above 7 wherein the P2 ring as a carbocyclic group is a phenyl group or a cyclohexyl group, or a heterocyclic group as the P2 ring is a thiazolyl group, a pyridyl group, a piperidyl group, a piperidino group, a quinolyl group, a benzo[1,3]dioxo group, a 2,3-dihydrobenzo[1,4]dioxo group or a 1,2,3,4-tetrahydroquinolyl group.

10

9. The condensed benzamide compound according to above 1 selected from the following group or a pharmaceutically acceptable salt thereof:
1) N-(4-tert-butylphenyl)-4-(3-chloropyridin-2-yl)-3,4-dihydro-2H-benzo[1,4]oxazine-8-carboxamide,
2) 8-(4-tert-butylphenyl)carbamoyl-4-(3-chloropyridin-2-yl)-3,4-dihydro-2H-benzo[1,4]oxazine-2-carboxylic acid,
3) N-(4-tert-butylphenyl)-4-(3-chloropyridin-2-yl)-3-methyl-3,4-dihydro-2H-benzo[1,4]oxazine-8-carboxamide,
4) N-(4-tert-butylphenyl)-1-(3-chloropyridin-2-yl)-4-methyl-1,2,3,4-tetrahydroquinoxaline-5-carboxamide,
5) N-(4-tert-butylphenyl)-9-(3-chloropyridin-2-yl)-6,7,8,9-tetrahydro-5-oxa-9-aza-benzocycloheptene-4-carboxamide,
6) N-(4-chlorophenyl)-4-(3-chloropyridin-2-yl)-3,4-dihydro-2H-benzo[1,4]oxazine-8-carboxamide,
7) 4-(3-chloropyridin-2-yl)-N-(4-isopropoxyphenyl)-3,4-dihydro-2H-benzo[1,4]oxazine-8-carboxamide,
8) N-(1-tert-butylpiperidin-4-yl)-4-(3-chloropyridin-2-yl)-3,4-dihydro-2H-benzo[1,4]oxazine-8-carboxamide,
9) 4-(3-chloropyridin-2-yl)-N-(4-methylphenyl)-3,4-dihydro-2H-benzo[1,4]oxazine-8-carboxamide,
10) 4-(3-chloropyridin-2-yl)-N-(trans-4-methylcyclohexyl)-3,4-dihydro-2H-benzo[1,4]oxazine-8-carboxamide,
11) 4-(3-chloropyridin-2-yl)-N-(4-isobutyloxyphenyl)-3,4-dihydro-2H-benzo[1,4]oxazine-8-carboxamide,
12) N-benzyl-4-(3-chloropyridin-2-yl)-3,4-dihydro-2H-benzo[1,4]oxazine-8-carboxamide,
13) N-(4-chlorophenyl)methyl-4-(3-chloropyridin-2-yl)-3,4-dihydro-2H-benzo[1,4]oxazine-8-carboxamide,
14) N-(4-tert-butylphenyl)methyl-4-(3-chloropyridin-2-yl)-3,4-dihydro-2H-benzo[1,4]oxazine-8-carboxamide,
15) 4-(3-chloropyridin-2-yl)-N-(4-trifluoromethylphenyl)methyl-3,4-dihydro-2H-benzo[1,4]oxazine-8-carboxamide,
16) N-(4-tert-butylphenyl)-4-(pyridin-2-yl)-3,4-dihydro-2H-benzo[1,4]oxazine-8-carboxamide,
17) N-(4-tert-butylphenyl)-4-(3-trifluoromethylpyridin-2-yl)-3,4-dihydro-2H-benzo[1,4]oxazine-8-carboxamide,
18) N-(4-tert-butylphenyl)-4-(3-chloropyridin-2-yl)-2,2-dimethyl-3,4-dihydro-2H-benzo[1,4]oxazine-8-carboxamide,
19) N-(4-tert-butylphenyl)-4-(3-chloropyridin-2-yl)-2-methyl-3,4-dihydro-2H-benzo[1,4]oxazine-8-carboxamide,
20) N-(4-tert-butylphenyl)-6-chloro-4-(3-chloropyridin-2-yl)-3,4-dihydro-2H-benzo[1,4]oxazine-8-carboxamide,
21) 4-(3-chloropyridin-2-yl)-N-(4-trifluoromethylphenyl)-3,4-dihydro-2H-benzo[1,4]oxazine-8-carboxamide,
22) 4-(3-chloropyridin-2-yl)-N-(4-trifluoromethoxyphenyl)-3,4-dihydro-2H-benzo[1,4]oxazine-8-carboxamide,
23) 4-(3-chloropyridin-2-yl)-N-(4-methoxyphenyl)-3,4-dihydro-2H-benzo[1,4]oxazine-8-carboxamide,
24) N-(trans-4-tert-butylcyclohexyl)-4-(3-chloropyridin-2-yl)-3,4-dihydro-2H-benzo[1,4]oxazine-8-carboxamide,
25) 4-(3-chloropyridin-2-yl)-N-(4-chloro-3-trifluoromethylphenyl)-3,4-dihydro-2H-benzo[1,4]oxazine-8-carboxamide,
26) 4-(3-chloropyridin-2-yl)-N-(4-fluorophenyl)-3,4-dihydro-2H-benzo[1,4]oxazine-8-carboxamide,
27) 4-(3-chloropyridin-2-yl)-N-(3-trifluoromethylphenyl)-3,4-dihydro-2H-benzo[1,4]oxazine-8-carboxamide,
28) 4-(3-chloropyridin-2-yl)-N-(4-trifluoromethylthiazol-2-yl)-3,4-dihydro-2H-benzo[1,4]oxazine-8-carboxamide,
29) 4-(3-chloropyridin-2-yl)-N-(5-trifluoromethylpyridin-2-yl)-3,4-dihydro-2H-benzo[1,4]oxazine-8-carboxamide,
30) 4-(3-chloropyridin-2-yl)-N-(2-trifluoromethylpyridin-5-yl)-3,4-dihydro-2H-benzo[1,4]oxazine-8-carboxamide, 31) 4-(3-chloropyridin-2-yl)-N-(4-isopropylphenyl)-3,4-dihydro-2H-benzo[1,4]oxazine-8-carboxamide,
32) 4-(3-chloropyridin-2-yl)-N-(quinolin-7-yl)-3,4-dihydro-2H-benzo[1,4]oxazine-8-carboxamide,
33) 4-(3-chloropyridin-2-yl)-N-(1-methyl-1,2,3,4-tetrahydroquinolin-7-yl)-3,4-dihydro-2H-benzo[1,4]oxazine-8-carboxamide,
34) 4-(3-chloropyridin-2-yl)-N-(4-methoxycarbonylphenyl)-3,4-dihydro-2H-benzo[1,4]oxazine-8-carboxamide,
35) 4-[4-(3-chloropyridin-2-yl)-3,4-dihydro-2H-benzo[1,4]oxazine-8-carbonyl]aminobenzoic acid,
36) N-(4-carbamoylphenyl)-4-(3-chloropyridin-2-yl)-3,4-dihydro-2H-benzo[1,4]oxazine-8-carboxamide,
37) 4-(3-chloropyridin-2-yl)-N-(4-methylcarbamoylphenyl)-3,4-dihydro-2H-benzo[1,4]oxazine-8-carboxamide,
38) 4-(3-chloropyridin-2-yl)-N-(4-dimethylcarbamoylphenyl)-3,4-dihydro-2H-benzo[1,4]oxazine-8-carboxamide,
39) N-(4-acetylphenyl)-4-(3-chloropyridin-2-yl)-3,4-dihydro-2H-benzo[1,4]oxazine-8-carboxamide,
40) 4-(3-chloropyridin-2-yl)-N-[4-(1-hydroxy-1-methyl)ethylphenyl]-3,4-dihydro-2H-benzo[1,4]oxazine-8-carboxamide,
41) 4-(3-chloropyridin-2-yl)-N-[4-(1-hydroxy-1-methyl)propylphenyl]-3,4-dihydro-2H-benzo[1,4]oxazine-8-carboxamide,
42) 4-(3-chloropyridin-2-yl)-N-(1-isobutyrylpiperidin-4-yl)phenyl-3,4-dihydro-2H-benzo[1,4]oxazine-8-carboxamide,
43) N-(trans-4-tert-butoxycyclohexyl)-4-(3-chloropyridin-2-yl)-3,4-dihydro-2H-benzo[1,4]oxazine-8-carboxamide,
44) 4-(3-chloropyridin-2-yl)-N-(3-isopropoxyphenyl)-3,4-dihydro-2H-benzo[1,4]oxazine-8-carboxamide,
45) 4-(3-chloropyridin-2-yl)-N-(3-isobutyloxyphenyl)-3,4-dihydro-2H-benzo[1,4]oxazine-8-carboxamide,
46) N-(4-tert-butylphenyl)-4-(pyridin-4-yl)-3,4-dihydro-2H-benzo[1,4]oxazine-8-carboxamide,
47) N-(4-tert-butylphenyl)-4-(3-methylpyridin-2-yl)-3,4-dihydro-2H-benzo[1,4]oxazine-8-carboxamide,
48) 4-(3-chloropyridin-2-yl)-N-(4-piperidinophenyl)-3,4-dihydro-2H-benzo[1,4]oxazine-8-carboxamide,
49) 4-(3-chloropyridin-2-yl)-N-(4-dimethylaminophenyl)-3,4-dihydro-2H-benzo[1,4]oxazine-8-carboxamide,
50) 4-(3-chloropyridin-2-yl)-N-(4-morpholinophenyl)-3,4-dihydro-2H-benzo[1,4]oxazine-8-carboxamide,
51) 4-(3-chloropyridin-2-yl)-N-(3-fluoro-4-isopropoxyphenyl)-3,4-dihydro-2H-benzo[1,4]oxazine-8-carboxamide,
52) 4-(3-chloropyridin-2-yl)-N-(2-fluoro-4-isopropoxyphenyl)-3,4-dihydro-2H-benzo[1,4]oxazine-8-carboxamide,
53) 4-(3-chloropyridin-2-yl)-N-(4-fluoro-3-trifluoromethylphenyl)-3,4-dihydro-2H-benzo[1,4]oxazine-8-carboxamide,
54) 4-(3-chloropyridin-2-yl)-N-(4-dimethylamino-3-trifluoromethylphenyl)-3,4-dihydro-2H-benzo[1,4]oxazine-8-carboxamide,
55) 4-(3-chloropyridin-2-yl)-N-(4-isopropoxy-3-trifluoromethylphenyl)-3,4-dihydro-2H-benzo[1,4]oxazine-8-carboxamide,
56) 4-(3-chloropyridin-2-yl)-N-(4-methoxy-3-trifluoromethylphenyl)-3,4-dihydro-2H-benzo[1,4]oxazine-8-carboxamide,
57) 4-(3-chloropyridin-2-yl)-N-(4-isobutyloxy-3-trifluoromethylphenyl)-3,4-dihydro-2H-benzo[1,4]oxazine-8-carboxamide,
58) N-(4-tert-butylphenyl)-4-(4-methylpyridin-2-yl)-3,4-dihydro-2H-benzo[1,4]oxazine-8-carboxamide,
59) N-(4-tert-butylphenyl)-4-(6-methylpyridin-2-yl)-3,4-dihydro-2H-benzo[1,4]oxazine-8-carboxamide,
60) N-(4-tert-butylphenyl)-4-(5-methylpyridin-2-yl)-3,4-dihydro-2H-benzo[1,4]oxazine-8-carboxamide,
61) N-(4-tert-butylphenyl)-4-(pyridin-3-yl)-3,4-dihydro-2H-benzo[1,4]oxazine-8-carboxamide,
62) N-(4-cyanophenyl)-4-(5-methylpyridin-2-yl)-3,4-dihydro-2H-benzo[1,4]oxazine-8-carboxamide,
63) N-(3-amino-4-chlorophenyl)-4-(5-methylpyridin-2-yl)-3,4-dihydro-2H-benzo[1,4]oxazine-8-carboxamide,
64) N-(3-acetamido-4-chlorophenyl)-4-(5-methylpyridin-2-yl)-3,4-dihydro-2H-benzo[1,4]oxazine-8-carboxamide,
65) N-[4-(4-carbamoylpiperidin-1-yl)-3-fluorophenyl]-4-(5-methylpyridin-2-yl)-3,4-dihydro-2H-benzo[1,4]oxazine-8-carboxamide,
66) N-[3-fluoro-4-(4-methylcarbamoylpiperidin-1-yl)phenyl]-4-(5-methylpyridin-2-yl)-3,4-dihydro-2H-benzo[1,4]oxazine-8-carboxamide,
67) N-[4-(4-dimethylcarbamoylpiperidin-1-yl)-3-fluorophenyl]-4-(5-methylpyridin-2-yl)-3,4-dihydro-2H-benzo[1,4]oxazine-8-carboxamide,
68) N-[4-(4-ethoxypiperidin-1-yl)-3-fluorophenyl]-4-(5-methylpyridin-2-yl)-3,4-dihydro-2H-benzo[1,4]oxazine-8-carboxamide,
69) N-[3-fluoro-4-(4-isopropoxypiperidin-1-yl)phenyl]-4-(5-methylpyridin-2-yl)-3,4-dihydro-2H-benzo[1,4]oxazine-8-carboxamide,
70) N-[3-fluoro-4-(3-methoxypiperidin-1-yl)phenyl]-4-(5-methylpyridin-2-yl)-3,4-dihydro-2H-benzo[1,4]oxazine-8-carboxamide,
71) N-[3-fluoro-4-(4-methoxymethylpiperidin-1-yl)phenyl]-4-(5-methylpyridin-2-yl)-3,4-dihydro-2H-benzo[1,4]oxazine-8-carboxamide,
72) N-[3-fluoro-4-(3-methoxypyrrolidin-1-yl)phenyl]-4-(5-methylpyridin-2-yl)-3,4-dihydro-2H-benzo[1,4]oxazine-8-carboxamide,
73) N-(4-isobutyloxy-3-methoxycarbonylphenyl)-4-(5-methylpyridin-2-yl)-3,4-dihydro-2H-benzo[1,4]oxazine-8-carboxamide,
74) 2-isobutyloxy-{[4-(5-methylpyridin-2-yl)-3,4-dihydro-2H-benzo[1,4]oxazine-8-carbonyl]amino}benzoic acid,
75) N-(3-carbamoyl-4-isobutyloxyphenyl)-4-(5-methylpyridin-2-yl)-3,4-dihydro-2H-benzo[1,4]oxazine-8-carboxamide,
76) N-(4-isobutyloxy-3-methylcarbamoylphenyl)-4-(5-methylpyridin-2-yl)-3,4-dihydro-2H-benzo[1,4]oxazine-8-carboxamide,
77) N-(3-dimethylcarbamoyl-4-isobutyloxyphenyl)-4-(5-methylpyridin-2-yl)-3,4-dihydro-2H-benzo[1,4]oxazine-8-carboxamide,
78) N-(4-acetylphenyl)-4-(5-methylpyridin-2-yl)-3,4-dihydro-2H-benzo[1,4]oxazine-8-carboxamide,
79) N-[4-(1-hydroxy-1-methyl)ethylphenyl]-4-(5-methylpyridin-2-yl)-3,4-dihydro-2H-benzo[1,4]oxazine-8-carboxamide,
80) N-(3-acetyl-4-chlorophenyl)-4-(5-methylpyridin-2-yl)-3,4-dihydro-2H-benzo[1,4]oxazine-8-carboxamide,
81) N-[4-chloro-3-(1-hydroxy-1-methyl)ethylphenyl]-4-(5-methylpyridin-2-yl)-3,4-dihydro-2H-benzo[1,4]oxazine-8-carboxamide,
82) N-[4-(1-methoxy-1-methyl)ethylphenyl]-4-(5-methylpyridin-2-yl)-3,4-dihydro-2H-benzo[1,4]oxazine-8-carboxamide,
83) N-(3-chloro-4-methoxyphenyl)-4-(5-methylpyridin-2-yl)-3,4-dihydro-2H-benzo[1,4]oxazine-8-carboxamide,
84) 4-(5-methylpyridin-2-yl)-N-(4-propoxyphenyl)-3,4-dihydro-2H-benzo[1,4]oxazine-8-carboxamide,
85) N-(3-fluoro-4-propoxyphenyl)-4-(5-methylpyridin-2-yl)-3,4-dihydro-2H-benzo[1,4]oxazine-8-carboxamide, 86) N-(4-ethoxy-3-fluorophenyl)-4-(5-methylpyridin-2-yl)-3,4-dihydro-2H-benzo[1,4]oxazine-8-carboxamide,
87) N-(3-ethoxy-4-methylphenyl)-4-(5-methylpyridin-2-yl)-3,4-dihydro-2H-benzo[1,4]oxazine-8-carboxamide,
88) N-(3-carbamoylmethyloxy-4-methylphenyl)-4-(5-methylpyridin-2-yl)-3,4-dihydro-2H-benzo[1,4]oxazine-8-carboxamide
89) N-(3-methoxyethyloxy-4-methylphenyl)-4-(5-methylpyridin-2-yl)-3,4-dihydro-2H-benzo[1,4]oxazine-8-carboxamide,
90) N-[3-fluoro-4-(2-methoxymethylpiperidin-1-yl)phenyl]-4-(5-methylpyridin-2-yl)-3,4-dihydro-2H-benzo[1,4]oxazine-8-carboxamide,
91) N-(4-chlorophenyl)-4-(5-methylpyridin-2-yl)-3,4-dihydro-2H-benzo[1,4]oxazine-8-carboxamide,
92) N-(3-fluoro-4-methylphenyl)-4-(5-methylpyridin-2-yl)-3,4-dihydro-2H-benzo[1,4]oxazine-8-carboxamide,
93) N-(2-chloropyridin-5-yl)-4-(5-methylpyridin-2-yl)-3,4-dihydro-2H-benzo[1,4]oxazine-8-carboxamide,
94) 4-(3-chloropyridin-2-yl)-N-(4-ethoxyphenyl)-3,4-dihydro-2H-benzo[1,4]oxazine-8-carboxamide,
95) 4-(3-chloropyridin-2-yl)-N-(3-fluoro-4-piperidinophenyl)-3,4-dihydro-2H-benzo[1,4]oxazine-8-carboxamide,
96) 4-(3-chloropyridin-2-yl)-N-(trans-4-ethoxycyclohexyl)-3,4-dihydro-2H-benzo[1,4]oxazine-8-carboxamide,
97) 4-(3-chloropyridin-2-yl)-N-(trans-4-isopropoxycyclohexyl)-3,4-dihydro-2H-benzo[1,4]oxazine-8-carboxamide,
98) 4-(3-chloropyridin-2-yl)-N-(trans-4-cyclopentyloxycyclohexyl)-3,4-dihydro-2H-benzo[1,4]oxazine-8-carboxamide,
99) 4-(3-chloropyridin-2-yl)-N-(trans-4-cyclohexyloxycyclohexyl)-3,4-dihydro-2H-benzo[1,4]oxazine-8-carboxamide,
100) 4-(3-chloropyridin-2-yl)-N-(4-trifluoromethylphenyl)-3,4-dihydro-2H-benzo[1,4]oxazine-8-carboxamide,
101) 4-(3-chloropyridin-2-yl)-N-[3-fluoro-4-(4-methoxypiperidin-1-yl)phenyl]-3,4-dihydro-2H-benzo[1,4]oxazine-8-carboxamide,
102) 4-(3-chloropyridin-2-yl)-N-[4-(4-ethoxypiperidin-1-yl)-3-fluorophenyl]-3,4-dihydro-2H-benzo[1,4]oxazine-8-carboxamide,
103) 4-(3-chloropyridin-2-yl)-N-[3-fluoro-4-(4-isopropoxypiperidin-1-yl)phenyl]-3,4-dihydro-2H-benzo[1,4]oxazine-8-carboxamide,
104) 4-(3-chloropyridin-2-yl)-N-(3-fluoro-4-isobutyloxyphenyl)-3,4-dihydro-2H-benzo[1,4]oxazine-8-carboxamide,
105) N-(trans-4-ethoxycyclohexyl)-4-(5-methylpyridin-2-yl)-3,4-dihydro-2H-benzo[1,4]oxazine-8-carboxamide,
106) N-(trans-4-isopropoxycyclohexyl)-4-(5-methylpyridin-2-yl)-3,4-dihydro-2H-benzo[1,4]oxazine-8-carboxamide,
107) N-(trans-4-cyclohexyloxycyclohexyl)-4-(5-methylpyridin-2-yl)-3,4-dihydro-2H-benzo[1,4]oxazine-8-carboxamide,
108) N-(trans-4-aminocyclohexyl)-4-(5-methylpyridin-2-yl)-3,4-dihydro-2H-benzo[1,4]oxazine-8-carboxamide,
109) N-(1,4-dioxa-spiro[4,5]deca-8-yl)-4-(5-methylpyridin-2-yl)-3,4-dihydro-2H-benzo[1,4]oxazine-8-carboxamide,
110) 4-(5-methylpyridin-2-yl)-N-(4-oxocyclohexyl)-3,4-dihydro-2H-benzo[1,4]oxazine-8-carboxamide,
111) 4-(5-methylpyridin-2-yl)-N-(cis-4-morpholinocyclohexyl)-3,4-dihydro-2H-benzo[1,4]oxazine-8-carboxamide,
112) N-(trans-4-dimethylaminocyclohexyl)-4-(5-methylpyridin-2-yl)-3,4-dihydro-2H-benzo[1,4]oxazine-8-carboxamide,
113) N-(trans-4-diethylaminocyclohexyl)-4-(5-methylpyridin-2-yl)-3,4-dihydro-2H-benzo[1,4]oxazine-8-carboxamide,
114) 4-(5-methylpyridin-2-yl)-N-[cis-4-(pyrrolidin-1-yl)cyclohexyl]-3,4-dihydro-2H-benzo[1,4]oxazine-8-carboxamide,
115) 4-(5-methylpyridin-2-yl)-N-[trans-4-(pyrrolidin-1-yl)cyclohexyl]-3,4-dihydro-2H-benzo[1,4]oxazine-8-carboxamide,
116) 4-(5-methylpyridin-2-yl)-N-(4-piperidinocyclohexyl)-3,4-dihydro-2H-benzo[1,4]oxazine-8-carboxamide,
117) 4-(5-methylpyridin-2-yl)-N-(cis-4-morpholinocyclohexyl)-3,4-dihydro-2H-benzo[1,4]oxazine-8-carboxamide,
118) N-(trans-4-acetamidocyclohexyl)-4-(5-methylpyridin-2-yl)-3,4-dihydro-2H-benzo[1,4]oxazine-8-carboxamide,
119) N-(trans-4-cyclohexyloxycyclohexyl)-4-(5-methylpyridin-2-yl)-3,4-dihydro-2H-benzo[1,4]oxazine-8-carboxamide,
120) 4-(5-chloropyridin-2-yl)-N-(4-ethoxyphenyl)-3,4-dihydro-2H-benzo[1,4]oxazine-8-carboxamide,
121) N-(4-chlorophenyl)-4-(5-chloropyridin-2-yl)-3,4-dihydro-2H-benzo[1,4]oxazine-8-carboxamide,
122) 4-(5-chloropyridin-2-yl)-N-[3-fluoro-4-(4-methoxypiperidin-1-yl)phenyl]-3,4-dihydro-2H-benzo[1,4]oxazine-8-carboxamide,
123) 4-(5-chloropyridin-2-yl)-N-(4-trifluoromethylphenyl)-3,4-dihydro-2H-benzo[1,4]oxazine-8-carboxamide,
124) 4-(5-methylpyridin-2-yl)-N-(2-phenylethyl)-3,4-dihydro-2H-benzo[1,4]oxazine-8-carboxamide,
125) N-[2-(4-chlorophenyl)ethyl]-4-(5-methylpyridin-2-yl)-3,4-dihydro-2H-benzo[1,4]oxazine-8-carboxamide,
126) N-[2-(3-chlorophenyl)ethyl]-4-(5-methylpyridin-2-yl)-3,4-dihydro-2H-benzo[1,4]oxazine-8-carboxamide,
127) N-[2-(2-chlorophenyl)ethyl]-4-(5-methylpyridin-2-yl)-3,4-dihydro-2H-benzo[1,4]oxazine-8-carboxamide,
128) 6-[8-(4-trifluoromethylphenyl)carbamoyl-2,3-dihydrobenzo[1,4]oxazin-4-yl]nicotinic acid,
129) 4-[3-chloro-5-(1-hydroxy-1-methyl)ethylpyridin-2-yl]-N-(4-trifluoromethylphenyl)-3,4-dihydro-2H-benzo[1,4]oxazine-8-carboxamide,
130) 4-[3-chloro-5-(1-hydroxyethyl)pyridin-2-yl]-N-(4-trifluoromethylphenyl)-3,4-dihydro-2H-benzo[1,4]oxazine-8-carboxamide,
131) 5-chloro-6-[8-(3-fluoro-4-trifluoromethylphenyl)carbamoyl-2,3-dihydro-benzo[1,4]oxazin-4-yl]nicotinic acid,
132) N-(4-tert-butylphenyl)-4-(5-methoxycarbonylpyridin-2-yl)-3,4-dihydro-2H-benzo[1,4]oxazine-8-carboxamide,
133) 6-[8-(4-tert-butylphenyl)carbamoyl-2,3-dihydro-benzo[1,4]oxazin-4-yl]nicotinic acid,
134) 5-chloro-6-[8-(4-trifluoromethylphenyl)carbamoyl-2,3-dihydro-benzo[1,4]oxazin-4-yl]nicotinic acid,
135) 5-chloro-6-[8-(4-tert-butylphenyl)carbamoyl-2,3-dihydro-benzo[1,4]oxazin-4-yl]nicotinic acid,
136) 4-(5-acetyl-3-chloropyridin-2-yl)-N-(4-trifluoromethylphenyl)-3,4-dihydro-2H-benzo[1,4]oxazine-8-carboxamide,
137) N-(4-tert-butylphenyl)-4-(5-methylcarbamoylpyridin-2-yl)-3,4-dihydro-2H-benzo[1,4]oxazine-8-carboxamide,
138) N-(4-tert-butylphenyl)-4-(5-carbamoylpyridin-2-yl)-3,4-dihydro-2H-benzo[1,4]oxazine-8-carboxamide,
139) N-(4-tert-butylphenyl)-4-(5-diethylaminopyridin-2-yl)-3,4-dihydro-2H-benzo[1,4]oxazine-8-carboxamide,
140) N-(4-tert-butylphenyl)-4-(5-nitropyridin-2-yl)-3,4-dihydro-2H-benzo[1,4]oxazine-8-carboxamide, 141) 4-(5-aminopyridin-2-yl)-N-(4-tert-butylphenyl)-3,4-dihydro-2H-benzo[1,4]oxazine-8-carboxamide,
142) 4-(5-acetamidopyridin-2-yl)-N-(4-tert-butylphenyl)-3,4-dihydro-2H-benzo[1,4]oxazine-8-carboxamide,
143) 4-(5-methoxymethylpyridin-2-yl)-N-(4-trifluoromethylphenyl)-3,4-dihydro-2H-benzo[1,4]oxazine-8-carboxamide,
144) 4-(5-ethoxypyridin-2-yl)-N-(4-trifluoromethylphenyl)-3,4-dihydro-2H-benzo[1,4]oxazine-8-carboxamide,
145) 4-(3-chloro-5-methoxypyridin-2-yl)-N-(4-trifluoromethylphenyl)-3,4-dihydro-2H-benzo[1,4]oxazine-8-carboxamide,
146) 4-(5-hydroxypyridin-2-yl)-N-(4-trifluoromethylphenyl)-3,4-dihydro-2H-benzo[1,4]oxazine-8-carboxamide,
147) 4-(5-methoxypyridin-2-yl)-N-(4-trifluoromethylphenyl)-3,4-dihydro-2H-benzo[1,4]oxazine-8-carboxamide,
148) N-(4-tert-butylphenyl)-4-(4-chloropyridin-2-yl)-3,4-dihydro-2H-benzo[1,4]oxazine-8-carboxamide,
149) 4-(5-fluoropyridin-2-yl)-N-(4-trifluoromethylphenyl)-3,4-dihydro-2H-benzo[1,4]oxazine-8-carboxamide,
150) 4-(3,5-difluoropyridin-2-yl)-N-(4-trifluoromethylphenyl)-3,4-dihydro-2H-benzo[1,4]oxazine-8-carboxamide,
151) N-(4-tert-butylphenyl)-4-(3-methoxypyridin-2-yl)-3,4-dihydro-2H-benzo[1,4]oxazine-8-carboxamide,
152) N-(4-tert-butylpiperidin-1-yl)-4-(5-methylpyridin-2-yl)-3,4-dihydro-2H-benzo[1,4]oxazine-8-carboxamide,
153) 4-[5-(2-hydroxyethoxy)pyridin-2-yl]-N-(4-trifluoromethylphenyl)-3,4-dihydro-2H-benzo[1,4]oxazine-8-carboxamide,
154) 4-[3-chloro-5-(2-hydroxyethyl)pyridin-2-yl]-N-(4-trifluoromethylphenyl)-3,4-dihydro-2H-benzo[1,4]oxazine-8-carboxamide,
155) 4-(5-methylpyridin-2-yl)-N-(4-neopentyloxyphenyl)-3,4-dihydro-2H-benzo[1,4]oxazine-8-carboxamide,
156) N-(3-fluoro-4-piperidinophenyl)-4-(5-methylpyridin-2-yl)-3,4-dihydro-2H-benzo[1,4]oxazine-8-carboxamide,
157) N-(3-fluoro-4-morpholinophenyl)-4-(5-methylpyridin-2-yl)-3,4-dihydro-2H-benzo[1,4]oxazine-8-carboxamide,
158) N-(3,4-difluorophenyl)-4-(5-methylpyridin-2-yl)-3,4-dihydro-2H-benzo[1,4]oxazine-8-carboxamide,
159) N-(3-fluoro-4-methoxyphenyl)-4-(5-methylpyridin-2-yl)-3,4-dihydro-2H-benzo[1,4]oxazine-8-carboxamide,
160) N-(4-ethoxyphenyl)-4-(5-methylpyridin-2-yl)-3,4-dihydro-2H-benzo[1,4]oxazine-8-carboxamide,
161) N-[4-(2-oxo-piperidin-1-yl)phenyl]-4-(5-methylpyridin-2-yl)-3,4-dihydro-2H-benzo[1,4]oxazine-8-carboxamide,
162) 4-(5-methylpyridin-2-yl)-N-(1-methyl-1,2,3,4-tetrahydroquinolin-7-yl)-3,4-dihydro-2H-benzo[1,4]oxazine-8-carboxamide,
163) N-(4-dimethylamino-3-fluorophenyl)-4-(5-methylpyridin-2-yl)-3,4-dihydro-2H-benzo[1,4]oxazine-8-carboxamide,
164) N-{3-fluoro-4-[N-(2-methoxyethyl)-isopropylamino]phenyl}-4-(5-methylpyridin-2-yl)-3,4-dihydro-2H-benzo[1,4]oxazine-8-carboxamide,
165) N-{4-[N-(2-acetoxyethyl)-isopropylamino]-3-fluorophenyl}-4-(5-methylpyridin-2-yl)-3,4-dihydro-2H-benzo[1,4]oxazine-8-carboxamide,
166) N-{3-fluoro-4-[N-(2-hydroxyethyl)-isopropylamino]phenyl}-4-(5-methylpyridin-2-yl)-3,4-dihydro-2H-benzo[1,4]oxazine-8-carboxamide,
167) N-[4-(4-ethoxycarbonylpiperidin-1-yl)-3-fluorophenyl]-4-(5-methylpyridin-2-yl)-3,4-dihydro-2H-benzo[1,4]oxazine-8-carboxamide,
168) 1-(4-{[4-(5-methylpyridin-2-yl)-3,4-dihydro-2H-benzo[1,4]oxazine-8-carbonyl]amino}phenyl)piperidine-4-carboxylic acid,
169) N-[3-fluoro-4-(4-methoxypiperidin-1-yl)phenyl]-4-(5-methylpyridin-2-yl)-3,4-dihydro-2H-benzo[1,4]oxazine-8-carboxamide,
170) N-[4-(4-acetoxypiperidin-1-yl)-3-fluorophenyl]-4-(5-methylpyridin-2-yl)-3,4-dihydro-2H-benzo[1,4]oxazine-8-carboxamide,
171) N-[3-fluoro-4-(4-hydroxypiperidin-1-yl)phenyl]-4-(5-methylpyridin-2-yl)-3,4-dihydro-2H-benzo[1,4]oxazine-8-carboxamide,
172) N-(3-methoxy-4-methylphenyl)-4-(5-methylpyridin-2-yl)-3,4-dihydro-2H-benzo[1,4]oxazine-8-carboxamide,
173) N-[3-(2-hydroxyethoxy)-4-methylphenyl]-4-(5-methylpyridin-2-yl)-3,4-dihydro-2H-benzo[1,4]oxazine-8-carboxamide,
174) N-[4-(1-tert-butoxycarbonylpiperidin-4-yl)oxy-3-fluorophenyl]-4-(5-methylpyridin-2-yl)-3,4-dihydro-2H-benzo[1,4]oxazine-8-carboxamide,
175) N-[4-(piperidin-4-yl)oxy-3-fluorophenyl]-4-(5-methylpyridin-2-yl)-3,4-dihydro-2H-benzo[1,4]oxazine-8-carboxamide,
176) N-(trans-4-ethoxycarbonylmethyloxycyclohexyl)-4-(5-methylpyridin-2-yl)-3,4-dihydro-2H-benzo[1,4]oxazine-8-carboxamide,
177) (trans-4-{[4-(5-methylpyridin-2-yl)-3,4-dihydro-2H-benzo[1,4]oxazine-8-carbonyl]amino}cyclohexyloxy) acetic acid,
178) N-(trans-4-carbamoylmethoxycyclohexyl)-4-(5-methylpyridin-2-yl)-3,4-dihydro-2H-benzo[1,4]oxazine-8-carboxamide,
179) N-(trans-4-methylcarbamoylmethoxycyclohexyl)-4-(5-methylpyridin-2-yl)-3,4-dihydro-2H-benzo[1,4]oxazine-8-carboxamide,
180) N-(trans-4-dimethylcarbamoylmethoxycyclohexyl)-4-(5-methylpyridin-2-yl)-3,4-dihydro-2H-benzo[1,4]oxazine-8-carboxamide,
181) N-[trans-4-(2-hydroxyethyloxy)cyclohexyl]-4-(5-methylpyridin-2-yl)-3,4-dihydro-2H-benzo[1,4]oxazine-8-carboxamide,
182) N-(trans-4-methoxymethylcyclohexyl)-4-(5-methylpyridin-2-yl)-3,4-dihydro-2H-benzo[1,4]oxazine-8-carboxamide,
183) N-(trans-4-isopropoxymethylcyclohexyl)-4-(5-methylpyridin-2-yl)-3,4-dihydro-2H-benzo[1,4]oxazine-8-carboxamide,
184) N-(cis-4-methoxymethylcyclohexyl)-4-(5-methylpyridin-2-yl)-3,4-dihydro-2H-benzo[1,4]oxazine-8-carboxamide,
185) N-(cis-4-isopropoxymethylcyclohexyl)-4-(5-methylpyridin-2-yl)-3,4-dihydro-2H-benzo[1,4]oxazine-8-carboxamide,
186) N-(trans-4-tert-butoxymethylcyclohexyl)-4-(5-methylpyridin-2-yl)-3,4-dihydro-2H-benzo[1,4]oxazine-8-carboxamide,
187) N-(trans-4-isobutyloxycyclohexyl)-4-(5-methylpyridin-2-yl)-3,4-dihydro-2H-benzo[1,4]oxazine-8-carboxamide,
188) N-(4,4-dimethylcyclohexyl)-4-(5-methylpyridin-2-yl)-3,4-dihydro-2H-benzo[1,4]oxazine-8-carboxamide,
189) N-[trans-4-(3-methylbutyloxy)cyclohexyl]-4-(5-methylpyridin-2-yl)-3,4-dihydro-2H-benzo[1,4]oxazine-8-carboxamide,
190) N-(trans-4-benzyloxycyclohexyl)-4-(5-methylpyridin-2-yl)-3,4-dihydro-2H-benzo[1,4]oxazine-8-carboxamide, 191) N-(trans-4-isopropylcyclohexyl)-4-(5-methylpyridin-2-yl)-3,4-dihydro-2H-benzo[1,4]oxazine-8-carboxamide,
192) N-(trans-4-propylcyclohexyl)-4-(5-methylpyridin-2-yl)-3,4-dihydro-2H-benzo[1,4]oxazine-8-carboxamide,
193) N-(trans-4-neopentyloxycyclohexyl)-4-(5-methylpyridin-2-yl)-3,4-dihydro-2H-benzo[1,4]oxazine-8-carboxamide,
194) N-(4-tert-butylphenyl)-4-(5-methoxymethylpyridin-2-yl)-3,4-dihydro-2H-benzo[1,4]oxazine-8-carboxamide,
195) 5-chloro-6-[8-(3-chloro-4-trifluoromethoxyphenyl)carbamoyl-2,3-dihydro-benzo[1,4]oxazin-4-yl]nicotinic acid,
196) 5-chloro-6-[8-(4-trifluoromethoxyphenyl)carbamoyl-2,3-dihydro-benzo[1,4]oxazin-4-yl]nicotinic acid,
197) 4-(5-methylaminopyridin-2-yl)-N-(4-trifluoromethoxyphenyl)-3,4-dihydro-2H-benzo[1,4]oxazine-8-carboxamide,
198) 4-(5-ethoxypyridin-2-yl)-N-(4-trifluoromethoxyphenyl)-3,4-dihydro-2H-benzo[1,4]oxazine-8-carboxamide,
199) 4-(3-chloro-5-methoxypyridin-2-yl)-N-(4-trifluoromethoxyphenyl)-3,4-dihydro-2H-benzo[1,4]oxazine-8-carboxamide,
200) 4-[5-(2-hydroxyethoxy)pyridin-2-yl]-N-(4-trifluoromethoxyphenyl)-3,4-dihydro-2H-benzo[1,4]oxazine-8-carboxamide,
201) 4-(5-hydroxypyridin-2-yl)-N-(4-trifluoromethoxyphenyl)-3,4-dihydro-2H-benzo[1,4]oxazine-8-carboxamide,
202) 4-(5-methoxypyridin-2-yl)-N-(4-trifluoromethoxyphenyl)-3,4-dihydro-2H-benzo[1,4]oxazine-8-carboxamide,
203) 4-(3-cyanopyridin-2-yl)-N-(4-trifluoromethoxyphenyl)-3,4-dihydro-2H-benzo[1,4]oxazine-8-carboxamide,
204) 4-(3-carbamoylpyridin-2-yl)-N-(4-trifluoromethoxyphenyl)-3,4-dihydro-2H-benzo[1,4]oxazine-8-carboxamide,
205) 4-(3-methylcarbamoylpyridin-2-yl)-N-(4-trifluoromethoxyphenyl)-3,4-dihydro-2H-benzo[1,4]oxazine-8-carboxamide,
206) 4-(3-dimethylcarbamoylpyridin-2-yl)-N-(4-trifluoromethoxyphenyl)-3,4-dihydro-2H-benzo[1,4]oxazine-8-carboxamide,
207) 4-(3-benzyloxycarbonylpyridin-2-yl)-N-(4-trifluoromethoxyphenyl)-3,4-dihydro-2H-benzo[1,4]oxazine-8-carboxamide,
208) 2-[8-(4-trifluoromethoxyphenyl)carbamoyl-2,3-dihydro-benzo[1,4]oxazin-4-yl]nicotinic acid,
209) 4-(3-benzyloxypyridin-2-yl)-N-(4-trifluoromethoxyphenyl)-3,4-dihydro-2H-benzo[1,4]oxazine-8-carboxamide,
210) 4-(3-hydroxypyridin-2-yl)-N-(4-trifluoromethoxyphenyl)-3,4-dihydro-2H-benzo[1,4]oxazine-8-carboxamide,
211) 4-[3-(2-hydroxyethoxy)pyridin-2-yl]-N-(4-trifluoromethoxyphenyl)-3,4-dihydro-2H-benzo[1,4]oxazine-8-carboxamide,
212) {2-[8-(4-trifluoromethoxyphenylcarbamoyl)-2,3-dihydro-benzo[1,4]oxazin-4-yl]pyridin-3-yl}oxyacetic acid,
213) 4-(3-carbamoylmethoxypyridin-2-yl)-N-(4-trifluoromethoxyphenyl)-3,4-dihydro-2H-benzo[1,4]oxazine-8-carboxamide,
214) 4-(3-methylcarbamoylmethoxypyridin-2-yl)-N-(4-trifluoromethoxyphenyl)-3,4-dihydro-2H-benzo[1,4]oxazine-8-carboxamide,
215) 4-(3-dimethylcarbamoylmethoxypyridin-2-yl)-N-(4-trifluoromethoxyphenyl)-3,4-dihydro-2H-benzo[1,4]oxazine-8-carboxamide,
216) 4-[3-(pyridin-2-yl)methyloxypyridin-2-yl]-N-(4-trifluoromethoxyphenyl)-3,4-dihydro-2H-benzo[1,4]oxazine-8-carboxamide,
217) 4-[3-(pyridin-3-yl)methyloxypyridin-2-yl]-N-(4-trifluoromethoxyphenyl)-3,4-dihydro-2H-benzo[1,4]oxazine-8-carboxamide,
218) 4-(5-cyanopyridin-2-yl)-N-(4-trifluoromethoxyphenyl)-3,4-dihydro-2H-benzo[1,4]oxazine-8-carboxamide,
219) 4-(5-acetamidomethylpyridin-2-yl)-N-(4-trifluoromethoxyphenyl)-3,4-dihydro-2H-benzo[1,4]oxazine-8-carboxamide,
220) 4-(3-chloro-5-methoxymethylpyridin-2-yl)-N-(4-trifluoromethoxyphenyl)-3,4-dihydro-2H-benzo[1,4]oxazine-8-carboxamide,
221) 4-[5-(N-methylacetamido)methylpyridin-2-yl]-N-(4-trifluoromethoxyphenyl)-3,4-dihydro-2H-benzo[1,4]oxazine-8-carboxamide,
222) 4-(5-aminomethylpyridin-2-yl)-N-(4-trifluoromethoxyphenyl)-3,4-dihydro-2H-benzo[1,4]oxazine-8-carboxamide,
223) 4-(5-dimethylaminomethylpyridin-2-yl)-N-(4-trifluoromethoxyphenyl)-3,4-dihydro-2H-benzo[1,4]oxazine-8-carboxamide,
224) 4-(3-chloropyridin-2-yl)-2-methylcarbamoyl-N-(4-trifluoromethoxyphenyl)-3,4-dihydro-2H-benzo[1,4]oxazine-8-carboxamide,
225) 4-(6-hydroxymethylpyridin-2-yl)-N-(4-trifluoromethylphenyl)-3,4-dihydro-2H-benzo[1,4]oxazine-8-carboxamide,
226) 4-(3-chloropyridin-2-yl)-2-dimethylcarbamoyl-N-(4-trifluoromethoxyphenyl)-3,4-dihydro-2H-benzo[1,4]oxazine-8-carboxamide,
227) 4-(5-carbamoyl-3-chloropyridin-2-yl)-N-(4-trifluoromethoxyphenyl)-3,4-dihydro-2H-benzo[1,4]oxazine-8-carboxamide,
228) (S)-3-acetamidomethyl-4-(3-chloropyridin-2-yl)-N-(4-trifluoromethylphenyl)-3,4-dihydro-2H-benzo[1,4]oxazine-8-carboxamide,
229) (R)-4-(3-chloropyridin-2-yl)-8-(4-trifluoromethylphenylcarbamoyl)-3,4-dihydro-2H-benzo[1,4]oxazine-3-carboxylic acid,
230) 4-(3-chloropyridin-2-yl)-2-methoxycarbonyl-N-(4-trifluoromethoxyphenyl)-3,4-dihydro-2H-benzo[1,4]oxazine-8-carboxamide,
231) 4-(3-chloropyridin-2-yl)-2-hydroxymethyl-N-(4-trifluoromethoxyphenyl)-3,4-dihydro-2H-benzo[1,4]oxazine-8-carboxamide,
232) 4-(3-chloropyridin-2-yl)-8-(4-trifluoromethoxyphenylcarbamoyl)-3,4-dihydro-2H-benzo[1,4]oxazine-2-carboxylic acid,
233) (S)-3-carbamoyl-4-(3-chloropyridin-2-yl)-N-(4-trifluoromethylphenyl)-3,4-dihydro-2H-benzo[1,4]oxazine-8-carboxamide,
234) (S)-4-(3-chloropyridin-2-yl)-3-methylcarbamoyl-N-(4-trifluoromethylphenyl)-3,4-dihydro-2H-benzo[1,4]oxazine-8-carboxamide,
235) 2-carbamoyl-4-(3-chloropyridin-2-yl)-N-(4-trifluoromethoxyphenyl)-3,4-dihydro-2H-benzo[1,4]oxazine-8-carboxamide,
236) N-(4-chlorophenyl)-N-methyl-4-(5-methylpyridin-2-yl)-3,4-dihydro-2H-benzo[1,4]oxazine-8-carboxamide,
237) N-(benzo[1,3]dioxol-5-yl)-4-(3-chloro-5-hydroxymethylpyridin-2-yl)-3,4-dihydro-2H-benzo[1,4]oxazine-8-carboxamide,
238) N-(2,3-dihydrobenzo[1,4]dioxin-6-yl)-4-(3-chloro-5-hydroxymethylpyridin-2-yl)-3,4-dihydro-2H-benzo[1,4]oxazine-8-carboxamide,
239) 4-(3-chloro-5-hydroxymethylpyridin-2-yl)-N-(4-trifluoromethoxyphenyl)-3,4-dihydro-2H-benzo[1,4]oxazine-8-carboxamide, 240) 4-(3-chloro-5-hydroxymethylpyridin-2-yl)-N-(3-chloro-4-trifluoromethoxyphenyl)-3,4-dihydro-2H-benzo[1,4]oxazine-8-carboxamide,
241) 4-(3-chloro-5-hydroxymethylpyridin-2-yl)-N-(4-trifluoromethylphenyl)-3,4-dihydro-2H-benzo[1,4]oxazine-8-carboxamide,
242) 4-(3-chloro-5-hydroxymethylpyridin-2-yl)-N-(3-fluoro-4-trifluoromethylphenyl)-3,4-dihydro-2H-benzo[1,4]oxazine-8-carboxamide,
243) 4-(5-hydroxymethylpyridin-2-yl)-N-(4-trifluoromethylphenyl)-3,4-dihydro-2H-benzo[1,4]oxazine-8-carboxamide,
244) 4-(5-hydroxymethylpyridin-2-yl)-N-(4-isobutyloxyphenyl)-3,4-dihydro-2H-benzo[1,4]oxazine-8-carboxamide,
245) 4-(3-chloro-5-methoxymethylpyridin-2-yl)-N-(4-trifluoromethylphenyl)-3,4-dihydro-2H-benzo[1,4]oxazine-8-carboxamide,
246) 4-(4-hydroxymethylpyridin-2-yl)-N-(4-trifluoromethylphenyl)-3,4-dihydro-2H-benzo[1,4]oxazine-8-carboxamide,
247) 4-(3-hydroxymethylpyridin-2-yl)-N-(4-trifluoromethoxyphenyl)-3,4-dihydro-2H-benzo[1,4]oxazine-8-carboxamide,
248) (+)-4-{3-chloro-5-(1-hydroxyethyl)pyridin-2-yl}-N-(4-trifluoromethylphenyl)-3,4-dihydro-2H-benzo[1,4]oxazine-8-carboxamide,
249) (−)-4-{3-chloro-5-(1-hydroxyethyl)pyridin-2-yl}-N-(4-trifluoromethylphenyl)-3,4-dihydro-2H-benzo[1,4]oxazine-8-carboxamide,
250) (+)-4-{3-chloro-5-(1-hydroxyethyl)pyridin-2-yl}-N-(4-trifluoromethoxyphenyl)-3,4-dihydro-2H-benzo[1,4]oxazine-8-carboxamide,
251) (−)-4-{3-chloro-5-(1-hydroxyethyl)pyridin-2-yl}-N-(4-trifluoromethoxyphenyl)-3,4-dihydro-2H-benzo[1,4]oxazine-8-carboxamide,
252) 4-(3-chloro-5-hydroxymethylpyridin-2-yl)-N-(2-trifluoromethylpyridin-5-yl)-3,4-dihydro-2H-benzo[1,4]oxazine-8-carboxamide,
253) N-(4-bromo-3-chlorophenyl)-4-(3-chloro-5-hydroxymethylpyridin-2-yl)-3,4-dihydro-2H-benzo[1,4]oxazine-8-carboxamide,
254) 4-[5-(1-hydroxy-1-methyl)ethylpyridin-2-yl]-N-(4-trifluoromethylphenyl)-3,4-dihydro-2H-benzo[1,4]oxazine-8-carboxamide,
255) 4-(3-chloro-5-hydroxymethylpyridin-2-yl)-N-(4-isopropoxy-3-trifluoromethylphenyl)-3,4-dihydro-2H-benzo[1,4]oxazine-8-carboxamide,
256) 4-(3-chloro-5-hydroxymethylpyridin-2-yl)-N-(2,3-dichloropyridin-5-yl)-3,4-dihydro-2H-benzo[1,4]oxazine-8-carboxamide,
257) 4-(3-chloro-5-hydroxymethylpyridin-2-yl)-N-(3,4,5-trichlorophenyl)-3,4-dihydro-2H-benzo[1,4]oxazine-8-carboxamide,
258) 4-(3-chloro-5-hydroxymethylpyridin-2-yl)-N-(6-fluorobenzothiazol-2-yl)-3,4-dihydro-2H-benzo[1,4]oxazine-8-carboxamide,
259) N-(4-bromo-3-trifluoromethylphenyl)-4-(3-chloro-5-hydroxymethylpyridin-2-yl)-3,4-dihydro-2H-benzo[1,4]oxazine-8-carboxamide,
260) 4-(3-chloro-5-hydroxymethylpyridin-2-yl)-N-(2-trifluoromethylbenzimidazol-5-yl)-3,4-dihydro-2H-benzo[1,4]oxazine-8-carboxamide,
261) 4-(3-chloro-5-hydroxymethylpyridin-2-yl)-N-(3,4,5-trifluorophenyl)-3,4-dihydro-2H-benzo[1,4]oxazine-8-carboxamide,
262) 4-(3-chloro-5-hydroxymethylpyridin-2-yl)-N-(4-fluoro-3-nitrophenyl)-3,4-dihydro-2H-benzo[1,4]oxazine-8-carboxamide,
263) N-(3-amino-4-fluorophenyl)-4-(3-chloro-5-hydroxymethylpyridin-2-yl)-3,4-dihydro-2H-benzo[1,4]oxazine-8-carboxamide,
264) N-(tert-butylphenyl)-4-(5-hydroxymethylpyridin-2-yl)-3,4-dihydro-2H-benzo[1,4]oxazine-8-carboxamide,
265) N-(3,5-bistrifluoromethylphenyl)-4-(3-chloro-5-hydroxymethylpyridin-2-yl)-3,4-dihydro-2H-benzo[1,4]oxazine-8-carboxamide,
266) 4-(3-chloro-5-hydroxymethylpyridin-2-yl)-N-[(2,2,2-trifluoroethoxy)phenyl]-3,4-dihydro-2H-benzo[1,4]oxazine-8-carboxamide,
267) 4-(3-chloro-5-hydroxymethylpyridin-2-yl)-N-[3-chloro-(2,2,2-trifluoroethoxy)phenyl]-3,4-dihydro-2H-benzo[1,4]oxazine-8-carboxamide,
268) 4-(3-chloro-5-hydroxymethylpyridin-2-yl)-N-(4-trifluoromethylmercaptophenyl)-3,4-dihydro-2H-benzo[1,4]oxazine-8-carboxamide,
269) N-(trans-4-tert-butylcyclohexyl)-4-(3-chloro-5-hydroxymethylpyridin-2-yl)-3,4-dihydro-2H-benzo[1,4]oxazine-8-carboxamide,
270) 4-(3-chloro-5-hydroxymethylpyridin-2-yl)-N-(3-fluoro-4-isopropoxyphenyl)-3,4-dihydro-2H-benzo[1,4]oxazine-8-carboxamide,
271) 4-(3-chloro-5-hydroxymethylpyridin-2-yl)-N-(3-fluoro-4-piperidinophenyl)-3,4-dihydro-2H-benzo[1,4]oxazine-8-carboxamide,
272) N-(4-tert-butylphenyl)-4-(3-chloro-5-hydroxymethylpyridin-2-yl)-3,4-dihydro-2H-benzo[1,4]oxazine-8-carboxamide,
273) 4-(3-chloro-5-hydroxymethylpyridin-2-yl)-N-[4-(1-hydroxy-2,2,2-trifluoro-1-trifluoromethyl)ethylphenyl]-3,4-dihydro-2H-benzo[1,4]oxazine-8-carboxamide,
274) 4-(3-chloro-5-hydroxymethylpyridin-2-yl)-N-(2,2,3,3-tetrafluoro-2,3-dihydrobenzo[1,4]dioxin-6-yl)-3,4-dihydro-2H-benzo[1,4]oxazine-8-carboxamide,
275) 4-(3-chloro-5-hydroxymethylpyridin-2-yl)-N-(4-isobutyloxyphenyl)-3,4-dihydro-2H-benzo[1,4]oxazine-8-carboxamide,
276) 4-(3-chloro-5-hydroxymethylpyridin-2-yl)-N-(2,3-dichlorophenyl)-3,4-dihydro-2H-benzo[1,4]oxazine-8-carboxamide,
277) N-(4-bromo-3-fluorophenyl)-4-(3-chloro-5-hydroxymethylpyridin-2-yl)-3,4-dihydro-2H-benzo[1,4]oxazine-8-carboxamide,
278) N-(4-bromophenyl)-4-(3-chloro-5-hydroxymethylpyridin-2-yl)-3,4-dihydro-2H-benzo[1,4]oxazine-8-carboxamide,
279) 4-(3-chloro-5-hydroxymethylpyridin-2-yl)-N-(3,5-dichlorophenyl)-3,4-dihydro-2H-benzo[1,4]oxazine-8-carboxamide,
280) 4-(3-chloro-5-hydroxymethylpyridin-2-yl)-N-(4-difluoromethoxyphenyl)-3,4-dihydro-2H-benzo[1,4]oxazine-8-carboxamide,
281) 4-(3-chloro-5-hydroxymethylpyridin-2-yl)-N-(4-chlorophenyl)-3,4-dihydro-2H-benzo[1,4]oxazine-8-carboxamide,
282) 4-(3-chloro-5-hydroxymethylpyridin-2-yl)-N-(4-isopropylphenyl)-3,4-dihydro-2H-benzo[1,4]oxazine-8-carboxamide,
283) 4-(3-chloro-5-hydroxymethylpyridin-2-yl)-N-(3-trifluoromethoxyphenyl)-3,4-dihydro-2H-benzo[1,4]oxazine-8-carboxamide, 284) 4-[3-chloro-5-(1-hydroxyethyl)pyridin-2-yl]-N-(3-trifluoromethoxyphenyl)-3,4-dihydro-2H-benzo[1,4]oxazine-8-carboxamide,
285) 4-(3-chloro-pyridin-2-yl)-N-(4-trifluoromethoxyphenyl)-3,4-dihydro-3-oxo-2H-benzo[1,4]oxazine-8-carboxamide,
286) (R)-4-(3-chloropyridin-2-yl)-3-hydroxymethyl-N-(4-trifluoromethoxyphenyl)-3,4-dihydro-2H-benzo[1,4]oxazine-8-carboxamide,
287) (R)-4-(3-chloropyridin-2-yl)-3-hydroxymethyl-N-(4-trifluoromethylphenyl)-3,4-dihydro-2H-benzo[1,4]oxazine-8-carboxamide,
288) (S)-4-(3-chloropyridin-2-yl)-3-hydroxymethyl-N-(4-trifluoromethoxyphenyl)-3,4-dihydro-2H-benzo[1,4]oxazine-8-carboxamide,
289) (S)-4-(3-chloropyridin-2-yl)-3-hydroxymethyl-N-(4-trifluoromethylphenyl)-3,4-dihydro-2H-benzo[1,4]oxazine-8-carboxamide,
290) (S)-4-(5-chloropyridin-2-yl)-3-hydroxymethyl-N-(4-trifluoromethoxyphenyl)-3,4-dihydro-2H-benzo[1,4]oxazine-8-carboxamide,
291) (S)-4-(5-chloropyridin-2-yl)-3-hydroxymethyl-N-(4-trifluoromethylphenyl)-3,4-dihydro-2H-benzo[1,4]oxazine-8-carboxamide,
292) (S)-3-hydroxymethyl-4-(5-methylpyridin-2-yl)-N-(4-trifluoromethoxyphenyl)-3,4-dihydro-2H-benzo[1,4]oxazine-8-carboxamide,
293) (S)-3-hydroxymethyl-4-(5-methylpyridin-2-yl)-N-(4-trifluoromethylphenyl)-3,4-dihydro-2H-benzo[1,4]oxazine-8-carboxamide,
294) (S)-4-(3-chloropyridin-2-yl)-N-(3-fluoro-4-isopropoxyphenyl)-3-hydroxymethyl-3,4-dihydro-2H-benzo[1,4]oxazine-8-carboxamide,
295) (S)-4-(3-chloropyridin-2-yl)-N-(3-fluoro-4-trifluoromethoxyphenyl)-3-hydroxymethyl-3,4-dihydro-2H-benzo[1,4]oxazine-8-carboxamide,
296) (S)-4-(3-chloropyridin-2-yl)-N-(3-chloro-4-piperidinophenyl)-3-hydroxymethyl-3,4-dihydro-2H-benzo[1,4]oxazine-8-carboxamide,
297) (S)-4-(3-chloropyridin-2-yl)-N-(4-dimethylamino-3-fluorophenyl)-3-hydroxymethyl-1,4-dihydro-2H-benzo[1,4]oxazine-8-carboxamide,
298) (S)-4-(3-chloropyridin-2-yl)-N-(3-fluoro-4-methylphenyl)-3-hydroxymethyl-3,4-dihydro-2H-benzo[1,4]oxazine-8-carboxamide,
299) (S)—N-(trans-4-tert-butylcyclohexyl)-4-(3-chloropyridin-2-yl)-3-hydroxymethyl-3,4-dihydro-2H-benzo[1,4]oxazine-8-carboxamide,
300) (S)-4-(3-chloropyridin-2-yl)-3-hydroxymethyl-N-(trans-4-neopentyloxycyclohexyl)-3,4-dihydro-2H-benzo[1,4]oxazine-8-carboxamide,
301) (S)—N-(4-chlorophenyl)-4-(3-chloropyridin-2-yl)-3-hydroxymethyl-3,4-dihydro-2H-benzo[1,4]oxazine-8-carboxamide,
302) (S)-4-(3-chloropyridin-2-yl)-3-hydroxymethyl-N-(4-isopropylphenyl)-3,4-dihydro-2H-benzo[1,4]oxazine-8-carboxamide,
303) (S)-4-(3-chloropyridin-2-yl)-N-(4-fluoro-3-trifluoromethylphenyl)-3-hydroxymethyl-3,4-dihydro-2H-benzo[1,4]oxazine-8-carboxamide,
304) (S)—N-(4-bromo-3-chlorophenyl)-4-(3-chloropyridin-2-yl)-3-hydroxymethyl-3,4-dihydro-2H-benzo[1,4]oxazine-8-carboxamide,
305) (S)-4-(3-chloropyridin-2-yl)-N-(4-dimethylamino-3-trifluoromethylphenyl)-3-hydroxymethyl-3,4-dihydro-2H-benzo[1,4]oxazine-8-carboxamide,
306) (S)-4-(3-chloropyridin-2-yl)-N-(4-isopropoxy-3-trifluoromethylphenyl)-3-hydroxymethyl-3,4-dihydro-2H-benzo[1,4]oxazine-8-carboxamide,
307) (S)-4-(3-chloropyridin-2-yl)-3-hydroxymethyl-N-(4-piperidino-3-trifluoromethylphenyl)-3,4-dihydro-2H-benzo[1,4]oxazine-8-carboxamide,
308) (S)-4-(3-chloropyridin-2-yl)-N-(4-ethoxy-3-fluorophenyl)-3-hydroxymethyl-3,4-dihydro-2H-benzo[1,4]oxazine-8-carboxamide,
309) (S)-4-(3-chloropyridin-2-yl)-3-hydroxymethyl-N-(4-methoxy-3-trifluoromethylphenyl)-3,4-dihydro-2H-benzo[1,4]oxazine-8-carboxamide,
310) (S)-4-(3-chloro-5-methoxypyridin-2-yl)-3-hydroxymethyl-N-(4-trifluoromethylphenyl)-3,4-dihydro-2H-benzo[1,4]oxazine-8-carboxamide,
311) (S)-4-(3-chloro-5-methoxypyridin-2-yl)-3-hydroxymethyl-N-(4-trifluoromethoxyphenyl)-3,4-dihydro-2H-benzo[1,4]oxazine-8-carboxamide,
312) (S)-3-hydroxymethyl-4-(5-methylpyridin-2-yl)-N-(2-trifluoromethylpyridin-5-yl)-3,4-dihydro-2H-benzo[1,4]oxazine-8-carboxamide,
313) (S)-3-hydroxymethyl-N-(4-methoxy-3-trifluoromethylphenyl)-4-(5-methylpyridin-2-yl)-3,4-dihydro-2H-benzo[1,4]oxazine-8-carboxamide,
314) (S)-3-hydroxymethyl-4-(5-methylpyridin-2-yl)-N-(4-piperidino-3-trifluoromethylphenyl)-3,4-dihydro-2H-benzo[1,4]oxazine-8-carboxamide,
315) (S)—N-(3-fluoro-4-trifluoromethylphenyl)-3-hydroxymethyl-4-(5-methylpyridin-2-yl)-3,4-dihydro-2H-benzo[1,4]oxazine-8-carboxamide,
316) (S)—N-(3-chloro-4-trifluoromethoxyphenyl)-3-hydroxymethyl-4-(5-methylpyridin-2-yl)-3,4-dihydro-2H-benzo[1,4]oxazine-8-carboxamide,
317) (S)—N-(3,4-dichlorophenyl)-3-hydroxymethyl-4-(5-methylpyridin-2-yl)-3,4-dihydro-2H-benzo[1,4]oxazine-8-carboxamide,
318) (S)-4-(3-chloropyridin-2-yl)-3-hydroxymethyl-N-(4-isobutyloxy-3-trifluoromethylphenyl)-3,4-dihydro-2H-benzo[1,4]oxazine-8-carboxamide,
319) (S)-4-(3-chloropyridin-2-yl)-N-(3,4-dichlorophenyl)-3-hydroxymethyl-3,4-dihydro-2H-benzo[1,4]oxazine-8-carboxamide,
320) (S)-4-(3-chloropyridin-2-yl)-N-(4-chloro-3-trifluoromethylphenyl)-3-hydroxymethyl-3,4-dihydro-2H-benzo[1,4]oxazine-8-carboxamide,
321) (S)—N-(4-bromo-3-fluorophenyl)-4-(3-chloropyridin-2-yl)-3-hydroxymethyl-3,4-dihydro-2H-benzo[1,4]oxazine-8-carboxamide,
322) (S)—N-(4-chloro-3-trifluoromethylphenyl)-3-hydroxymethyl-4-(5-methylpyridin-2-yl)-3,4-dihydro-2H-benzo[1,4]oxazine-8-carboxamide,
323) (S)-3-hydroxymethyl-N-(4-isopropoxy-3-trifluoromethylphenyl)-4-(5-methylpyridin-2-yl)-3,4-dihydro-2H-benzo[1,4]oxazine-8-carboxamide,
324) (S)-4-(3-chloropyridin-2-yl)-3-hydroxymethyl-N-(4-morpholino-3-trifluoromethylphenyl)-3,4-dihydro-2H-benzo[1,4]oxazine-8-carboxamide,
325) (S)—N-(2-chloro-4-trifluoromethylphenyl)-3-hydroxymethyl-4-(5-methylpyridin-2-yl)-3,4-dihydro-2H-benzo[1,4]oxazine-8-carboxamide,
326) (S)-3-hydroxymethyl-4-(3-methylpyridin-2-yl)-N-(4-trifluoromethoxyphenyl)-3,4-dihydro-2H-benzo[1,4]oxazine-8-carboxamide,
327) (S)-3-hydroxymethyl-4-(3-methylpyridin-2-yl)-N-(4-trifluoromethylphenyl)-3,4-dihydro-2H-benzo[1,4]oxazine-8-carboxamide, 328) (S)—N-(4-tert-butoxy-3-fluorophenyl)-4-(3-chloropyridin-2-yl)-3-hydroxymethyl-3,4-dihydro-2H-benzo[1,4]oxazine-8-carboxamide,
329) (S)-4-(3-chloropyridin-2-yl)-N-(3-fluoro-4-isobutyloxyphenyl)-3-hydroxymethyl-3,4-dihydro-2H-benzo[1,4]oxazine-8-carboxamide,
330) (S)-3-hydroxymethyl-N-(4-isobutyloxy-3-trifluoromethylphenyl)-4-(5-methylpyridin-2-yl)-3,4-dihydro-2H-benzo[1,4]oxazine-8-carboxamide,
331) (S)—N-(3-fluoro-4-isopropoxyphenyl)-3-hydroxymethyl-4-(5-methylpyridin-2-yl)-3,4-dihydro-2H-benzo[1,4]oxazine-8-carboxamide,
332) (S)—N-(3-fluoro-4-morpholinophenyl)-3-hydroxymethyl-4-(5-methylpyridin-2-yl)-3,4-dihydro-2H-benzo[1,4]oxazine-8-carboxamide,
333) (S)—N-(4-chlorophenyl)-3-hydroxymethyl-4-(5-methylpyridin-2-yl)-3,4-dihydro-2H-benzo[1,4]oxazine-8-carboxamide,
334) (S)-3-hydroxymethyl-4-(5-methylpyridin-2-yl)-N-(2-morpholino-4-trifluoromethylphenyl)-3,4-dihydro-2H-benzo[1,4]oxazine-8-carboxamide,
335) (S)—N-(4-tert-butoxy-3-fluorophenyl)-3-hydroxymethyl-4-(5-methylpyridin-2-yl)-3,4-dihydro-2H-benzo[1,4]oxazine-8-carboxamide,
336) (S)—N-(4-bromo-3-fluorophenyl)-3-hydroxymethyl-4-(5-methylpyridin-2-yl)-3,4-dihydro-2H-benzo[1,4]oxazine-8-carboxamide,
337) 4-(3-chloropyridin-2-yl)-3-hydroxymethyl-N-(4-trifluoromethoxyphenyl)-3,4-dihydro-2H-benzo[1,4]oxazine-8-carboxamide,
338) (S)-4-(3-chloropyridin-2-yl)-N-(3-fluoro-4-trifluoromethylphenyl)-3-hydroxymethyl-3,4-dihydro-2H-benzo[1,4]oxazine-8-carboxamide,
339) (S)—N-(3-fluoro-4-isobutyloxyphenyl)-3-hydroxymethyl-4-(5-methylpyridin-2-yl)-3,4-dihydro-2H-benzo[1,4]oxazine-8-carboxamide,
340) (S)—N-(4-fluoro-3-trifluoromethylphenyl)-3-hydroxymethyl-4-(5-methylpyridin-2-yl)-3,4-dihydro-2H-benzo[1,4]oxazine-8-carboxamide,
341) 4-(3-chloropyridin-2-yl)-3-(1-hydroxyethyl)-N-(4-trifluoromethoxyphenyl)-3,4-dihydro-2H-benzo[1,4]oxazine-8-carboxamide,
342) (R)-9-(3-chloropyridin-2-yl)-7-hydroxy-N-(4-trifluoromethoxyphenyl)-6,7,8,9-tetrahydro-5-oxa-9-azabenzocycloheptane-4-carboxamide,
343) (R)-9-(3-chloropyridin-2-yl)-7-hydroxy-N-(4-trifluoromethylphenyl)-6,7,8,9-tetrahydro-5-oxa-9-azabenzocycloheptane-4-carboxamide,
344) (S)-9-(3-chloropyridin-2-yl)-7-hydroxy-N-(4-trifluoromethoxyphenyl)-6,7,8,9-tetrahydro-5-oxa-9-azabenzocycloheptane-4-carboxamide,
345) N-(4-tert-butylphenyl)-4-(pyrazin-2-yl)-3,4-dihydro-2H-benzo[1,4]oxazine-8-carboxamide,
346) N-(4-chlorophenyl)-4-(5-ethylpyrimidin-2-yl)-3,4-dihydro-2H-benzo[1,4]oxazine-8-carboxamide,
347) N-(4-ethoxyphenyl)-4-(5-ethylpyrimidin-2-yl)-3,4-dihydro-2H-benzo[1,4]oxazine-8-carboxamide,
348) 4-(6-chloropyridazin-3-yl)-N-(4-trifluoromethylphenyl)-3,4-dihydro-2H-benzo[1,4]oxazine-8-carboxamide,
349) 4-(4-methylthiazol-2-yl)-N-(4-trifluoromethoxyphenyl)-3,4-dihydro-2H-benzo[1,4]oxazine-8-carboxamide,
350) 4-(5-methylthiazol-2-yl)-N-(4-trifluoromethoxyphenyl)-3,4-dihydro-2H-benzo[1,4]oxazine-8-carboxamide,
351) (S)-3-hydroxymethyl-4-(5-methylthiazol-2-yl)-N-(4-trifluoromethoxyphenyl)-3,4-dihydro-2H-benzo[1,4]oxazine-8-carboxamide,
352) (S)-3-hydroxymethyl-4-(5-methylthiazol-2-yl)-N-(4-trifluoromethylphenyl)-3,4-dihydro-2H-benzo[1,4]oxazine-8-carboxamide,
353) (S)—N-(3,4-dichlorophenyl)-3-hydroxymethyl-4-(5-methylthiazol-2-yl)-3,4-dihydro-2H-benzo[1,4]oxazine-8-carboxamide,
354) (S)—N-(3-fluoro-4-isopropoxyphenyl)-3-hydroxymethyl-4-(5-methylthiazol-2-yl)-3,4-dihydro-2H-benzo[1,4]oxazine-8-carboxamide,
355) (S)—N-(3-fluoro-4-tert-butoxyphenyl)-3-hydroxymethyl-4-(5-methylthiazol-2-yl)-3,4-dihydro-2H-benzo[1,4]oxazine-8-carboxamide,
356) (S)—N-(3-fluoro-4-isobutyloxyphenyl)-3-hydroxymethyl-4-(5-methylthiazol-2-yl)-3,4-dihydro-2H-benzo[1,4]oxazine-8-carboxamide,
357) (S)—N-(4-bromo-3-fluorophenyl)-3-hydroxymethyl-4-(5-methylthiazol-2-yl)-3,4-dihydro-2H-benzo[1,4]oxazine-8-carboxamide,
358) (S)—N-(4-fluoro-3-trifluoromethylphenyl)-3-hydroxymethyl-4-(5-methylthiazol-2-yl)-3,4-dihydro-2H-benzo[1,4]oxazine-8-carboxamide,
359) (S)—N-(3-fluoro-4-morpholinophenyl)-3-hydroxymethyl-4-(5-methylthiazol-2-yl)-3,4-dihydro-2H-benzo[1,4]oxazine-8-carboxamide,
360) (S)-3-hydroxymethyl-4-(5-methylthiazol-2-yl)-N-(2-trifluoromethylpyridin-5-yl)-3,4-dihydro-2H-benzo[1,4]oxazine-8-carboxamide,
361) (S)-3-hydroxymethyl-4-(5-methyloxazol-2-yl)-N-(4-trifluoromethoxyphenyl)-3,4-dihydro-2H-benzo[1,4]oxazine-8-carboxamide,
362) (S)-3-hydroxymethyl-4-(5-methyloxazol-2-yl)-N-(4-trifluoromethylphenyl)-3,4-dihydro-2H-benzo[1,4]oxazine-8-carboxamide,
363) (S)-4-(4,5-dimethylthiazol-2-yl)-3-hydroxymethyl-N-(4-trifluoromethoxyphenyl)-3,4-dihydro-2H-benzo[1,4]oxazine-8-carboxamide,
364) (S)-4-(4,5-dimethylthiazol-2-yl)-3-hydroxymethyl-N-(4-trifluoromethylphenyl)-3,4-dihydro-2H-benzo[1,4]oxazine-8-carboxamide,
365) (S)-3-hydroxymethyl-4-(5-methyl[1,3,4]thiadiazol-2-yl)-N-(4-trifluoromethoxyphenyl)-3,4-dihydro-2H-benzo[1,4]oxazine-8-carboxamide,
366) (S)-3-hydroxymethyl-4-(5-methyl[1,3,4]thiadiazol-2-yl)-N-(4-trifluoromethylphenyl)-3,4-dihydro-2H-benzo[1,4]oxazine-8-carboxamide,
367) 4-(4,5-dimethylthiazol-2-yl)-N-(4-trifluoromethoxyphenyl)-3,4-dihydro-2H-benzo[1,4]thiazine-8-carboxamide,
368) 4-(4,5-dimethylthiazol-2-yl)-N-(4-trifluoromethoxyphenyl)-1-oxo-3,4-tetrahydro-benzo[1,4]thiazine-8-carboxamide,
369) N-(4-tert-butylphenyl)-4-(4-methoxyphenyl)-3,4-dihydro-2H-benzo[1,4]oxazine-8-carboxamide,
370) N-(4-isobutyloxyphenyl)-4-(4-methoxyphenyl)-3,4-dihydro-2H-benzo[1,4]oxazine-8-carboxamide,
371) N-(4-chlorophenyl)-4-(4-methoxyphenyl)-3,4-dihydro-2H-benzo[1,4]oxazine-8-carboxamide,
372) (S)-4-(2-chlorophenyl)-3-hydroxymethyl-N-(4-trifluoromethoxyphenyl)-3,4-dihydro-2H-benzo[1,4]oxazine-8-carboxamide,
373) (S)-4-(2-chlorophenyl)-3-hydroxymethyl-N-(4-trifluoromethylphenyl)-3,4-dihydro-2H-benzo[1,4]oxazine-8-carboxamide,
374) (S)-4-(2-chlorophenyl)-N-(3-fluoro-4-trifluoromethylphenyl)-3-hydroxymethyl-3,4-dihydro-2H-benzo[1,4]oxazine-8-carboxamide, 375) (S)-4-(4-chlorophenyl)-3-hydroxymethyl-N-(4-trifluoromethoxyphenyl)-3,4-dihydro-2H-benzo[1,4]oxazine-8-carboxamide,
376) (S)-3-hydroxymethyl-4-(4-methoxyphenyl)-N-(4-trifluoromethoxyphenyl)-3,4-dihydro-2H-benzo[1,4]oxazine-8-carboxamide,
377) (S)-3-hydroxymethyl-4-(4-methoxyphenyl)-N-(4-trifluoromethylphenyl)-3,4-dihydro-2H-benzo[1,4]oxazine-8-carboxamide,
378) (S)-4-(4-chlorophenyl)-3-hydroxymethyl-N-(4-trifluoromethylphenyl)-3,4-dihydro-2H-benzo[1,4]oxazine-8-carboxamide, and
379) (S)-4-(4-chlorophenyl)-N-(4-chlorophenyl)-3-hydroxymethyl-3,4-dihydro-2H-benzo[1,4]oxazine-8-carboxamide.

10. A pharmaceutical composition comprising a condensed benzamide compound or a pharmaceutically acceptable salt thereof according to any of above 1 to 9 and a pharmaceutically acceptable carrier.

11. A pharmaceutical composition comprising a condensed benzamide compound or a pharmaceutically acceptable salt thereof according to any of above 1 to 9 and a pharmaceutically acceptable carrier for treating and/or preventing a disease selected from pain, acute pain, chronic pain, neuropathic pain, rheumatoid arthritis pain, neuralgia, neuropathy, hyperalgesia, migraine, joint pain, acute postherpetic neuralgia, postherpetic neuralgia, chronic postherpetic neuralgia, postoperative pain, cancer pain, inflammatory pain, interstitial cystitis, posttraumatic neuralgia, diabetic neuropathy, neurodegenerative disease, cerebral apoplexy, ischemic symptom, nerve injury, neurogenic skin disorder, inflammatory disease, pruritus, allergic rhinitis, apoplexy, irritable bowel syndrome, asthma, chronic obstructive pulmonary disease, dermatitis, mucositis, stomach and duodenal ulcer and inflammatory bowel disease, bladder hypersensitivity, and overactive bladder type frequent urination and urinary incontinence.

12. A pharmaceutical composition for treating and/or preventing pain comprising a condensed benzamide compound or a pharmaceutically acceptable salt thereof according to any of above 1 to 9 and a pharmaceutically acceptable carrier.

13. The pharmaceutical composition according to above 12 wherein the pain is acute pain, chronic pain, neuropathic pain, rheumatoid arthritis pain, neuralgia, neuropathy, hyperalgesia, migraine, joint pain, acute postherpetic neuralgia, postherpetic neuralgia, chronic postherpetic neuralgia, postoperative pain, cancer pain, inflammatory pain, interstitial cystitis, posttraumatic neuralgia, diabetic neuropathy or neurodegenerative disease.

14. An inhibitor of vanilloid receptor subtype 1 (VR1) activity comprising a condensed benzamide compound or a pharmaceutically acceptable salt thereof according to any of above 1 to 9 and a pharmaceutically acceptable carrier.

15. A method for treating and/or preventing a disease selected from pain, acute pain, chronic pain, neuropathic pain, rheumatoid arthritis pain, neuralgia, neuropathy, hyperalgesia, migraine, joint pain, acute postherpetic neuralgia, postherpetic neuralgia, chronic postherpetic neuralgia, postoperative pain, cancer pain, inflammatory pain, interstitial cystitis, posttraumatic neuralgia, diabetic neuropathy, neurodegenerative disease, cerebral apoplexy, ischemic symptom, nerve injury, neurogenic skin disorder, inflammatory disease, pruritus, allergic rhinitis, apoplexy, irritable bowel syndrome, asthma, chronic obstructive pulmonary disease, dermatitis, mucositis, stomach and duodenal ulcer and inflammatory bowel disease, bladder hypersensitivity, and overactive bladder type frequent urination and urinary incontinence characterized in that the method comprises administering a pharmacologically effective amount of a condensed benzamide compound or a pharmaceutically acceptable salt thereof according to any of above 1 to 9.

16. A method for treating and/or preventing pain characterized in that the method comprises administering a pharmacologically effective amount of a condensed benzamide compound or a pharmaceutically acceptable salt thereof according to any of above 1 to 9.

17. The treating and/or preventing method according to above 16 wherein the pain is acute pain, chronic pain, neuropathic pain, rheumatoid arthritis pain, neuralgia, neuropathy, hyperalgesia, migraine, joint pain, acute postherpetic neuralgia, postherpetic neuralgia, chronic postherpetic neuralgia, postoperative pain, cancer pain, inflammatory pain, interstitial cystitis, posttraumatic neuralgia, diabetic neuropathy or neurodegenerative disease.

18. A commercial package comprising a pharmaceutical composition according to any of above 10 to 13 and written instructions concerning this pharmaceutical composition stating that said composition can be used or should be used for treating and/or preventing a disease selected from pain, acute pain, chronic pain, neuropathic pain, rheumatoid arthritis pain, neuralgia, neuropathy, hyperalgesia, migraine, joint pain, acute postherpetic neuralgia, postherpetic neuralgia, chronic postherpetic neuralgia, postoperative pain, cancer pain, inflammatory pain, interstitial cystitis, posttraumatic neuralgia, diabetic neuropathy, neurodegenerative disease, cerebral apoplexy, ischemic symptom, nerve injury, neurogenic skin disorder, inflammatory disease, pruritus, allergic rhinitis, apoplexy, irritable bowel syndrome, asthma, chronic obstructive pulmonary disease, dermatitis, mucositis, stomach and duodenal ulcer and inflammatory bowel disease, bladder hypersensitivity, and overactive bladder type frequent urination and urinary incontinence.

19. Use of a condensed benzamide compound or a pharmaceutically acceptable salt thereof according to any of above 1 to 9 for preparing a pharmaceutical composition according to above 11 for treating and/or preventing a disease selected from pain, acute pain, chronic pain, neuropathic pain, rheumatoid arthritis pain, neuralgia, neuropathy, hyperalgesia, migraine, joint pain, acute postherpetic neuralgia, postherpetic neuralgia, chronic postherpetic neuralgia, postoperative pain, cancer pain, inflammatory pain, interstitial cystitis, posttraumatic neuralgia, diabetic neuropathy, neurodegenerative disease, cerebral apoplexy, ischemic symptom, nerve injury, neurogenic skin disorder, inflammatory disease, pruritus, allergic rhinitis, apoplexy, irritable bowel syndrome, asthma, chronic obstructive pulmonary disease, dermatitis, mucositis, stomach and duodenal ulcer and inflammatory bowel disease, bladder hypersensitivity, and overactive bladder type frequent urination and urinary incontinence.

20. Use of a condensed benzamide compound or a pharmaceutically acceptable salt thereof according to any of above 1 to 9 for preparing a pharmaceutical composition for treating and/or preventing pain according to above 12.

21. The use of a condensed benzamide compound or a pharmaceutically acceptable salt thereof according to above 20 wherein the pain is acute pain, chronic pain, neuropathic pain, rheumatoid arthritis pain, neuralgia, neuropathy, hyperalgesia, migraine, joint pain, acute postherpetic neuralgia, postherpetic neuralgia, chronic postherpetic neuralgia, postoperative pain, cancer pain, inflammatory pain, interstitial cystitis, posttraumatic neuralgia, diabetic neuropathy or neurodegenerative disease.

22. A drug comprising a combination of a pharmaceutical composition comprising a condensed benzamide compound or a pharmaceutically acceptable salt thereof according to any of above 1 to 9 and a pharmaceutically acceptable carrier with one or more agents selected from the group which consists of an anti-virus agent, an antidepressant, an anticonvulsant, an antiarrhythmic drug, a local anesthetic, an anesthetic drug, an N-methyl-D-aspartate receptor antagonist, adrenal cortical steroid, a nerve block, a nonsteroidal antiinflammatory analgesic, narcotics, an antagonist analgesic, $\alpha_2$-adrenaline receptor agonist, a medicine for external application, a calcium channel antagonist, and a potassium channel opener.

23. Use of a condensed benzamide compound or a pharmaceutically acceptable salt thereof according to any of above 1 to 9 for preparing a drug according to above 22.

24. A method for treating and/or preventing a disease selected from pain, acute pain, chronic pain, neuropathic pain, rheumatoid arthritis pain, neuralgia, neuropathy, hyperalgesia, migraine, joint pain, acute postherpetic neuralgia, postherpetic neuralgia, chronic postherpetic neuralgia, postoperative pain, cancer pain, inflammatory pain, interstitial cystitis, posttraumatic neuralgia, diabetic neuropathy, neurodegenerative disease, cerebral apoplexy, ischemic symptom, nerve injury, neurogenic skin disorder, inflammatory disease, pruritus, allergic rhinitis, apoplexy, irritable bowel syndrome, asthma, chronic obstructive pulmonary disease, dermatitis, mucositis, stomach and duodenal ulcer and inflammatory bowel disease, bladder hypersensitivity, and overactive bladder type frequent urination and urinary incontinence characterized in that one or more agents selected from the group which consists of an anti-virus agent, an antidepressant, an anticonvulsant, an antiarrhythmic drug, a local anesthetic, an anesthetic drug, an N-methyl-D-aspartate receptor antagonist, adrenal cortical steroid, a nerve block, a nonsteroidal antiinflammatory analgesic, narcotics, an antagonist analgesic, $\alpha_2$-adrenaline receptor agonist, a medicine for external application, a calcium channel antagonist, and a potassium channel opener are used in combination with a pharmacologically effective amount of an inhibitor of vanilloid receptor subtype 1 (VR1) activity.

25. The treating and/or preventing method according to above 24 wherein the inhibitor of vanilloid receptor subtype 1 (VR1) activity is a condensed benzamide compound or a pharmaceutically acceptable salt thereof according to any of above 1 to 9.

26. A method for treating and/or preventing pain characterized in that the method uses administration of an inhibitor of vanilloid receptor subtype 1 (VR1) activity in combination with stimulation-produced analgesia selected from acupuncture, transcutaneous electroacupuncture stimulation therapy, transcutaneous electrical nerve stimulation therapy, silver spike point (SSP) therapy, peripheral nerve stimulation therapy, spinal cord electrical stimulation therapy, electroconvulsive therapy, laser therapy and low-frequency therapy.

27. The treating and/or preventing method according to above 26 wherein the inhibitor of vanilloid receptor subtype 1 (VR1) activity is a condensed benzamide compound or a pharmaceutically acceptable salt thereof according to any of above 1 to 9.

28. A method for treating and/or preventing postoperative neuralgia characterized in that an inhibitor of vanilloid receptor subtype 1 (VR1) activity is administered after performing a surgical operation selected from cicatrectomy, nerve freezing solidification, peripheral nerve excision, spinal cord dorsal root excision, sympathectomy, spinal cord dorsal root entry zone destruction, cordotomy, and frontal lobe excision.

29. The treating and/or preventing method according to above 28 wherein the inhibitor of vanilloid receptor subtype 1 (VR1) activity is a condensed benzamide compound or a pharmaceutically acceptable salt thereof according to any of above 1 to 9.

The condensed benzamide compound of the present invention effectively inhibits vanilloid receptor subtype 1 (VR1) activity, and therefore it is effective in the medical treatment and/or prevention of diseases such as pain, acute pain, chronic pain, neuropathic pain, rheumatoid arthritis pain, neuralgia, neuropathy, hyperalgesia, migraine, joint pain, acute postherpetic neuralgia, postherpetic neuralgia, chronic postherpetic neuralgia, postoperative pain, cancer pain, inflammatory pain, interstitial cystitis, posttraumatic neuralgia, diabetic neuropathy, neurodegenerative disease, cerebral apoplexy, ischemic symptom, nerve injury, neurogenic skin disorder, inflammatory disease, pruritus, allergic rhinitis, apoplexy, irritable bowel syndrome, asthma, chronic obstructive pulmonary disease, dermatitis, mucositis, stomach and duodenal ulcer and inflammatory bowel disease, bladder hypersensitivity, and overactive bladder type frequent urination and urinary incontinence. Particularly, it is effective as a therapeutic agent and preventive agent of diseases accompanied with pain condition such as pain, acute pain, chronic pain, neuropathic pain, rheumatoid arthritis pain, neuralgia, neuropathy, hyperalgesia, migraine, joint pain, acute postherpetic neuralgia, postherpetic neuralgia, chronic postherpetic neuralgia, postoperative pain, cancer pain, inflammatory pain, interstitial cystitis, posttraumatic neuralgia, diabetic neuropathy and neurodegenerative disease. In addition, effects by different mechanism from the conventional analgesics are also expected.

BEST MODE FOR CARRYING OUT THE INVENTION

The definition of each term used in this specification is as follows.

A "C1-6 alkyl group" represents a linear or branched alkyl group having 1 to 6 carbon atoms, and specifically includes a methyl group, an ethyl group, a propyl group, an isopropyl group, a butyl group, an isobutyl group, a sec-butyl group, a tert-butyl group, a pentyl group, an isopentyl group, a tert-pentyl group, a hexyl group, etc. A "C1-4 alkyl group" represents a linear or branched alkyl group having 1 to 4 carbon atoms, and specifically includes a methyl group, an ethyl group, a propyl group, an isopropyl group, a butyl group, an isobutyl group, a sec-butyl group, and a tert-butyl.

A preferred "C1-6 alkyl group" as $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$ and $R^{27}$ is a "C1-4 alkyl group," particularly a methyl group and an ethyl group. A preferred C1-6 alkyl group in a P1 ring and a P2 ring which may be substituted is a C1-4 alkyl group, particularly a methyl group, an ethyl group, a propyl group, an isopropyl group, a butyl group, an isobutyl group, a sec-butyl group and a tert-butyl group.

A "halogen atom" is a fluorine atom, a chlorine atom, a bromine atom or an iodine atom, and a fluorine atom and a chlorine atom are preferred.

As $R^4$, preferred is a chlorine atom, and as a halogen atom in a P1 ring and a P2 ring which may be substituted, preferred are a chlorine atom and a fluorine atom.

A "halo C1-6 alkyl group" is a "C1-6 alkyl group" of the above-mentioned definition substituted with "halogen atom" of the above-mentioned definition, and preferably a halogenated alkyl group in which the alkyl group thereof is a linear or branched alkyl group having 1 to 4 carbon atoms. Specifically, it includes a fluoromethyl group, a difluoromethyl group, a trifluoromethyl group, a bromomethyl group, a chloromethyl group, a 1,2-dichloromethyl group, a 2,2-dichloromethyl group, a 2,2,2-trifluoroethyl group, etc.

A "C1-6 alkoxy group" is an alkoxy group in which the alkyl part thereof is a "C1-6 alkyl group" of the above-mentioned definition. Specifically, it includes a methoxy group, an ethoxy group, a propoxy group, an isopropoxy group, a butoxy group, an isobutoxy group, a s-butoxy group, a tert-butyloxy group, a pentyloxy group, an isopentyloxy group, a 2-methylbutoxy group, a neopentyloxy group, a 1-ethylpropoxy group, a hexyloxy group, a 4-methylpentyloxy group, a 3-methylpentyloxy group, a 2-methylpentyloxy group, a 1-methylpentyloxy group, a 3,3-dimethylbutoxy group, a 2,2-dimethylbutoxy group, a 1,1-dimethylbutoxy group, a 1,2-dimethylbutoxy group, a 1,3-dimethylbutoxy group, a 2,3-dimethylbutoxy group, a 2-ethylbutoxy group, etc. Preferred is an alkoxy group in which the alkyl part thereof is a linear or branched alkyl group having 1 to 4 carbon atoms.

A "halo C1-6 alkoxy group" is a haloalkoxy group in which the "C1-6 alkyl group" which constitutes the C1-6 alkoxy-group part thereof is substituted with one or more and the same or different halogen atoms, and, specifically includes a fluoromethoxy group, a difluoromethoxy group, a trifluoromethoxy group, a bromomethoxy group, a chloromethoxy group, a 1,2-dichloromethoxy group, a 2,2-dichloromethoxy group, a 2,2,2-trifluoroethoxy group, etc.

A "C1-6 alkylthio group" is a "C1-6 alkyl group" mentioned above attached to a sulfur atom, and for example, a linear or branched alkylthio group having 1 to 6 carbon atoms such as a methylthio group, ethylthio group, propylthio group, isopropylthio group, butylthio group, isobutylthio group, s-butylthio group, t-butylthio group, pentylthio group, isopentylthio group, 2-methylbutylthio group, neopentylthio group, hexylthio group, 4-methylpentylthio group, 3-methylpentylthio group, 2-methylpentylthio group, 3,3-dimethylbutylthio group, 2,2-dimethylbutylthio group, 1,1-dimethylbutylthio group, 1,2-dimethylbutylthio group, 1,3-dimethylbutylthio group, 2,3-dimethylbutylthio group, and preferably a C1-4 alkylthio group.

A "C1-6 alkoxycarbonyl group" is a linear or branched "C1-6 alkoxy group" attached to a carbonyl group, and specifically includes a methoxycarbonyl group, an ethoxycarbonyl group, a propoxycarbonyl group, an isopropoxycarbonyl group, a butoxycarbonyl group, an isobutoxycarbonyl group, a s-butoxycarbonyl group, a t-butoxycarbonyl group, a pentyloxycarbonyl group, an isopentyloxycarbonyl group, a 2-methylbutoxycarbonyl group, a neopentyloxycarbonyl group, a 1-ethyl propoxycarbonyl group, a hexyloxycarbonyl group, a 4-methylpentyloxycarbonyl group, a 3-methylpentyloxycarbonyl group, a 2-methylpentyloxycarbonyl group, a 1-methylpentyloxycarbonyl group, a 3,3-dimethylbutoxycarbonyl group, a 2,2-dimethylbutoxycarbonyl group, a 1,1-dimethylbutoxycarbonyl group, a 1,2-dimethylbutoxycarbonyl group, a 1,3-dimethylbutoxycarbonyl group, a 2,3-dimethylbutoxycarbonyl group, a 2-ethylbutoxycarbonyl group, etc. Preferred is an alkoxycarbonyl group in which the alkoxy group part thereof is a linear or branched alkoxy group having 1 to 4 carbon atoms.

Preferable examples of an "acyl group" include a formyl group; a carboxyl group; a carbamoyl group; a thiocarbamoyl group; a C1-6 alkyl-carbonyl group (e.g. an acetyl group, propionyl group, butyryl group, isobutyryl group, valeryl group, isovaleryl group, pivaloyl group and hexanoyl group); a C2-7 alkenyl-carbonyl group (e.g. a crotonyl group); a C3-8 cycloalkyl-carbonyl group (e.g. a cyclobutanecarbonyl group, cyclopentanecarbonyl group, cyclohexanecarbonyl group and cycloheptanecarbonyl group); a C3-8 cycloalkenyl-carbonyl group (e.g. a 2-cyclohexanecarbonyl group); a C6-14 aryl-carbonyl group (e.g. a benzoyl group, 1-naphthoyl group and 2-naphthoyl group); a C7-14 aralkyl-carbonyl group (e.g. a benzylcarbonyl group, phenethylcarbonylphenylpropylcarbonyl group and phenylbutylcarbonyl group); a C8-13 arylalkenyl-carbonyl group (e.g. a styrylcarbonyl group); a C8-13 arylalkynyl-carbonyl group (e.g. a phenylethynylcarbonyl group); an aromatic heterocyclic carbonyl group (e.g. a nicotinoyl group, isonicotinoyl group, furylcarbonyl group, thienylcarbonyl group, pyrimidinylcarbonyl group, benzofuranylcarbonyl group, 1H-indazolylcarbonyl group and quinolylcarbonyl group); a non-aromatic heterocyclic carbonyl group (e.g. a pyrrolidinylcarbonyl group, piperidinocarbonyl group, morpholinocarbonyl group, thiomorpholinocarbonyl group, piperazinocarbonyl group, thiazolidinylcarbonyl group, hexamethyleneiminylcarbonyl group and tetrahydroisoquinolylcarbonyl group); a C1-6 alkoxy-carbonyl group (e.g. a methoxycarbonyl group, ethoxycarbonyl group, propoxycarbonyl group, butoxycarbonyl group and tert-butoxycarbonyl group); a C6-14 aryloxy-carbonyl group (e.g. a phenyloxycarbonyl group and naphthyloxycarbonyl group); a C7-14 aralkyloxy-carbonyl group (e.g. a benzyloxycarbonyl group and phenethyloxycarbonyl group); a mono or di-C1-6 alkylcarbamoyl group (e.g. a methylcarbamoyl group, ethylcarbamoyl group, dimethylcarbamoyl group, diethylcarbamoyl group, ethylmethylcarbamoyl group, propylcarbamoyl group, butylcarbamoyl group, tert-butylcarbamoyl group, pentylcarbamoyl group, hexylcarbamoyl group); a mono or di-C1-6 alkyl-thiocarbamoyl group (e.g. a methylthiocarbamoyl group and ethylthiocarbamoyl group); a C6-14 aryl-carbamoyl group (e.g. a phenylcarbamoyl group); a C3-10 cycloalkyl-carbamoyl group (e.g. a cyclopropylcarbamoyl group, cyclopentylcarbamoyl group and cyclohexylcarbamoyl group); a C7-14 aralkyl-carbamoyl group (e.g. a benzylcarbamoyl group, phenethylcarbamoyl group and diphenylethylcarbamoyl group); a C4-13 cycloalkylalkyl-carbamoyl group (e.g. a cyclohexylmethylcarbamoyl group); an aromatic heterocyclic carbamoyl group (e.g. an isoxazolylcarbamoyl group and benzothiazolylcarbamoyl group); a non-aromatic heterocyclic carbamoyl group (e.g. a pyrrolidinylcarbamoyl group); a C1-10 alkylsulfinyl group (e.g. a methylsulfinyl group and ethylsulfinyl group); a C1-10 alkylsulfonyl group (e.g. a methylsulfonyl group and ethylsulfonyl group); a C6-14 arylsulfonyl group (e.g. a phenylsulfonyl group); a (mono or di-C1-10 alkyl) phosphono group which may form a ring (e.g. a dimethylphosphono group; a diethylphosphono group; a diisopropropylphosphono group; a dibutylphosphono group; a 2-oxide-1,3,2-dioxaphosphinanyl group; a mono or di-(C1-6 alkyl group which may be substituted with 1 to 3 halogen)-sulfamoyl group (e.g. a methylsulfamoyl group and ethylsulfamoyl group), etc.

Preferable examples of "acyloxy group" include an acyloxy group with 2 to 13 carbon atoms, for example, a C1-6 alkyl-carbonyloxy etc (e.g. an acetyloxy, propionyloxy, butyryloxy and isobutyryloxy).

Preferable examples of "heteroaryloxy group" include 5 to 7-membered single ring type heteroaryloxy group, for example, 2-pyridyloxy, 3-pyridyloxy, 2-imidazolyloxy, 2-pyrimidinyloxy, 1,2,4-triazol-5-yloxy etc.

A "carbocyclic group" is a saturated or unsaturated cyclic hydrocarbon group having 3 to 14 carbon atoms, and specifically means an aryl group, a cycloalkyl group, cycloalkenyl group described below or a condensed carbocyclic ring in which these rings are condensed.

Here, an "aryl group" is an aromatic hydrocarbon group having 6 to 14 carbon atoms, and specifically includes a phenyl group, a naphthyl group, a biphenyl group, an anthryl group, an indenyl group, a pentalenyl group, an azulenyl group, a fluorenyl group, a phenanthryl group, etc. Preferably, it is a phenyl group, a naphthyl group, and a biphenyl group. Particularly preferred is a phenyl group.

Here, a "cycloalkyl group" is a saturated cycloalkyl group having 3 to 8 carbon atoms, and specifically includes a cyclopropyl group, a cyclobutyl group, a cyclopentyl group, a cyclohexyl group, a cycloheptyl group, and a cyclooctyl group.

A "cycloalkenyl group" is a cycloalkenyl group having 3 to 8 carbon atoms, and preferably contains at least one, preferably one or two double bonds. Specifically it includes a cyclopropenyl group, a cyclobutenyl group, a cyclopentenyl group, a cyclopentadienyl group, a cyclohexenyl group, cyclohexadienyl groups (2,4-cyclohexadien-1-yl group, 2,5-cyclohexadien-1-yl group, etc.), a cycloheptenyl group, a cyclooctenyl group, etc.

A "condensed carbocyclic group" in which the "aryl group," "cycloalkyl group," and "cycloalkenyl group" are condensed specifically includes an indenyl group, an indanyl group, a 1,4-dihydronaphthyl group, a 1,2,3,4-tetrahydronaphthyl group (a 1,2,3,4-tetrahydro-2-naphthyl group, a 5,6,7,8-tetrahydro-2-naphthyl group, etc.), a perhydronaphthyl group, etc. As a P2 ring, preferred is an aryl group and a cycloalkyl group, and a phenyl group, a biphenyl group and a cyclohexyl group are more preferably.

An "aralkyl group" is an arylalkyl group in which the aryl part thereof is an aryl group as mentioned above, particularly a phenyl group and the alkyl part thereof is a "C1-6 alkyl group" of the above-mentioned definition, and specifically it includes a benzyl group, a phenethyl group, a 3-phenyl propyl group, a 4-phenylbutyl group, a 6-phenyl hexyl group, etc.

A "aralkoxy group" is an arylalkoxy group in which the aryl part thereof is an aryl group as mentioned above, particularly a phenyl group and the alkoxy part thereof is a "C1-6 alkoxy group" of the above-mentioned definition, and, specifically it includes a benzyloxy group, a 3-phenylpropyloxy group, a 4-phenylbutyloxy group, a 6-phenylhexyloxy group, etc.

A "cycloalkylalkoxy group" is a cycloalkylalkoxy group in which the cycloalkyl part thereof is a "cycloalkyl group" of the above-mentioned definition and the alkoxy part thereof is a "C1-6 alkoxy group" of the above-mentioned definition, and, specifically it includes a cyclopropylmethoxy group, a cyclobutylmethoxy group, a cyclopentylmethoxy group, a cyclohexylmethoxy group, etc.

A "heterocyclic group" means a saturated or unsaturated (including partial unsaturation and complete unsaturation) 5-membered or 6-membered monocyclic heterocyclic ring containing at least one, preferably 1 to 4 hetero atoms selected from a nitrogen atom, an oxygen atom and a sulfur atom besides the carbon atoms, or a condensed ring of these heterocyclic rings or a condensed ring of these heterocyclic rings and a carbocyclic ring selected from benzene, cyclopentane and cyclohexane.

A "saturated monocyclic heterocyclic group" includes a pyrrolidinyl group, a tetrahydrofuryl group, a tetrahydrothienyl group, an imidazolidinyl group, a pyrazolidinyl group, a 1,3-dioxolanyl group, a 1,3-oxathiolanyl group, an oxazolidinyl group, a thiazolidinyl group, a piperidinyl group, a piperidino group, a piperazinyl group, a piperazino group, a tetrahydropyranyl group, a tetrahydrothiopyranyl group, a dioxanyl group, a morpholinyl group, a thiomorpholinyl group, a 2-oxopyrrolidinyl group, a 2-oxopiperidinyl group, a 4-oxopiperidinyl group, a 2,6-dioxopiperidinyl group etc.

A "unsaturated monocyclic heterocyclic group" includes a pyrrolyl group, a furyl group, a thienyl group, an imidazolyl group, a 1,2-dihydro-2-oxoimidazolyl group, a pyrazolyl group, a diazolyl group, an oxazolyl group, an isoxazolyl group, a thiazolyl group, an isothiazolyl group, a 1,2,4-triazolyl group, a 1,2,3-triazolyl group, a tetrazolyl group, a 1,3,4-oxadiazolyl group, a 1,2,4-oxadiazolyl group, a 1,3,4-thiadiazolyl group, a 1,2,4-thiadiazolyl group, a furazanyl group, a pyridyl group, a pyrimidinyl group, a 3,4-dihydro-4-oxopyrimidinyl group, a pyridazinyl group, a pyrazinyl group, a 1,3,5-triazinyl group, an imidazolinyl group, a pyrazolinyl group and an oxazolinyl group (a 2-oxazolinyl group, a 3-oxazolinyl group and a 4-oxazolinyl group), an isooxazolinyl group, a thiazolinyl group, an isothiazolinyl group, a pyranyl group, a 2-oxopyranyl group, a 2-oxo-2,5-dihydrofuranyl group, a 1,1-dioxo-1H-isothiazolyl group.

A "condensed heterocyclic ring" includes an indolyl group (for example, a 4-indolyl group, a 7-indolyl group, etc.), an isoindolyl group, a 1,3-dihydro-1,3-dioxo isoindolyl group, a benzofuranyl group (for example, a 4-benzofuranyl group, a 7-benzofuranyl group, etc.), an indazolyl group, an isobenzofuranyl group, a benzothiophenyl group (for example, a 4-benzothiophenyl group, a 7-benzothiophenyl group, etc.) a benzooxazolyl group (for example, a 4-benzooxazolyl group, a 7-benzooxazolyl group, etc.), a benzimidazolyl group (for example, a 4-benzimidazolyl group, a 7-benzimidazolyl group, etc.), a benzothiazolyl group (for example, a 4-benzothiazolyl group, a 7-benzothiazolyl group, etc.), an indolidinyl group, a quinolyl group, an iso quinolyl group, a 1,2-dihydro-2-oxoquinolyl group, a quinazolinyl group, a quinoxalinyl group, a cinnolinyl group, a phthalazinyl group, a quinolidinyl group, a puryl group, a pteridinyl group, an indolinyl group, an isoindolinyl group, a 5,6,7,8-tetrahydroquinolyl group, a 1,2,3,4-tetrahydroquinolyl group, a 2-oxo-1,2,3,4-tetrahydroquinolyl group, a benzo[1,3]dioxolyl group, a 2,3-dihydrobenzo[1,4]dioxosilyl group, a 3,4-methylene dioxypyridyl group, a 4,5-ethylene dioxypyrimidinyl group, a chromenyl group, a chromanyl group, an isochromanyl group, etc.

As for the group not specifically defined here, usual definition is to be followed.

In the general formula [1], preferable examples and particularly preferable examples of each symbol are as follows. However, the present invention is not limited thereto.

[Preferable Z]

Z is preferably —O—, —NR$^5$—, —S— or —SO—, and R$^5$ is preferably a hydrogen atom or a C1-4 alkyl group. Preferable Z is —O—, —S— or —SO—.

[Preferable l and m]

Preferably l is 0 or 1 and preferably m is 0 or 1. Preferably l+m is 1 or 2 and it is more preferably 1.

[Preferable R$^1$]

R$^1$ is preferably a C1-6 alkyl group which may be preferably substituted with a hydroxyl group, or a hydrogen atom. Particularly preferable R$^1$ is a hydrogen atom.

[Preferable R$^2$]

R$^2$ is preferably a hydrogen atom, a hydroxyl group, a C1-6 alkyl group (preferably a C1-4 alkyl group), a carboxyl group, a C1-6 alkoxycarbonyl group (preferably a C1-4 alkoxycarbonyl group), a C1-6 alkyl group substituted with a hydroxyl group (preferably a hydroxy substituted C1-4 alkyl group), a carbamoyl group (preferably a carbamoyl group, a mono C1-4 alkyl substituted carbamoyl group or a di-C1-4 alkyl substituted carbamoyl group), a C1-6 alkyl group substituted with a acylamino group (preferably an acylamino substituted C1-4 alkyl group) or R$^1$ and R$^2$ combined together form a carbonyl group.

$R^2$ is particularly preferably a hydrogen atom or a C1-4 alkyl group substituted with a hydroxy group.
[Preferable $R^3$]
$R^3$ is a hydrogen atom or a C1-6 alkyl group and preferably a hydrogen atom or a methyl group.
[Preferable $R^4$]
$R^4$ is preferably a hydrogen atom or a halogen atom.
[Preferable V]
V is preferably a single bond or —$(CH_2)_n$— wherein n is 1 or 2. It is particularly preferably a single bond.
[Preferable P1 and P2 Rings]
P1 and P2 rings each is a heterocyclic group (preferably a 5-membered or 6-membered heterocyclic ring containing 1 to 4, more preferably 1 to 3 hetero atoms preferably selected from a nitrogen atom, an oxygen atom and a sulfur atom, or a condensed ring of these heterocyclic rings which may be the same or different, or a condensed ring of these heterocyclic rings and a carbocyclic ring selected from benzene, cyclopentane and cyclohexane (particularly preferably a pyridyl group, a thiazolyl group, a pyrazinyl group, a pyridazinyl group, a pyrimidinyl group, more preferably a pyridyl group), or a carbocyclic group selected from C3-8 cycloalkyl groups (for example, a cyclohexyl group, a cyclopentyl group, etc.), a C3-8 cycloalkenyl group (for example, a cyclohexenyl group), and an aryl group (for example, a phenyl group, etc.).
[Preferable P1 Ring]
The P1 ring is preferably a 5-membered or 6-membered monocyclic aromatic heterocyclic group or aromatic carbocyclic group.
[Preferable Aromatic Heterocyclic Group for P1 Ring]
The preferable aromatic heterocyclic group for the P1 ring is a 5-membered or 6-membered monocyclic aromatic heterocyclic group having at least one nitrogen atom and preferably an aromatic heterocyclic group as follows.

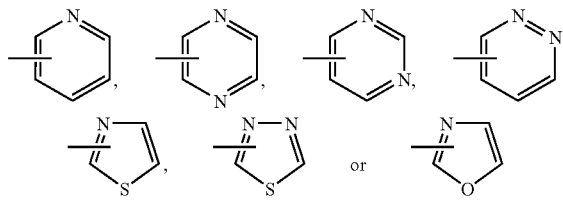

It is more preferably an aromatic heterocyclic group as follows.

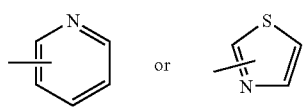

[Preferable Aromatic Carbocyclic Group for P1 Ring]
The preferable aromatic carbocyclic group for the P1 ring is a phenyl group, a biphenyl group or a naphthyl group and particularly preferably a phenyl group.
[Particularly Preferable P1 Group]
A pyridyl group or a phenyl group is particularly preferably as a P1 ring.
[Preferable P2 Ring]
A ring preferable as P2 is an aromatic carbocyclic group, a 5-membered or 6-membered cycloalkyl group, a 5-membered or 6-membered saturated heterocyclic group or a 5-membered or 6-membered aromatic heterocyclic group and more details are as follows.

[Preferable Aromatic Carbocyclic Group in P2 Ring]
The preferable aromatic carbocyclic group in the P2 ring is a phenyl group, a biphenyl group or a naphthyl group and particularly preferably a phenyl group. These aromatic carbocyclic groups may be substituted with a methylenedioxy group or an ethylenedioxy group as shown below.

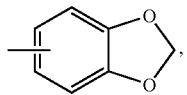 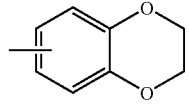

[Preferable Cycloalkyl Group for P2 Ring]
Preferable 5-membered or 6-membered cycloalkyl group for the P2 ring is specifically a cyclopentyl group or a cyclohexyl group, and may be substituted with an oxo group as shown below, and may form an ethylenedioxy group and a spiro ring.

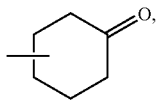 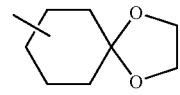

[Preferable Saturated Heterocyclic Group for P2 Ring]
The saturated 5-membered or 6-membered heterocyclic group which may form a preferable condensed ring in the P2 ring may be substituted with an oxo group as follows.

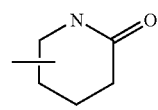

It is preferably a piperidyl group, a piperidino group and a tetrahydroquinolyl group as follows.

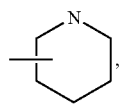 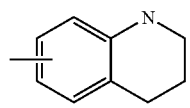

[Preferable Aromatic Heterocyclic Group for P2 Ring]
The 5-membered or 6-membered aromatic heterocyclic group which may form a preferable condensed ring for the P2 ring is 5-membered or 6-membered monocyclic aromatic heterocyclic group which preferably has at least one nitrogen atom, and is specifically an aromatic heterocyclic group as follows.

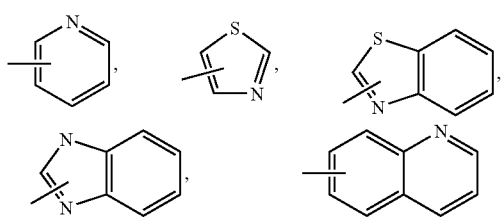

[Particularly Preferable P2 Group]
Particularly preferred as P2 ring is a ring group as follows.

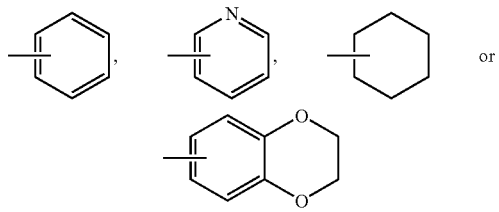

[Preferable Substituent Group of P1 Ring and P2 Ring]
The heterocyclic group and carbocyclic group of these rings P1 and P2 may be substituted with 1 to 3 substituents selected from the following group, respectively:
a halogen atom,
a hydroxyl group,
a C1-6 alkoxy group (wherein the C1-6 alkoxy group may be substituted with a carboxyl group, a hydroxyl group, and
$CONR^6R^7$ (wherein $R^6$ and $R^7$ are the same or different and each represents a hydrogen atom or a C1-6 alkyl group, and the alkyl group may be substituted with a hydroxyl group or an acyloxy group)),
a C1-6 alkyl group (wherein the C1-6 alkyl group may be substituted with 1 to 5, preferably 1 to 3 substituents selected from a halogen atom, a hydroxyl group, a C1-6 alkoxy group,
$NR^6R^7$ (wherein $R^6$ and $R^7$ are the same or different and each represents a hydrogen atom or a C1-6 alkyl group, and the alkyl group may be substituted with a hydroxyl group or an acyloxy group), $-NR^6COR^7$ (wherein $R^6$ and $R^7$ are the same or different and each represents a hydrogen atom or a C1-6 alkyl group, and the alkyl group may be substituted with a hydroxyl group or an acyloxy group)),
$-CONR^{23}R^{24}$ (wherein $R^{23}$ and $R^{24}$ are the same or different and each represents a hydrogen atom or a C1-6 alkyl group which may be substituted with 1 to 5 substituents selected from or the above-mentioned Group A),
$-NR^{123}R^{124}$ (wherein $R^{123}$ and $R^{124}$ are the same or different and each represents a hydrogen atom or a C1-6 alkyl group which may be substituted with 1 to 5 substituents selected from the Group A),
$-NR^{223}COR^{224}$ (wherein $R^{223}$ and $R^{224}$ are the same or different and each represents a hydrogen atom or a C1-6 alkyl group which may be substituted with 1 to 5 substituents selected from the Group A),
$-COR^{27}$ (wherein $R^{27}$ is a C1-6 alkyl group, C1-6 alkoxy group, a C3-8 cycloalkyl group, an aralkyl group, an aralkoxy group, a cycloalkylalkoxy group or a hydroxyl group),
$-O-(CR^{121}R^{122})_n-R^{128}$ (wherein $R^{112}$ and $R^{122}$ are the same or different and each represents a hydrogen atom or a C1-6 alkyl group, n is 1 or 2, and $R^{128}$ is an acyl group, a carbocyclic group which may be substituted with 1 to 5 substituents selected from (a) to (i) of the Group C or a heterocyclic group which may be substituted with 1 to 5 substituents selected from (a) to (l) of the Group C, wherein $R^{128}$ is preferably a 5-membered or 6-membered heterocyclic group which preferably contains 1 to 3 nitrogen atoms and/or sulfur atoms, more preferably an unsaturated monocyclic heterocyclic group such as a pyridyl group, or an aryl group such as a phenyl group), and
a cyano group.
The P2 ring is preferably a carbocyclic group (more preferably an aryl group such as a phenyl group or a C3-8 cycloalkyl group, particularly preferably a phenyl group or a C5-6 cycloalkyl group), or a heterocyclic group (wherein this heterocyclic group is a saturated or unsaturated 5-membered or 6-membered heterocyclic group which contains 1 to 3 hetero atoms, preferably nitrogen atoms and/or sulfur atoms, particularly preferably 1 to 3 nitrogen atoms, a condensed ring group of these heterocyclic rings or a condensed heterocyclic group of these heterocyclic rings which may be the same or different and a carbocyclic ring selected from benzene, cyclopentane and cyclohexane. Specific examples of the preferable heterocyclic group are a thiazolyl group, a pyridyl group, a piperidyl group, a piperidino group, a quinolyl group or a 1,2,3,4-tetrahydroquinolyl group, a benzothiazolyl group, a benzimidazolyl group, a pyrrolidino group, etc.), and the carbocyclic group and heterocyclic group may be substituted with a substituent group selected from the following:
a halogen atom,
a hydroxyl group,
a C1-6 alkoxy group which may be substituted with a halogen atom, $-CONR^{23}R^{24}$ (wherein $R^{23}$ and $R^{24}$ are the same or different and each represents a hydrogen atom or a C1-6 alkyl group. The alkyl group may be further substituted with a hydroxyl group or an acyloxy group), a C3-8 cycloalkyl group, a C1-6 alkoxy group, a carboxyl group or a C1-6 alkoxycarbonyl group,
a C1-6 alkyl group which may be substituted with a halogen atom, a hydroxyl group or a C1-6 alkoxy group,
$-NR^{123}R^{124}$ (wherein $R^{123}$ and $R^{124}$ are the same or different and each represents a hydrogen atom or a C1-6 alkyl group),
$-NR^{223}COR^{224}$ (wherein $R^{223}$ and $R^{224}$ are the same or different and each represents a hydrogen atom or a C1-6 alkyl group which may be substituted with 1 to 5 substituents selected from the Group A),
$-COR^{27}$ (wherein $R^{27}$ is preferably a C1-6 alkyl group, C1-6 alkoxy group, a C3-8 cycloalkyl group, an aralkyl group, an aralkoxy group, a cycloalkylalkoxy group or a hydroxyl group),
a saturated or unsaturated heterocyclic group having 1 to 3 nitrogen atoms as hetero atom (preferably a piperidinyl group, a piperidino group, a 2-oxopiperidino group, a morpholino group or a piperazino group, a 1,3-dioxolanyl group (spiro), a pyrrolidino group, etc., and these heterocyclic rings group may be substituted with a substituent group selected from a hydroxyl group, $-CONR^{23}R^{24}$ (wherein $R^{23}$ and $R^{24}$ are the same as above), a C1-6 alkoxy group, a carboxyl group, a C1-6 alkyl group which may be substituted with a C1-6 alkoxy group, a C1-6 alkoxycarbonyl group and an acyloxy group),
$-O-R^{28}$ (wherein $R^{28}$ is an acyl group, a carbocyclic group which may be substituted with 1 to 5 substituents selected from (a) to (l) of the Group C or a heterocyclic group which may be substituted with 1 to 5 substituents selected from (a) to (l) of the Group C),
$-O-(CR^{121}R^{122})_n-R^{128}$ (wherein $R^{121}$ and $R^{122}$ are the same or different and each represents a hydrogen atom or a C1-6 alkyl group, n is 1 or 2, and $R^{128}$ is an acyl group, a carbocyclic group which may be substituted with 1 to 5 substituents selected from (a) to (i) of the Group C or a heterocyclic group which may be substituted with 1 to 5 substituents selected from (a) to (l) of the Group C),
a nitro group, and
a cyano group.

[Substituent Group Preferable as a Substituent Group in P1 Ring]

More specifically, the following is preferable as a substituent group in P1 ring:
- a halogen atom, particularly preferably a fluorine atom, a chlorine atom,
- a C1-6 alkyl group (preferably a C1-4 alkyl group),
- a cyano group,
- a hydroxyl group,
- a carboxyl group,
- a C1-6 alkoxycarbonyl group (preferably a C1-4 alkoxycarbonyl group),
- —$NR^{123}R^{124}$ (wherein $R^{123}$ and $R^{124}$ are the same or different and each represents a hydrogen atom or a C1-6 alkyl group which may be substituted with 1 to 5 substituents selected from the Group A),
- a C1-6 alkoxy group (preferably a C1-4 alkoxy group (wherein the alkoxy group may be substituted with 1 to 2 substituents selected from a hydroxyl group, a carboxyl group, —$CONR^{23}R^{24}$ (wherein $R^{23}$ and $R^{24}$ are the same as above) and a 5-membered or 6-membered monocyclic aromatic heterocyclic group (preferably a pyridyl group),
- an aralkoxy group (preferably a benzyloxy group),
- an aralkoxycarbonyl group (preferably a benzyloxycarbonyl group),
- a C1-6 alkyl group (preferably a C1-4 alkyl group) substituted with 1 to 2 substituents selected from a hydroxyl group, a C1-4 alkoxy group and —$NR^{123}R^{124}$ (wherein $R^{123}$ and $R^{124}$ are the same as above), or
- —$CONR^{23}R^{24}$ (wherein $R^{23}$ and $R^{24}$ are the same as above).

Preferable substituent group for the aromatic carbocyclic group which constitutes P2 ring is a substituent group as follows:
- a halogen atom,
- a C1-6 alkyl group (preferably a C1-4 alkyl group) which may be branched,
- a C1-6 alkoxy group (preferably a C1-4 alkoxy group) (wherein the C1-6 alkoxy group may be substituted with a hydroxyl group, a carbamoyl group or a C1-6 alkoxy group),
- a nitro group,
- a cyano group,
- a carboxyl group,
- a halo C1-6 alkoxy group (preferably a halo C1-4 alkoxy group),
- a halo C1-6 alkylthio group (preferably a halo C1-4 alkylthio group),
- a C1-6 alkoxycarbonyl group (preferably a C1-4 alkoxycarbonyl group),
- an acyl group,
- a C1-6 alkyl group substituted with 1 to 3 substituents selected a hydroxyl group, a halogen atom and a C1-6 alkoxy group (preferably a C1-4 alkoxy group),
- —$NR^{123}R^{124}$ (wherein $R^{123}$ and $R^{124}$ are the same as above),
- —$CONR^{23}R^{24}$ (wherein $R^{23}$ and $R^{24}$ are the same as above),
- a saturated 5-membered or 6-membered heterocyclic ring containing at least one nitrogen atom (preferably a piperidino group, a pyrrolidino group or a morpholino group which may be substituted with an oxo group) which may be substituted with a substituent group selected from a hydroxyl group, a C1-6 alkoxy group, a carboxyl group, a C1-6 alkoxycarbonyl group, a C1-6 alkyl group (wherein the C1-6 alkyl group may be substituted with a hydroxyl group or a C1-6 alkoxy group), a carbamoyl group, and an acyloxy group, or
- a piperidyloxy group which may be substituted with a C1-6 alkoxycarbonyl group.

[Substituent Group Particularly Preferable as a Substituent Group in P1 Ring]

Particularly preferable substituent group as a substituent group in P1 ring is a halogen atom (particularly a fluorine atom and a chlorine atom), a C1-4 alkyl group, a C1-4 alkyl group substituted with a hydroxyl group, a C1-4 alkyl group substituted with a C1-4 alkyl group, a C1-4 alkoxy group, an amino group, an amino group substituted with a C1-4 alkyl group or an amino group substituted with two identical or different C1-4 alkyl groups.

[Substituent Group for an Aromatic Carbocyclic Group in P2 Ring]
- a halogen atom,
- a C1-6 alkyl group (preferably a C1-4 alkyl group) which may be branched,
- a C1-6 alkoxy group (wherein the C1-6 alkoxy group may be substituted with a hydroxyl group, a carbamoyl group or a C1-6 alkoxy group),
- a nitro group,
- a cyano group,
- a carboxyl group,
- a halo C1-6 alkoxy group (preferably a halo C1-4 alkoxy group),
- a halo C1-6 alkylthio group (preferably a halo C1-4 alkylthio group),
- a C1-6 alkoxycarbonyl group (preferably a C1-4 alkoxycarbonyl group),
- an acyl group,
- a C1-6 alkyl group substituted with 1 to 3 substituents selected from a hydroxyl group, a halogen atom and a C1-6 alkoxy group (preferably a C1-4 alkoxy group),
- —$NR^{123}R^{124}$ (wherein $R^{123}$ and $R^{124}$ are the same as above),
- —$CONR^{23}R^{24}$ (wherein $R^{23}$ and $R^{24}$ are the same as above),
- a saturated 5-membered or 6-membered heterocyclic ring containing at least one nitrogen atom (preferably a piperidino group, a pyrrolidino group or a morpholino group which may be substituted with an oxo group) which may be substituted with a substituent group selected from a hydroxyl group, a C1-6 alkoxy group, a carboxyl group, a C1-6 alkoxycarbonyl group, a C1-6 alkyl group (wherein the C1-6 alkyl group may be substituted with a hydroxyl group or a C1-6 alkoxy group), a carbamoyl group, and an acyloxy group, or
- a piperidyloxy group which may be substituted with a C1-6 alkoxycarbonyl group.

[Particularly Preferable Substituent Group for an Aromatic Carbocyclic Group in P2 Ring]

Particularly preferable substituents for an aromatic carbocyclic group in P2 ring are the following substituents:
- a halogen atom,
- a C1-6 alkyl group (preferably C1-4 alkyl group) which may be branched,
- a C1-6 alkoxy group (wherein the C1-6 alkoxy group may be substituted with a hydroxyl group, a carbamoyl group or a C1-6 alkoxy group), a halo C1-6 alkyl group (preferably a halo C1-4 alkyl group, particularly preferably a trifluoromethyl group), a halo C1-6 alkoxy group (preferably a halo C1-4 alkoxy group), —NR$^{123}$R$^{124}$ (wherein R$^{123}$ and R$^{124}$ are the same as above, and particularly, it may be a di-C1-4 alkylamino group), a saturated 5-membered or 6-membered heterocyclic ring containing at least one nitrogen atom (preferably a piperidino group, a pyrrolidino group or a morpholino group which may be substituted with an oxo group), which may be substituted with a substituent group selected from a C1-6 alkoxy group, a C1-6 alkoxycarbonyl group, and a C1-6 alkyl group (wherein the C1-6 alkyl group may be substituted with a C1-6 alkoxy group), or a piperidyloxy group which may be substituted with a C1-6 alkoxycarbonyl group.

[Substituent Group Preferable for a Saturated Hydrocarbocyclic Group in P2 Ring]

a C1-6 alkyl group (wherein the C1-6 alkyl group may be substituted with a hydroxyl group or a C1-6 alkoxy group), a C1-6 alkoxy group (wherein the C1-6 alkoxy group may be substituted with a carboxyl group, a C1-6 alkoxycarbonyl group, a carbamoyl group), an aralkoxy group, —NR$^{123}$R$^{124}$ (wherein R$^{123}$ and R$^{124}$ are the same as above), an oxo group, a C3-6 cycloalkyl C1-6 alkoxy group, a —C3-6 cycloalkyloxy group or a saturated 5-membered or 6-membered heterocyclic ring containing at least one nitrogen atom (preferably a piperidino group, a pyrrolidino group, a morpholino group which may be substituted with an oxo group),

[Substituents Particularly Preferable for a Saturated Hydrocarbocyclic Group in P2 Ring]

a C1-6 alkyl group (particularly a C1-4 alkyl group), a C1-6 alkoxy group (particularly a C1-4 alkoxy group), or

[Substituents Preferable for a Saturated Heterocyclic Group in P2 Ring]

a C1-6 alkyl group (wherein the C1-6 alkyl group may be substituted with a hydroxyl group or a C1-6 alkoxy group), a C1-6 alkoxy group, a carbamoyl group or an acyl group.

[Substituents Preferable for an Aromatic Heterocyclic Group in P2 Ring]

a halogen atom, a C1-6 alkyl group or a halo C1-6 alkyl group.

A "pharmaceutically acceptable salt" may be any kind of salt as long as it forms a nontoxic salt with a compound represented by the above-mentioned general formula [1], and can be obtained by reacting it with, for example, an inorganic acid such as hydrochloric acid, sulfuric acid, phosphoric acid, or hydrobromic acid; an organic acid such as oxalic acid, malonic acid, citric acid, fumaric acid, lactic acid, malic acid, succinic acid, tartaric acid, acetic acid, trifluoroacetic acid, gluconic acid, ascorbic acid, methylsulfonic acid, or benzylsulfonic acid; an inorganic base such as sodium hydroxide, potassium hydroxide, calcium hydroxide, magnesium hydroxide, or ammonium hydroxide; an organic base such as methylamine, diethylamine, triethylamine, triethanolamine, ethylenediamine, tris(hydroxymethyl)methylamine, guanidine, choline, or cinchonine; or an amino acid such as lysine, arginine or alanine. A hydrated compound, hydrate and solvate of each compound are also included in the present invention.

In addition, various isomers exist for the compound represented by the above-mentioned general formula [1]. For example, E isomer and Z isomer exist as geometric isomers, and when an asymmetric carbon atom exists, enantiomers and diastereomers exist as stereoisomers based on these, and tautomers may exist. Therefore, all of these isomers and the mixtures thereof are included in the range of the present invention. In addition, the present invention also encompasses prodrug compounds of these compounds and metabolite compounds as equivalent compounds besides the compound represented by the above-mentioned general formula [1].

A "prodrug" is a derivative of the compound of the present invention having a group which may be decomposed chemically or metabolically and after administered to a living body, it goes through a chemical change to a compound which has an activity as a drug and exhibits original pharmacological effect, and complexes and salts not by a covalent bond are included.

A prodrug is used for improving absorption upon oral administration or targeting to a target site. Moieties to be modified for forming a prodrug include reactive functional groups such as a hydroxyl group, a carboxyl group, an amino group, and a thiol group in the compound of the present invention. Specific examples of the modifying group for a hydroxyl group include an acetyl group, a propionyl group, an isobutyryl group, a pivaloyl group, a benzoyl group, a 4-methylbenzoyl group, a dimethylcarbamoyl group, a sulfo group, etc. Specific examples of the modifying group for a carboxyl group include an ethyl group, a pivaloyloxymethyl group, a 1-(acetyloxy)ethyl group, a 1-(ethoxycarbonyloxy) ethyl group, a 1-(cyclohexyloxycarbonyloxy)ethyl group, a carboxylmethyl group, a methyl(5-methyl-2-oxo-1,3-dioxol-4-yl) group, a phenyl group, an o-tolyl group, etc. Specific examples of the modifying group for an amino group include a hexylcarbamoyl group, a 3-methylthio-1-(acetylamino) propylcarbonyl group, a 1-sulfo-1-(3-ethoxy-4-hydroxyphenyl)methyl group, a methyl(5-methyl-2-oxo-1,3-dioxol-4-yl) group, etc.

A "pharmaceutical composition" encompasses a combination drug with another drugs, etc., besides the so-called "composition" which comprises an active ingredient as a drug and a combinational agent, etc. Needless to say, the pharmaceutical composition of the present invention may be used in combination with any kind of other drugs as long as it is permitted in the medical scene. Therefore, it can also be said that this pharmaceutical composition is a pharmaceutical composition for the combined use with other drugs.

A "pain" means every type of pain condition no matter what the condition is (for example, no matter whether it is a dull pain or a sharp pain, chronic or acute, etc.), no matter which disease causes the pain (for example, no matter whether the pain is resulted from rheumatism, or the pain resulted from cancer, etc.). Therefore, the "pain" as used herein encompasses, in addition to the so-called "pain," acute pain, chronic pain, neuropathic pain, rheumatoid arthritis pain, neuralgia, neuropathy, hyperalgesia, migraine, joint pain, acute postherpetic neuralgia, postherpetic neuralgia, chronic postherpetic neuralgia, postoperative pain, cancer pain, inflammatory pain, interstitial cystitis, posttraumatic neuralgia, diabetic neuropathy, and neurodegenerative disease.

An "inhibitor of vanilloid receptor subtype 1 (VR1) activity" means a substance which inhibits the function of the vanilloid receptor subtype 1 as an ion channel, and eliminates or attenuates the activity. Specifically, it includes vanilloid receptor subtype 1 antagonist, etc. The vanilloid receptor subtype 1 antagonist means a substance which inhibits the effect of the agonist which acts on the vanilloid receptor subtype 1, thereby inhibiting the function of the vanilloid receptor subtype 1 as an ion channel. The inhibitor of the present invention has not to compete with the agonist but may also inhibit the function as a VR1 ion channel. Specifically, agonists which act on the vanilloid receptor subtype 1 include capsaicin, capsaicin derivatives, acid stimulation (proton), heat stimulation, etc., the inhibitor of vanilloid receptor subtype 1 (VR1) activity may be a substance which inhibits the $Ca^{2+}$ inflow into the cell caused by agonist stimulation of capsaicin, acid stimulation (proton) or heat stimulation.

The pharmaceutical composition of the present invention can be administered to human as well as other mammals (mouse, rat, hamster, rabbit, cat, dog, cow, horse, sheep, monkey, etc.). Therefore, the pharmaceutical composition of the present invention is useful also as a drug for animal not to mention for human.

When the compound of the present invention is used as a pharmaceutical preparation, it can be mixed with a pharmacologically acceptable carrier usually known in itself, excipient, diluent, extender, disintegrating agent, stabilizer, preservative, buffer, emulsifier, flavor, colorant, sweetener, thickner, corrigent, dissolution auxiliary agent, and other additive agents, specifically water, plant oil, alcohol such as ethanol or benzyl alcohol, carbohydrates such as polyethylene glycol, glycerol triacetate, gelatin, lactose and starch, magnesium stearate, talc, lanolin, vaseline, etc. to prepare a drug in the form such as tablet, pill, powder, granule, suppository, injection agent, eye-drops, liquid medicine, capsule agent, troche, aerosol agent, elixir agent, suspension, emulsion and syrup for systemic or local administration by oral or parenteral route.

Although the dosage varies depending on age, weight, condition, therapeutical effect, administration methods, etc., it is usually administered at a dose in the range of 0.01 mg to 1 g per dose, 1 time to several times per day, to adults, in the form of an oral preparate or injection preparation such as an intravenous injection, etc.

"Preventing" is the so-called prevention, and means, for example, suppressing the onset of neuralgia or chronicity of neuralgia prophylactically. As for pain, specifically included is prophylactically suppressing the onset of acute postherpetic neuralgia, onset of postherpetic neuralgia, transition to postherpetic neuralgia from acute herpetic pain, chronicity of postherpetic neuralgia, onset of postoperative pain, chronicity of postoperative pain, onset of symptoms of cancer pain, chronicity of cancer pain, onset of symptoms of inflammatory pain, onset of interstitial cystitis, chronicity of inflammatory pain, onset of posttraumatic neuralgia or chronicity of posttraumatic neuralgia.

A "drug comprising a combination" means a drug characterized in that it is a formulation containing a pharmaceutical composition or an agent to be combined, a drug characterized in that it is a kit comprising a pharmaceutical composition or an agent to be combined, a drug characterized in that a pharmaceutical composition or an agent to be combined is administered via the same or different administration routes, respectively.

The compound and pharmaceutical composition of the present invention can be used in combination with one or more other agents following a general method currently performed in the usual medical site. When used in combination, the drug to be used with may be administered simultaneously or separately with a time lag. Although there are various compounds which can be used in combination with the compound of the present invention, particularly preferred are an anti-virus agent, an antidepressant, an anticonvulsant, an antiarrhythmic drug, a local anesthetic, an anesthetic drug, a N-methyl-D-aspartate receptor antagonist, adrenal cortical steroid, a nerve block, a nonsteroidal antiinflammatory analgesic, narcotics, an antagonist analgesic, an $\alpha_2$-adrenaline receptor agonist, a stimulation analgesic method, drugs for external application, a calcium channel antagonist, and a potassium channel opener.

The anti-virus agent specifically includes vidarabine, acyclovir, ganciclovir, zidovudine, didanosine, amantadine, and idoxuridine, interferon, etc.

The antidepressant specifically includes amitriptyline, imipramine, clomipramine, trimipramine, lofepramine, dosulepin, desipramine, amoxapine, nortriptyline, fluoxetine, fluvoxamine, maprotiline, mianserin, setiptiline, trazodone, etc.

The anticonvulsant specifically includes gabapentin, pregabalin, phenobarbital, primidone, phenytoin, mephenytoin, nirvanol, ethotoin, trimethadione, ethosuximide, acetylpheneturide, carbamazepine, zonisamide, acetazolamide, diazepam, clonazepam, nitrazepam, diphenylhydantoin, valproic acid, baclofen, etc.

The antiarrhythmic drug specifically includes quinidine, disopyramide, procainamide, ajmaline, prajmalium, cibenzoline, lidocaine, mexiletine, aprindine, tonicaid, phenytoin, flecainide, pilcicainide, propafenone, propranolol, amiodarone, verapamil, bepridil, etc.

The local anesthetic specifically includes lidocaine, mexiletine, cocaine, procaine, bupivacaine, mepivacaine, prilocaine, tetracaine, dibucaine, ethyl aminobenzoate, etc.

The anesthetic drug specifically includes benzodiazepine, diazepam, midazolam, thiopental, thiamylal, propofol, baclofen, droperidol, sufentanil, etc. are mentioned. The N-methyl-D-aspartate receptor antagonist specifically includes ketamine, dextromethorphan, memantine, amantadine, etc. are included.

The adrenal cortical steroid specifically includes cortisol, cortisone, prednisolone, triamcinolone, dexamethasone, betamethasone, paramethasone, fluocinolone acetonide, fluocinonide, beclomethasone, fludrocortisone, etc.

The nerve block specifically includes stellate ganglion block, epidural ganglion block, brachial plexus ganglion block, nerve root block, thoracic/lumbar sympathetic ganglion, trigger point block, subarachnoid ganglion block, trigeminal nerve block, sympathetic nerve block, local infiltration block, peripheral nerve block, etc.

The nonsteroidal antiinflammatory analgesic specifically includes celecoxib, rofecoxib, etodolac, meloxicam, nimesulid, sodium diclofenac, mefenamic acid, zaltoprofen, sodium loxoprofen, sulindac, nabumetone, diflunisal, piroxicam, ibuprofen, naproxen, fenoprofen, acetylsalicylic acid, tolmetin, indomethacin, flurbiprofen, oxaprozin, ketoprofen, mofezolac, acetaminophen, ketorolac, zomepirac, nitroaspirin, tiaprofen, ampiroxicam, tiaramide, epirizole, etc.

The narcotics specifically include morphine, fentanyl, oxycodone, methadon, codeine, cocaine, pethidine, opium, ipecac, etc.

The antagonist analgesic specifically includes pentagyn, buprenorphine, nalorphine, cyclazocine, butorphanol, etc.

The $\alpha_2$-adrenaline receptor agonist specifically includes clonidine, dexmedetomidine, tizanidine, guanfacine, guanabenz, etc.

The medicine for external application specifically includes capsaicin cream etc.

The stimulation analgesic method specifically includes acupuncture, a percutaneous electricity needle stimulation therapy, a percutaneous electricity nerve stimulation therapy, a silver spike point (SSP) treatment, a peripheral nerve stimulus, a spine electricity stimulus, an electric spasm treatment, laser surgery, a low-frequency therapy, etc.

In addition, the compound of the present invention can be used following the general method usually performed in the art by administration after performing a surgical operation to prevent or treat pain. Although various surgical operations can be performed in combination with the compound of the present invention, cicatrectomy, nerve freezing, peripheral nerve excision, spinal dorsal root excision, sympathectomy, spinal cord dorsal root entry zone destruction, cordotomy, and frontal lobe excision are particularly preferable.

Although application of the compound of the present invention has been described mainly as a use for preventing or treating pain, the compound of the present invention can be applied to the conditions in which C fibers participates, for example, pruritus, allergic and allergic rhinitis, overactive bladder type frequent urination and urinary incontinence, apoplexy, irritable bowel syndrome, respiratory ailment such as asthma and a chronic obstructive pulmonary disease, dermatitis, mucositis, stomach and duodenal ulcer, inflammatory bowel disease, etc.

Next, a preparation method of the compound represented by the general formula [1] of the present invention is described specifically but, needless to say, the present invention is not limited to these preparation methods. Therefore, the compound of the present invention may be synthesized according to the following manufacture methods A, B or C, but it can be prepared according to the below-mentioned examples, or referring to these processes. In preparation of the compound of the present invention, the order of reaction operation can be changed suitably. It can be performed starting from the reaction step or substitution part considered to be rational. For example, the P2 ring may be introduced before the P1 ring is introduced, and this order may be reversed. As for the formation of the hetero ring condensed to the benzene ring (of benzamide group), a closed ring reaction may be performed to form this hetero ring before introducing the P1 ring and/or P2 ring or alternatively, a closed ring reaction may be performed to form this hetero ring after introducing the P1 ring and/or P2 ring. Protection and deprotection may be suitably conducted when there is a reactant functional group. In order to enhance development of the reaction, reagents other than those illustrated can be used suitably.

The following production process flow is an example of the typical preparation method, but preparation of the compound of the present invention is not particularly limited to the following method. Each compound obtained at each step can be isolated and purified by a usual method, but depending on the case the compound can be used in the next step without being isolated and purified.

1. Preparation Method A;

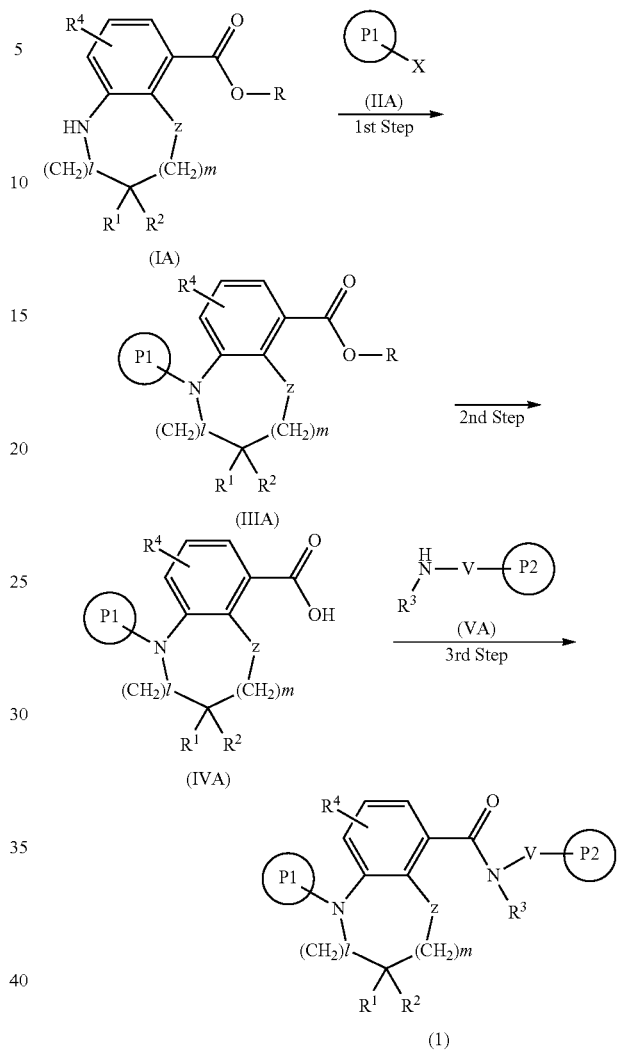

(wherein, R represents a carboxyl protecting group (the carboxyl protecting group here includes, for example, a methyl group, an ethyl group, a propyl group, a tert-butyl group, a benzyl group, a paramethoxy benzyl group, etc.), and forms an ester which is easily led to a carboxylic acid by hydrolysis or catalytic hydrogenation reaction. X represents a halogen atom such as chloro and bromo or a sulfonyloxy group such as a 3-nitrobenzene sulfonyloxy group, a p-toluenesulfonyloxy group, a benzene sulfonyloxy group, a p-bromobenzenesulfonyloxy group, a methanesulfonyloxy group or a trifluoromethanesulfonyloxy group, and each other symbol is the same as above.)

First Step

This is the reaction for obtaining a compound (IIIA) by the palladium catalyzed Buchwald/Hartwig type amination reaction from a compound (IA) and a compound (IIA).

The compound (IIIA) can be obtained by reacting the (IA) with the compound (IIA) in toluene, 1,4-dioxane, tetrahydrofuran or the like or a mixed solvent of these, using a palladium catalyst such as a mixture of palladium acetate and 2,2'-bis(diphenylphosphino)-1,1'-binaphthyl, bis(diphenylphosphino)ferrocene palladium chloride (II) or tris(dibenzylideneacetone)dipalladium together with a base such as sodium carbonate, tripotassium phosphate (K₃PO₄), potassium carbonate, cesium carbonate, sodium bicarbonate, potassium bicarbonate or potassium tert butoxide, at a temperature of 20° C. to reflux temperature, preferably 60° C. to reflux temperature for 5 hours to 96 hours preferably for 8 hours to 48 hours.

When the P1 ring is an aromatic hetero ring such as oxazole, thiazole or 1,3,4-thiadiazole, the compound (IIA) is not used and the reaction builds up the aromatic hetero ring by a known method and proceeds to the Second Step.

For example, when the P1 ring is 5-methyloxazole, the compound (IA) is reacted with thiophosgene or 1,1-thiocarbonyldiimidazole etc., in tetrahydrofuran, ethyl acetate, toluene, water or a mixed solvent of these, in the presence or absence of a base such as triethylamine, sodium bicarbonate, potassium carbonate or pyridine to form an isothiocyanate compound which is then allowed to react with 1-azidoacetone and triphenylphosphine in a solvent such as dichloromethane, dichloroethane and chloroform at a temperature of –20° C. to reflux temperature, preferably 0° C. to 50° C. for 0.5 hour to 24 hours, preferably 2 hours to 8 hours to obtain the compound (IIIA).

When the P1 ring is 4-methylthiazole, the compound (IA) is reacted with thiophosgene or 1,1-thiocarbonyldiimidazole, etc., in tetrahydrofuran, ethyl acetate, toluene, water or a mixed solvent of these, in the presence or absence of a base such as triethylamine, sodium bicarbonate, potassium carbonate or pyridine to form an isothiocyanate compound which is then allowed to react with ammonia water and the like to obtain a thiourea compound, and this compound is allowed to react with 1-chloroacetone, 1-bromoacetone, etc. in a solvent such as methanol, ethanol, tetrahydrofuran or acetone at a temperature of –20° C. to reflux temperature, preferably 0° C. to reflux temperature for 0.5 hour to 24 hours, preferably 1 hour to 12 hours to obtain the compound (IIIA).

Second Step

This is a step to remove R from the compound (IIIA) and obtain a carboxylic acid (IVA).

For example, when R is a methyl group, ethyl group, propyl group, etc., the compound (IIIA) can be hydrolyzed in water, methanol, ethanol, propanol, tetrahydrofuran, or a mixed solvent of these using a base such as sodium hydroxide, potassium hydroxide, lithium hydroxide, potassium carbonate or sodium carbonate, at a temperature of –20° C. to reflux temperature, preferably 20° C. to reflux temperature for 0.5 hour to 24 hours, preferably 0.5 hour to 8 hours to obtain the compound (IVA).

For example, when R is a tert-butyl group, the compound (IVA) can be obtained by the reaction of the compound (IIIA) without a solvent or in water, methanol, ethanol, propanol, tetrahydrofuran or a mixed solvent of these using an acid such as hydrochloric acid or trifluoroacetic acid at a temperature of 0° C. to reflux temperature, preferably 0° C. to 50° C. for 0.5 hour to 24 hours, preferably 0.5 hour to 8 hours.

When R is a benzyl group, paramethoxybenzyl group, etc., the compound (IVA) can be obtained by the reaction in methanol, ethanol, propanol, tetrahydrofuran or a mixed solvent of these in the presence of palladium carbon catalyst, etc. using hydrogen or ammonium formate at a temperature of about 0° C. to reflux temperature, preferably about 20° C. to reflux temperature for 0.5 hour to 96 hours, preferably 1 hour to 48 hours.

Third Step

This is a reaction to obtain a compound (1) by condensation reaction of a compound (IVA) and a compound (VA).

The condensation reaction can be performed using a condensing agent, or via an acid chloride etc.

When a direct condensation reaction is performed using a condensing agent, a compound (IVA) is reacted with a compound (VA) in N,N-dimethylformamide, methylene chloride, chloroform etc. or a mixed solvent of these using a condensing agent such as dicyclohexylcarbodiimide or 1-ethyl-3-(3-dimethylaminopropyl)carbodiimide at a temperature of –20° C. to reflux temperature, preferably about 0° C. to 50° C. for 1 hour to 48 hours, preferably about 1 hour to 24 hours. In this case, it is preferable to add additives such as hydroxybenzotriazole or N-hydroxysuccinic acid imide.

When the process goes via an acid chloride, the compound (IVA) is reacted with thionylchloride, oxalyl chloride, etc. in chloroform, methylene chloride, tetrahydrofuran, etc. or a mixed solvent of these to obtain an acid chloride of (IVA) and this is reacted with a compound (VA) in toluene, chloroform, tetrahydrofuran or a mixed solvent of these in the presence of a base such as triethylamine or pyridine at a temperature of –20° C. to reflux temperature, preferably about 0° C. to 40° C. for 0.5 hour to 24 hours, preferably about 0.5 hour to 12 hours to obtain the compound (1).

2. Preparation Method B;

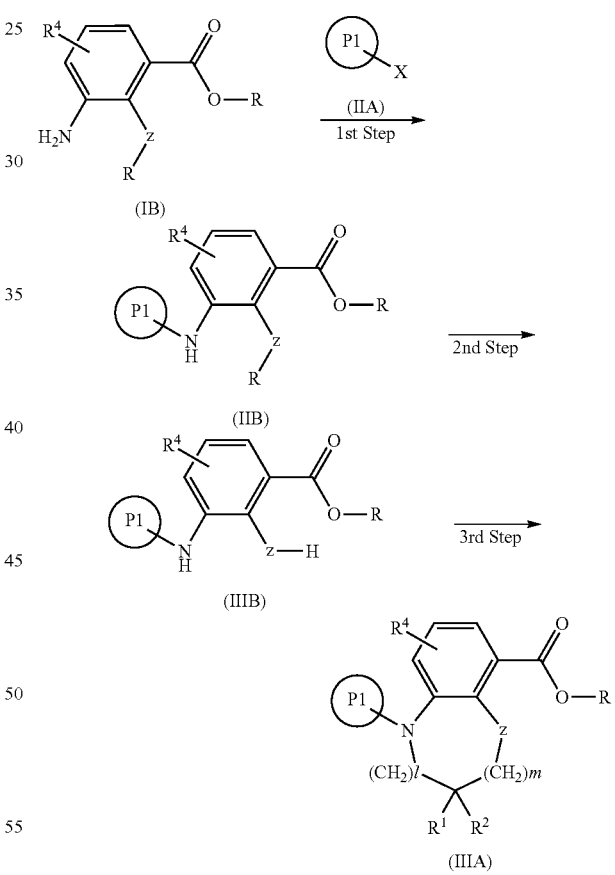

This is an alternative method of preparing a compound (IIIA) in which Z is an oxygen atom in the Preparation method A.

(wherein, Z is an oxygen atom, R is a C1-6 alkyl group and forms an ester which is easily led to a carboxylic acid by hydrolysis or catalytic hydrogenation reaction. R' represents a protecting group of a phenolic hydroxyl group easily removable by hydrolysis or catalytic hydrogenation reaction. Each other symbol is the same as above.)

First Step

This is the reaction for obtaining a compound (IIB) by the palladium catalyzed Buchwald/Hartwig type amination reaction from a compound (IB) and a compound (IIA).

The compound (IIB) can be obtained by reacting the (IB) with the compound (IIA) in toluene, 1,4-dioxane, tetrahydrofuran or the like or a mixed solvent of these, using a palladium catalyst such as a mixture of palladium acetate and 2,2'-bis(diphenylphosphino)-1,1'-binaphthyl, bis(diphenylphosphino)ferrocene palladium chloride (II) or tris(dibenzylideneacetone)dipalladium together with a base such as sodium carbonate, tripotassium phosphate ($K_3PO_4$), potassium carbonate, cesium carbonate, sodium bicarbonate, potassium bicarbonate or potassium tert butoxide, at a temperature of 20° C. to reflux temperature, preferably 60° C. to reflux temperature for 5 hours to 96 hours preferably for 8 hours to 48 hours.

When P1 ring is an aromatic hetero ring such as oxazole, thiazole or 1,3,4-thiadiazole, the compound (IIA) is not used and the reaction builds up the aromatic hetero ring by a known method and proceeds to the Second Step.

For example, when the P1 ring is 5-methyloxazole, the compound (IB) is reacted with thiophosgene or 1,1-thiocarbonyldiimidazole etc., in tetrahydrofuran, ethyl acetate, toluene, water or a mixed solvent of these, in the presence or absence of a base such as triethylamine, sodium bicarbonate, potassium carbonate or pyridine to form an isothiocyanate compound which is then allowed to react with 1-azidoacetone and triphenylphosphine in a solvent such as dichloromethane, dichloroethane or chloroform at a temperature of −20° C. to reflux temperature, preferably 0° C. to 50° C. for 0.5 hour to 24 hours, preferably 2 hours to 8 hours to obtain the compound (IIB).

When the P1 ring is 4-methylthiazole, the compound (IB) is reacted with thiophosgene or 1,1-thiocarbonyldiimidazole etc., in tetrahydrofuran, ethyl acetate, toluene, water or a mixed solvent of these, in the presence or absence of a base such as triethylamine, sodium bicarbonate, potassium carbonate or pyridine to form an isothiocyanate compound which is then allowed to react with ammonia water or the like to obtain a thiourea compound, and this compound is allowed to react with 1-chloroacetone, 1-bromoacetone, etc. in a solvent such as methanol, ethanol, tetrahydrofuran or acetone at a temperature of −20° C. to reflux temperature, preferably 0° C. to reflux temperature for 0.5 hour to 24 hours, preferably 1 hour to 12 hours to obtain the compound (IIB).

Second Step

This is a step to remove R' which is a protecting group of the phenolic hydroxyl group of the compound (IIB).

For example, when R' is a methoxymethyl group, a tetrahydropyranyl group, etc., the compound (IIIB) can be obtained by reacting the compound (IIB) without solvent or in water, methanol, ethanol, isopropanol, tetrahydrofuran, chloroform or a mixed solvent of these using an acid such as sulfuric acid, hydrochloric acid or trifluoroacetic acid at a temperature of 0° C. to reflux temperature, preferably 0° C. to 50° C. for 0.5 hour to 24 hours, preferably 0.5 hour to 8 hours.

Third Step

This is a step to obtain a cyclic compound (IIIA) from the compound (IIIB).

For example, when l is 1, R1 and R2 are hydrogen atoms and m is 0, the compound (IIIB) is reacted with a dihalo reagent such as 1,2-dibromoethane, 1,2-dichloroethane or 1-bromo-2-chloroethane, in chloroform, tetrahydrofuran, N,N-dimethylformamide, dimethylsulfoxide, ethyl acetate, methanol, water or a mixed solvent of these in the presence of a base such as sodium carbonate, potassium carbonate, sodium hydroxide, potassium hydroxide or triethylamine at a temperature of 0° C. to reflux temperature, preferably 0° C. to 60° C. for 0.5 hour to 24 hours to obtain a compound (IIIA). Alternatively, after making it react with a haloacetic acid chloride such as acetyl chloride, and forming a cyclic lactam, the compound (IIIA) can also obtained by performing a reduction reaction in tetrahydrofuran using a borane-tetrahydrofuran complex reagent etc at 0° C. to reflux temperature for 0.5 hour to 8 hours.

For example, when l is 1; R1 is a hydroxymethyl group; R2 is a hydrogen atom and m is 0, the similar reaction as a dihalo reagent can be performed using glycidyl chloride, glycidyl tosylate or glycidyl nosylate to obtain a compound (IIIA). In this case, the produced hydroxyl group may be subjected to a step to introduce a widely used protecting group such as an acetyl group, a methoxymethyl group, a tetrahydropyranyl group or a benzyl group, and used in the following steps, and can be suitably deprotected to the compound (1).

3. Preparation Method C;

This is an alternative method of preparing a compound (1) in which Z is an oxygen atom in the Preparation method A.

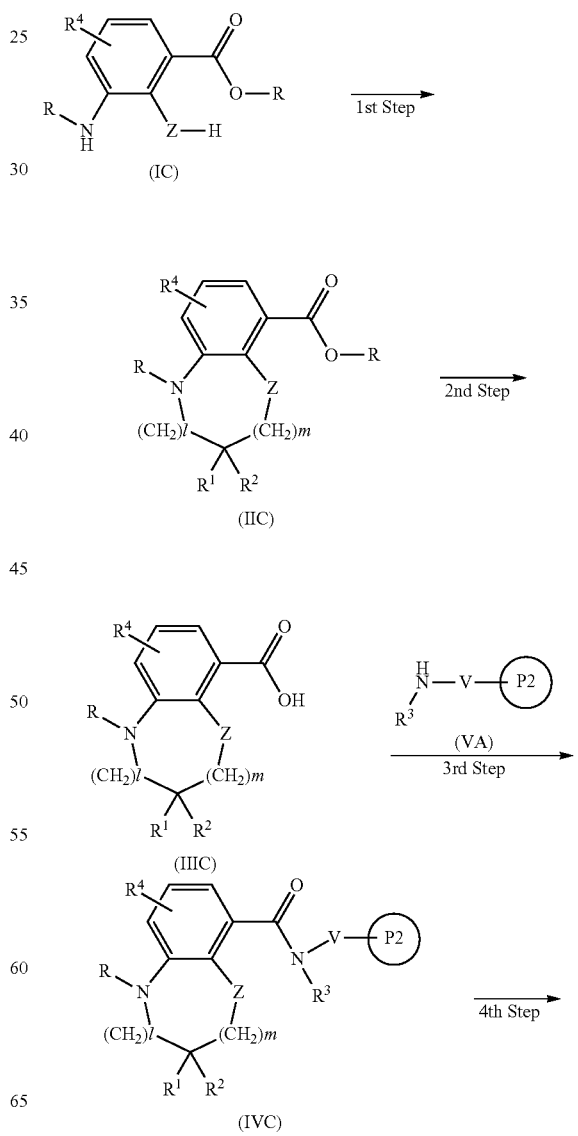

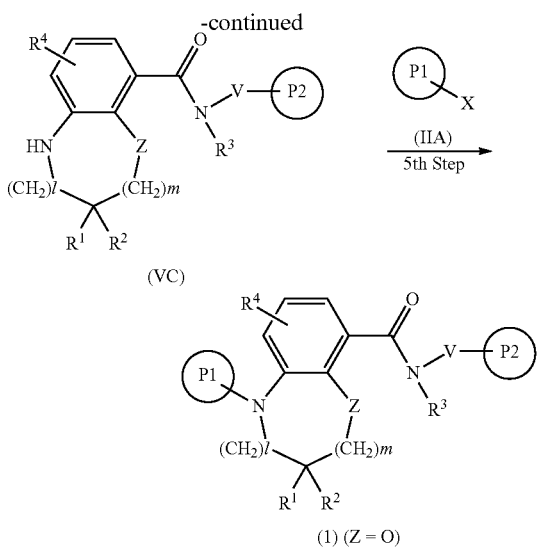

(wherein, R is a C1-6 alkyl group and forms an ester which is easily led to a carboxylic acid by hydrolysis or catalytic hydrogenation reaction. R" represents a protecting group of an amino group easily re movable by hydrolysis or catalytic hydrogenation reaction. Each other symbol is the same as above.)

First Step

This is a step to obtain a cyclic compound (IIC) from a compound (IC).

For example, when l is 1, R1 and R2 are hydrogen atoms, and m is 0, the compounds (IC) is reacted with a dihalo reagent such as 1,2-dibromoethane, 1,2-dichloroethane or 1-bromo-2-chloroethane in chloroform, tetrahydrofuran, N,N-dimethylformamide, dimethylsulfoxide, ethyl acetate, methanol, water or a mixed solvent of these in the presence of a base such as s odium carbonate, potassium carbonate, sodium hydroxide, potassium hydroxide or triethylamine at a temperature of 0° C. to reflux temperature for 0.5 hour to 8 hours to obtain a compound (IIC).

For example, when l is 1, R1 is a hydroxymethyl group, R2 is a hydrogen atom, and m is 0, the compound (IIC) can be obtained using the compound (IC) along with glycidyl chloride, glycidyl tosylate or glycidyl nosylate in the similar reaction as with a dihalo reagent. In this case, the produced hydroxyl group may be subjected to a step to introduce a widely used protection group such as an acetyl group, a methoxymethyl group, a tetrahydropyranyl group or a benzyl group, and used in the following steps, and can be suitably deprotected to the compound (1).

Second Step

This is a step to remove R of the compound (IIC) to obtain a carboxylic acid compound (IIIC).

For example, when R is a methyl group, ethyl group, propyl group, etc., the compound (IIIC) can be obtained by hydrolyzing the compound (IIC) in water, methanol, ethanol, propanol, tetrahydrofuran, etc. or a mixed solvent of these using a base such as sodium hydroxide, potassium hydroxide, lithium hydroxide, potassium carbonate and sodium carbonate or an aqueous solution of these at a temperature of −20° C. to reflux temperature preferably 20° C. to reflux temperature for 0.5 hour to 24 hours, preferably 0.5 hour to 8 hours.

For example, when R is a tert-butyl group, the compound (IIIC) can be obtained by reacting the compound (IIC) without solvent or in water, methanol, ethanol, propanol, or tetrahydrofuran, etc. or a mixed solvent of these using an acid such as hydrochloric acid or trifluoroacetic acid, at a temperature of 0° C. to reflux temperature preferably 0° C. to 50° C. for 0.5 hour to 24 hours, preferably 0.5 hour to 8 hours.

When R is a benzyl or paramethoxybenzyl group, etc., the compound (IIIC) can be obtained by reacting in methanol, ethanol, propanol, tetrahydrofuran, etc. or a mixed solvent of these using hydrogen or ammonium formate in the presence of a palladium carbon catalyst, etc. at a temperature of about 0° C. to reflux temperature, preferably about 20° C. to 50° C. for 0.5 hour to 96 hours, preferably 1 hour to 48 hours.

Third Step

This is a reaction which obtains a compound (IVC) by the condensation reaction of a compound (IIIC) and a compound (VA) The condensation reaction can be performed either by a method using a condensing agent or by a method via an acid chloride, etc.

When a direct condensation reaction using a condensing agent is performed, the compound (IVC) can be obtained by reacting the compound (IIIC) with the compound (VA) in N,N-dimethylformamide, methylene chloride, chloroform, etc. or a mixed solvent of these using a condensing agent such as dicyclohexylcarbodiimide or 1-ethyl-3-(3-dimethylaminopropyl)-carbodiimide at a temperature of −20° C. to reflux temperature, preferably about 0° C. to 50° C. for 1 hour to 48 hours, preferably 1 hour to 24 hours. In this case, it is preferable to add additives such as hydroxybenzotriazole and N-hydroxysuccinic acid imide.

When a reaction via an acid chloride is performed, the compound (IIIC) is reacted with thionyl chloride, oxalyl chloride etc. in chloroform, methylene chloride, tetrahydrofuran, etc. or a mixed solvent of these to obtain an acid chloride of (IIIC), and this compound is reacted with the compound (VA) in toluene, chloroform, or tetrahydrofuran, etc. or a mixed solvent of these in the presence of a base such as triethylamine or pyridine at a temperature of −20° C. to reflux temperature, preferably about 0° C. to 40° C. for 0.5 hour to 24 hours, preferably 0.5 hour to 12 hours and thereby the compound (IVC) can be obtained.

Fourth Step

This is a step to remove the amino protecting group R" of compound (IVC) and obtain a compound (VC).

For example, when R' is an acetyl group or a formyl group, the compound (VC) can be obtained by reacting the compound (IVC) in tetrahydrofuran, methanol, ethanol, isopropanol, water or a mixed solvent of these in the presence of a base such as sodium hydroxide, potassium hydroxide, lithium hydroxide or sodium methoxide or in the presence of an acid such as sulfuric acid, hydrochloric acid or trifluoroacetic acid at a temperature of −20° C. to reflux temperature, preferably about 0° C. to reflux temperature for 0.5 hour to 24 hours, preferably 0.5 hour to 8 hours.

For example, when R" is a tert-butoxycarbonyl group, the compound (VC) can be obtained by reacting the compound (IVC) without solvent or in tetrahydrofuran, methanol, ethanol, isopropanol, chloroform, water or a mixed solvent of these in the presence of an acid such as hydrochloric acid or trifluoroacetic acid at a temperature of 0° C. to reflux temperature, preferably about 0° C. to 50° C. for 0.5 hour to 24 hours, preferably 0.5 hour to 8 hours.

When R' is a benzyloxycarbonyl group, a benzyl group, etc., the compound (VC) can be obtained by reacting the compound (IVC) in methanol, ethanol, propanol, tetrahydrofuran, etc. or a mixed solvent of these using hydrogen or ammonium formate in the presence of a palladium carbon catalyst, etc. at a temperature of about 0° C. to reflux temperature, preferably about 20° C. to 50° C. for 0.5 hour to 96 hours, preferably 1 hour to 48 hours.

Fifth Step

This is a reaction for obtaining a compound (1) by the palladium catalyzed Buchwald/Hartwig type amination reaction from a compound (VC) and a compound (IIA).

The compound (1) can be obtained by reacting the compound (VC) with the compound (IIA) in toluene, 1,4-dioxane, tetrahydrofuran or the like or a mixed solvent of these, using a palladium catalyst such as a mixture of palladium acetate and 2,2'-bis(diphenylphosphino)-1,1'-binaphthyl, bis(diphenylphosphino) ferrocene palladium chloride (II) or tris(dibenzylideneacetone)dipalladium together with a base such as sodium carbonate, tripotassium phosphate ($K_3PO_4$), potassium carbonate, cesium carbonate, sodium bicarbonate, potassium bicarbonate, or potassium tert-butoxide, at a temperature of 20° C. to reflux temperature, preferably 60° C. to reflux temperature for 5 hours to 96 hours preferably for 8 hours to 48 hours.

When the P1 ring is an aromatic hetero ring such as oxazole, thiazole or 1,3,4-thiadiazole, the compound (IIA) is not used and the reaction builds up the aromatic hetero ring by a known method and proceeds to the Second Step.

When the P1 ring is 5-methyloxazole, the compound (VC) is reacted with thiophosgene or 1,1-thiocarbonyldiimidazole etc., in tetrahydrofuran, ethyl acetate, toluene, water, etc. or a mixed solvent of these in the presence or absence of a base such as triethylamine, sodium bicarbonate, potassium carbonate or pyridine to form an isothiocyanate compound which is then allowed to react with 1-azidoacetone and triphenylphosphine in a solvent such as dichloromethane, dichloroethane or chloroform at a temperature of −20° C. to reflux temperature, preferably 0° C. to 50° C. for 0.5 hour to 24 hours, preferably 2 hours to 8 hours to obtain the compound (1).

When the P1 ring is 4-methylthiazole, the compound (VC) is reacted with thiophosgene or 1,1-thiocarbonyldiimidazole etc., in tetrahydrofuran, ethyl acetate, toluene, water, etc. or a mixed solvent of these in the presence or absence of a base such as triethylamine, sodium bicarbonate, potassium carbonate or pyridine to form an isothiocyanate compound which is then allowed to react with ammonia water and the like to obtain a thiourea compound, and this compound is allowed to react with 1-chloroacetone, 1-bromoacetone, etc. in a solvent such as methanol, ethanol, tetrahydrofuran or acetone at a temperature of −20° C. to reflux temperature, preferably 0° C. to reflux temperature for 0.5 hour to 24 hours, preferably 1 hour to 12 hours to obtain the compound (1).

Example 1

Example 1-001

Production of N-(4-tert-butylphenyl)-4-(3-chloropyridin-2-yl)-3,4-dihydro-2H-benzo[1,4]oxazine-8-carboxamide First Step Production of methyl 3-nitrosalicylate:

3-Nitrosalycylic acid (7.5 g) was dissolved in methanol (75 ml), concentrated sulfuric acid (2 ml) was added, and the mixture was refluxed for 24 hours. Reaction mixture was left cool to and the precipitated pale yellowish solid was collected by filtration, washed with water and dried in vacuo to obtain the title compound (7.19 g).

Second Step

Production of methyl 3-aminosalicylate:

Methyl 3-nitrosalicylate (7.19 g) obtained in the First Step was dissolved in tetrahydrofuran (100 ml) and ethyl acetate (50 ml), 5% palladium-carbon (water content 50%) (0.70 g) was added, and the mixture was stirred at room temperature for 2 hours under hydrogen atmosphere. Palladium-carbon was filtered off from the reaction suspension, the filtrate was concentrated, and n-hexane was added. The precipitated white solid was filtered off and dried to obtain the title compound (5.59 g).

Third Step

Production of methyl 3-chloroacetylaminosalicylate:

Methyl 3-aminosalicylate (5.59 g) obtained in the Second Step was dissolved in chloroform (100 ml), aqueous saturated sodium hydrogencarbonate (50 ml) was added, further chloroacetyl chloride (3.2 ml) was added with vigorous stirring under ice-cooling, then the mixture was stirred for 1.5 hours under ice-cooling. The reaction mixture was partitioned, and the chloroform layer was dried over anhydrous magnesium sulfate and concentrated to obtain the title compound (white solid 8.07 g).

Fourth Step

Production of methyl-3,4-dihydro-3-oxo-2H-benzo[1,4]oxazine-8-carboxylate:

Methyl 3-chloroacetylaminosalicylate (8.07 g) obtained in the Third Step was dissolved in N,N-dimethylformamide (80 ml), potassium carbonate (9.15 g) was added, and the mixture was stirred at 80° C. for 1 hour. The reaction suspension was concentrated, and white solid precipitate obtained by adding water was filtered, washed with water and dried to obtain the title compound (6.37 g).

Fifth Step

Production of methyl 3,4-dihydro-2H-benzo[1,4]oxazine-8-carboxylate:

Methyl-3,4-dihydro-3-oxo-2H-benzo[1,4]oxazine-8-carboxylate (2.07 g) obtained in the Fourth Step was suspended in tetrahydrofuran (20 ml), 1 M solution of borane-tetrahydrofuran complex in tetrahydrofuran (12 ml) was added under ice-cooling with stirring, and the mixture was refluxed for 1 hour in a stream of argon. The reaction mixture was cooled on ice, water (10 ml) and acetone (5 ml) were added in this order to terminate the reaction, further 6 N hydrochloric acid (10 ml) was added, and the mixture was stirred for 1 hour. The reaction mixture was adjusted to pH 8-9 by adding 4 N sodium hydroxide and aqueous saturated sodium hydrogencarbonate, and extracted with ethyl acetate. The ethyl acetate layer was washed with water and saturated sodium chloride solution in this order, dried over anhydrous sodium sulfate and concentrated to obtain the title compound (1.82 g) as colorless oil.

Sixth Step

Production of methyl 4-(3-chloropyridin-2-yl)-3,4-dihydro-2H-benzo[1,4]oxazine-8-carboxylate:

Methyl 3,4-dihydro-2H-benzo[1,4]oxazine-8-carboxylate (0.58 g) obtained in the Fifth Step was dissolved in toluene (7.5 ml), 2,3-dichloropyridine (0.44 g), tris(dibenzylideneacetone)dipalladium (69 mg), 2,2'-bis(diphenylphosphino)-1,1'-binaphthyl (93 mg) and cesium carbonate (1.47 g) were added in this order, and the mixture was stirred at 80° C. for 24 hours. 2,3-Dichloropyridine (0.44 g), tris(dibenzylideneacetone)dipalladium (69 mg) and 2,2'-bis(diphenylphosphino)-1,1'-binaphthyl (93 mg) were added again and stirring was further continued for 15 hours under excessive heating. After cooling, the reaction mixture was partitioned between the ethyl acetate and water. The obtained ethyl acetate layer was washed with saturated sodium chloride solution, dried over anhydrous sodium sulfate and then concentrated. The thus obtained residue was purified by the use of silica gel chromatography (hexane-tetrahydrofuran=3:1) to obtain the orange colored oily compound in the title (0.53 g).

Seventh Step

Production of 4-(3-chloropyridin-2-yl)-3,4-dihydro-2H-benzo[1,4]oxazine-8-carboxylic acid:

Methyl 4-(3-chloropyridin-2-yl)-3,4-dihydro-2H-benzo[1,4]oxazine-8-carboxylate (0.53 g) obtained in the Sixth Step was dissolved in methanol (5 ml), 4 M sodium hydroxide solution (1 ml) was added, and the mixture was stirred at 60° C. for 1 hour under heating. After cooling, the reaction mixture was neutralized by adding 1 M hydrochloric acid (4 ml), water (20 ml) was added, the precipitated solid was filtered off and dried to obtain the pale orange solid compound in the title (0.43 g).

Eighth Step

Production of N-(4-tert-butylphenyl)-4-(3-chloropyridin-2-yl)-3,4-dihydro-2H-benzo[1,4]oxazine-8-carboxamide:

4-(3-chloropyridin-2-yl)-3,4-dihydro-2H-benzo[1,4]oxazine-8-carboxylic acid (0.43 g) obtained in the Seventh Step was dissolved in N,N-dimethylformamide (5 ml), 4-tert-butylaniline (0.24 g), 1-hydroxybenzotriazole (0.25 g) and 1-ethyl-3-(3-dimethylaminopropyl)-carbodiimide hydrochloride (0.31 g) were added in this order, and the mixture was stirred at room temperature for 1 hour. After adding water and saturated sodium hydrogencarbonate solution, the mixture was extracted with ethyl acetate. The ethyl acetate layer was washed with saturated sodium chloride solution, dried over anhydrous sodium sulfate and then concentrated. The thus obtained residue was purified by the use of silica gel chromatography (hexane-ethyl acetate=3:2) to obtain the white amorphous solid compound in the title (0.42 g).

$^1$H-NMR 400 MHz (CDCl$_3$) δ=1.33 (s, 9H), 3.88-3.97 (m, 2H), 4.57-4.65 (m, 2H), 6.66 (dd, J=8.00, 1.28 Hz, 1H), 6.90 (t, J=7.88 Hz, 1H), 7.11 (dd, J=7.88, 4.87 Hz, 1H), 7.38 (d, J=8.58 Hz, II H), 7.60 (d, J=8.58 Hz, 2H), 7.77-7.82 (m, 2H), 8.37 (dd, J=4.75, 1.28 Hz, 1H), 9.57 (s, 1H).

Example 1-002

Production of 8-(4-tert-butylphenyl)carbamoyl-4-(3-chloropyridin-2-yl)-3,4-dihydro-2H-benzo[1,4]oxazine-2-carboxylic acid First Step Production of N-(4-tert-butylphenyl)-3-nitro-2-hydroxybenzamide:

3-Nitrosalysilic acid (10.0 g) was dissolved in methylene chloride (100 ml), oxalyl chloride (6.2 ml) and N,N-dimethylformamide (0.1 ml) were added, and the mixture was stirred at room temperature for 2 hours. The reaction mixture was concentrated, and the concentrate was added to a solution of 4-tert-butylaniline (5.2 g) and triethylamine (5.1 ml) in acetonitrile (100 ml), then the mixture was stirred at room temperature for 3 hours. After concentrating the reaction mixture, the reaction mixture was partitioned between chloroform and water. The obtained chloroform layer was washed with water, dried over anhydrous sodium sulfate and then concentrated. The thus obtained residue was purified by the use of silica gel chromatography (hexane-ethyl acetate=1:1) to obtain the title compound (3.0 g).

Second Step

Production of 3-amino-N-(4-tert-butylphenyl)-2-hydroxybenzamide:

N-(4-tert-butylphenyl)-3-nitro-2-hydroxybenzamide (3.0 g) obtained in the First Step was dissolved in methanol (100 ml), iron (III) chloride hexahydrate (0.27 g) and active charcoal (0.5 g) were added, and the mixture was stirred at 80° C., and hydrazine hydrate (2.6 ml) was added dropwise. After stirring under heating for 1 hour, the reaction mixture was cooled and insoluble substance was filtered off, then the solvent was evaporated in vacuo. The residue was partitioned between ethyl acetate and water. The obtained ethyl acetate layer was washed with saturated sodium chloride solution, dried over anhydrous magnesium sulfate and then concentrated. The thus obtained residue was dissolved in ethyl acetate, n-hexane was added, the precipitated solid was filtered off and dried to obtain the title compound (1.61 g).

Third Step

Production of ethyl 8-(4-tert-butylphenyl)carbamoyl-3,4-dihydro-2H-benzo[1,4]oxazine-2-carboxylate:

3-Amino-N-(4-tert-butylphenyl)-2-hydroxybenzamide (1.6 g) obtained in the Second Step was dissolved in acetone (20 ml), ethyl 2,3-dibromopropionate (2.2 g) and potassium carbonate (2.3 g) were added, and the mixture was stirred at room temperature for 16 hours. The reaction mixture was concentrated, water was added, and the precipitated solid substance was filtered off. The thus obtained solid substance was suspended in and washed with a mixed solvent of ethyl acetate and n-hexane, filtered off and dried to obtain the title compound (1.67 g).

Fourth Step

Production of ethyl 8-(4-tert-butylphenyl)carbamoyl-4-(3-chloropyridin-2-yl)-3,4-dihydro-2H-benzo[1,4]oxazine-2-carboxylate:

8-(4-tert-butylphenyl)carbamoyl-3,4-dihydro-2H-benzo[1,4]oxazine-2-carboxylate (1.66 g) obtained in the Third Step was dissolved in toluene (10 ml), 2,3-dichloropyridine (0.64 g), tris(dibenzylideneacetone)dipalladium (394 mg), 2,2'-bis(diphenylphosphino)-1,1'-binaphthyl (270 mg) and caesium carbonate (3.5 g) were added in this order, and the mixture was stirred at 80° C. for 24 hours. The reaction mixture was diluted with ethyl acetate (10 ml), active charcoal (1 g) was added, and the mixture was stirred and filtered with Celite. The filtrate was concentrated and purified by the use of silica gel chromatography (gradient elution with n-hexane-ethyl acetate) to obtain the pale yellowish solid in the title (1.03 g).

Fifth Step

Production of 8-(4-tert-butylphenyl)carbamoyl-4-(3-chloropyridin-2-yl)-3,4-dihydro-2H-benzo[1,4]oxazine-2-carboxylic acid:

8-(4-tert-butylphenyl)carbamoyl-4-(3-chloropyridin-2-yl)-3,4-dihydro-2H-benzo[1,4]oxazine-2-carboxylate (1.03 g) obtained in the Fourth Step was dissolved in tetrahydrofuran (10 ml) and ethanol (10 ml), 2 M sodium hydroxide (2 ml) was added, and the mixture was stirred at room temperature for 3 hours. The reaction mixture was concentrated, water (20 ml) was added, the mixture was neutralized by adding 1N potassium hydrogen sulfate, and the precipitated solid substance was filtered off. The thus obtained solid substance was suspended and washed with a mixed solvent of ethyl acetate and n-hexane, filtered off and dried to obtain the title compound (0.60 g).

$^1$H-NMR 400 MHz (DMSO-d$_6$) δ=1.29 (m, 9H), 3.62 (m, 1H), 4.18 (m, 1H), 4.70 (m, 1H), 6.47 (dd, J=8.07, 1.47 Hz, 1H), 6.79 (t, J=7.89 Hz, 1H), 7.21-7.35 (m, 4H), 7.84-7.92 (m, 2H), 7.98 (dd, J=7.70, 1.47 Hz, 1H), 8.43 (dd, J=4.99, 1.51 Hz, 1H), 12.34 (s, 1H).

Example 1-003

Production of N-(4-tert-butylphenyl)-4-(3-chloropyridin-2-yl)-3-methyl-3,4-dihydro-2H-benzo[1,4]oxazine-8-carboxamide First Step
Production of methyl 3-nitro-2-(2-oxopropoxy)benzoate:
Methyl 3-nitrosalycilate (1.95 g) obtained in the First Step of Example 1-001 was dissolved in N,N-dimethylformamide (20 ml), potassium carbonate (2.73 g) and bromoacetone (1.1 ml) were added, and the mixture was stirred at room temperature overnight. The reaction mixture was partitioned between water and ethyl acetate, and the ethyl acetate layer was washed twice with saturated sodium chloride solution, dried over anhydrous sodium sulfate and concentrated to obtain brownish oily compound in the title (2.46 g).

Second Step
Production of methyl 3-methyl-3,4-dihydro-2H-benzo[1,4]oxazine-8-carboxylate:
Methyl 3-nitro-2-(2-oxopropoxy)benzoate (2.46 g) obtained in the First Step was dissolved in tetrahydrofuran (25 ml), 10% palladium carbon (containing 50% water) (0.25 g) was added, and the mixture was stirred at room temperature for 24 hours under hydrogen atmosphere. The catalyst was filtered off from the reaction mixture and the filtrate was concentrated. The concentrate was purified by the use of silica gel chromatography (n-hexane-ethyl acetate=1:1) to obtain pale yellowish oily compound in the title (0.45 g)

Third Step
Production of methyl 4-(3-chloropyridin-2-yl)-3-methyl-3,4-dihydro-2H-benzo[1,4]oxazine-8-carboxylate:
methyl 2-methyl-3,4-dihydro-2H-benzo[1,4]oxazine-8-carboxylate (0.62 g) obtained in the method of Second Step was subjected to the reaction in a similar manner as in the Fourth Step in Example 2, and purified by the use of silica gel chromatography (n-hexane-acetone=5:1) to obtain pale yellowish oily compound in the title (0.10 g).

Fourth Step
Production of 4-(3-chloropyridin-2-yl)-3-methyl-3,4-dihydro-2H-benzo[1,4]oxazine-8-carboxylic acid:
Methyl 4-(3-chloropyridin-2-yl)-3-methyl-3,4-dihydro-2H-benzo[1,4]oxazine-8-carboxylate (0.09 g) obtained in the Third Step was dissolved in tetrahydrofuran (1 ml) and methanol (1 ml), 4 M sodium hydroxide solution (0.5 ml) was added, and the mixture was stirred at 60° C. for 1 hour. The reaction mixture was neutralized with 1 M hydrochloric acid and the solvent was evaporated in vacuo. The residue was partitioned between water and ethyl acetate, and the ethyl acetate layer was washed with saturated sodium chloride solution, dried over anhydrous sodium sulfate and concentrated to obtain pale yellowish oily compound in the title (75 mg).

Fifth Step
Production of N-(4-tert-butylphenyl)-4-(3-chloropyridin-2-yl)-3-methyl-3,4-dihydro-2H-benzo[1,4]oxazine-8-carboxamide:
4-(3-Chloropyridin-2-yl)-3-methyl-3,4-dihydro-2H-benzo[1,4]oxazine-8-carboxylic acid (75 mg) obtained in the Fourth Step was subjected to the reaction in a similar manner as in the Eighth Step in Example 1-001, and water and saturated aqueous sodium hydrogencarbonate solution were added in this order. The precipitated pale brownish solid substance was filtered off and dried to obtain the title compound (95 mg).

$^1$H-NMR 400 MHz (DMSO-$d_6$) δ=1.23 (d, J=6.49 Hz, 3H), 1.28 (s, 9H), 4.07-4.15 (m, 1H), 4.22-4.32 (m, 2H), 6.38 (dd, J=8.12, 1.62 Hz, 1H), 6.80 (t, J=7.88 Hz, 1H), 7.04 (dd, J=7.54, 1.51 Hz, 1H), 7.31-7.39 (m, 3H), 7.64-7.71 (m, 2H), 8.07 (dd, J=7.88, 1.62 Hz, 1H), 8.45 (dd, J=4.64, 1.62 Hz, 1H), 10.10 (s, 1H).

Example 1-004

Production of N-(4-tert-butylphenyl)-1-(3-chloropyridin-2-yl)-4-methyl-1,2,3,4-tetrahydroquinoxaline-5-carboxamide First Step
Production of methyl 2-chloro-3-nitrobenzoate:
2-Chloro-3-nitrobenzoic acid (15.0 g) was subjected to the reaction in a similar manner as in the First Step in Example 1-001 to obtain pale yellowish compound in the title (9.0 g)

Second Step
Production of methyl 2-[(ethoxycarbonylmethyl)-(N-methyl)amino]-3-nitrobenzoate:
Methyl 2-chloro-3-nitrobenzoate (2.0 g) obtained in the First Step was dissolved in n-butanol (20 ml), sodium carbonate (2.46 g) and sarcosine ethyl ester hydrochloride (2.14 g) were added, and the mixture was refluxed for 4.5 hours with stirring. The cooled reaction mixture was poured into a mixture of 1 M hydrochloric acid (50 ml)/ethyl acetate (50 ml) under ice-cooling with stirring. The ethyl acetate layer was washed with saturated sodium chloride solution, dried over anhydrous sodium sulfate, and concentrated to obtain red oily substance containing the title compound which was supplied to the subsequent step without purification.

Third Step
Production of methyl 4-methyl-2-oxo-1,2,3,4-tetrahydroquinoxaline-5-carboxylate:
The oily substance containing methyl 2-[(ethoxycarbonylmethyl)-(N-methyl)amino]-3-nitrobenzoate obtained in the Second Step was dissolved in methanol (20 ml), 5% palladium carbon (0.2 g) was added, and the mixture was stirred at room temperature for 2 hours under hydrogen atmosphere. The catalyst was filtered off from the reaction suspension. The filtrate was concentrated and then purified by the use of silica gel chromatography (n-hexane-ethyl acetate=1:3), diethyl ether was added, and the precipitated pale brownish solid substance was filtered off and dried to obtain the title compound (0.41 g).

Fourth Step
Production of methyl 4-methyl-1,2,3,4-tetrahydroquinoxaline-5-carboxylate:
Methyl 4-methyl-2-oxo-1,2,3,4-tetrahydroquinoxaline-5-carboxylate (0.41 g) obtained in the Third Step was subjected to the reaction in a similar manner as in the Fifth Step in Example 1 to obtain yellowish oily compound in the title (203 mg).

Fifth Step
Production of methyl 1-(3-chloropyridin-2-yl)-4-methyl-1,2,3,4-tetrahydroquinoxaline-5-carboxylate:
Methyl 4-methyl-1,2,3,4-tetrahydroquinoxaline-5-carboxylate (206 mg) obtained in the Fourth Step was subjected to the reaction in a similar manner as in the Fourth Step in Example 1-002 to obtain pale yellowish brown solid compound in the title (179 mg).

Sixth Step
Production of methyl 1-(3-chloropyridin-2-yl)-4-methyl-1,2,3,4-tetrahydroquinoxaline-5-carboxylic acid:
Methyl 1-(3-chloropyridin-2-yl)-4-methyl-1,2,3,4-tetrahydroquinoxaline-5-carboxylate (176 mg) obtained in the Fifth Step was subjected to the reaction in a similar manner as in the Fourth Step in Example 1-003 to obtain pale yellowish brown solid compound in the title (130 mg).

Seventh Step

Production of N-(4-tert-butylphenyl)-1-(3-chloropyridin-2-yl)-4-methyl-1,2,3,4-tetrahydroquinoxaline-5-carboxamide:

Methyl 1-(3-chloropyridin-2-yl)-4-methyl-1,2,3,4-tetrahydroquinoxaline-5-carboxylic acid (130 mg) obtained in the Sixth Step was subjected to the reaction in a similar manner as in the Eighth Step in Example 1-001, and the reaction mixture was partitioned between aqueous saturated sodium hydrogencarbonate solution and ethyl acetate. The ethyl acetate layer was washed with saturated sodium chloride solution, washed with saturated sodium chloride solution, dried over anhydrous sodium sulfate and then concentrated. The residue was purified by the use of silica gel chromatography (n-hexane-ethyl acetate=3:2) to obtain pale yellowish amorphous compound in the title (100 mg).

$^1$H-NMR 400 MHz (DMSO-d$_6$) δ=1.28 (s, 9H), 2.83 (s, 3H), 3.34-3.39 (m, 2H), 3.69-3.74 (m, II H), 6.33 (dd, J=8.12, 1.39, 1 Hz, 1H), 6.72 (t, J=7.77 Hz, 1H), 7.03 (dd, J=7.65, 1.39 Hz, 1H), 7.30 (dd, J=7.88, 4.64 Hz, 1H), 7.33-7.38 (m, 2H), 7.63-7.68 (m, 2H) 8.02 dd, J=7.88, 1.62 Hz, 1H), 8.44 (dd, J=4.75, 1.74 Hz, 1H), 10.62 (s, 1H).

Example 1-005

Production of N-(4-tert-butylphenyl)-9-(3-chloropyridin-2-yl)-6,7,8,9-tetrahydro-5-oxa-9-aza-benzocycloheptene-4-carboxamide First Step Production of methyl 5-chloro-3-nitrosalicylate Methyl 5-chlorosalicylate (5.0 g) was dissolved in concentrated sulfuric acid (15 ml), a mixture of concentrated nitric acid (1.2 ml) and concentrated sulfuric acid (1.2 ml) was added dropwise with stirring under ice-cooling, and further stirred after finishing the dropwise addition. The reaction mixture was poured into ice-water, the precipitated solid substance was filtered off, washed with water, then and dried to obtain the title compound (5.51 g).

Second Step

Production of methyl 3-amino-5-chlorosalicylate

Methyl 5-chloro-3-nitrosalicylate (9.16 g) obtained in the method of First Step was subjected to the reaction in a similar manner as in the Second Step in Example 2, and purified by the use of silica gel chromatography (n-hexane-ethyl acetate=1:1) to obtain white solid compound in the title (4.46 g).

Third Step

Production of methyl 3-acetamide-5-chlorosalicylate

Methyl 3-amino-5-chlorosalicylate (4.46 g) obtained in the Second Step was dissolved in tetrahydrofuran (50 ml), and pyridine (2 ml) and acetyl chloride (1.6 ml) were added with stirring under ice-cooling. After 30 minutes, the reaction mixture was concentrated and partitioned between water and ethyl acetate. The ethyl acetate layer was washed with 1 M hydrochloric acid, saturated sodium chloride solution, saturated aqueous sodium hydrogencarbonate and saturated sodium chloride solution, in this order, dried over anhydrous sodium sulfate and concentrated to obtain the white solid compound in the title (4.86 g).

Fourth Step

Production of methyl 9-acetyl-2-chloro-6,7,8,9-tetrahydro-5-oxa-9-aza-benzocycloheptene-4-carboxylate:

Methyl 3-acetamide-5-chlorosalicylate obtained in the Third Step was dissolved in N,N-dimethylformamide (10 ml), potassium carbonate (1.38 g) and 1-bromo-3-chloropropane (2.0 ml) were added, and the mixture was stirred at room temperature for 1 hour. Then the temperature to 120° C. was increased and the mixture was stirred for 3 hours. After cooling the reaction mixture, water was added, and the mixture was extracted with ethyl acetate. The ethyl acetate layer was washed with water and saturated sodium chloride solution, in this order, dried over anhydrous sodium sulfate and then concentrated. The residue was purified by the use of silica gel chromatography (n-hexane-ethyl acetate=1:1) to obtain the white solid compound in the title (630 mg).

Fifth Step

Production of methyl 9-acetyl-6,7,8,9-tetrahydro-5-oxa-9-aza-benzocycloheptene-4-carboxylate:

Methyl 9-acetyl-2-chloro-6,7,8,9-tetrahydro-5-oxa-9-aza-benzocycloheptene-4-carboxylate (1.9 g) obtained by the same method of the Fourth Step was dissolved in tetrahydrofuran (20 ml) and methanol (20 ml), 5% palladium carbon (0.2 g) and triethylamine (1.2 ml) were added, and the mixture was stirred at room temperature for 45 hours under hydrogen atmosphere. The catalyst was filtered off from the reaction suspension, the filtrate was concentrated, and the concentrate was partitioned between water and ethyl acetate. The ethyl acetate layer was washed with water and saturated sodium chloride solution in this order, dried over anhydrous sodium sulfate and concentrated to obtain the colorless oily compound in the title (1.45 g).

Sixth Step

Production of 6,7,8,9-tetrahydro-5-oxa-9-aza-benzocycloheptene-4-carboxylic acid:

Water (25 ml) and concentrated sulfuric acid (5 ml) were added to methyl 9-acetyl-6,7,8,9-tetrahydro-5-oxa-9-aza-benzocycloheptene-4-carboxylate (1.43 g) obtained in the Fifth Step and the mixture was refluxed with stirring overnight. The reaction mixture was left to cool, neutralized by adding 2 M sodium hydroxide solution to slightly acidic and extracted twice with ethyl acetate. The ethyl acetate layer was washed twice with saturated sodium chloride solution, dried over anhydrous sodium sulfate and concentrated to obtain the title compound (530 mg). The aqueous layer was extracted with tetrahydrofuran, dried over anhydrous sulfate and concentrated to further obtain the compound (320 mg).

Seventh Step

Production of ethyl 6,7,8,9-tetrahydro-5-oxa-9-aza-benzocycloheptene-4-carboxylate:

6,7,8,9-Tetrahydro-5-oxa-9-aza-benzocycloheptene-4-carboxyl acid (850 mg) was dissolved in ethanol (30 ml), concentrated sulfuric acid (2 ml) was added, and the mixture was refluxed with stirring for 2 hours. The reaction mixture was cooled, neutralized with saturated sodium hydrogencarbonate solution and extracted with ethyl acetate. The ethyl acetate layer was concentrated to obtain the oily compound in the title (721 mg).

Eighth Step

Production of ethyl 9-(3-chloropyridin-2-yl)-6,7,8,9-tetrahydro-5-oxa-9-aza-benzocycloheptene-4-carboxylate:

Ethyl 6,7,8,9-tetrahydro-5-oxa-9-aza-benzocycloheptene-4-carboxylate (720 mg) obtained in the Seventh Step was subjected to the reaction in a similar manner as in the Fourth Step in Example 1-002, and the crude product was purified by the use of silica gel chromatography (n-hexane-ethyl acetate=3:1) to obtain the oily compound in the title (154 mg).

Ninth Step

Production of 9-(3-chloropyridin-2-yl)-6,7,8,9-tetrahydro-5-oxa-9-aza-benzocycloheptene-4-carboxylic acid:

Ethyl 9-(3-chloropyridin-2-yl)-6,7,8,9-tetrahydro-5-oxa-9-aza-benzocycloheptene-4-carboxylate (150 mg) was dissolved in tetrahydrofuran (2 ml) and ethanol (2 ml), 2 M sodium hydroxide solution (2 ml) was added, and the mixture was stirred at 60° C. for 1.5 hours. The reaction mixture was concentrated, acidified with 1 M aqueous potassium hydrogen sulfate and extracted twice with ethyl acetate. The ethyl acetate layer was washed with saturated sodium chloride solution, washed over anhydrous sodium sulfate and concentrated to obtain the oily compound in the title (102 mg).

Tenth Step

Production of N-(4-tert-butylphenyl)-9-(3-chloropyridin-2-yl)-6,7,8,9-tetrahydro-5-oxa-9-aza-benzocycloheptene-4-carboxamide:

9-(3-Chloropyridin-2-yl)-6,7,8,9-tetrahydro-5-oxa-9-aza-benzocycloheptene-4-carboxylic acid (100 mg) obtained in the Ninth Step was subjected to the reaction in a similar manner as in the Eighth Step in Example 1-001, and the crude product was purified by the use of silica gel chromatography (n-hexane-ethyl acetate=2:1), n-hexane was added, precipitated white solid substance was filtered off and dried to obtain the title compound (35 mg).

$^1$H-NMR 400 MHz (DMSO-d$_6$) δ=1.25 (s, 9H), 1.95 (m, 2H), 3.97 (m, 2H), 4.27 (m, 2H), 6.61 (dd, J=8.00, 1.51 Hz, 1H), 6.93 (t, J=7.77 Hz, 1H), 7.06 (dd, J=7.77, 4.75 Hz, 1H), 7.26 (dd, J=7.54, 1.51 Hz, 1H), 7.30-7.38 (m, 2H), 7.63 (ddd, J=9.04, 2.55, 2.32 Hz, 2H), 7.76 (dd, J=7.65, 1.62 Hz, 1H), 8.31 (dd, J=4.64, 1.62 Hz, 1H), 10.15 (s, 1H).

Example 1-006

In the method similar to Example 1-001, corresponding carboxylic acid and amine were used to obtain the compound of Example 1-006 shown in the following table.

Example 1-007

In the method similar to Example 1-001, corresponding carboxylic acid and amine were used to obtain the compound of Example 1-007 shown in the following table.

Example 1-008

In the method similar to Example 1-001, corresponding carboxylic acid and amine were used to obtain the compound of Example 1-008 shown in the following table.

Example 1-009

In the method similar to Example 1-001, corresponding carboxylic acid and amine were used to obtain the compound of Example 1-009 shown in the following table.

Example 1-010

In the method similar to Example 1-001, corresponding carboxylic acid and amine were used to obtain the compound of Example 1-010 shown in the following table.

Example 1-011

In the method similar to Example 1-001, corresponding carboxylic acid and amine were used to obtain the compound of Example 1-011 shown in the following table.

Example 1-012

In the method similar to Example 1-001, corresponding carboxylic acid and amine were used to obtain the compound of Example 1-012 shown in the following table.

Example 1-013

In the method similar to Example 1-001, corresponding carboxylic acid and amine were used to obtain the compound of Example 1-013 shown in the following table.

Example 1-014

In the method similar to Example 1-001, corresponding carboxylic acid and amine were used to obtain the compound of Example 1-014 shown in the following table.

Example 1-015

In the method similar to Example 1-001, corresponding carboxylic acid and amine were used to obtain the compound of Example 1-015 shown in the following table.

Example 1-016

In the Sixth Step in Example 1-001, 2-bromopyridine was used in the place of 2,3-dichloropyridine, and others were treated by the same manner as in the example to obtain the compound of Example 1-016 shown in the following table.

Example 1-017

In the Sixth Step in Example 1-001, 2-chloro-3-trifluoromethylpyridine was used in the place of 2,3-dichloropyridine, and others were treated by the same manner as in the example to obtain the compound of Example 1-017 shown in the following table.

Example 1-018

In the Third Step in Example 1-001, 2-bromoisobutyl bromide was used in the place chloroacetyl chloride, and others were treated by the same manner as in the example to obtain the compound of Example 1-018 shown in the following table.

Example 1-019

In the Third Step in Example 1-001, 2-chloropropionyl chloride was used in the place chloroacetyl chloride, and others were treated by the same manner as in the example to obtain the compound of Example 1-019 shown in the following table.

Example 1-020

3-amino-5-chlorosalicylic acid produced by the method of the Second Step in Example 1-005 was used in the method subsequent to the Third Step in Example 1-001 to obtain the compound of Example 1-020 shown in the following table.

Example 1-021

Production of 4-(3-chloropyridin-2-yl)-N-(4-trifluoromethylphenyl)-3,4-dihydro-2H-benzo[1,4]oxazine-8-carboxamide 4-(3-chloropyridin-2-yl)-3,4-dihydro-2H-benzo[1,4]oxazine-8-carboxylic acid (100 mg) obtained in the Seventh Step in Example 1-001 was dissolved in tetrahydrofuran (1 ml), oxalyl chloride (0.05 ml) and N,N-dimethylformamide (0.01 ml) were added, the mixture was stirred at room temperature for 30 minutes, and the reaction mixture was concentrated to obtain acid chloride as yellowish solid. Tetrahydrofuran (1 ml) and 1 M sodium hydroxide solution (1 ml) were added to 4-trifluoroaniline (48 mg), and a solution of the acid chloride in tetrahydrofuran (1 ml) was added with stirring under ice-cooling, and the reaction mixture was stirred at room temperature for 30 minutes. The reaction mixture was concentrated, partitioned between ethyl acetate and water, and the ethyl acetate layer was washed with 1 M sodium hydroxide and saturated sodium chloride solution in this order, dried over anhydrous magnesium sulfate and then concentrated. The residue was suspended in n-hexane, filtered off and dried to obtain the title compound (72 mg).

Example 1-022

In the method similar to Example 1-021, corresponding carboxylic acid and amine were used to obtain the compound of Example 1-022 shown in the following table.

Example 1-023

In the method similar to Example 1-021, corresponding carboxylic acid and amine were used to obtain the compound of Example 1-023 shown in the following table.

Example 1-024

In the method similar to Example 1-021, corresponding carboxylic acid and amine were used to obtain the compound of Example 1-024 shown in the following table.

Example 1-025

In the method similar to Example 1-021, corresponding carboxylic acid and amine were used to obtain the compound of Example 1-025 shown in the following table.

Example 1-026

In the method similar to Example 1-021, corresponding carboxylic acid and amine were used to obtain the compound of Example 1-026 shown in the following table.

Example 1-027

In the method similar to Example 1-021, corresponding carboxylic acid and amine were used to obtain the compound of Example 1-027 shown in the following table.

Example 1-028

In the method similar to Example 1-021, corresponding carboxylic acid and amine were used to obtain the compound of Example 1-028 shown in the following table.

Example 1-029

In the method similar to Example 1-021, corresponding carboxylic acid and amine were used to obtain the compound of Example 1-029 shown in the following table.

Example 1-030

In the method similar to Example 1-021, corresponding carboxylic acid and amine were used to obtain the compound of Example 1-030 shown in the following table.

Example 1-031

In the method similar to Example 1-021, corresponding carboxylic acid and amine were used to obtain the compound of Example 1-031 shown in the following table.

Example 1-032

In the method similar to Example 1-021, corresponding carboxylic acid and amine were used to obtain the compound of Example 1-032 shown in the following table.

Example 33

In the method similar to Example 1-021, corresponding carboxylic acid and amine were used to obtain the compound of Example 1-033 shown in the following table.

Example 1-034

Production of 4-(3-chloropyridin-2-yl)-N-(methoxycarbonylphenyl)-3,4-dihydro-2H-benzo[1,4]oxazine-8-carboxamide Methyl 4-aminobenzoate (260 mg) was used in the method similar to Example 1-021 to obtain the title compound (515 mg).

Example 1-035

Production of N-(4-carboxyphenyl)-4-(3-chloropyridin-2-yl)-3,4-dihydro-2H-benzo[1,4]oxazine-8-carboxamide 4-(3-Chloropyridin-2-yl)-N-(methoxycarbonylphenyl)-3,4-dihydro-2H-benzo[1,4]oxazine-8-carboxamide (500 mg) produced in Example 1-034 was dissolved in tetrahydrofuran (5 ml) and methanol (5 ml), 4 M sodium hydroxide solution (1 ml) was added, and the mixture was stirred at 60° C. for 5 hours. The reaction mixture was neutralized by adding 1 M hydrochloric acid and then concentrated. The concentrate was diluted with water and stirred, and white solid substance was collected by filtration and dried to obtain the title compound (433 mg)

Example 1-036

Production of N-(4-carbamoylphenyl)-4-(3-chloropyridin-2-yl)-3,4-dihydro-2H-benzo[1,4]oxazine-8-carboxamide N-(4-carboxyphenyl)-4-(3-chloropyridin-2-yl)-3,4-dihydro-2H-benzo[1,4]oxazine-8-carboxamide (100 mg) obtained in Example 1-035 was dissolved in N,N-dimethylformamide (2 ml), ammonium chloride (65 mg), 1-hydroxybenzotriazole (56 mg), 1-ethyl-3-(3-dimethylaminopropyl)-carbodiimide hydrochloride (70 mg) and triethylamine (0.20 ml) were added in this order, and the mixture was stirred at room temperature for 10 hours. After adding water and saturated sodium hydrogencarbonate solution to the reaction mixture, the mixture was partitioned by adding ethyl acetate.

After ethyl acetate layer was washed with water, concentrated and dried, the concentrate was suspended in and washed with water, the white solid substance was collected by filtration and dried to obtain the title compound (80 mg).

Example 1-037

In the method similar to Example 1-036, corresponding carboxylic acid and amine were used to obtain the compound of Example 1-037 shown in the following table.

Example 1-038

In the method similar to Example 1-036, corresponding carboxylic acid and amine were used to obtain the compound of Example 1-038 shown in the following table.

Example 1-039

Production of N-(4-acetylphenyl)-4-(3-chloropyridin-2-yl)-3,4-dihydro-2H-benzo[1,4]oxazine-8-carboxamide 4'-aminoacetophenone (279 mg) was used in the similar method of Example 1-021 to obtain the title compound (673 mg)

Example 1-040

Production of 4-(3-chloropyridin-2-yl)-N-[4-(1-hydroxy-1-methyl)ethyl]phenyl-3,4-dihydro-2H-benzo[1,4]oxazine-8-carboxamide N-(4-acetylphenyl)-4-(3-chloropyridin-2-yl)-3,4-dihydro-2H-benzo[1,4]oxazine-8-carboxamide (150 mg) obtained in Example 1-039 was dissolved in tetrahydrofuran (15 ml), 1 M methyl magnesium bromide-tetrahydrofuran solution (1.1 ml) was added under ice-cooling, and then the mixture was stirred at room temperature for 30 minutes. Then, 1 M methyl magnesium bromide-tetrahydrofuran solution (0.37 ml) was further added and stirred and the mixture was at room temperature for 30 minutes. The reaction mixture was cooled on ice, the reaction was terminated by adding saturated aqueous ammonium chloride, and the mixture was extracted with ethyl acetate. The ethyl acetate layer was washed with saturated sodium chloride solution, dried over anhydrous sodium sulfate and then concentrated. The residue was purified by the use of silica gel chromatography (n-hexane-ethyl acetate=1:4) to obtain the white amorphous compound in the title (79 mg).

Example 1-041

Production of 4-(3-chloropyridin-2-yl)-N-[4-(1-hydroxy-1-methyl)propyl]phenyl-3,4-dihydro-2H-benzo[1,4]oxazine-8-carboxamide In the reaction similar to Example 1-040, 2 M ethyl magnesium bromide was used to obtain the white amorphous compound in the title (100 mg) from N-(4-acetylphenyl)-4-(3-chloropyridin-2-yl)-3,4-dihydro-2H-benzo[1,4]oxazine-8-carboxamide (150 mg).

Example 1-042

In the method similar to Example 1-001, corresponding carboxylic acid and amine were used to obtain the compound of Example 1-042 shown in the following table.

Example 1-043

In the method similar to Example 1-001, corresponding carboxylic acid and amine were used to obtain the compound of Example 1-043 shown in the following table.

Example 1-044

In the method similar to Example 1-001, corresponding carboxylic acid and amine were used to obtain the compound of Example 1-044 shown in the following table.

Example 1-045

In the method similar to Example 1-001, corresponding carboxylic acid and amine were used to obtain the compound of Example 1-045 shown in the following table.

Example 1-046

In the Sixth Step in Example 1-001, 4-bromopyridine was used in the place of 2,3-dichloropyridine and others were treated by the same manner as in the example to obtain the compound of Example 1-046 shown in the following table.

Example 1-047

In the Sixth Step in Example 1-001, 2-bromo-3-picoline was used in the place of 2,3-dichloropyridine and others were treated by the same manner as in the example to obtain the compound of Example 1-047 shown in the following table.

Example 1-048

In the method similar to Example 1-021, corresponding carboxylic acid and amine were used to obtain the compound of Example 1-048 shown in the following table.

Example 1-049

In the method similar to Example 1-021, corresponding carboxylic acid and amine were used to obtain the compound of Example 1-049 shown in the following table.

Example 1-050

In the method similar to Example 21, corresponding carboxylic acid and amine were used to obtain the compound of Example 1-050 shown in the following table.

Example 1-051

In the method similar to Example 1-021, corresponding carboxylic acid and amine were used to obtain the compound of Example 1-051 shown in the following table.

Example 1-052

In the method similar to Example 1-021, corresponding carboxylic acid and amine were used to obtain the compound of Example 1-052 shown in the following table.

Example 1-053

In the method similar to Example 1-021, corresponding carboxylic acid and amine were used to obtain the compound of Example 1-053 shown in the following table.

Example 1-054

In the method similar to Example 1-021, corresponding carboxylic acid and amine were used to obtain the compound of Example 1-054 shown in the following table.

Example 1-055

In the method similar to Example 1-021, corresponding carboxylic acid and amine were used to obtain the compound of Example 1-055 shown in the following table.

Example 1-056

In the method similar to Example 1-021, corresponding carboxylic acid and amine were used to obtain the compound of Example 1-056 shown in the following table.

Example 1-057

In the method similar to Example 1-021, corresponding carboxylic acid and amine were used to obtain the compound of Example 1-057 shown in the following table.

Example 1-058

Production of N-(4-tert-butylphenyl)-4-(4-chloropyridin-2-yl)-3,4-dihydro-2H-benzo[1,4]oxazine-8-carboxamide First Step
Production of 4-(3-chloropyridin-2-yl)-3,4-dihydro-2H-benzo[1,4]oxazine-8-carboxylic acid:
In the Sixth Step in Example 1-001, 2-chloro-4-picoline (890 mg) was used in the place of 2,3-dichloropyridine and others were treated by the same manner as in the Seventh Step of Example 1-001 to obtain the title compound (690 mg).
Second Step
Production of N-(4-tert-butylphenyl)-4-(4-methylpyridin-2-yl)-3,4-dihydro-2H-benzo[1,4]oxazine-8-carboxamide:
N-(4-tert-butylphenyl)-4-(4-methylpyridin-2-yl)-3,4-dihydro-2H-benzo[1,4]oxazine-8-carboamide (150 mg) obtained in the process 1-001 was used in the similar method in Example 21 to obtain the title compound (130 mg).

Example 1-059

Example 1-059 compound shown in the following table was obtained from the corresponding bromopicoline by applying the similar method as of Example 21.

Example 1-060

Example 1-060 compound shown in the following table was obtained from the corresponding bromopicoline by applying the similar method as of Example 1-021.

Example 1-061 to Example 1-236

A compound of Examples 1-061 to 1-236 hereinbelow were obtained by similarly performing any methods described in the general processes A to C for producing the compound and/or a method described in Examples 1-001 to 1-060 hereinbefore.

Example 2

Example 2-01

Production of N-(benzo[1,3]dioxol-5-yl)-4-(3-chloro-5-hydroxymethylpyridin-2-yl)-3,4-dihydro-2H-benzo[1,4]oxazine-8-carboxamide First Step
Production of methyl 4-{3-chloro-5-(tetrahydropyran-2-yl)oxymethylpyridin-2-yl}-3,4-dihydro-2H-benzo[1,4]oxazine-8-carboxylate:
3,4-Dihydro-2H-benzo[1,4]oxazine-8-carboxylate (2.0 g) obtained by the method of Fifth Step in Example 1-001 was dissolved in toluene (30 ml), 2,3-dichloro-5-(tetrahydropyran-2-yl)oxymethylpyridine (2.76 g), palladium acetate (0.25 g), 2,2'-bis(diphenylphosphino)-1,1'-binaphthyl (0.7 g) and caesium carbonate (7.4 g) were added, and the mixture was stirred at 90° C. overnight. The reaction mixture was filtered and concentrated, and the thus obtained residue was purified by the use of silica gel column chromatography (hexane-tetrahydrofuran=2:1) to obtain oily compound in the title (2.48 g).
Second Step
Production of 4-{3-chloro-5-(tetrahydropyran-2-yl)oxymethylpyridin-2-yl}-3,4-dihydro-2H-benzo[1,4]oxazine-8-carboxylic acid:
Methyl 4-{3-chloro-5-(tetrahydropyran-2-yl)oxymethylpyridin-2-yl}-3,4-dihydro-2H-benzo[1,4]oxazine-8-carboxylate (2.48 g) obtained in the First Step was subjected to the reaction similar to that of the Fourth Step in Example 1-003 to obtain the title compound (1.33 g).
Third Step
Production of N-(benzo[1,3]dioxol-5-yl)-4-{3-chloro-5-(tetrahydropyran-2-yl)oxymethylpyridin-2-yl}-3,4-dihydro-2H-benzo[1,4]oxazine-8-carboxamide:
4-{3-chloro-5-(tetrahydropyran-2-yl)oxymethylpyridin-2-yl}-3,4-dihydro-2H-benzo[1,4]oxazine-8-carboxylic acid (0.20 g) obtained in the Second Step and 5-amino-benzo[1,3]dioxolane (0.10 g) were subjected to the reaction similar to that of the Eighth Step in Example 1-001 to obtain the title compound (0.21 g).
Fourth Step
Production of N-(benzo[1,3]dioxol-5-yl)-4-(3-chloro-5-hydroxymethylpyridin-2-yl)-3,4-dihydro-2H-benzo[1,4]oxazine-8-carboxamide:
N-(benzo[1,3]dioxol-5-yl)-4-{3-chloro-5-(tetrahydropyran-2-yl)oxymethylpyridin-2-yl}-3,4-dihydro-2H-benzo[1,4]oxazine-8-carboxamide (0.21 g) obtained in the Third Step was dissolved in tetrahydrofuran (3 ml), 6 M hydrochloric acid (3 ml) was added, and the mixture was stirred at room temperature overnight. The reaction mixture was concentrated, and the residue was purified by the use of silica gel column chromatography to obtain the title compound (0.12 g).

Example 2-02

Production of N-(2,3-dihydrobenzo[1,4]dioxine-6-yl)-4-(3-chloro-5-hydroxymethylpyridin-2-yl)-3,4-dihydro-2H-benzo[1,4]oxazine-8-carboxamide In the Third Step of Example 2-01, 6-amino-2,3-dihydrobenzo[1,4]dioxin (111 mg) was used in the place of 5-amino-benzo[1,3]dioxolane, and others were treated by the same manner as in the process to obtain the title compound (109 mg).

Example 2-03

Production of N-(4-trifluoromethoxyphenyl)-4-(3-chloro-5-hydroxymethylpyridin-2-yl)-3,4-dihydro-2H-benzo[1,4]oxazine-8-carboxamide In the Third Step of Example 2-01, 4-trifluoromethoxyaniline (87 mg) was used in the place of 5-amino-benzo[1,3] dioxolane, and others were treated by the same manner as in the process to obtain the title compound (101 mg).

Example 2-04

Production of N-(3-chloro-4-trifluoromethoxypheny)-4-(3-chloro-5-hydroxymethylpyridin-2-yl)-3,4-dihydro-2H-benzo[1,4]oxazine-8-carboxamide In the Third Step of Example 2-01, 3-chloro-4-trifluoromethoxyaniline (87 mg) was used in the place of 5-amino-benzo[1,3]dioxolane, and others were treated by the same manner as in the process to obtain the title compound (58 mg).

Example 2-05

Production of N-(4-trifluoromethylphenyl)-4-(3-chloro-5-hydroxymethylpyridin-2-yl)-3,4-dihydro-2H-benzo[1,4]oxazine-8-carboxamide First Step
Production of N-(4-trifluoromethylphenyl)-4-{3-chloro-5-(tetrahydropyran-2-yl)oxymethylpyridin-2-yl}-3,4-dihydro-2H-benzo[1,4]oxazine-8-carboxamide:
4-{3-Chloro-5-(tetrahydropyran-2-yl)oxymethylpyridin-2-yl}-3,4-dihydro-2H-benzo[1,4]oxazine-8-carboxylic acid (300 mg) obtained in the Second Step of Example 2-01 was dissolved in pyridine (5 ml), thionyl chloride (88 mg) was added, and the mixture was stirred at 80° C. for 1 hour. The reaction mixture was cooled to room temperature, 4-trifluoromethylaniline (80 mg) was added, and the mixture was stirred for 1 hour. The reaction mixture was partitioned between water and ethyl acetate, and the ethyl acetate layer was washed with water, diluted aqueous potassium hydrogen sulfate, diluted aqueous sodium hydroxide and saturated sodium chloride solution, dried over magnesium sulfate and then concentrated to obtain residue containing the title compound, which was supplied to the subsequent process without purification.
Second Step
Production of N-(4-trifluoromethylphenyl)-4-(3-chloro-5-hydroxymethylpyridin-2-yl)-3,4-dihydro-2H-benzo[1,4]oxazine-8-carboxamide:
The concentrated residue obtained in the First Step was dissolved in tetrahydrofuran (3 ml), 6 M hydrochloric acid (3 ml) was added, and the mixture was stirred at room temperature for 1 hour. The reaction mixture was partitioned between water and ethyl acetate, and the ethyl acetate layer was washed with water and saturated sodium chloride solution in this order, dried over anhydrous magnesium sulfate and then concentrated. The thus obtained concentrated residue was purified by the use of silica gel chromatography to obtain the title compound (71 mg).

Example 2-06

Production of N-(3-fluoro-4-trifluoromethylphenyl)-4-(3-chloro-5-hydroxymethylpyridin-2-yl)-3,4-dihydro-2H-benzo[1,4]oxazine-8-carboxamide In the First Step of Example 2-05, 3-fluoro-4-trifluoromethylaniline (110 mg) was used in the place of 4-trifluoromethylaniline, and others were treated by the same manner as in the process to obtain the title compound (50 mg).

Example 2-07

Production of N-(4-trifluoromethylphenyl)-4-(5-hydroxymethylpyridin-2-yl)-3,4-dihydro-2H-benzo[1,4]oxazine-8-carboxamide First Step
Production of 4-{5-(tetrahydropyran-2-yl)oxymethylpyridin-2-yl}-3,4-dihydro-2H-benzo[1,4]oxazine-8-carboxylic acid:
Methyl 4-{5-(tetrahydropyran-2-yl)oxymethylpyridin-2-yl}-3,4-dihydro-2H-benzo[1,4]oxazine-8-carboxylate (560 mg), which was obtained by using 2-chloro-5-(tetrahydropyran-2-yl)oxymethylpyridine in the place of 2,3-dichloro-5-(tetrahydropyran-2-yl)oxymethylpyridine in the First Step of Example 2-01, was dissolved in methanol (8 ml), 4 M sodium hydroxide solution (1.1 ml) was added, and the mixture was stirred at 60° C. for 2 hours. The reaction mixture was concentrated, and the concentrate was partitioned by adding water and ethyl acetate. The aqueous layer was adjusted to pH 4 by adding hydrochloric acid and was extracted with ethyl acetate. The ethyl acetate layer was dried over anhydrous sodium sulfate and then concentrated. Precipitated solid obtained by adding diisopropyl ether was collected by filtration and dried to obtain the title compound (420 mg).
Second Step
Production of N-(4-trifluoromethylphenyl)-4-{5-(tetrahydropyran-2-yl)oxymethylpyridin-2-yl}-3,4-dihydro-2H-benzo[1,4]oxazine-8-carboxamide:
A reaction similar to that of the First Step of Example 2-05 was performed by using 4-{5-(tetrahydropyran-2-yl)oxymethylpyridin-2-yl}-3,4-dihydro-2H-benzo[1,4]oxazine-8-carboxylic acid (200 g) obtained in the First Step of Example 2-05 to obtain a concentrated residue containing the title compound.
Third Step
Production of N-(4-trifluoromethylphenyl)-4-(5-hydroxymethylpyridin-2-yl)-3,4-dihydro-2H-benzo[1,4]oxazine-8-carboxamide hydrochloride:
The concentrated residue containing N-(4-trifluoromethylphenyl)-4-{5-(tetrahydropyran-2-yl)oxymethylpyridin-2-yl}-3,4-dihydro-2H-benzo[1,4]oxazine-8-carboxamide was dissolved in methanol (2 ml) and tetrahydrofuran (2 ml), 6 M hydrochloric acid (1 ml) was added, and the mixture was stirred at room temperature for 1 hour. The reaction mixture was concentrated, water and diethyl ether were added, then precipitated yellow solid substance was collected by filtration and dried to obtain the title compound (170 mg)

Example 2-08

Production of 4-(5-hydroxymethylpyridin-2-yl)-N-(4-isobutyloxyphenyl)-3,4-dihydro-2H-benzo[1,4]oxazine-8-carboxamide 4-{5-(tetrahydropyran-2-yl)oxymethylpyridin-2-yl}-3,4-dihydro-2H-benzo[1,4]oxazine-8-carboxylic acid (200 mg)

obtained in the First Step of Example 2-07 and 4-isobutyloxyaniline (110 mg) were used and the others were subjected to the reaction similar to Example 2-05 to obtain the title compound (140 mg).

Example 2-09

Production of 4-(3-chloro-5-methoxymethylpyridin-2-yl)-N-(4-trifluoromethylpheny)-3,4-dihydro-2H-benzo[1,4]oxazine-8-carboxamide First Step
Production of methyl 4-{3-chloro-5-hydroxymethylpyridin-2-yl}-3,4-dihydro-2H-benzo[1,4]oxazine-8-carboxylate:
Methyl 4-{3-chloro-5-(tetrahydropyran-2-yl)oxymethylpyridin-2-yl}-3,4-dihydro-2H-benzo[1,4]oxazine-8-carboxylate (1.3 g) obtained in the First Step of Example 2-01 was dissolved in tetrahydrofuran (5 ml), 6 M hydrochloric acid was (5 ml) added, and the mixture was stirred at room temperature for 2 hours. The reaction mixture was neutralized and extracted with ethyl acetate. The extract was concentrated to obtain a concentrated residue containing the title compound.

Second Step
Production of methyl 4-(3-chloro-5-methoxymethylpyridin-2-yl)-3,4-dihydro-2H-benzo[1,4]oxazine-8-carboxylate:
The concentrated residue obtained in the First Step was dissolved in N,N-dimethylformamide (5 ml), sodium hydride (50%) (0.32 g) was added, and the mixture was stirred at room temperature until foaming was terminated. Subsequently, sodium iodide (1 ml) was added and the mixture was further stirred for 1 hour. The reaction mixture was partitioned between water and ethyl acetate, and the ethyl acetate layer was washed with water, dried over anhydrous sodium sulfate and then concentrated. The concentrate was purified by the use of silica gel chromatography to obtain the oily compound in the title (1.20 g).

Third Step
Production of 4-(3-chloro-5-methoxymethylpyridin-2-yl)-3,4-dihydro-2H-benzo[1,4]oxazine-8-carboxylic acid:
Methyl 4-(3-chloro-5-methoxymethylpyridin-2-yl)-3,4-dihydro-2H-benzo[1,4]oxazine-8-carboxylate (1.20 g) obtained in the Second Step was dissolved in tetrahydrofuran (10 ml) and methanol (10 ml), 2 M sodium hydroxide (5 ml) was added, and the mixture was stirred at 60° C. for 1 hour. The reaction mixture was concentrated and neutralized to obtain black colored solid substance by filtration and dried to obtain the title compound (915 mg).

Fourth Step
Production of 4-(3-chloro-5-methoxymethylpyridin-2-yl)-N-(4-trifluoromethylpheny)-3,4-dihydro-2H-benzo[1,4]oxazine-8-carboxamide:
4-(3-chloro-5-methoxymethylpyridin-2-yl)-3,4-dihydro-2H-benzo[1,4]oxazine-8-carboxylic acid (200 mg) obtained in the Third Step was dissolved in chloroform (2 ml), oxalyl chloride (60 µl) and N,N-dimethylformamide (one drop) were added, and the mixture was stirred at room temperature for 1 hour. The reaction mixture was concentrated, pyridine (2 ml) and 4-trifluoromethylaniline (75 µl) were added, and the mixture was stirred at room temperature for 1 hour. The reaction mixture was partitioned between water and ethyl acetate, and the ethyl acetate layer was washed with water, dried over anhydrous magnesium sulfate and then concentrated. Precipitated solid obtained by adding n-hexane and diethyl ether to the concentrate was collected by filtration and dried to obtain the title compound (64 mg).

Example 2-10

Production of N-(4-trifluoromethylphenyl)-4-(4-hydroxymethylpyridin-2-yl)-3,4-dihydro-2H-benzo[1,4]oxazine-8-carboxamide First Step
Production of 4-{4-(tetrahydropyran-2-yl)oxymethylpyridin-2-yl}-3,4-dihydro-2H-benzo[1,4]oxazine-8-carboxylic acid:
Methyl 4-{4-(tetrahydropyran-2-yl)oxymethylpyridin-2-yl}-3,4-dihydro-2H-benzo[1,4]oxazine-8-carboxylate, which was obtained by the process, in which, in the First Step of Example 2-01, the reaction was performed by the similar manner using 2-chloro-4-(tetrahydropyran-2-yl)oxymethylpyridine (1.52 g) in the place of 2,3-dichloro-5-(tetrahydropyran-2-yl)oxymethylpyridine, and the reaction mixture was filtered, concentrated and purified by the use of silica gel column chromatography, was dissolved in methanol (10 ml) and tetrahydrofuran (10 ml), 4 M sodium hydroxide solution (5 ml) was added, and the mixture was stirred at 60° C. for 1.5 hour. The reaction mixture was neutralized and then concentrated. The concentrate was partitioned by adding water and ethyl acetate. The ethyl acetate layer was washed with water and saturated sodium chloride solution in this order, dried over anhydrous magnesium sulfate and concentrated to obtain the title compound (913 mg).

Second Step
Production of N-(4-trifluoromethylphenyl)-4-(4-hydroxymethylpyridin-2-yl)-3,4-dihydro-2H-benzo[1,4]oxazine-8-carboxamide:
4-{4-(tetrahydropyran-2-yl)oxymethylpyridin-2-yl}-3,4-dihydro-2H-benzo[1,4]oxazine-8-carboxylic acid (300 mg) obtained in the First Step was dissolved in pyridine (5 ml), thionyl chloride (89 µl) was added, and the mixture was stirred at room temperature for 2 hours. Subsequently, 4-trifluoromethylaniline (102 µl) was added and stirred at the same temperature overnight. The reaction mixture was partitioned between water and ethyl acetate. The ethyl acetate layer was washed with water and saturated sodium chloride in this order, dried over anhydrous magnesium sulfate and then concentrated. The concentrate was purified by the use of silica gel chromatography. To the purified concentrated substance was added tetrahydrofuran (5 ml) and 6 M hydrochloric acid (2 ml) and stirred at room temperature for 2 hours. The reaction mixture was partitioned between water and ethyl acetate. The ethyl acetate layer was washed with water and saturated sodium chloride solution in this order, dried over anhydrous magnesium sulfate and then concentrated. The concentrate was purified by the use of silica gel chromatography to obtain the title compound (12 mg).

Example 2-11

Production of N-(4-trifluoromethoxyphenyl)-4-(3-hydroxymethylpyridin-2-yl)-3,4-dihydro-2H-benzo[1,4]oxazine-8-carboxamide First Step
Production of methyl 4-{3-(tetrahydropyran-2-yl)oxymethylpyridin-2-yl}-3,4-dihydro-2H-benzo[1,4]oxazine-8-carboxylate:
In the First Step of Example 2-01, the similar reaction was performed by using 2-chloro-3-(tetrahydropyran-2-yl)oxymethylpyridine (712 mg) in the place of 2,3-dichloro-5-(tetrahydropyran-2-yl)oxymethylpyridine to obtain the title compound (536 mg).

Second Step

Production of 4-{3-(tetrahydropyran-2-yl)oxymethylpyridin-2-yl}-3,4-dihydro-2H-benzo[1,4]oxazine-8-carboxylic acid:

Methyl 4-{3-(tetrahydropyran-2-yl)oxymethylpyridin-2-yl}-3,4-dihydro-2H-benzo[1,4]oxazine-8-carboxylate (536 mg) obtained in the First Step was dissolved in ethanol (10 ml), 2 M sodium hydroxide solution (2 ml) was added, and the mixture was stirred at 60° C. for 1 hour. The reaction mixture was neutralized by adding hydrochloric acid and concentrated, partitioned between water and ethyl acetate. The thus obtained ethyl acetate layer was dried over anhydrous sodium sulfate and concentrated to obtain the title compound (493 mg).

Third Step

Production of N-(4-trifluoromethoxyphenyl)-4-{3-(tetrahydropyran-2-yl)oxymethylpyridin-2-yl}-3,4-dihydro-2H-benzo[1,4]oxazine-8-carboxamide:

4-{3-(Tetrahydropyran-2-yl)oxymethylpyridin-2-yl}-3,4-dihydro-2H-benzo[1,4]oxazine-8-carboxylic acid (266 mg) obtained in the Second Step and 4-trifluoromethoxyaniline (97 μl) was subjected to the reaction similar to that of the Eighth Step of Example 1-001 to obtain the title compound (222 mg).

Fourth Step

Production of N-(4-trifluoromethoxyphenyl)-4-(3-hydroxymethylpyridin-2-yl)-3,4-dihydro-2H-benzo[1,4]oxazine-8-carboxamide:

N-(4-trifluoromethoxyphenyl)-4-{3-(tetrahydropyran-2-yl)oxymethylpyridin-2-yl}-3,4-dihydro-2H-benzo[1,4]oxazine-8-carboxamide (217 mg) obtained in the Third Step was dissolved in methanol (5 ml), 6 M hydrochloric acid (0.3 ml) added, and the mixture was stirred at room temperature for 1 hour. The reaction mixture was diluted with water, neutralized by adding sodium hydroxide solution and extracted with ethyl acetate. The ethyl acetate layer was dried over anhydrous sodium sulfate, concentrated and purified by the use of silica gel chromatography to obtain the title compound (164 mg).

Example 2-12

Production of (+)-N-(4-trifluoromethylphenyl)-4-{3-chloro-5-(1-hydroxyethyl)pyridin-2-yl}-3,4-dihydro-2H-benzo[1,4]oxazine-8-carboxamide First Step Production of methyl 3-acetamide-2-hydroxybenzoate:

Methyl 3-aminosalicylate (10 g) obtained in the Second Step of Example 1-001 was dissolved in ethyl acetate (30 ml), water (30 ml) and sodium hydrogencarbonate (5.54 g) were added, and acetyl chloride (5 ml) was added with stirring under ice-cooling. After stirring at room temperature for 30 minutes, the ethyl acetate layer was dried over anhydrous sodium sulfate and concentrated to obtain the title compound (11.47 g).

Second Step

Production of methyl 4-acetyl-3,4-dihydro-2H-benzo[1,4]oxazine-8-carboxylate:

Methyl 3-acetamide-2-hydroxybenzoate obtained in the First Step was dissolved in N,N-dimethylformamide (42 ml), potassium carbonate (9.67 g) and 1-bromo-2-chloroethane (4.99 ml) were added, and the mixture was stirred at 50° C. overnight. The reaction mixture was partitioned between ethyl acetate and water, and ethyl acetate layer was washed with water, dried over anhydrous sodium sulfate and concentrated to obtain the title compound (4.32 g).

Third Step

Production of 4-acetyl-3,4-dihydro-2H-benzo[1,4]oxazine-8-carboxylic acid:

To methyl 4-acetyl-3,4-dihydro-2H-benzo[1,4]oxazine-8-carboxylate (4.32 g) obtained in the Second Step, 2 M sodium hydroxide solution, was added and the mixture was refluxed with stirring for 1.5 hour. The reaction mixture was cooled on ice, and tetrahydrofuran (10 ml) solution containing acetyl chloride (2.62 ml) was added dropwise. 2 M sodium hydroxide and acetyl chloride were further added until the reaction finished. The thus obtained reaction mixture was acidified with aqueous citric acid solution and extracted with ethyl acetate. The ethyl acetate layer was washed with saturated sodium chloride, dried over anhydrous sodium sulfate and then concentrated. Isopropanol was added to the concentrate, and the precipitated solid substance was collected by filtration and dried to obtain the title compound (2.25 g).

Fourth Step

Production of 4-acetyl-N-(4-trifluoromethylphenyl)-3,4-dihydro-2H-benzo[1,4]oxazine-8-carboxamide:

4-Acetyl-3,4-dihydro-2H-benzo[1,4]oxazine-8-carboxylic acid (2.75 g) obtained by the similar method of the Third Step was dissolved in tetrahydrofuran (30 ml), oxalyl chloride (1.3 ml) and N,N-dimethylformamide (one drop) were added, and the mixture was stirred at room temperature for 1 hour. To the reaction mixture was pyridine (30 ml) and 4-trifluoromethylaniline (1.9 ml) were added, and stirred at room temperature for 1 hour. The reaction mixture was partitioned between water and ethyl acetate, and the ethyl acetate layer was washed with water, dried over anhydrous sodium sulfate and then concentrated. Precipitated solid obtained by adding n-hexane and diethyl ether to the concentrate was collected by filtration and dried to obtain the title compound (2.70 g).

Fifth Step

Production of N-(4-trifluoromethylphenyl)-3,4-dihydro-2H-benzo[1,4]oxazine-8-carboxamide:

Tetrahydrofuran (15 ml) was added to 4-acetyl-N-(4-trifluoromethylphenyl)-3,4-dihydro-2H-benzo[1,4]oxazine-8-carboxamide (2.70 g) obtained in the Fourth Step, water (15 ml) and concentrated sulfuric acid (5 ml) were added, and the mixture was refluxed for 4 hours with stirring. The reaction mixture was cooled, neutralized with sodium hydroxide solution and extracted with ethyl acetate. The ethyl acetate layer was concentrated and purified by the use of silica gel column chromatography to obtain the title compound (1.94 g).

Sixth Step

Production of (2R)-2-phenylpronionate 1-(5,6-dichloropyridine-3-yl)ethyl ester:

2,3-dichloro-5-(1-hydroxy)ethylpyridine (7.58 g) was dissolved in tetrahydrofuran (65 ml), (R)-2-phenylpropionic acid (5.5 ml), diisopropyl azodicarboxylate (9.5 ml) and triphenylphosphine (12.54 g) were added, and the mixture was stirred for 1 hour under ice-cooling. A mixed solution of hexane-ethyl acetate (9:1) was added to the reaction mixture, the precipitated solid was filtered off, the filtrate was concentrated and purified by the use of silica gel chromatography to obtain more polar isomer (4.54 g) and less polar isomer (5.38 g) of the title compound.

Seventh Step

Production of 4-{3-chloro-5-[1-(2R)-2-phenylpropionyl)oxyethyl]pyridin-2-yl}-N-(4-trifluoromethylphenyl)-3,4-dihydro-2H-benzo[1,4]oxazine-8-carboxamide:

The more polar isomer of (2R)-2-phenylpropionate 1-(5,6-dichloropyridine-3-yl)ethyl ester (324 mg) obtained in the Sixth Step and N-(4-trifluoromethylphenyl)-3,4-dihydro-2H-benzo[1,4]oxazine-8-carboxamide (322 mg) were subjected to the reaction similar to that of the First Step of Example 2-01 to obtain the title compound (80 mg).

Eighth Step

Production of (+)-N-(4-trifluoromethylphenyl)-4-{3-chloro-5-(1-hydroxyethyl)pyridin-2-yl}-3,4-dihydro-2H-benzo[1,4]oxazine-8-carboxamide:

4-{3-chloro-5-[1-{(2R)-2-phenylpropionyl] oxyethyl}pyridin-2-yl}-N-(4-trifluoromethylphenyl)-3,4-dihydro-2H-benzo[1,4]oxazine-8-carboxamide (80 mg) obtained in the Seventh Step was dissolved in methanol (0.3 ml) and tetrahydrofuran (0.3 ml), 4 M sodium hydroxide (0.3 ml) was added, and the mixture was stirred at 60° C. for 1 hour. The reaction mixture was concentrated, and the precipitated solid obtained by adding water was collected by filtration and dried to obtain the dextro-compound in the title (32 mg).

Example 2-13

Production of (−)-N-(4-trifluoromethylphenyl)-4-{3-chloro-5-(1-hydroxyethyl)pyridin-2-yl}-3,4-dihydro-2H-benzo[1,4]oxazine-8-carboxamide Low polar isomer of (2R)-2-phenylpronionate 1-(5,6-dichloropyridine-3-yl)ethyl ester (324 mg) obtained in the Sixth Step of Example 2-12 was used, and the similar process subsequent to the Seventh Step of Example 2-12 was performed to obtain the levo-compound in the title (115 mg)

Example 2-14

Production of (+)-N-(4-trifluoromethoxyphenyl)-4-{3-chloro-5-(1-hydroxyethyl)pyridin-2-yl}-3,4-dihydro-2H-benzo[1,4]oxazine-8-carboxamide First Step Production of N-(4-trifluoromethoxyphenyl)-3,4-dihydro-2H-benzo[1,4]oxazine-8-carboxamide:

In the Fourth Step of Example 2-12, 4-trifluoromethoxyaniline (2.25 g) was used in the place of 4-trifluoromethylaniline, and the reaction similar to that of the processes 4 and 5 of Example 2-12 was performed to obtain the title compound (1.77 g).

Second Step

Production of (+)-N-(4-trifluoromethoxyphenyl)-4-{3-chloro-5-(1-hydroxyethyl)pyridin-2-yl}-3,4-dihydro-2H-benzo[1,4]oxazine-8-carboxamide:

N-(4-trifluoromethoxyphenyl)-3,4-dihydro-2H-benzo[1,4]oxazine-8-carboxamide (334 mg) obtained in the First Step and a more polar isomer of (2R)-2-phenylpropionate 1-(5,6-dichloropyridine-3-yl)ethyl ester (320 mg) obtained in the Sixth Step of Example 2-12 were used, and the reaction subsequent to the Seventh Step of Example 2-12 was performed to obtain dextro-compound in the title (197 mg).

Example 2-15

Production of (−)-N-(4-trifluoromethoxyphenyl)-4-{3-chloro-5-(1-hydroxyethyl)pyridin-2-yl}-3,4-dihydro-2H-benzo[1,4]oxazine-8-carboxamide In the Second Step of Example 2-14, the more polar isomer of (2R)-2-phenylpropionate 1-(5,6-dichloropyridine-3-yl) ethyl ester was replaced by the low polar isomer (320 mg), and others were performed similarly to obtain levo-compound in the title (180 mg).

Example 2-16 to Example 2-48

Compounds of Examples 2-16 to 2-48 shown in the following tables were obtained by similarly performing any methods described in the general processes A to C for producing the compound and/or the methods described in Examples 2-01 to 2-15 hereinbefore.

Example 3

N-(4-trifluoromethoxyphenyl)-4-(3-chloropyridin-2-yl)-3,4-dihydro-3-oxo-2H-benzo[1,4]oxazine-8-carboxamide First Step Production of methyl 2-methoxymethyloxy-3-nitrobenzoate:

Methyl 3-nitrosalicylate (5.91 g) obtained in the First Step of Example 1-001 was dissolved in N,N-dimethylformamide (60 ml), potassium carbonate (8.29 g) was added, methoxymethyl chloride (2.73 ml) was added with stirring under ice-cooling, and the mixture was stirred for 4.5 hours. The reaction mixture was concentrated and was partitioned between ethyl acetate and water. The ethyl acetate layer was washed with water, dried over anhydrous sodium sulfate and concentrated to obtain the title compound (6.98 g).

Second Step

Production of methyl 3-amino-2-methoxymethyloxybenzoate:

Methyl 2-methoxymethyloxy-3-nitrobenzoate (6.98 g) obtained in the First Step was subjected to hydrogenation similar to the Second Step of Example 1-001 to obtain the title compound (6.11 g).

Third Step

Production of methyl 3-(3-chloropyridin-2-yl)amino-2-methoxymethyloxybenzoate:

Methyl 3-amino-2-methoxymethyloxybenzoate (6.11 g) obtained in the Second Step and 2,3-dichloropyridine (4.29 g) were subjected to the reaction similar to that of the First Step of Example 2-01 to obtain the title compound (7.46 g)

Fourth Step

Production of methyl 3-(3-chloropyridin-2-yl)aminosalicylate:

Methyl 3-(3-chloropyridin-2-yl)amino-2-methoxymethyloxybenzoate (7.46 g) obtained in the Third Step was dissolved in methanol (50 ml), 6 M hydrochloric acid was added, and the mixture was stirred at 40° C. for 1 hour. The reaction mixture was concentrated. The solid substance precipitated by adding water was collected by filtration and dried to obtain the title compound (5.64 g).

Fifth Step

Production of 3-(3-chloropyridin-2-yl)aminosalicylic acid:

Methyl 3-(3-chloropyridin-2-ylamino)salicylate (3.08 g) obtained in the Fourth Step was dissolved in methanol (20 ml), 4 M sodium hydroxide (8.3 ml) was added, and the mixture was stirred at 70° C. for 3 hours. The reaction mixture was concentrated. Aqueous citric acid solution was added to the residue, and the solid was substance precipitated collected by filtration and dried to obtain the title compound (2.73 g)).

Sixth Step

Production of 3-(3-chloropyridin-2-yl)amino-N-(4-trifluoromethoxy)benzamide Obtained in the Previous Fifth Step:

(2.73 g) and 4-trifluoromethoxyaniline (1.46 ml) were subjected to condensation similar to the Eighth Step of Example 1-001 to obtain the title compound (2.90 g).

Seventh Step

Production of 3-[(3-chloropyridin-2-yl)-(chloroacetyl)]amino-N-(4-trifluoromethoxy)benzamide:

3-(3-chloropyridin-2-yl)amino-N-(4-trifluoromethoxy)benzamide (0.84 g) obtained in the Sixth Step was dissolved in tetrahydrofuran (10 ml), triethylamine (0.30 ml) and chloroacetylchloride (0.175 ml) under ice-cooling were added in this order, and the mixture was stirred for 1 hour. The reaction mixture was partitioned between ethyl acetate and water. The ethyl acetate layer was washed with water, aqueous citric acid solution, aqueous sodium hydrogencarbonate and saturated sodium chloride solution, in this order, dried over anhydrous sodium sulfate and concentrated to obtain residue containing the title compound.

Eighth Step

Production of N-(4-trifluoromethoxyphenyl)-4-(3-chloropyridin-2-yl)-3,4-dihydro-3-oxo-2H-benzo[1,4]oxazine-8-carboxamide:

The residue obtained in the previous step was dissolved in N,N-dimethylformamide (10 mL), potassium carbonate (0.55 g) was added, and the mixture was stirred at 80° C. for 1 hour. After concentrating the reaction solution, the solution was partitioned between ethyl acetate and water. The ethyl acetate layer was washed with water, aqueous citric acid solution, and saturated saline solution, in this order, dried over anhydrous sodium sulfate and then concentrated. The concentrated residue was purified by the use of silica gel chromatography to obtain the title compound (519 mg).

Example 4

Example 4-01

Production of (R)-4-(3-chloropyridin-2-yl)-3-hydroxylmethyl-N-(4-trifluoromethoxyphenyl)-3,4-dihydro-2H-benzo[1,4]oxazine-8-carboxamide First Step Production of (S)-methyl 3-(3-chloropyridin-2-yl)amino-2-(oxirane-2-yl)methyloxybenzoate:

Methyl 3-(3-chloropyridin-2-yl)aminosalicylate (6.08 g) obtained in the Fourth Step of Example 3 was dissolved in N,N-dimethylformamide (60 ml), potassium carbonate (3.01 g) and (S)-glycidyl nosylate (6.78) were added, and the mixture was stirred at room temperature for 13 hours. The reaction mixture was partitioned between diethyl ether and water. Ether layer was washed with water, aqueous sodium hydrogencarbonate solution and saturated sodium chloride solution, dried over anhydrous sodium sulfate and then concentrated. The residue was purified by the use of silica gel chromatography to obtain the title compound (7.22 g).

Second Step

Production of (R)-methyl 4-(3-chloropyridin-2-yl)-3-hydroxylmethyl-3,4-dihydro-2H-benzo[1,4]oxazine-8-carboxylate:

(S)-Methyl 3-(3-chloropyridin-2-yl)amino-2-(oxirane-2-yl)methyloxybenzoate (7.10 g) obtained in the First Step was dissolved in N,N-dimethylformamide (70 ml), potassium carbonate (3.66 g) was added, and the mixture was stirred at 60° C. for 2 hours. The reaction mixture was partitioned between water and ethyl acetate. The ethyl acetate layer was washed with saturated sodium chloride solution, dried over anhydrous sodium sulfate and then concentrated. The residue was purified by the use of silica gel chromatography to obtain the colorless oily compound in the title (3.42 g).

Third Step

Production of (R)-methyl 4-(3-chloropyridin-2-yl)-3-(tetrahydropyran-2-yl)oxymethyl-3,4-dihydro-2H-benzo[1,4]oxazine-8-carboxylate:

(R)-methyl 4-(3-chloropyridin-2-yl)-3-hydroxylmethyl-3,4-dihydro-2H-benzo[1,4]oxazine-8-carboxylate (3.33 g) obtained in the Second Step was dissolved in chloroform (35 ml), 2,3-dihydropyran (1.0 g) and tin chloride dihydrate (225 mg) were added, and the mixture was stirred at room temperature for 17 hours. The reaction mixture was concentrated and purified by the use of silica gel chromatography to obtain the oily compound in the title (3.49 g).

Fourth Step

Production of (R)-4-(3-chloropyridin-2-yl)-3-(tetrahydropyran-2-yl)oxymethyl-3,4-dihydro-2H-benzo[1,4]oxazine-8-carboxylic acid:

(R)-methyl 4-(3-chloropyridin-2-yl)-3-(tetrahydropyran-2-yl)oxymethyl-3,4-dihydro-2H-benzo[1,4]oxazine-8-carboxylate (3.39 g) obtained in the Third Step was dissolved in tetrahydrofuran (15 ml) and methanol (15 ml), 4 M sodium hydroxide (10 ml) was added, and stirred at 60° C. for 0.5 hour. The reaction mixture was neutralized with hydrochloric acid concentrated, and partitioned between water and ethyl acetate. The ethyl acetate layer was washed with saturated sodium chloride solution, dried over anhydrous sodium sulfate and concentrated to obtain the title compound (3.15 g).

Fifth Step

Production of (R)-4-(3-chloropyridin-2-yl)-3-(tetrahydropyran-2-yl)oxymethyl-N-(4-trifluoromethoxyphenyl)-3,4-dihydro-3-oxo-2H-benzo[1,4]oxazine-8-carboxamide:

(R)-4-(3-chloropyridin-2-yl)-3-(tetrahydropyran-2-yl)oxymethyl-3,4-dihydro-2H-benzo[1,4]oxazine-8-carboxylic acid (1.20 g) obtained in the Fourth Step and 4-trifluoromethoxyaniline (525 mg) were subjected to condensation similar to the Eighth Step of Example 1-001 to obtain the white amorphous compound in the title (1.40 g).

Sixth Step

Production of (R)-4-(3-chloropyridin-2-yl)-3-hydroxylmethyl-N-(4-trifluoromethoxyphenyl)-3,4-dihydro-2H-benzo[1,4]oxazine-8-carboxamide:

(R)-4-(3-chloropyridin-2-yl)-3-(tetrahydropyran-2-yl)oxymethyl-N-(4-trifluoromethoxyphenyl)-3,4-dihydro-2H-benzo[1,4]oxazine-8-carboxamide (1.33 g) obtained in the Fifth Step was dissolved in tetrahydrofuran (15 ml), 6 M hydrochloric acid (2 ml) was added, and the mixture was stirred at room temperature for 1 hour. The reaction mixture was partitioned between water and ethyl acetate. The ethyl acetate layer was washed with water and saturated sodium chloride solution, in this order, dried over anhydrous sodium sulfate and then concentrated. The concentrated residue was purified by the use of silica gel column chromatography to obtain the title compound (930 mg).

Example 4-02

Production of (R)-4-(3-chloropyridin-2-yl)-3-hydroxylmethyl-N-(4-trifluoromethylphenyl)-3,4-dihydro-2H-benzo[1,4]oxazine-8-carboxamide First Step Production of (R)-4-(3-chloropyridin-2-yl)-3-(tetrahydropyran-2-yl)oxymethyl-N-(4-trifluoromethylphenyl)-3,4-dihydro-2H-benzo[1,4]oxazine-8-carboxamide:

(R)-4-(3-chloropyridin-2-yl)-3-(tetrahydropyran-2-yl) oxymethyl-3,4-dihydro-2H-benzo[1,4]oxazine-8-carboxylic acid (1.63 g) obtained in the Fourth Step of Example 4-01 was dissolved in pyridine (15 ml), thionyl chloride (0.352 ml) was added, and the mixture was stirred at room temperature for 1 hour. A solution of 4-trifluoromethylaniline (0.973 ml) in pyridine (1 ml) was added and the mixture was further stirred for 1 hour. The reaction mixture was concentrated and partitioned between water and ethyl acetate. The thus obtained ethyl acetate layer was washed with aqueous citric acid solution, aqueous sodium hydrogencarbonate and saturated sodium chloride solution, in this order, dried over anhydrous sodium sulfate and then concentrated. The thus obtained residue was purified by the use of silica gel column chromatography to obtain the white amorphous compound in the title (2.03 g).

Second Step

Production of (R)-4-(3-chloropyridin-2-yl)-3-hydroxylmethyl-N-(4-trifluoromethylphenyl)-3,4-dihydro-2H-benzo [1,4]oxazine-8-carboxamide:

(R)-4-(3-chloropyridin-2-yl)-3-(tetrahydropyran-2-yl) oxymethyl-N-(4-trifluoromethylphenyl)-3,4-dihydro-2H-benzo[1,4]oxazine-8-carboxamide (1.93 g) obtained in the First Step was subjected to the reaction similar to that of the Sixth Step of Example 4-01 to obtain the title compound (1.34 g)

Example 4-03

Production of (S)-4-(3-chloropyridin-2-yl)-3-hydroxylmethyl-N-(4-trifluoromethoxyphenyl)-3,4-dihydro-2H-benzo[1,4]oxazine-8-carboxamide First Step Production of (S)-4-(3-chloropyridin-2-yl)-3-(tetrahydropyran-2-yl)oxymethyl-3,4-dihydro-2H-benzo[1,4]oxazine-8-carboxylic acid:

In the First Step of Example 4-01, (R)-glycidyl nosylate (6.74 g) was used in the place of (S)-glycidyl nosylate, and the reaction was performed in the similar manner from the First Step to the Fourth Step to obtain the title compound (3.88 g).

Second Step

Production of (S)-4-(3-chloropyridin-2-yl)-3-hydroxylmethyl-N-(4-trifluoromethoxyphenyl)-3,4-dihydro-2H-benzo [1,4]oxazine-8-carboxamide:

(S)-4-(3-chloropyridin-2-yl)-3-(tetrahydropyran-2-yl) oxymethyl-3,4-dihydro-2H-benzo[1,4]oxazine-8-carboxylic acid (1.88 g) obtained in the First Step was used, and the reactions similar to the Fifth Step and the Sixth Step of Example 4-01 were performed to obtain the title compound (1.126 g)

Example 4-04

Production of (S)-4-(3-chloropyridin-2-yl)-3-hydroxylmethyl-N-(4-trifluoromethylphenyl)-3,4-dihydro-2H-benzo[1,4]oxazine-8-carboxamide (S)-4-(3-chloropyridin-2-yl)-3-(tetrahydropyran-2-yl) oxymethyl-3,4-dihydro-2H-benzo[1,4]oxazine-8-carboxylic acid (2.0 g) obtained in the First Step of Example 4-03 was used, and the reaction similar to that of the process of Example 4-02 was performed to obtain the title compound (0.872 g).

Example 4-05

Production of (S)-4-(5-chloropyridin-2-yl)-3-hydroxylmethyl-N-(4-trifluoromethoxyphenyl)-3,4-dihydro-2H-benzo[1,4]oxazine-8-carboxamide First Step Production of methyl 3-(5-chloropyridin-2-yl)amino-2-methoxymethyloxybenzoate:

Methyl 3-amino-2-methoxymethyloxybenzoate (4.2 g) obtained by the same method in the Second Step of Example 3 and 2,5-dichloropyridine (3.0 g) were subjected to the reaction similar to that of the First Step of Example 2-01 to obtain the title compound (1.0 g).

Second Step

Production of (S)-4-(5-chloropyridin-2-yl)-3-hydroxylmethyl-N-(4-trifluoromethoxyphenyl)-3,4-dihydro-2H-benzo [1,4]oxazine-8-carboxamide:

Methyl 3-(5-chloropyridin-2-yl)amino-2-methoxymethyloxybenzoate (330 mg) obtained in the First Step was used, and others were treated by the similar way to Example 4-03 to obtain the title compound (83 mg).

Example 4-06

Production of (S)-4-(5-chloropyridin-2-yl)-3-hydroxylmethyl-N-(4-trifluoromethylphenyl)-3,4-dihydro-2H-benzo[1,4]oxazine-8-carboxamide First Step Production of methyl 3-(5-chloropyridin-2-yl)amino-2-hydroxybenzoate:

In the Third Step of Example 3, 2,5-dichloropyridine (3.0 g) was used in the place of 2,3-dichloropyridine, methyl 3-amino-2-methoxymethyloxybenzoate (4.20 g) was subjected to the reaction similar to that of the Fourth Step to obtain the title compound (1.0 g).

Second Step

Production of (S)-4-(5-chloropyridin-2-yl)-3-(tetrahydropyran-2-yl)oxymethyl-3,4-dihydro-2H-benzo[1,4]oxazine-8-carboxylic acid:

Methyl 3-(5-chloropyridin-2-yl)amino-2-hydroxybenzoate (1.0 g) obtained in the First Step was used in the First Step of Example 4-01 except that (R)-glycidyl nosylate (1.1 g) was used in the place of (S)-glycidyl nosylate and others were performed in a similar manner as from the First Step to the Fourth Step to obtain the title compound (830 mg).

Third Step

Production of (S)-4-(5-chloropyridin-2-yl)-3-hydroxylmethyl-N-(4-trifluoromethlphenyl)-3,4-dihydro-2H-benzo[1, 4]oxazine-8-carboxamide:

The process similar to Example 4-02 was performed by using (S)-4-(5-chloropyridin-2-yl)-3-(tetrahydropyran-2-yl) oxymethyl-3,4-dihydro-2H-benzo[1,4]oxazine-8-carboxylic acid (500 mg) obtained in the Second Step to obtain the title compound (104 mg).

Example 4-07

Production of (S)-4-(5-picoline-2-yl)-3-hydroxylmethyl-N-(4-trifluoromethoxyphenyl)-3,4-dihydro-2H-benzo[1,4]oxazine-8-carboxamide In Example 4-05, 6-chloro-3-picoline was used in the place of 2,5-dichloropyridine, and was subjected to the reaction similar to that of the process to obtain the title compound (91 mg).

Example 4-08

Production of (S)-4-(5-picoline-2-yl)-3-hydroxylmethyl-N-(4-trifluoromethylphenyl)-3,4-dihydro-2H-benzo[1,4]oxazine-8-carboxamide In Example 4-06, 6-chloro-3-picoline was used in the place of 2,5-dichloropyridine, and subjected to the reaction similar to that of the process to obtain the title compound (167 mg)

Example 4-09 to Example 4-56

Compounds of Examples 4-09 to 4-56 shown in the following tables were obtained by similarly performing any methods described in the general processes A to C for producing the compound and/or the methods described in Examples 4-01 to 4-08 hereinbefore.

Example 4-57

Production of (R)-9-(3-chloropyridin-2-yl)-7-hydroxy-N-(4-trifluoromethoxyphenyl)-6,7,8,9-tetrahydro-5-oxa-9-azabenzocycloheptane-4-carboxamide First Step Production of methyl (R)-9-(3-chloropyridin-2-yl)-7-hydro-6,7,8,9-tetrahydro-5-oxa-9-azabenzocycloheptane-4-carboxylate:

(S)-3-(3-chloropyridin-2-yl)amino-2-(oxirane-2-yl)methyloxybenzoate (0.30 g), which was obtained by using (R)-glycidyl nosylate in the place of (S)-glycidyl nosylate in the process of Example 4-01, was dissolved in N,N-dimethylformamide (5 ml), sodium methoxide (72 mg) was added, and the mixture was stirred at room temperature for 1.5 hour. The reaction mixture was partitioned between ethyl acetate and water. The ethyl acetate layer was washed with water and dried over anhydrous sodium sulfate. Solvent was distilled off to obtain the oily substance containing the title compound.

Second Step

Production of (R)-9-(3-chloropyridin-2-yl)-7-hydro-6,7,8,9-tetrahydro-5-oxa-9-azabenzocycloheptane-4-carboxylic acid:

Methyl (R)-9-(3-chloropyridin-2-yl)-7-hydro-6,7,8,9-tetrahydro-5-oxa-9-azabenzocycloheptane-4-carboxylate (520 mg) obtained by the method similar to the previous step was dissolved in methanol (5 ml), 4 N sodium hydroxide (1.6 ml) was added, and the mixture was stirred at 65° C. for 3 hours. The reaction mixture was concentrated and partitioned between water and ethyl acetate. The aqueous layer was adjusted to pH 3 by adding 6 N hydrochloric acid. The precipitated solid substance was collected by filtration, washed with water and dried to obtain the title compound (415 mg).

Third Step

Production of (R)-9-(3-chloropyridin-2-yl)-7-hydroxy-N-(4-trifluoromethoxyphenyl)-6,7,8,9-tetrahydro-5-oxa-9-azabenzocycloheptane-4-carboxamide:

(R)-9-(3-chloropyridin-2-yl)-7-hydro-6,7,8,9-tetrahydro-5-oxa-9-azabenzocycloheptane-4-carboxylic acid (321 mg) obtained in the Second Step was subjected to the condensation reaction similar to that of the Eighth Step of Example 1-001 to obtain the title compound (310 mg).

Example 4-58

Production of (R)-9-(3-chloropyridin-2-yl)-7-hydroxy-N-(4-trifluoromethylphenyl)-6,7,8,9-tetrahydro-5-oxa-9-azabenzocycloheptane-4-carboxamide In the production process of Example 4-04, when the reaction similar to that of the Sixth Step of Example 4-01 was performed, the title compound of white solid substance was obtained as the by-product.

Example 4-59

Production of (S)-9-(3-chloropyridin-2-yl)-7-hydroxy-N-(4-trifluoromethoxyphenyl)-6,7,8,9-tetrahydro-5-oxa-9-azabenzocycloheptane-4-carboxamide (S)-glycidyl nosylate was used in the method similar to Example 4-57 to obtain the title compound.

Example 5

Example 5-01

Production of N-(4-tert-butylphenyl)-4-(pyrazine-2-yl)-3,4-dihydro-2H-benzo[1,4]oxazine-8-carboxamide First Step Production of methyl 4-(pyrazine-2-yl)-3,4-dihydro-2H-benzo[1,4]oxazine-8-carboxylate:

Methyl 3,4-dihydro-2H-benzo[1,4]oxazine-8-carboxylate (1.0 g) obtained in the Fifth Step of Example 1-001 and chloropyrazine (0.6 g) were used, and the coupling reaction similar to that of the Fourth Step of Example 1-002 was performed to obtain the oily compound in the title (0.84 g).

Second Step

Production of 4-(pyrazine-2-yl)-3,4-dihydro-2H-benzo[1,4]oxazine-8-carboxylic acid:

Methyl 4-(pyrazine-2-yl)-3,4-dihydro-2H-benzo[1,4]oxazine-8-carboxylate (0.84 g) obtained in the First Step was dissolved in tetrahydrofuran (2 ml) and methanol (2 ml), 2 N sodium hydroxide (3 ml) was added, and the mixture was stirred at 60° C. for 3 hours. The reaction mixture was concentrated and 1 N potassium hydrogen sulfate was added. The precipitated yellowish solid substance was collected by filtration and dried to obtain the title compound (0.40 g).

Third Step

Production of N-(4-tert-butylphenyl)-4-(pyrazine-2-yl)-3,4-dihydro-2H-benzo[1,4]oxazine-8-carboxamide:

4-(pyrazine-2-yl)-3,4-dihydro-2H-benzo[1,4]oxazine-8-carboxylic acid (150 mg) obtained in the Second Step was dissolved in tetrahydrofuran (3 ml), oxalyl chloride (0.05 ml) and N,N-dimethylformamide (one drop) were added, and the mixture was stirred at room temperature for 0.5 hour. The reaction mixture was concentrated. The concentrated residue was dissolved in tetrahydrofuran (3 ml), tert-butylaniline (74 mg) and triethylamine (0.5 ml) were added, and the mixture was stirred at room temperature for 0.5 hour. The reaction mixture was partitioned between water and ethyl acetate, and the ethyl acetate layer was dried over anhydrous sodium sulfate and then concentrated. The residue was dissolved in methanol with heating. The solution was cooled to obtain a solid substance, which was collected by filtration and dried to obtain the title compound (12 mg).

Example 5-02

Production of N-(4-chlorophenyl)-4-(5-ethylpyrimidin-2-yl)-3,4-dihydro-2H-benzo[1,4]oxazine-8-carboxamide First Step
Production of methyl 4-(5-ethylpyrimidin-2-yl)-3,4-dihydro-2H-benzo[1,4]oxazine-8-carboxylate:
Methyl 3,4-dihydro-2H-benzo[1,4]oxazine-8-carboxylate (677 mg) obtained in the Fifth Step of Example 1-001 and 2-chloro-4-ethylpyrimidine (500 mg) were used, and the coupling reaction similar to that of the Fourth Step of Example 1-002 was performed to obtain the yellowish oily compound in the title (944 mg).

Second Step
Production of 4-(5-ethylpyrimidin-2-yl)-3,4-dihydro-2H-benzo[1,4]oxazine-8-carboxylic acid:
Methyl 4-(5-ethylpyrimidin-2-yl)-3,4-dihydro-2H-benzo[1,4]oxazine-8-carboxylate (944 mg) obtained in the First Step was subjected to the reaction similar to that of the Second Step of example 5-02 to obtain white solid compound in the title (820 mg).

Third Step
Production of N-(4-chlorophenyl)-4-(5-ethylpyrimidin-2-yl)-3,4-dihydro-2H-benzo[1,4]oxazine-8-carboxamide:
4-(5-ethylpyrimidin-2-yl)-3,4-dihydro-2H-benzo[1,4]oxazine-8-carboxylic acid (100 mg) obtained in the Second Step and 4-chloroaniline (45 mg) were subjected to the condensation reaction similar to that of the Eighth Step of Example 1-001 to obtain the title compound (99 mg).

Example 5-03

Production of N-(4-ethoxyphenyl)-4-(5-ethylpyrimidin-2-yl)-3,4-dihydro-2H-benzo[1,4]oxazine-8-carboxamide 4-(5-ethylpyrimidin-2-yl)-3,4-dihydro-2H-benzo[1,4]oxazine-8-carboxylic acid (100 mg) obtained in the Second Step of example 5-02 and p-phenetidine (48 mg) were subjected to the condensation reaction similar to that of the Eighth Step of Example 1-001 to obtain the title compound (84 mg).

Example 5-04

Production of 4-(6-chloropyridazine-3-yl)-N-(4-trifluoromethylphenyl)-3,4-dihydro-2H-benzo[1,4]oxazine-8-carboxamide First Step
Production of methyl 4-(6-chloropyridazine-3-yl)-3,4-dihydro-2H-benzo[1,4]oxazine-8-carboxylate:
Methyl 3,4-dihydro-2H-benzo[1,4]oxazine-8-carboxylate (0.5 g) obtained in the Fifth Step of Example 1-001 and 3,6-dichloropiridazine (0.575 g) were used, and the coupling reaction similar to that of the Fourth Step of Example 1-002 was performed to obtain the title compound (0.24 g).

Second Step
Production of 4-(6-chloropyridazine-3-yl)-3,4-dihydro-2H-benzo[1,4]oxazine-8-carboxylic acid:
Methyl 4-(6-chloropyridazine-3-yl)-3,4-dihydro-2H-benzo[1,4]oxazine-8-carboxylate (240 mg) obtained in the First Step was subjected to the reaction similar to that of the Second Step of example 5-02 to obtain the solid compound in the title (145 mg).

Third Step
Production of 4-(6-chloropyridazine-3-yl)-N-(4-trifluoromethylphenyl)-3,4-dihydro-2H-benzo[1,4]oxazine-8-carboxamide:
4-(6-chloropyridazine-3-yl)-3,4-dihydro-2H-benzo[1,4]oxazine-8-carboxylic acid (145 mg) obtained in the Second Step and 4-trifluoromethylaniline (89 mg) were subjected to the condensation reaction similar to example 5-01, and purified by the use of silica gel chromatography (n-hexane:ethylacetate=3:1) to obtain the title compound (38 mg)

Example 5-05

Production of 4-(4-methylthiazol-2-yl)-N-(4-trifluoromethoxyphenyl)-3,4-dihydro-2H-benzo[1,4]oxazine-8-carboxamide First Step
Production of methyl 4-thiocarbamide-3,4-dihydro-2H-benzo[1,4]oxazine-8-carboxylate:
Methyl 3,4-dihydro-2H-benzo[1,4]oxazine-8-carboxylate (1.93 g) obtained in the Fifth Step of Example 1-001 was dissolved in tetrahydrofuran (20 ml), 9-fluorenylmethyloxycarbonyl isothiocyanate (2.95 g) was added under ice-cooling, and the mixture was stirred for 0.5 hour. Piperidine (5 ml) was added and the mixture was further stirred for 0.5 hour. The thus obtained reaction mixture was concentrated, and the residue was purified by the use of silica gel chromatography to obtain the title compound (2.27 g).

Second Step
Production of methyl 4-(4-methylthiazol-2-yl)-3,4-dihydro-2H-benzo[1,4]oxazine-8-carboxylate:
Methyl 4-thiocarbamide-3,4-dihydro-2H-benzo[1,4]oxazine-8-carboxylate (1.10 g) obtained in the First Step was dissolved in methanol (15 ml), chloroacetone (0.4 ml) was added, and the mixture was refluxed for 5 hours. The reaction mixture was concentrated and partitioned between ethyl acetate and saturated sodium hydrogencarbonate solution. The ethyl acetate layer was washed with water, aqueous citric acid and saturated sodium chloride solution, in this order, dried over anhydrous sodium sulfate and concentrated to obtain the residue containing the title compound.

Third Step
Production of 4-(4-methylthiazol-2-yl)-3,4-dihydro-2H-benzo[1,4]oxazine-8-carboxylic acid:
The residue containing methyl 4-(4-methylthiazol-2-yl)-3,4-dihydro-2H-benzo[1,4]oxazine-8-carboxylate obtained in the Second Step was dissolved in methanol (10 ml), 4 N sodium hydroxide (3 ml) was added, and the mixture was refluxed for 0.5 hour. The reaction mixture was concentrated. The solid precipitated by adding aqueous citric acid was collected by filtration and dried to obtain the title compound (1.10 g).

Fourth Step
Production of 4-(4-methylthiazol-2-yl)-N-(4-trifluoromethoxyphenyl)-3,4-dihydro-2H-benzo[1,4]oxazine-8-carboxamide:
4-(4-methylthiazol-2-yl)-3,4-dihydro-2H-benzo[1,4]oxazine-8-carboxylic acid (0.55 g) obtained in the Third Step and 4-trifluoromethoxyaniline (0.28 ml) were subjected to the reaction similar to that of the Eighth Step of Example 1-001 and purified by the use of silica gel chromatography to obtain the title compound (0.722 g).

Example 5-06

Production of 4-(5-methylthiazol-2-yl)-N-(4-trifluoromethoxyphenyl)-3,4-dihydro-2H-benzo[1,4]oxazine-8-carboxamide First Step
Production of methyl 4-(5-methylthiazol-2-yl)-3,4-dihydro-2H-benzo[1,4]oxazine-8-carboxylate:

2,4,6-tris(1-chloroethyl)-1.3.5-trioxane (0.64 g) and montmorillonite K-10 (39 mg) were heated at 110° C. for 10 minutes. Toluene (10 ml) and methyl 4-thiocarbamide-3,4-dihydro-2H-benzo[1,4]oxazine-8-carboxylate (1.17 g) obtained in the First Step of example 5-05 were added, then 2,4,6-tris(1-chloroethyl)-1.3.5-trioxane was added appropriately under heated to reflux until the reaction was terminated. The reaction mixture was concentrated and partitioned between ethyl acetate and saturated sodium hydrogencarbonate solution. The ethyl acetate layer was concentrated to obtain the title compound (0.68 g).

Second Step
Production of 4-(5-methylthiazol-2-yl)-3,4-dihydro-2H-benzo[1,4]oxazine-8-carboxylic acid:

Methyl 4-(5-methylthiazol-2-yl)-3,4-dihydro-2H-benzo[1,4]oxazine-8-carboxylate (0.68 g) obtained in the Second Step was dissolved in methanol (7 ml), 4 N sodium hydroxide (1.77 ml) was added, and the mixture was refluxed for 20 minutes with stirring. The reaction mixture was concentrated. The solid precipitated by adding aqueous citric acid was collected by filtration and dried to obtain the title compound (0.66 g).

Third Step
Production of 4-(5-methylthiazol-2-yl)-N-(4-trifluoromethoxyphenyl)-3,4-dihydro-2H-benzo[1,4]oxazine-8-carboxamide:

4-(5-methylthiazol-2-yl)-3,4-dihydro-2H-benzo[1,4]oxazine-8-carboxylic acid (0.66 g) obtained in the Second Step and 4-trifluoromethoxyaniline (0.28 ml) were subjected to the reaction similar to that of the Eighth Step of Example 1-001 to obtain the title compound (0.878 g).

Example 6

Example 6-01

Production of (S)-3-hydroxymethyl-4-(5-methylthiazol-2-yl)-N-(4-trifluoromethoxyphenyl)-3,4-dihydro-2H-benzo[1,4]oxazine-8-carboxamide First Step
Production of methyl 2-methoxymethyloxy-3-thioureid benzoate:

Methyl 3-amino-2-methoxymethyloxybenzoate (2.11 g) obtained in the Second Step of Example 3 was dissolved in tetrahydrofuran (20 ml), and 9-fluorenylmethyloxycarbonyl isothiocyanate (3.09 g) was added under ice-cooling, and the mixture was stirred for 3 hours. The reaction mixture was concentrated, N,N-dimethylformamide and piperidine (1 ml) were added, and the mixture was further stirred for 2 hours. The thus obtained reaction mixture was concentrated and partitioned between ethyl acetate and water. The ethyl acetate layer was washed with aqueous citric acid, saturated sodium hydrogencarbonate solution and saturated sodium chloride solution, in this order, dried over anhydrous sodium sulfate and concentrated to obtain the title compound (1.91 g).

Second Step
Production of methyl 3-(5-methylthiazol-2-yl)aminosalicylate:

Methyl 2-methoxymethyloxy-3-thioureidbenzoate (1.64 g) obtained in the First Step was subjected to the reaction similar to that of the First Step of example 5-06 to obtain the title compound (734 mg).

Third Step
Production of methyl (R)-3-(5-methylthiazol-2-yl)amino-2-(oxirane-2-yl)methyloxybenzoate:

Methyl 3-(5-methylthiazol-2-yl)aminosalicylate (848 mg) obtained by the similar method as in the Second Step was dissolved in N,N-dimethylformamide (8 ml), potassium carbonate (452 mg) and (R)-glycidyl nosylate (915 mg) were added, and the mixture was stirred at room temperature for 5 hours. The reaction mixture was partitioned between ethyl acetate and water. The ethyl acetate layer was washed with water and saturated sodium chloride solution, dried over anhydrous sodium sulfate and then concentrated. The residue was purified by the use of silica gel chromatography (n-hexane:ethyl acetate=3:1) to obtain the title compound (719 mg)

Fourth Step
Production of methyl (S)-3-hydroxymethyl-4-(5-methylthiazol-2-yl)-3,4-dihydro-2H-benzo[1,4]oxazine-8-carboxylate:

Methyl (R)-3-(5-methylthiazol-2-yl)amino-2-(oxirane-2-yl)methyloxybenzoate (700 mg) obtained in the Third Step was dissolved in dimethyl sulfoxide (5 ml), 1,8-diazabicyclo[5.4.0]undece-7-ene (166 mg) was added, and the mixture was stirred at room temperature for 1.5 hour. The reaction mixture was partitioned between ethyl acetate and water. The ethyl acetate layer was washed with water and saturated sodium chloride solution, dried over anhydrous sodium sulfate and concentrated to obtain the colorless oily compound in the title (695 mg).

Fifth Step
Production of methyl (S)-4-(5-methylthiazol-2-yl)-3-(tetrahydropyran-2-yl)oxymethyl-3,4-dihydro-2H-benzo[1,4]oxazine-8-carboxylate:

Methyl (S)-3-hydroxymethyl-4-(5-methylthiazol-2-yl)-3,4-dihydro-2H-benzo[1,4]oxazine-8-carboxylate (695 mg) obtained in the Fourth Step was dissolved in chloroform (7 ml), 2,3-dihydropyran (700 mg) and p-toluenesulfonic acid hydrate (453 mg) were added, and the mixture was stirred at room temperature for 7 hours. The reaction mixture was concentrated and partitioned between ethyl acetate and saturated sodium hydrogencarbonate solution. The thus obtained ethyl acetate layer was washed with saturated sodium chloride solution, dried over anhydrous sodium sulfate and then concentrated. The concentrated residue was purified by the use of silica gel chromatography (n-hexane:ethyl acetate=3:1) to obtain the title compound (552 mg).

Sixth Step
Production of (S)-4-(5-methylthiazol-2-yl)-3-(tetrahydropyran-2-yl)oxymethyl-3,4-dihydro-2H-benzo[1,4]oxazine-8-carboxylic acid:

Methyl (S)-4-(5-methylthiazol-2-yl)-3-(tetrahydropyran-2-yl)oxymethyl-3,4-dihydro-2H-benzo[1,4]oxazine-8-carboxylate (552 mg) was dissolved in tetrahydrofuran (2.5 ml) and methanol (2.5 ml), 4 M sodium hydroxide (1.0 ml) was added, and the mixture was stirred at 60° C. for 1 hour. The reaction mixture was neutralized with diluted hydrochloric acid and extracted with ethyl acetate. The ethyl acetate layer was washed with saturated sodium chloride solution, dried over anhydrous sodium sulfate and concentrated to obtain the title compound (563 mg).

Seventh Step

Production of (S)-3-hydroxymethyl-4-(5-methylthiazol-2-yl)-3-(tetrahydropyran-2-yl)oxymethyl-N-(4-trifluoromethoxyphenyl)-3,4-dihydro-2H-benzo[1,4]oxazine-8-carboxamide:

(S)-4-(5-methylthiazol-2-yl)-3-(tetrahydropyran-2-yl) oxymethyl-3,4-dihydro-2H-benzo[1,4]oxazine-8-carboxylic acid (250 mg) obtained in the Sixth Step and 4-trifluoromethoxyaniline (170 mg) were subjected to condensation similar to the Eighth Step of Example 1-001 to obtain the title compound (379 mg).

Eighth Step

Production of (S)-3-hydroxymethyl-4-(5-methylthiazol-2-yl)-N-(4-trifluoromethoxyphenyl)-3,4-dihydro-2H-benzo[1,4]oxazine-8-carboxamide:

(S)-3-hydroxymethyl-4-(5-methylthiazol-2-yl)-3-(tetrahydropyran-2-yl)oxymethyl-N-(4-trifluoromethoxyphenyl)-3,4-dihydro-2H-benzo[1,4]oxazine-8-carboxamide (379 mg) obtained in the Seventh Step was dissolved in tetrahydrofuran (5 ml), added 6 N hydrochloric acid (1 ml) was added and the mixture was stirred at room temperature for 1 hour. The reaction mixture was neutralized with saturated sodium hydrogencarbonate solution and extracted with ethyl acetate. The ethyl acetate layer was washed with saturated sodium chloride solution, dried over anhydrous sodium sulfate and then concentrated. The residue was purified by the use of silica gel column chromatography. To the purified substance was added n-hexane, and the precipitated solid substance was collected by filtration and dried to obtain the title compound (216 mg).

Example 6-02

Production of (S)-3-hydroxymethyl-4-(5-methylthiazol-2-yl)-N-(4-trifluoromethylphenyl)-3,4-dihydro-2H-benzo[1,4]oxazine-8-carboxamide First Step Production of (S)-3-hydroxymethyl-4-(5-methylthiazol-2-yl)-3-(tetrahydropyran-2-yl)oxymethyl-N-(4-trifluoromethylphenyl)-3,4-dihydro-2H-benzo[1,4]oxazine-8-carboxamide:

(S)-4-(5-methylthiazol-2-yl)-3-(tetrahydropyran-2-yl) oxymethyl-3,4-dihydro-2H-benzo[1,4]oxazine-8-carboxylic acid (260 mg) obtained in the Sixth Step of Example 6-01 was dissolved in pyridine (5 ml), thionyl chloride (0.097 ml) was added, and the mixture was stirred at room temperature for 1 hour. Subsequently, 4-trifluoromethylaniline was added, and the mixture was stirred overnight. The reaction mixture was concentrated and partitioned between ethyl acetate and 5% aqueous citric acid solution. The ethyl acetate layer was washed with water and saturated sodium chloride solution, in this order, dried over anhydrous sodium sulfate and concentrated to obtain the residue containing the title compound.

Second Step

Production of (S)-3-hydroxymethyl-4-(5-methylthiazol-2-yl)-N-(4-trifluoromethylphenyl)-3,4-dihydro-2H-benzo[1,4]oxazine-8-carboxamide The residue containing (S)-3-hydroxymethyl-4-(5-methylthiazol-2-yl)-3-(tetrahydropyran-2-yl)oxymethyl-N-(4-trifluoromethylphenyl)-3,4-dihydro-2H-benzo[1,4]oxazine-8-carboxamide obtained in the First Step was subjected to the reaction similar to that of the Eighth Step of Example 6-01 to obtain the title compound (227 mg).

Example 6-03

Production of (S)—N-(3,4-dichlorophenyl)-3-hydroxymethyl-4-(5-methylthiazol-2-yl)-3,4-dihydro-2H-benzo[1,4]oxazine-8-carboxamide hydrochloride First Step Production of methyl 2-methoxymethyloxy-3-(3-prop-2-ynyl)thioureidobenzoate:

Methyl 3-amino-2-methoxymethyloxybenzoate (21.12 g) obtained in the Second Step of Example 3 was dissolved in ethyl acetate (100 ml), water (100 ml) and sodium hydrogencarbonate (25.2 g) were added, and thiophosgene (7.62 ml) was added dropwise with stirring under ice-cooling. After passing 0.5 hour, propargylamine (7.2 ml) was added, and the mixture was stirred at room temperature for 2 hours. The reaction mixture was partitioned and ethyl acetate layer was washed with water, dried over anhydrous sodium sulfate and concentrated to obtain the brownish oily substance (36.16 g) containing the title compound.

Second Step

Production of methyl 2-methoxymethyloxy-3-(5-methylene-4,5-dihydrothiazol-2-yl) aminobenzoate:

The brownish oily substance (36.16 g) obtained in the First Step was dissolved in methanol (200 ml), p-toluenesulfonic acid (1.90 g) was added, and the mixture was refluxed for 2 hours with stirring. The reaction mixture was concentrated and partitioned between ethyl acetate and saturated aqueous sodium hydrogencarbonate. The ethyl acetate layer was washed with water and saturated sodium chloride solution in this order, dried over anhydrous sodium sulfate and concentrated to obtain the title compound (34.42 g).

Third Step

Production of methyl 3-(5-methylthiazol-2-yl)aminosalicylate:

Methyl 2-methoxymethyloxy-3-(5-methylene-4,5-dihydrothiazol-2-yl) aminobenzoate (34.42 g) obtained in the Second Step was stirred at 50° C. for 30 minutes in a solution of 25% hydrogen bromide/acetic acid (60 ml). The reaction mixture was cooled, 4 N sodium hydroxide (75 ml) was added with stirring, and the precipitated solid substance was collected by filtration and dried to obtain the title compound.

Fourth Step

Production of methyl (S)-3-hydroxymethyl-4-(5-methylthiazol-2-yl)-3,4-dihydro-2H-benzo[1,4]oxazine-8-carboxylate:

Methyl 3-(5-methylthiazol-2-yl)aminosalicylate (3.54 g) obtained in the Third Step was subjected to the reaction similar to that of the Third Step and Fourth Step of Example 6-01 to obtain the title compound (4.29 g).

Fifth Step

Production of (S)-3-hydroxymethyl-4-(5-methylthiazol-2-yl)-3,4-dihydro-2H-benzo[1,4]oxazine-8-carboxylic acid:

Methyl (S)-3-hydroxymethyl-4-(5-methylthiazol-2-yl)-3,4-dihydro-2H-benzo[1,4]oxazine-8-carboxylate (4.29 g) obtained in the Fourth Step was dissolved in tetrahydrofuran (10 ml) and methanol (10 ml), 4 N sodium hydroxide solution (10 ml) was added, and the mixture was stirred at 60° C. for 0.5 hour. The reaction mixture was neutralized, concentrated and partitioned between ethyl acetate and water. The ethyl acetate layer was washed with saturated sodium chloride solution and then concentrated. Ethyl acetate was added to the residue, the insoluble substance was filtered off and concentrated to obtain the title compound (3.53 g).

Sixth Step

Production of (S)-3-acetoxymethyl-4-(5-methylthiazol-2-yl)-3,4-dihydro-2H-benzo[1,4]oxazine-8-carboxylic acid hydrochloride:

(S)-3-hydroxymethyl-4-(5-methylthiazol-2-yl)-3,4-dihydro-2H-benzo[1,4]oxazine-8-carboxylic acid (2.53 g) obtained in the Fifth Step was dissolved in tetrahydrofuran (25 ml), 4-(dimethylamino)pyridine (1.01 g) was added, and the mixture was stirred at room temperature for 1 hour. Subsequently, acetic anhydride (0.779 ml) was added and the mixture was further stirred for 0.5 hour. The reaction mixture was partitioned between ethyl acetate and 5% aqueous citric acid solution. The ethyl acetate layer was washed with saturated sodium chloride solution, dried over anhydrous sodium sulfate and then concentrated. The concentrated residue was dissolved in ethyl acetate (50 ml) and 4 N hydrogen chloride/ethyl acetate solution (2.5 ml) was added. The precipitated solid substance was collected by filtration and dried to obtain the title compound (2.60 g).

Seventh Step

Production of (S)-3-acetoxymethyl-N-(3,4-dichlorophenyl)-4-(5-methylthiazol-2-yl)-3,4-dihydro-2H-benzo[1,4]oxazine-8-carboxamide:

(S)-3-acetoxymethyl-4-(5-methylthiazol-2-yl)-3,4-dihydro-2H-benzo[1,4]oxazine-8-carboxylic acid hydrochloride (445 mg) obtained in the Sixth Step was dissolved in pyridine (5 ml), thionyl chloride (0.168 ml) was added, and the mixture was stirred at room temperature for 1 hour. 3,4-Dichloroaniline (187 mg) was added and the mixture was further stirred for 0.5 hour. The reaction mixture was concentrated and partitioned between ethyl acetate and 5% aqueous citric acid solution. The ethyl acetate layer was washed with water and saturated sodium chloride solution, in this order, dried over anhydrous sodium sulfate and then concentrated. The residue was purified by the use of silica gel chromatography (n-hexane:ethyl acetate=2:1) to obtain the title compound (398 mg).

Eighth Step

Production of (S)—N-(3,4-dichlorophenyl)-3-hydroxymethyl-4-(5-methylthiazol-2-yl)-3,4-dihydro-2H-benzo[1,4]oxazine-8-carboxamide hydrochloride:

(S)-3-acetoxymethyl-N-(3,4-dichlorophenyl)-4-(5-methylthiazol-2-yl)-3,4-dihydro-2H-benzo[1,4]oxazine-8-carboxamide (398 mg) obtained in the Seventh Step was dissolved in tetrahydrofuran (5 ml) and methanol (5 ml), 1 N sodium hydroxide (1.25 ml) was added, and the mixture was stirred at room temperature for 0.5 hour. The reaction mixture was concentrated, and partitioned between ethyl acetate and water. The ethyl acetate layer was washed with water and saturated sodium chloride solution, dried over anhydrous sodium sulfate and then concentrated. The residue was dissolved in diethyl ether (10 ml), and 4 N hydrogen chloride/ethyl acetate solution (1 ml) was added. The precipitated solid substance was collected by filtration and dried to obtain the title compound (352 mg).

Example 6-04 to Example 6-10

Compounds of Examples 6-04 to 6-10 shown in the following tables were obtained by similarly performing any methods described in the general processes A to C for producing the compound and/or the methods described in Examples 6-01 to 6-03 hereinbefore.

Example 6-11

Production of (S)-3-hydroxymethyl-4-(5-methyloxazol-2-yl)-N-(4-trifluoromethoxyphenyl)-3,4-dihydro-2H-benzo[1,4]oxazine-8-carboxamide First Step Production of methyl 3-isothiocyano-2-methoxymethyloxybenzoate:

Methyl 3-amino-2-methoxymethyloxybenzoate (2.0 g) obtained in the Second Step of Example 3 was dissolved in tetrahydrofuran (20 ml), and triethylamine (4 ml) was added, and thiophosgene (0.76 ml) was added dropwise under ice-cooling and stirred at room temperature for 1 hour. After adding water, the reaction mixture was concentrated and partitioned by adding ethyl acetate. The ethyl acetate layer was washed with water, dried over anhydrous sodium sulfate and concentrated to obtain the title compound (2.4 g).

Second Step

Production of methyl 3-(5-methyloxazol-2-yl)amino-3-methoxymethyloxybenzoate:

1-azidoacetone (0.94 g) was dissolved in methylene chloride (10 ml), methyl 3-isothiocyano-2-methoxymethyloxybenzoate (2.4 g) obtained in the First Step and triphenylphosphine (2.5 g) were added, and the mixture was stirred at room temperature for 3 hours. The reaction mixture was concentrated, diethyl ether was added, and the precipitated solid substance was removed off by filtration. The filtrate was concentrated. The residue was purified by the use of silica gel chromatography (n-hexane:ethyl acetate=5:1) to obtain the title compound (1.82 g)

Third Step

Production of methyl 3-(5-methyloxazol-2-yl)aminosalicylate:

Methyl 3-(5-methyloxazol-2-yl)amino-3-methoxymethyloxybenzoate (1.77 g) obtained in the Second Step was dissolved in tetrahydrofuran (20 ml), 6 N hydrochloric acid (3 ml) was added, and the mixture was stirred at room temperature for 1 hour. The reaction mixture was concentrated and partitioned between water and ethyl acetate. The aqueous layer was neutralized with hydrochloric acid, collected the precipitated solid substance by filtration and dried to obtain the title compound (1.4 g).

Fourth Step

Production of (S)-4-(5-methyloxazol-2-yl)-3-(tetrahydropyran-2-yl)oxymethyl-3,4-dihydro-2H-benzo[1,4]oxazine-8-carboxylic acid:

Methyl 3-(5-methyloxazol-2-yl)aminosalicylate (1.4 g) obtained in the Third Step was subjected to the reaction similar to that of the Third Step to Sixth Step of Example 6-01 to obtain the title compound (760 mg).

Fifth Step

Production of (S)-3-hydroxymethyl-4-(5-methyloxazol-2-yl)-N-(4-trifluoromethoxyphenyl)-3,4-dihydro-2H-benzo[1,4]oxazine-8-carboxamide:

(S)-4-(5-methyloxazol-2-yl)-3-(tetrahydropyran-2-yl)oxymethyl-3,4-dihydro-2H-benzo[1,4]oxazine-8-carboxylic acid (200 mg) obtained in the Fourth Step was subjected to the reaction similar to that of the Seventh Step and the Eighth Step of Example 6-01 to obtain the title compound (78 mg).

Example 6-12

Production of (S)-3-hydroxymethyl-4-(5-methyloxazol-2-yl)-N-(4-trifluoromethylphenyl)-3,4-dihydro-2H-benzo[1,4]oxazine-8-carboxamide (S)-4-(5-methyloxazol-2-yl)-3-(tetrahydropyran-2-yl)oxymethyl-3,4-dihydro-2H-benzo [1,4]oxazine-8-carboxylic acid (200 mg) obtained in the Fourth Step of Example 6-11 was subjected to the reaction similar to that of the First Step and the Second Step of Example 6-02 to obtain the title compound (80 mg).

Example 6-13

Production of (S)-4-(4,5-dimethylthiazol-2-yl)-3-hydroxymethyl-N-(4-trifluoromethoxyphenyl)-3,4-dihydro-2H-benzo[1,4]oxazine-8-carboxamide First Step Production of methyl 3-(4,5-dimethylthiazol-2-yl)amino-3-methoxymethyloxybenzoate:

Methyl 2-methoxymethyloxy-3-thioureidbenzoate (2.00 g) obtained in the First Step of Example 6-01, 3-bromo-2-butanone (1.34 g) and sodium hydrogencarbonate (746 mg) in ethanol (20 ml) was refluxed for 1.5 hour with stirring. The reaction mixture was concentrated and partitioned between water and ethyl acetate. Ethyl acetate layer was washed with saturated sodium chloride solution, dried over anhydrous sodium sulfate and concentrated to obtain the title compound (2.65 g).

Second Step

Production of methyl 3-(4,5-dimethylthiazol-2-yl)aminosalicylate:

Methyl 3-(4,5-dimethylthiazol-2-yl)amino-3-methoxymethyloxybenzoate (2.65 g) was dissolved in tetrahydrofuran (10 ml), 6 N hydrochloric acid (2 ml) was added, and the mixture was stirred at 60° C. for 1 hour. The reaction mixture was neutralized by adding saturated sodium hydrogencarbonate solution and then concentrated. The precipitated solid substance was collected by filtration and dried to obtain the title compound (2.00 g).

Third Step

Production of (S)-4-(4,5-dimethylthiazol-2-yl)-3-hydroxymethyl-N-(4-trifluoromethoxyphenyl)-3,4-dihydro-2H-benzo[1,4]oxazine-8-carboxamide:

Methyl 3-(4,5-dimethylthiazol-2-yl)aminosalicylate obtained in the Second Step was subjected to the reaction similar to those of the process Third Step to Eighth Step of Example 6-001 to obtain the title compound.

Example 6-14

Production of (S)-4-(4,5-dimethylthiazol-2-yl)-3-hydroxymethyl-N-(4-trifluoromethylphenyl)-3,4-dihydro-2H-benzo[1,4]oxazine-8-carboxamide Methyl 3-(4,5-dimethylthiazol-2-yl)aminosalicylate obtained in the Second Step of Example 6-13 was subjected to the reaction similar to those of the process Third Step to Sixth Step of Example 6-01 and the First Step and Second Step of Example 6-02 to obtain the title compound.

Example 6-15

Production of (S)-3-hydroxymethyl-4-(5-methyl[1,3,4]thiazol-2-yl)-N-(4-trifluoromethoxyphenyl)-3,4-dihydro-2H-benzo[1,4]oxazine-8-carboxamide First Step Production of methyl 3-(acetylhydrazinothioxomethyl)amino-2-methoxymethyloxybenzoate:

Methyl 3-isothicyano-2-methoxymethyloxybenzoate (6.12 g) obtained in the First Step of Example 6-11 was dissolved in tetrahydrofuran (100 ml), acetohydrazide (2.5 g) was added, and the mixture was refluxed overnight with stirring. The reaction mixture was partitioned between water and ethyl acetate. The ethyl acetate layer was washed with water and saturated sodium chloride solution, dried over anhydrous sodium sulfate and then concentrated. The residue was purified by the use of silica gel chromatography (n-hexane:ethyl acetate=1:1) to obtain the title compound (4.97 g)

Second Step

Production of methyl 3-(5-methyl[1,3,4]thiadizol-2-yl)aminosalicylate:

Methyl 3-(acetylhydrazinothioxomethyl)amino-2-methoxymethyloxybenzoate (4.97 g) obtained in the First Step was dissolved in ethanol (100 ml), and concentrated sulfuric acid (50 ml) was added under ice-cooling. The mixture was further stirred at room temperature for 1 hour. The reaction mixture was neutralized and partitioned between water and ethyl acetate. The ethyl acetate layer was washed with water and saturated sodium chloride solution in this order, dried over anhydrous sodium sulfate and then concentrated. The residue was purified by the use of silica gel chromatography (n-hexane:ethyl acetate=2:1) to obtain the title compound (1.11 g)

Third Step

Production of (S)-3-hydroxymethyl-4-(5-methyl[1,3,4]thiadiazol-2-yl)-N-(4-trifluoromethoxyphenyl)-3,4-dihydro-2H-benzo[1,4]oxazine-8-carboxamide:

Methyl 3-(5-methyl[1,3,4]thiadiazol-2-yl)aminosalicylate obtained in the Second Step was subjected to the reaction similar to those of the process Third Step to Eighth Step of Example 6-001 to obtain the title compound.

Example 6-16

Production of (S)-3-hydroxymethyl-4-(5-methyl[1,3,4]thiadiazol-2-yl)-N-(4-trifluoromethylphenyl)-3,4-dihydro-2H-benzo[1,4]oxazine-8-carboxamide Methyl 3-(5-methyl[1,3,4]thiadiazol-2-yl)aminosalicylate obtained in the Second Step of Example 6-15 was subjected to the reaction similar to those of the process Third Step to Sixth Step of Example 6-001 and the First Step and Second Step of Example 6-02 to obtain the title compound.

Example 6-17

Production of 4-(4,5-dimethylthiazol-2-yl)-N-(4-trifluoromethoxyphenyl)-3,4-dihydro-2H-benzo[1,4]thiazine-8-carboxamide First Step Production of methyl 2-carbomethoxymethylsulfanyl-3-nitrobenzoate:

Methyl 2-chloro-3-nitrobenzoate (11.6 g) obtained in the First Step of Example 1-004 was dissolved in methanol (100 mL), sodium hydrogencarbonate (6.83 g) and mercaptoacetic acid (2.64 mL) were added, and the mixture was refluxed with stirring for 16 hours. The reaction solution was left to cool, poured into 2 M hydrochloric acid (100 mL)-ethyl acetate (100 mL) with stirring under ice-cooling, and partitioned. The ethyl acetate layer was washed with a saturated sodium chloride solution, dried over anhydrous sodium sulfate, and concentrated. The residue was purified by silica gel chromatography (chloroform:methanol:acetic acid=19:0.9:0.1) to obtain the title compound (4.84 g) as a pale orange solid.

Second Step

Production of methyl 3-oxo-3,4-dihydro-2H-benzo[1,4]thiazine-8-carboxylate:

Ammonium chloride (379 mg) was dissolved in water (10 mL), and reduced iron (3.66 g) was added while heating to 85° C. and stirring. A solution of methyl 2-carbomethoxymethylsulfanyl-3-nitrobenzoate obtained in the above step (4.81 g) in N,N-dimethylformamide (20 mL) was added dropwise thereto over 15 minutes, and the mixture was heated and stirred at 85° C. for a further one hour. The reaction solution was left to cool, water, ethyl acetate and tetrahydrofuran were added. After removing the insoluble substance, the mixture was partitioned. The organic layer was dried over anhydrous sodium sulfate and concentrated. The pale gray solid precipitated with diisopropyl ether was collected by filtration and dried to obtain the title compound (2.99 g).

Third Step

Production of methyl 3,4-dihydro-2H-benzo[1,4]thiazine-8-carboxylate:

Methyl 3-oxo-3,4-dihydro-2H-benzo[1,4]thiazine-8-carboxylate obtained in the above step (2.99 g) was subjected to the same reaction as in the Fifth Step of Example 1-001 to obtain the title compound (2.53 g) as an yellow solid.

Fourth Step

Production of methyl 4-thiocarbamide-3,4-dihydro-2H-benzo[1,4]thiazine-8-carboxylate:

The same reaction as in the First Step of Example 5-05 was performed for methyl 3,4-dihydro-2H-benzo[1,4]thiazine-8-carboxylate obtained in the above step to obtain the title compound (1.44 g) as a white solid.

Fifth Step

Production of methyl 4-(4,5-dimethylthiazol-2-yl)-3,4-dihydro-2H-benzo[1,4]thiazine-8-carboxylate:

Methyl 4-thiocarbamide-3,4-dihydro-2H-benzo[1,4]thiazine-8-carboxylate obtained in the above step (1.44 g), 3-bromo-2-butanone (972 mg) and sodium hydrogencarbonate (541 mg) were refluxed with stirring in methanol (15 mL) and tetrahydrofuran (10 mL) for 17 hours. The reaction solution was concentrated and partitioned between water and ethyl acetate. The resulting ethyl acetate layer was washed with saturated sodium chloride solution, dried over anhydrous sodium sulfate, and concentrated to obtain the title compound (1.91 g).

Sixth Step

Production of 4-(4,5-dimethyl-thiazol-2-yl)3,4-dihydro-2H-benzo[1,4]thiazine-8-carboxylic acid:

Methyl 4-(4,5-dimethyl-thiazol-2-yl)-3,4-dihydro-2H-benzo[1,4]thiazine-8-carboxylate obtained in the above step (1.91 g) was dissolved in methanol (5 mL) and tetrahydrofuran (5 mL), 4 N sodium hydroxide (2.0 mL) was added, and the mixture was refluxed with stirring for one hour. The reaction solution was concentrated, and neutralized by the addition of 2 N hydrochloric acid under ice-cooling. The precipitated solid was filtered off and dried to obtain the title compound (1.41 g).

Seventh Step

Production of 4-(4,5-dimethylthiazol-2-yl)-N-(4-trifluoromethoxyphenyl)-3,4-dihydro-2H-benzo[1,4]thiazine-8-carboxamide:

The same reaction as in the Eighth Step of Example 1-001 was performed for 4-(4,5-dimethyl-thiazol-2-yl)-3,4-dihydro-2H-benzo[1,4]thiazine-8-carboxylic acid obtained in the above step (1.40 g) and 4-trifluoromethoxyaniline (809 mg) to obtain the title compound (1.03 g) as a white solid.

Example 6-18

Production of 4-(4,5-dimethylthiazol-2-yl)-N-(4-trifluoromethoxyphenyl)-1-oxo-3,4-tetrahydro-benzo[1,4]thiazine-8-carboxamide 4-(4,5-dimethylthiazol-2-yl)-N-(4-trifluoromethoxyphenyl)-3,4-dihydro-2H-benzo[1,4]thiazine-8-carboxamide obtained in Example 6-17 (500 mg) was suspended in chloroform (15 mL), meta chloroperbenzoic acid (247 mg) was added, and the mixture was stirred at room temperature for two hours. A saturated sodium hydrogencarbonate solution was added to the reaction solution and partitioned. The chloroform layer was washed with a saturated sodium chloride solution, dried over anhydrous sodium sulfate and concentrated. The residue was purified by silica gel chromatography (chloroform:methanol=9:1), and the white solid precipitated with diisopropyl ether was filtered off and dried to obtain the title compound (290 mg).

Example 7

Example 7-01

Production of N-(4-tert-butylphenyl)-4-(4-methoxyphenyl)-3,4-dihydro-2H-benzo[1,4]oxazine-8-carboxamide First Step Production of methyl 4-(4-methoxyphenyl)-3,4-dihydro-2H-benzo[1,4]oxazine-8-carboxylate:

Methyl 3,4-dihydro-2H-benzo[1,4]oxazine-8-carboxylate (1.0 g) obtained in the Fifth Step of Example 1-001 and 4-bromoanisole (1.0 g) were used, and the coupling reaction similar to that of the Fourth Step of Example 1-002 was performed to obtain the oily compound in the title (0.58 g).

Second Step

Production of 4-(4-methoxyphenyl)-3,4-dihydro-2H-benzo[1,4]oxazine-8-carboxylic acid:

Methylmethyl 4-(4-methoxyphenyl)-3,4-dihydro-2H-benzo[1,4]oxazine-8-carboxylate (0.58 g) obtained in the First Step was dissolved in tetrahydrofuran (10 ml) and methanol (10 ml), 2 N sodium hydroxide solution (5 ml) was added, and the mixture was stirred at 60° C. for 1.5 hour. After concentrating the reaction mixture, yellow solid substance precipitated by adding 1 N potassium hydrogen sulfate was collected by filtration and dried to obtain the title compound (0.552 g).

Third Step

Production of N-(4-tert-butylphenyl)-4-(4-methoxyphenyl)-3,4-dihydro-2H-benzo[1,4]oxazine-8-carboxamide:

4-(4-methoxyphenyl)-3,4-dihydro-2H-benzo[1,4]oxazine-8-carboxylic acid (57 mg) obtained in the Second Step was dissolved in tetrahydrofuran (5 ml), oxalyl chloride (0.03 ml) and N,N-dimethylformamide (one drop) were added, and the mixture was stirred at room temperature for 0.5 hour, then the reaction mixture was concentrated. The concentrated residue was dissolved in tetrahydrofuran (5 ml), tert-butylaniline (30 mg) and triethylamine (0.5 ml) were added, and stirred at room temperature for 1 hour. The reaction mixture was partitioned between water and ethyl acetate. The ethyl acetate layer was dried over anhydrous sodium sulfate and then concentrated. Precipitated solid obtained by adding hexane to the residue was collected by filtration, and dried to obtain the title compound (48 mg).

Example 7-02

Production of N-(4-isobutyloxyphenyl)-4-(4-methoxyphenyl)-3,4-dihydro-2H-benzo[1,4]oxazine-8-carboxamide 4-(4-methoxyphenyl)-3,4-dihydro-2H-benzo[1,4]oxazine-8-carboxylic acid (57 mg) obtained in the Second Step of Example 7-01 and 4-isobutyloxyaniline (40 mg) were subjected to the reaction similar to that of the Third Step of example 7-01 to obtain the title compound (31 mg).

Example 7-03

Production of N-(4-chlorophenyl)-4-(4-methoxyphenyl)-3,4-dihydro-2H-benzo[1,4]oxazine-8-carboxamide 4-(4-methoxyphenyl)-3,4-dihydro-2H-benzo[1,4]oxazine-8-carboxylic acid (57 mg) obtained in the Second Step of Example 7-01 and 4-chloroaniline (40 mg) were subjected to the reaction similar to that of the Third Step of example 7-01 to obtain the title compound (29 mg).

Example 7-04

Production of (S)-4-(2-chlorophenyl)-3-hydroxymethyl-N-(4-trifluoromethoxyphenyl)-3,4-dihydro-2H-benzo[1,4]oxazine-8-carboxamide First Step
Production of methyl 3-(2-chlorophenyl)amino-2-methoxymethyloxybenzoate:
Methyl 3-amino-2-methoxymethyloxybenzoate (3.5 g) obtained in the Second Step of Example 3 and 2-iodochlorobenzene (2.62 ml) were subjected to the reaction similar to that of the First Step of Example 2-01 to obtain the title compound (2.33 g).

Second Step
Production of methyl 3-(2-chlorophenyl)aminosalicylate methyl:
Methyl 3-(2-chlorophenyl)amino-2-methoxymethyloxybenzoate (2.33 g) obtained in the First Step was subjected to the reaction similar to that of the Fourth Step of Example 3 to obtain the title compound (1.75 g).

Third Step
Production of (S)-4-(2-chlorophenyl)-3-hydroxymethyl-N-(4-trifluoromethoxyphenyl)-3,4-dihydro-2H-benzo[1,4]oxazine-8-carboxamide:
Methyl 3-(2-chlorophenyl)aminosalicylate methyl obtained in the Second Step was subjected to the reaction of the Third Step below in Example 6-01 to obtain the title compound.

Example 7-05 to Example 7-11

Compounds of Examples 7-05 to 7-11 hereinbelow were obtained by similarly performing any methods described in the general processes A to C for producing the compound and/or the methods described in Examples 4-01 to 4-59 hereinbefore and a method described in example 7-04.

Chemical structures, molecular weights thereof and NMR data of compounds obtained in Examples 1-001 to 7-11 are shown in Table 1 to Table 50.

TABLE 1

| | Ex. No. | Chemical Compounds | NMR |
|---|---|---|---|
| 1 | 1-001 | | (400 MHz, CHLOROFORM-D) 1.33(s, 9H) 3.88-3.97(m, 2H) 4.57-4.65(m, 2H) 6.66(dd, J=8.00, 1.28 Hz, 1H) 6.90(t, J=7.88 Hz, 1H) 7.11(dd, J=7.88, 4.67 Hz, 1H) 7.38 (d, J=8.58 Hz, 2H) 7.60(d, J=8.58 Hz, 2H) 7.77-7.82(m, 2H) 8.37(dd, J=4.75, 1.28 Hz, 1H) 9.57(s, 1H) |
| 2 | 1-002 | | (300 MHz, DMSO-D6) 1.29(m, 9H) 3.62(m, 1H) 4.18(m, 1H) 4.70(m, 1H) 6.47(dd, J=8.07, 1.47 Hz, 1H) 6.79(t, J=7.89 Hz, 1H) 7.21-7.35(m, 4H) 7.84-7.92(m, 2H) 7.98(dd, J=7.70, 1.47 Hz, 1H) 8.43(dd, J=4.99, 1.51 Hz, 1H) 12.34(s, 1H) |
| 3 | 1-003 | | (400 MHz, DMSO-D6) 1.23(d, J=6.49 Hz, 3H) 1.28(s, 9H) 4.07-4.15(m, 1H) 4.22-4.32(m, 2H) 6.38(dd, J=8.12, 1.62 Hz, 1H) 6.80(t, J=7.88 Hz, 1H) 7.04(dd, J=7.54, 1.51 Hz, 1H) 7.31-7.39(m, 3H) 7.84-7.71(m, 2H) 8.07(dd, J=7.88, 1.62 Hz, 1H) 8.45(dd, J=4.64, 1.62 Hz, 1H) 10.10 (s, 1H) |
| 4 | 1-004 | | (400 MHz, DMSO-D6) 1.28(s, 9H) 2.83(s, 3H) 3.34-3.39 (m, 2H) 3.69-3.74(m, 2H) 6.33(dd, J=8.12, 1.39 Hz, 1H) 6.72(t, J=7.77 Hz, 1H) 7.03(dd, J=7.65, 1.39 Hz, 1H) 7.30 (dd, J=7.88, 4.64 Hz, 1H) 7.33-7.38(m, 2H) 7.63-7.68 (m, 2H) 8.02(dd, J=7.88, 1.62 Hz, 1H) 8.44(dd, J=4.75, 1.74 Hz, 1H) 10.62(a, 1H) |

TABLE 1-continued

| Ex. No. | | Chemical Compounds | NMR |
|---|---|---|---|
| 5 | 1-005 | | (400 MHz, DMSO-D6) 1.25(s, 9H) 1.95(m, 2H) 3.97(m, 2H) 4.27(m, 2H) 6.61(dd, J=8.00, 1.51 Hz, 1H) 6.93(t, J=7.77 Hz, 1H) 7.06(dd, J=7.77, 4.75 Hz, 1H) 7.26(dd, J=7.54, 1.51 Hz, 1H) 7.30-7.38(m, 2H) 7.63(ddd, J=9 04, 2.55, 2.32 Hz, 2H) 7.76(dd, J=7.65, 1.62 Hz, 1H) 8.31(dd, J=4.84, 1.62 Hz, 1H) 10.15(s, 1H) |
| 6 | 1-006 | | (400 MHz, DMSO-D6) 3.76(m, 2H) 4.37(m, 2H) 6.48(dd, J=8.12, 1.39 Hz, 1H) 6.73-6.83(m, 1H) 7.02(dd, J=7.54, 1.51 Hz, 1H) 7.28(dd, J=7.88, 4.84 Hz, 1H) 7.36(dd, J=6.80, 2.10 Hz, 1H) 7.75(dd, J=6.00, 1.74 Hz, 2H) 8.01(dd, J=8.00, 1.74 Hz, 2H) 8.39(dd, J=4.84, 1.62 Hz, 1H) 10.28(a, 1H) |
| 7 | 1-007 | | (400 MHz, DMSO-D6) 1.17-1.26(d, J=6.00 Hz, 6H) 3.75(m, 2H) 4.39(m, 2H) 4.53(m, 1H) 6.46(dd, J=8.12, 1.39 Hz, 1H) 6.76(t, J=7.88 Hz, 1H) 6.86(m, 2H) 7.03(dd, J=7.54, 1.51 Hz, 1H) 7.27(dd, J=8.00, 4.75 Hz, 1H) 7.60(m, 2H) 8.01(dd, J=7.88, 1.62 Hz, 1H) 8.39(dd, J=4.84, 1.62 Hz, 1H) 9.98(s, 1H) |
| 8 | 1-008 | | (400 MHz, DMSO-D6) 1.02(m, 9H) 1.43-1.54(m, 2H) 1.77-1.87(m, 2H) 2.12-2.17(m, 2H) 2.86-2.95(m, 2H) 3.69-3.80(m, 3H) 4.37-4.47(m, 2H) 6.46(dd, J=8.12, 1.62 Hz, 1H) 6.73-6.77(m, 1H) 7.12(dd, J=7.65, 1.62 Hz, 1H) 7.29(dd, J=7.88, 4.46 Hz, 1H) 7.98(d, J=7.88 Hz, 1H) 8.02(dd, J=7.86, 1.62 Hz, 1H) 8.41(dd, J=4.75, 1.74 Hz, 1H) |

TABLE 2

| Ex. No. | | Chemical Compounds | NMR |
|---|---|---|---|
| 9 | 1-009 | | (300 MHz, OMSO-D6) 2.28(s, 3H) 3.77-3.84(m, 2H) 4.40-4.48(m, 2H) 6.50(dd, J=8.07, 1.47 Hz, 1H) 6.79(t, J=7.70 Hz, 1H) 7.07-7.10(m, 1H) 7.14(d, J=8.44 Hz, 2H) 7.31(dd, J=8.07, 4.77 Hz, 1H) 7.63(d, J=8.44 Hz, 2H) 8.05(dd, J=8.07, 1.47 Hz, 1H) 8.43(dd, J=4.77, 1.47 Hz, 1H) 10.06(s, 1H) |
| 10 | 1-010 | | (300 MHz, OMSO-D6) 0.89(d, J=6.60 Hz, 3H) 0.93-1.11(m, 2H) 1.19-1.40(m, 3H) 1.64-1.76(m, 2H) 1.81-1.93(m, 2H) 3.60-3.81(m, 3H) 4.38-4.44(m, 2H) 6.45(dd, J=7.89, 1.65 Hz, 1H) 6.72-6.77(m, 1H) 7.10(dd, J=7.70, 1.47 Hz, 1H) 7.28(dd, J=7.89, 4.59 Hz,H) 7.89(d, J=7.70 Hz, 1H) 8.02(dd, J=7.89, 1.65 1H) 8.40 J=4.59, 1.65 Hz, 1H) |
| 11 | 1-011 | | (400 MHz, DMSO-D6) 0.97(d, J=16.4 Hz, 6H) 2.01(m, 1H) 3.72(d, J=6.49 Hz, 2H) 3.79-3.84(m, 2H) 4.40-4.48(m, 2H) 6.50(dd, J=8.12, 1.62 Hz, 1H) 6.80(t, J=7.77 Hz, 1H) 6.87-6.95(m, 2H) 7.08(dd, J=7.54, 1.51 Hz, 1H) 7.31(dd, J=8.00, 4.75 Hz, 1H) 7.60-7.69(m, 2H) 8.04(dd, J=8.12, 1.62 Hz, 1H) 5.43(dd, J=4.64, 1.62 Hz, 1H) 10.01(s, 1H) |

TABLE 2-continued

| Ex. No. | | Chemical Compounds | NMR |
|---|---|---|---|
| 12 | 1-012 | | (300 MHz, DMSO-D6) 3.77-3.82(m, 2H) 4.41-4.45(m, 2H) 4.50(d, J=6.24 Hz, 2H) 6.49(dd, J=8.07, 1.47 Hz, 1H) 6.77(t, J=7.89 Hz, 1H) 7.19(dd, J=7.70, 1.47 Hz, 1H) 7.23-7.36(m, 6H) 8.03(dd, J=7.89, 1.65 Hz, 1H) 8.42(dd, J=4.59, 1.65 Hz, 1H) 8.71(t, J=6.05 Hz, 1H) |
| 13 | 1-013 | | (300 MHz, DMSO-D6) 3.77-3.83(m, 2H) 4.43-4.58(m, 4H) 6.49(dd, J=7.89, 1.65 Hz, 1H) 6.77(t, J=7.89 Hz, 1H) 7.18(dd, J=7.70, 1.83 Hz, 1H) 7.30(dd, J=8.07, 4.77 Hz, 1H) 7.39(m, 4H) 8.03(dd, J=7.89, 1.65 Hz, 1H) 8.42(dd, J=4.77, 1.47 Hz, 1H) 8.75(t, J=6.05 Hz, 1H) |
| 14 | 1-014 | | (300 MHz, OMSO-D6) 1.27(s, 9H) 3.69-3.84(m, 8H) 4.41-4.48(m, 5H) 6.49(dd, J=8.07, 1.83 Hz, 1H) 6.77(t, J=7.70 Hz, 1H) 7.19(dd, J=7.70, 1.47 Hz, 1H) 7.26-7.38(m, 5H) 8.03(dd, J=7.89, 1.65 Hz, 1H) 8.42(dd, J=4.59, 1.65 Hz, 1H) 8.64-8.68(m, 1H) |
| 15 | 1-015 | | (300 MHz, DMSO-D6) 3.78-3.83(m, 2H) 4.41-4.48(m, 2H) 4.58(d, J=6.24 Hz, 2H) 6.50(dd, J=8.07, 1.47 Hz, 1H) 6.78(t, J=7.89 Hz, 1H) 7.19(dd, J=7.52, 1.65 Hz, 1H) 7.30(dd, J=7.89, 4.59 Hz, 1H) 7.58(d, J=8.07 Hz, 2H) 7.72(d, J=8.07 Hz, 2H) 8.04(d, J=8.07 Hz, 1H) 8.42(dd, J=459, 1.65 Hz, 1H) 8.84(t, J=6.24 Hz, 1H) |
| 16 | 1-016 | | (300 MHz, DMSO-D6) 1.28(s, 9H) 4.03-4.10(m, 2H) 4.31-4.35(m, 2H) 6.90-6.97(m, 2H) 7.21-7.24,(m, 2H) 7.35(d, J=8.44 Hz, 2H) 7.47-7.52(m, 1H) 7.62-7.72(m, 3H) 8.31(d, J=3.30 Hz, 1H) 10.06(s, 1H) |

TABLE 3

| Ex. No. | | Chemical Compounds | NMR |
|---|---|---|---|
| 17 | 1-017 | | (400 MHz, DMSO-D6) 1.25(s, 9H) 3.59-3.69(m, 2H) 4.38-4.48(m, 2H) 6.23(dd, J=8.12, 1.39 Hz, 1H) 6.74(t, J=7.77 Hz, 1H) 7.01(dd, J=7.65, 1.39 Hz, 1H) 7.32-7.42(m, 2H) 7.62(dd, J=7.42, 4.87 Hz, 1H) 7.64-7.73(m, 2H) 8.37(dd, J=8.00, 1.74 Hz, 1H) 8.81(dd, J=4.75, 1.51 Hz, 1H) 10.08(s, 1H) |
| 18 | 1-018 | | (300 MHz, DMSO-D6) 1.28(s, 9H) 1.44(s, 6H) 3.65(s, 2H) 6.52-6.61(m, 1H) 6.82(t, J=7.89 Hz, 1H) 7.23(dd, J=7.70, 1.47 Hz, 1H) 7.30(dd, J=8.07, 4.77 Hz, 1H) 7.37(d, J=8.80 Hz, 2H) 7.64(d, J=8.44 Hz, 2H) 8.03(dd, J=7.89, 1.65 Hz, 1H) 8.44(dd, J=4.77, 1.47 Hz, 1H) 9.99(s, 1H) |
| 19 | 1-019 | | DMSO-D6, 1.28(s, 9H) 1.39(d, J=6.26 Hz, 3H) 3.51(dd, J=12.75, 7.88 Hz, 1H) 3.86(dd, J=12.75, 2.55 Hz, 1H) 4.49-4.59(m, 1H) 6.53(dd, J=8.00, 1.51 Hz, 1H) 6.81(t, J=7.88 Hz, 1H) 7.15(dd, J=7.65, 1.62 Hz, 1H) 7.30(dd, J=7.88, 4.64 Hz, 1H) 7.33-7.38(m, 2H) 7.59-7.68(m, 2H) 8.04(dd, J=8.00, 1.51 Hz, 1H) 8.42(dd, J=4.46, 1.62 Hz, 1H) 10.05(s, 1H) |

TABLE 3-continued

| Ex. No. | | Chemical Compounds | NMR |
|---|---|---|---|
| 20 | 1-020 | | (300 MHz, DMSO-D6) 1.28(s, 9H) 3.78-3.83(m, 2H) 4.39-4.45(m, 2H) 6.46(d, J=2.20 Hz, 1H) 7.0.4(d, J=2.57 Hz, 1H) 7.34-7.40(m, 4H) 7.64(d, J=8.80 Hz, 2H) 8.10 (dd, J=8.07, 1.47 Hz, 1H) 8.47(d, J=4.77 Hz, 1H) 10.16(s, 1H) |
| 21 | 1-021 | | (300 MHz, DMSO-D6) 3.81(m, 2H) 4.44(m, 2H) 6.53(dd, J=8.10, 1.50 Hz, 1H) 6.82(t, J=z7.90 Hz, 1H) 7.08(dd, J=7.30, 1.40 Hz, 1H) 7.33(dd, J=8.10, 4.80 Hz, 1H) 7.72(d, J=8.80 Hz, 2H) 7.98(d, J=8.80 Hz, 2H) 8.06(dd, J=8.30, 1.50 Hz, 1H) 8.44(dd, J=4.80, 1.50 Hz, 1H) 10.52(s, 1H) |
| 22 | 1-022 | | (300 MHz, DMSO-D6) 3.81(m, 2H) 4.42(m, 2H) 6.52(dd, J=8.10, 1.50 Hz, 1H) 6.83(t, J=7.90 Hz, 1H) 7.08(dd, J=7.30, 1.40 Hz, 1H) 7.33(dd, J=4.80, 8.10 Hz, 1H) 7.35(d, J=8.80 Hz, 2H) 7.86(d, J=8.80 Hz, 2H) 8.06(dd, J=1.50, 8.30 Hz, 1H) 8.45(dd, J=1.50, 4.80 Hz, 1H) 10.36(s, 1H) |
| 23 | 1-023 | | (300 MHz, DMSO-D6) 3.74(S, 3H) 3.80(m, 2H) 4.43(m, 2H) 6.51(dd, J=8.12, 1.39 Hz, 1H) 6.80(t, J=7.89 Hz, 1H) 6.91(d, J=9.17 Hz, 2H) 7.08(dd, J=7.70, 1.47 Hz, 1H) 7.31(dd, J=7.89, 4.59 Hz, 1H) 7.66(d, J=9.17 Hz, 2H) 8.05(dd, J=7.89, 1.65 Hz, 1H) 8.43(dd, J=4.59, 1.65 Hz, 1 H) 10.01(s, 1H) |
| 24 | 1-024 | | (400 MHz, DMSO-D6) 0.82(s, 9H) 0.91-1.00(m, 1H) 1.03(m, 2H) 1.22(m, 2H) 1.72(m, 2H) 1.90(m, 2H) 3.61 (m, 1H) 3.74(m, 2H) 4.36(m, 2H) 6.41(dd, J=8.12, 1.62 Hz, 1H) 6.70(t, J=7.88 Hz, 1H) 7.05(dd, J=7.54, 1.51 Hz, 1H) 7.25(dd, J=7.88, 4.64 Hz, 1H) 7.87(d, J=7.88 Hz, 1 H) 7.99(dd, J=7.88, 1.62 Hz, 1H) 8.37(dd, J=4.87, 1.62 Hz, 1H) |

TABLE 4

| Ex. No. | | Chemical Compounds | NMR |
|---|---|---|---|
| 25 | 1-025 | | (300 MHz, DMSO-D6) 3.81(m, 2H) 4.44(m, 2H) 6.53(dd, J=8.10, 1.50 Hz, 1H) 6.82(t, J=7.90 Hz, 1H) 7.08(dd, J=7.30, 1.40 Hz, 1H) 7.33(dd, J=4.80, 8.10 Hz, 1H) 7.70(d, J=8.80 Hz, 2H) 8.01-8.07(m, 2H) 8.40(m, 1H) 10.59(s, 1H) |
| 26 | 1-026 | | (400 MHz, DMSO-D6) 3.70(m, 2H) 4.34(m, 2H) 6.42(dd, J=8.00, 1.51 Hz, 1H) 6.71(t, J=7.88 Hz, 1H) 6.97(dd, J=7.54, 1.51 Hz, 1H) 7.06-7.16(m, 2H) 7.22(dd, J=7.88, 4.64 Hz, 1H) 7.68(dd, J=9.04, 5.10 Hz, 2H) 7.96(dd, J=8.00, 1.51 Hz, 1H) 8.34(dd, J=4.64, 1.62 Hz, 1H) 10.13 (s, 1H) |

TABLE 4-continued

| Ex. No. | | Chemical Compounds | NMR |
|---|---|---|---|
| 27 | 1-027 | | (400 MHz, DMSO-D6) 3.78(m, 2H) 4.40(m, 2H) 6.50(dd, J=8.12, 1.39 Hz, 1H) 6.78(t, J=7.88 Hz, 1H) 7.04(dd, J=7.65, 1.39 Hz, 1H) 7.28(dd, J=7.65, 4.64 Hz, 1H) 7.42 (s, 1H) 7.55(t, J=7.88 Hz, 1H) 7.92(s, 1H) 8.02(dd, J=7.88, 1.62 Hz, 1H) 8.23(s, 1H) 8.40(dd, J=4.99, 1.51 Hz, 1H)10.47(s, 1H) |
| 28 | 1-028 | | (300 MHz, DMSO-D6) 3.81(m, 2H) 4.47(m, 2H) 6.59(dd, J=8.10, 1.50 Hz, 1H) 6.84(t, J=7.90 Hz, 1H) 7.15(dd, J=7.30, 1.40 Hz, 1H) 7.33(dd, J=4.80, 8.10 Hz, 1H) 8.02(s, 1H) 8.06(d, J=1.50 Hz, 1H) 8.45(d, J=1.90 Hz, 1H) 12.42 (s, 1H) |
| 29 | 1-029 | | (300 MHz, DMSO-D6) 3.85(m, 2H) 4.52(m, 2H) 6.60(dd, J=7.89, 1.65 Hz, 1H) 6.86(t, J=8.07 Hz, 1H) 7.30-7.35 (m, 2H) 8.06(dd, J=7.89, 1.65 Hz, 1H) 8.26(d, J=8.99, 2.38 Hz, 1H) 8.42-8.48(m, 2H) 8.76(s, 1H) 10.87(s, 1H) |
| 30 | 1-030 | | (300 MHz, DMSO-D6) 3.82(m, 2H) 4.45(m, 2H) 6.55(dd, J=7.89, 1.47 Hz, 1H) 6.84(t, J=7.89 Hz, 1H) 7.12(d, J=6.60 Hz, 1H) 7.33(dd, J=6.25, 4.95 Hz, 1H) 7.92(d, J=8.80 Hz, 1H) 8.06(d, J=7.70 Hz, 1H) 8.45(td, J=5.14, 1.83 Hz, 1H) 8.50(s, 1H) 9.04(d, J=2.20 Hz, 1H) 10.74 (s, 1H) |
| 31 | 1-031 | | (400 MHz, DMSO-D6) 1.16(d, J=6.26 Hz, 6H) 2.83(m, 1H) 3.77(m, 2H) 4.39(m, 2H) 6.46(dd, J=8.12, 1.62 Hz, 1H) 6.76(dd, J=7.89, 1.47 Hz, 1H) 7.04(dd, J=7.65, 1.62 Hz, 1H) 7.16(d, J=8.58 Hz, 2H) 7.27(dd, J=7.88, 4.64 Hz, 1H) 7.60(m, 2H) 8.01(dd, J=7.88, 1.62 Hz, 1H) 8.39(dd, J=4.64, 1.62 Hz, 1H) 10.03(s, 1H) |
| 32 | 1-032 | | (300 MHz, DMSO-D6) 3.81-3.85(m, 2H) 4.45-4.49(m, 2H) 6.55(dd, J=8.07, 1.47 Hz, 1H) 6.84-6.87(m, 1H)7.13 (d, J=1.47 Hz, 1H) 7.33(dd, J=8.07, 4.77 Hz, 1H) 7.42-7.47(m, 1H) 7.91(d, J=1.83 Hz, 1H) 7.94-7.98(m, 1H) 8.06(dd, J=8.07, 1.47 Hz, 1H) 8.31(d, J=8.44 Hz, 1H) 8.44(dd, J=4.59, 1.65 Hz, 1H) 8.60(S, 1H) 8.87(dd, J=4.22, 1.65 Hz, 1H) 10.54(s, 1H) |

TABLE 5

| Ex. No. | | Chemical Compounds | NMR |
|---|---|---|---|
| 33 | 1-033 | | (300 MHz, DMSO-D6) 1.96(m, 2H) 2.72(m, 2H) 2.92(s, 3H) 326(m, 2H) 3.81(m, 2H) 4.43(m, 2H) 6.51(dd, J=8.07, 1.47 Hz, 1H) 6.80(t, J=7.89 Hz, 1H) 6.99(m, 1H) 7.08(dd, J=7.70, 1.47 Hz, 1H) 7.19(m, 1H) 7.31(dd, J=7.89, 4.59 Hz, 1H) 7.40(m, 1H) 8.05(dd, J=7.89, 1.65 Hz, 1H) 8.43(dd, J=4.77, 1.83 Hz, 1H) 10.04(s, 1H) |
| 34 | 1-034 | | (400 MHz, DMSO-D6) 3.72-3.83(m, 2H) 3.84(s, 3H) 4.36-4.46(m, 2H) 8.53(dd, J=8.12, 1.62 Hz, 1H) 6.76-6.84(m, 1H) 7.07(dd, J=7.65, 1.62 Hz, 1H) 7.32(dd, J=8.00, 4.75 Hz, 1H) 7.86-7.97(m, 4H) 8.05(dd, J=8.12, 1.62 Hz, 1H) 8.43(dd, J=4.64, 1.62 Hz, 1H) 10.53(s, 1H) |

TABLE 5-continued

| Ex. No. | | Chemical Compounds | NMR |
|---|---|---|---|
| 35 | 1-035 | | (400 MHz, DMSO-D6) 3.76-3.87(m, 2H) 4.37-4.48(m, 2H) 6.53(dd, J=8.12, 1.39 Hz, 1H) 6.80-6.83(m, 1H) 7.07(dd, J=7.65, 1.62 Hz, 1H) 7.32(dd, J=8.12, 4.64 Hz, 1H) 7.85-7.95(m, 4H) 8.05(dd, J=7.88, 1.62 Hz, 1H) 8.43(dd, J=4.64, 1.62 Hz, 1H) 10.48(s, 1H) 12.75(brs, 1H) |
| 36 | 1-036 | | (400 MHz, DMSO-D6) 3.75-3.85(m, 2H) 4.38-4.48(m, 2H) 6.52(dd, J=8.00, 1.51 Hz, 1H) 6.77-6.85(m, 1H) 7.08(dd, J=7.65, 1.62 Hz, 1H) 7.26(brs, 2H) 7.32(dd, J=7.88, 4.64 Hz, 1H) 7.79-7.90(m, 4H) 8.05(dd, J=8.00, 1.74 Hz, 1H) 8.43(dd, J=4.64, 1.62 Hz, 1H) 10.38(s, 1H) |
| 37 | 1-037 | | (400 MHz, DMSO-D6) 2.78(d, J=4.64 Hz, 3H) 3.76-3.86(m, 2H) 4.38-4.49(m, 2H) 6.52(dd, J=8.00, 1.51 Hz, 1H) 6.81(t, J=7.88 Hz, 1H) 7.08(dd, J=7.54, 1.51 Hz, 1H) 7.32(dd, J=7.88, 4.64 Hz, 1H) 7.82(s, 4H) 8.05(dd, J=8.12, 1.62 Hz, 1H) 8.31-8.37(m, 1H) 8.43(dd, J=4.64, 1.62 Hz, 1H) 10.38(s, 1H) |
| 38 | 1-038 | | (400 MHz, DMSO-D6) 2.97(s, 6H) 3.76-3.86(m, 2H) 4.39-4.50(m, 2H) 6.52(dd, J=8.12, 1.62 Hz, 1H), 6.79-6.83(m, 1H) 7.06(dd, J=7.54, 1.51 Hz, 1H) 7.32(dd, J=8.12, 4.64 Hz, 1H) 7.37-7.49(m, 2H) 7.78-7.85(m, 2H) 8.05(dd, J=7.88, 1.62 Hz, 1H) 8.43(dd, J=4.64, 1.62 Hz, 1H) 10.34(s, 1H) |
| 39 | 1-039 | | (400 MHz, DMSO-D6) 2.55(s, 3H) 3.74-3.85(m, 2H) 4.37-4.47(m, 2H) 6.53(dd, J=8.12, 1.62 Hz, 1H) 6.82(t, J=7.77 Hz, 1H) 7.08(dd, J=7.65, 1.62 Hz, 1H) 7.32(dd, J=7.88, 4.64 Hz, 1H) 7.83-7.93(m, 2H) 7.93-8.00(m, 2H) 8.05(dd, J=7.88, 1.62 Hz, 1H) 8.43(dd, J=4.64, 1.62 Hz, 1H) 10.51(s, 1H) |
| 40 | 1-040 | | (400 MHz, DMSO-D6) 1.42(s, 6H) 3.76-3.86(m, 2H) 4.37-4.48(m, 2H) 4.96(s, 1H) 6.49-6.52(m, 1H) 6.78-6.82(m, 1H) 7.07-7.09(m, 1H) 7.30-7.33(m, 1H) 7.37-7.46(m, 2H) 7.60-7.71(m, 2H) 8.04-8.06(m, 1H) 8.42-8.44(m, 1H) 10.08(s, 1H) |

TABLE 6

| Ex. No. | | Chemical Compounds | NMR |
|---|---|---|---|
| 41 | 1-041 | | (400 MHz, DMSO-D6) 0.68(t, J=7.42 Hz, 3H) 1.40(s, 3H) 1.63-1.73(m, 2H) 3.75-3.85(m, 2H) 4.38-4.48(m, 2H) 4.76(s, 1H) 6.50(dd, J=8.12, 1.62 Hz, 1H) 6.80(t, J=7.88 Hz, 1H) 7.07(dd, , J=7.65, 1.62 Hz, 1H) 7.29-7.39(m, 3H) 7.62-7.68(m, 2H) 8.05(dd, J=8.12, 1.62 Hz, 1H) 8.42-8.44(m, 1H) 10.08(s, 1H) |

TABLE 6-continued

| Ex. No. | | Chemical Compounds | NMR |
|---|---|---|---|
| 42 | 1-042 | | (400 MHz, DMSO-D6) 0.94-1.03(m, 6H) 1.30-1.52(m, 2 H)1.77-1.93(m, 2H)2.74-2.82(m, 1H)2.84-2.93(m, 1 H) 3.13-3.23(m, 1H) 3.72-3.82(m, 2H) 3.87-3.96(m, 1 H) 3.97-4.08(m, 1H) 4.23-4.31(m, 1H) 4.33-4.44(m, 2 H) 6.46(dd, J=8.12, 1.62 Hz, 1H) 6.88(t, J=7.88 Hz, 1H) 7.10(dd, J=7.65, 1.39 Hz, 1H) 7.29(dli, J=8.12, 4.75 Hz, 1 H) 8.02(dd, J=7.88, 1.62 Hz, 1H) 8.07(d, J=7.65 Hz, 1H) 8.41(dd, J=4.64, 1.62 Hz, 1H) |
| 43 | 1-043 | | (400 MHz, DMSO-D6) 1.13(s, 9H) 1.21-1.44(m, 4H) 1.71-1.79(m, 2H) 1.82-1.90(m, 2H) 3.37-3.46(m, 1H) 3.62-3.73(m, 1H) 3.75-3.50(m, 2H) 4.33-4.44(m, 2H) 6.45(dd, J=8.00, 1.51 Hz, 1H)6.74(t, J=7.88 Hz, 1H) 7.09 (dd, J=7.65, 1.62 Hz, 1H) 7.28(dd, J=7.88, 4.64 Hz, 1H) 7.92(d, J=7.65 Hz, 1H) 8.02(dd, J=8.12, 1.62 Hz, 1H) 8.40(dd, J=4.64, 1.62 Hz, 1H) |
| 44 | 1-044 | | (400 MHz, DMSO-D6) 1.28(d, J=6.03 Hz, 6H) 3.76-3.86 (m, 2H) 4.38-4.49(m, 3H) 4.56(m, 1H) 6.51(dd, J=8.00, 1.51 Hz, 1H) 6.62-6.71(m, 1H) 6.80(t, J=7.77 Hz, 1H) 7.06(dd, J=7.54, 1.51 Hz, 1H)7.20(t, J=8, 12 Hz, 1H) 7.25-7.35(m, 2H) 7.43(t, J=2.20 Hz, 1H) 8.05(dd, J=7.88, 1.62 Hz, 1H) 8.43(dd, J=4.87, 1.62 Hz, 1H) 10.11(s, 1H) |
| 45 | 1-045 | | (400 MHz, DMSO-D6) 0.99(d, J=6.49 Hz, 6H) 1.97-2.08 (m, 1H) 3.73(d, J=6.49 Hz, 2H) 3.77-3.86(m, 2H) 4.38-4.49(m, 2H) 6.50(dd, J=8.00, 1.51 Hz, 1H) 6.63-6.68 (m, 1H) 6.80(t, J=7.77 Hz, 1H) 7.06(dd, J=7.65, 1.62 Hz, 1H) 7.21(t, J=8.00 Hz, 1H) 7.24-7.29(m, 1H) 7.31(dd, J=8.00, 4.75 Hz, 1H) 7.48(t, J=2.09 Hz, 1H) 8.05(dd, J=7.88, 1.62 Hz, 1H) 8.43(dd, J=4.64, 1.62 Hz, 1H) 10.12 (s, 1H) |
| 46 | 1-046 | | (400 MHz, DMSO-D6) 1.28(s, 9H) 3.82-3.92(m, 2H) 4.27-4.38(m, 2H) 6.88-6.98(m, 1H) 7.16(dd, J=4.87, 1.62 Hz, 2H) 7.24(dd, J=7.65, 1.62 Hz, 1H) 7.29-7.39(m, 3H) 7.56-7.67(m, 2H) 8.31-8.38(m, 2H) 10.06(s, 1H) |
| 47 | 1-047 | | (400 MHz, DMSO-D6) 1.24-1.32(s, 9H) 2.13(s, 3H) 3.79-3.90(m, 2H) 4.46-4.56(m, 2H) 6.40(dd, J=8.00, 1.51 Hz, 1H) 6.80(t, J=7.88 Hz, 1H) 7.08(dd, J=7.65, 1.39 Hz, 1H) 7.33-7.45(m, 3H) 7.63-7.73(m, 2H) 7.98(d. J=6.26 Hz, 1H) 8.41(dd, J=5.10, 1.62 Hz, 1H) 10.08(s, 1 H) |

TABLE 7

| Ex. No. | | Chemical Compounds | NMR |
|---|---|---|---|
| 48 | 1-048 | | (400 MHz, DMSO-D6) 1.56(m, 2H) 1.58(m, 2H) 1.96(m, 2H) 3.44(m, 2H)3.68(m, 2H)3.75-3.79(m, 2H)4.34-4.42(m, 2H) 6.49(dd, J=8.12, 1.62 Hz, 1H) 6.72-6.82(m, 1H) 7.03(dd, J=7.65, 1.62 Hz, 1H) 7.29(dd, J=7.88, 4.64 Hz, 1H) 7.66(m, 2H) 7.83(m, 2H) 8.02(dd, J=7.88, 1.62 Hz, 1H) 8.40(dd, J=4.64, 1.62 Hz, 1H) 10.34(s, 1H) |
| 49 | 1-049 | | (400 MHz, DMSO-D6) 3.08(s, 6H) 3.78(m, 2H) 4.40(m, 2 H) 6.49(dd, J=8.12, 1.39 Hz, 1H) 6.79(m, 1H) 7.03(dd, J=7.54, 1.51 Hz, 1H) 7.28(dd, J=7.88, 4.64 Hz, 1H) 7.66 (m, 1H) 7.85(d, J=8.81 Hz, 2H) 8.02(dd, J=7.88, 1.62 Hz, 1H) 8.40(dd, J=4.64, 1.62 Hz, 1H) 10.35(s, 1H) |

TABLE 7-continued

| Ex. No. | | Chemical Compounds | NMR |
|---|---|---|---|
| 50 | 1-050 | | (400 MHz, DMSO-D6) 2.97-3.07(m, 4H) 3.65-3.74(m, 4H) 3.74-3.82(m, 2H) 4.35-4.45(m, 2H) 6.46(dd, J=8.12, 1.62 Hz, 1H) 6.76(t, J=7.77 Hz, 1H) 6.89(d, J=9.04 Hz, 2H) 7.05(dd, J=7.65, 1.62 Hz, 1H) 7.28(dd, J=7.88, 4.64 Hz, 1H) 7.55-7.66(m, 2H) 8.01(dd, J=7.88, 1.62 Hz, 1H) 8.39(dd, J=4.64, 1.62 Hz, 1H) 9.92(s, 1H) |
| 51 | 1-051 | | (400 MHz, DMSO-D6) 1.26(d, J=6.02 Hz, 6H) 3.71-3.81(m, 2H) 4.35-4.42(m, 2H) 4.44(dt, J=12.00, 6.02 Hz, 1H) 6.47(dd, J=8.12, 1.62 Hz, 1H) 6.71-6.81(m, 1H) 7.02(dd J=7.65, 1.39 Hz, 1H) 7.11(t, J=9.39 Hz, 1H) 7.28(dd, J=7.88, 4.64 Hz, 1H) 7.38(ddd, J=8.99, 2.38, 1.39 Hz, 1H) 7.70(dd, J=13.57, 2.43 Hz, 1H) 8.01(dd, J=7.88, 1.62 Hz, 1H) 8.39(dd, J=4.64, 1.62 Hz, 1H) 10.15(s, 1H) |
| 52 | 1-052 | | (400 MHz, DMSO-D6) 1.26(d, J=5.94 Hz, 6H) 3.77-3.86(m, 2H) 4.43-4.52(m, 2H) 4.59(dt, J=12.00, 5.94 Hz, 1H) 6.53(dd, J=8.00, 1.51 Hz, 1H) 6.73-6.84(m, 2H) 6.89(dd J=12.75, 2.78 Hz, 1H) 7.26-7.36(m, 2H) 7.79(t, J=9.04 Hz, 1H) 8.01(dd, J=7.88, 1.62 Hz, 1H) 8.39(dd, J=4.64, 1.62 Hz, 1H) 9.84(s, 1H) |
| 53 | 1-053 | | (300 MHz, DMSO-D6) 3.81(m, 2H) 4.44(m, 2H) 6.53(dd, J=8.10, 1.50 Hz, 1H) 6.82(t, J=7.90 Hz, 1H) 7.08(dd, J=7.30, 1.40 Hz, 1H) 7.33(dd, J=4.80, 8.10 Hz, 1H) 7.70(d, J=8.80 Hz, 2H) 8.01-8.07(m, 2H) 8.26(m, 1H), 8.40(m, 1H) 10.50(s, 1H) |
| 54 | 1-054 | | (300 MHz, DMSO-D6) 2.62(s, 6H) 3.81(m, 2H) 4.43(m, 2H) 6.53(dd, J=8.10, 1.50 Hz, 1H) 6.82(t, J=7.90 Hz, 1H) 7.08(dd, J=7.30, 1.40 Hz, 1H) 7.33(dd, J=4.80, 8.10 Hz, 1H) 7.94-8.14(m, 3H) 8.40(m, 1H) 10.34(s, 1H) |
| 55 | 1-055 | | (300 MHz, DMSO-D6) 1.28(d, J=5.86 Hz, 6H) 3.81(m, 2H) 4.43(m, 2H) 4.78(dt, J=12.00, 5.86 Hz, 1H) 6.50(dd, J=8.10, 1.50 Hz, 1H) 6.80(t, J=7.90 Hz, 1H) 7.08(dd, J=7.30, 1.40 Hz, 1H) 7.30(dd, J=4.80, 8.10 Hz, 1H) 7.88(d, J=8.80 Hz, 2H) 8.03-8.09(m, 2H) 8.26(m, 1H), 8.44(m, 1H) 10.50(s, 1H) |

TABLE 8

| Ex. No. | | Chemical Compounds | NMR |
|---|---|---|---|
| 56 | 1-056 | | (300 MHz, DMSO-D6) 3.29(s, 3H) 3.81(m, 2H) 4.43(m, 2H) 4.78(dt, J=12.00, 5.86 Hz, 1H) 6.50(dd, J=8.10, 1.50 Hz, 1H) 6.80(t, J=7.90 Hz, 1H) 7.08(dd, J=7.30, 1.40 Hz, 1H) 7.30(dd, J=4.80, 8.10 Hz, 1H) 7.88(d, J=8.80 Hz, 2H) 8.03-8.09(m, 2H) 8.26(m, 1H), 8.44(m, 1H) 10.25(s, 1H) |
| 57 | 1-057 | | (400 MHz, DMSO-D6) 0.93-1.00(d, J=6.82 Hz, 6H) 2.01(ddd, J=13.33, 6.61, 6.49 Hz, 1H) 3.72-3.81(m, 2H) 3.84(d, J=6.26 Hz, 2H) 4.34-4.45(m, 2H) 6.48(dd, J=8.12, 1.39 Hz, 1H) 6.77(t, J=7.68 Hz, 1H) 7.05(dd, J=7.54, 1.51 Hz, 1H) 7.20(d, J=9.04 Hz, 1H) 7.28(dd, J=8.00, 4.75 Hz, 1H) 7.88(dd, J=9.04, 2.55 Hz, 1H) 8.02(dd, J=7.88, 1.62 Hz, 1H) 8.08(d, J=2.78 Hz, 1H) 8.40(dd, J=4.64, 1.62 Hz, 1H) 10.22(s, 1H) |

TABLE 8-continued

| Ex. No. | | Chemical Compounds | NMR |
|---|---|---|---|
| 58 | 1-058 | 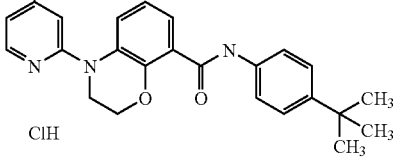 | (400 MHz, DMSO-D6) 1.20(s, 9H) 2.29(s, 3H) 3.96-4.06 (m, 2H) 4.29-4.38(m, 2H) 6.93(t, J=7.68 Hz, 2H) 7.13 (s, 1H) 7.21-7.28(m, 1H) 7.29-7.35(m, 2H) 7.46(dd, J=8.12, 1.39 Hz, 1H) 7.56-7.66(m, 2H) 8.16(d, J=5.33 Hz, 1H)10.03(s, 1H) |
| 59 | 1-059 | 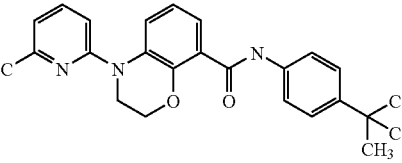 | (400 MHz, DMSO-D6) 1.24(s, 9H) 2.37(s, 3H) 3.97-4.07 (m, 2H)4.24-4.34(m, 2H) 6.76(d, J=7.42 Hz 1H) 6.87-6.93(m, 1H) 6.97(d, J=8.35 Hz, 1H) 7.17(dd, J=7.42. 1.62 Hz, 1H) 7.28-7.35(m, 2H) 7.43(dd, J=8.12, 1.62 Hz, 1H) 7.53(dd, J=8.35, 7.42 Hz, 1H) 7.58-7.65(m, 2H) 10.03(s, 1H) |
| 60 | 1-060 | 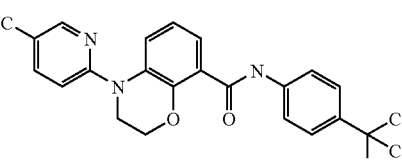 | (300 MHz, DMSO-D6) 1.27(s, 9H) 2.22(s, 3H) 3.97-4.01 (m, 2H) 4.30-4.34(m, 2H) 6.87-6.93(m, 1H) 7.11-7.20 (m, 2H) 7.34(d, J=7.89 Hz, 2H) 7.41(dd, J=8.23, 1.47 Hz, 1H) 7.52(dd, J=8.79, 2.20 Hz, 1H) 7.64(d, J=8.79 Hz, 2 H) 8.15(d, J=2.56 Hz, 1H) 10.04(s, 1H) |
| 61 | 1-061 | 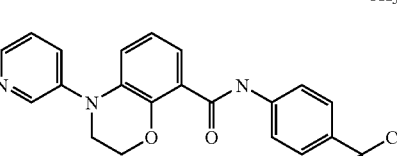 | (300 MHz, DMSO-d6) δ : 1.28(s, 9H), 3.80(t, J=4.4 Hz, 2H), 4.39(t, J=4.4 Hz, 2H), 6.83(t, J=7.9 Hz, 1H), 6.93 (dd, J=8.1, 1.5 Hz, 1H), 7.07(dd, J=7.5, 1.7 Hz, 1H), 7.35 (d, J=4.2 Hz, 2H), 7.42(dt, J=9.8, 2.5 Hz, 1H), 7.63-7.71 (m, 3H), 8.32(dd, J=4.8, 1.5 Hz, 1H), 8.55(d, J=2.6 Hz, 1H), 10.04(s, 1H). |
| 62 | 1-062 | 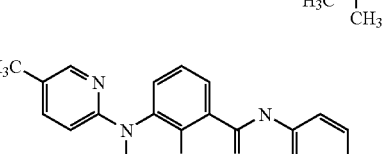 | (400 MHz, DMSO-D6) 2.23(s, 3H), 3.97(t, J=4.4 Hz, 2H), 4.31(t, J=4.4 Hz, 2H), 6.92(t, J=8 Hz,1H), 7.15(m, 2H) 7.44(dd, J=8, 1.4 Hz, 1H), 7.53(dd, J=8.8, 2.2 Hz, 1H) 7.80(d, J=8.8, 2H) 7.92(d, J=8.8 Hz, 2H) 8.15(d, J=2.56 Hz, 1H)10.58(s, 1H) |

TABLE 9

| Ex. No. | | Chemical Compounds | NMR |
|---|---|---|---|
| 63 | 1-063 | 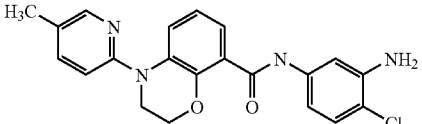 | (300 MHz, DMSO-d6) δ : 2.25(s, 3H), 3.99(t, J=4.6 Hz, 2H), 4.31(t, J=4.4 Hz, 2H), 5.34(br s, 2H), 6.81-6.92(m, 2H), 7.11-7.14(m, 3H), 7.39(td, J=7.7, 1.7 Hz, 2H), 7.52 (dt,.1 9.5, 1.3 Hz, 1H), 8.15(t, J=1.1 Hz, 1H), 9.97(s, 1H). |
| 64 | 1-064 | 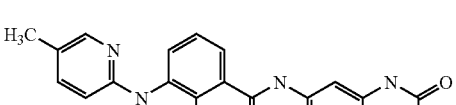 | (300 MHz, DMSO-d6) δ : 2.08(s, 3H), 2.23(s, 3H), 3.98(t, J= 4.4 Hz, 2H), 4.31(t, J=4.4 Hz, 2H), 6.90(t, .1 7.7 Hz, 1H), 7.13-7.16(m, 2H), 7.42(dd, J=8.3, 1.7 Hz, 2H), 7.53-7.59(m, 2H), 8.09-8.15(m, 2H), 9.50(s, 1H), 10.27(s, 1H). |
| 65 | 1-065 | 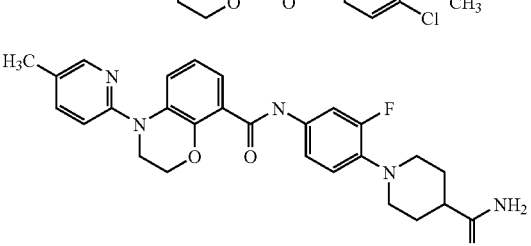 | (300 MHz, DMSO-d6) δ : 1.70-1.73(m, 2H), 1.93-1.97(m, 2H), 2.24(s, 3H), 2.71-2.74(m, 1H), 3.24-3.28(m, 2H), 3.99 (t, J=4.2 Hz, 2H), 4.33(t, .1 4.4 Hz, 2H), 6.91(t, J=7.9 7.04(t, J=10.0 Hz, 1H), 7.17-7.18(m, 2H), 7.38-7.44(m, 2H), 7.57-7.69(m, 2H), 8.16(s, 1H), 10.14(s, 1H). |

TABLE 9-continued

| Ex. | No. | Chemical Compounds | NMR |
|---|---|---|---|
| 66 | 1-066 | | (300 MHz, DMSO-d6) δ : 1.75-1.78(m, 4H), 2.22-2.25(m, 4H), 2.58(d, J=4.4 Hz, 3H), 2.70-2.72(m, 2H), 3.31-3.35 (m, 2H), 4.00(t, J=4.2 Hz, 2H), 4.34(t, J=4.2 Hz, 2H), 6.92(t, J=7.9 Hz, 1H), 7.07(t, J=9.2 Hz, 1H), 7.20(d, J= 7.7 Hz, 2H), 7.39-7.44(m, 2H), 7.63-7.72(m, 3H), 8.14-8.18 (m, 1H), 10.15(s, 1H). |
| 67 | 1-067 | | (300 MHz, DMSO-d6) δ : 1.73(s, 6H), 2.24-2.25(m, 3H), 2.80-2.83(m, 4H), 3.04-3.05(m, 3H), 3.35-3.45(m, 2H), 4.01(t, J=3.7 Hz, 2H), 4.34(t, J=4.2 Hz, 2H), 6.93(t, J= 2H), 7.09-7.12(m, 1H), 7.19-7.21(m, 2H), 7.42-7.45 (m, 3H), 7.66(t, J=13.9 Hz, 1H), 8.15-8.17(m, 1H), 10.18 (s, 1H). |
| 68 | 1-068 | | (300 MHz, DMSO-d6) δ : 1.13(t, J=7.0 Hz, 3H), 1.56-1.60 (m, 2H), 1.93-1.96(m, 2H), 2.23(s, 3H), 2.71-2.79(m, 2H), 3.17-3.20(m, 2H), 3.40-3.51(m, 3H), 3.99(t, J=4.4 Hz, 2H), 4.32(t, J=4.2 Hz, 2H), 6.90(t, J=7.7 Hz, 1H), 7.00 (q, J=8.4 Hz, 1H), 7.15(dt, J=10.1, 4.5 Hz, 2H), 7.40(dt, J=13.1, 4.8 Hz, 2H), 7.52(dd, J=8.6, 2.0 Hz, 1H), 7.65 (dd, J=15.0, 2.2 Hz, 1H), 8.15(d, J=2.6 Hz, 1H), 10.12(s, 1H). |
| 69 | 1-069 | | (300 MHz, DMSO-d6) δ : 1.09(d, J=6.2 Hz, 6H), 1.52-1.58 (m, 2H), 1.86-1.91(m, 2H), 2.23(s, 3H), 2.74-2.77(m, 2H), 3.17-3.19(m, 2H), 3.47-3.53(m, 1H), 3.59-3.61(m, 1H), 3.70-3.72(m, 1H), 3.98(t, J=4.4 Hz, 2H), 4.32(t, J=4.4 Hz, 2H), 6.90(t, J=7.9 Hz, 1H), 7.01(t, J=9.5 Hz, 1H), 7.15(dt, J=10.1,4.5 Hz, 2H), 7.40(dt, .1013.6,5.0 Hz, 2H), 7.52(dd, J=8.4, 1.8 Hz, 1H), 7.64(dd, J=14.9, 2.4 Hz, 1H), 8.15(d, J=2.2 Hz, 1H), 10.11(s, 1H). |

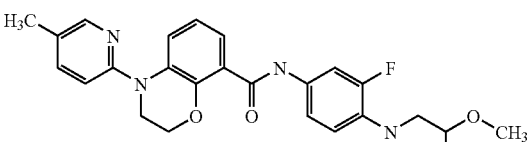

TABLE 10

| Ex. | No. | Chemical Compounds | NMR |
|---|---|---|---|
| 70 | 1-070 | | (300 MH, DMSO-d6) δ : 1.21-1.30(m, 1H), 1.51-1.63(m, 1H), 1.78-1.79(m, 1H), 1.96-2.02(m, 1H), 2.23(s, 3H), 2.53-2.68(m, 1H), 3.08-3.12(m, 1H), 3.32-3.38(m, 6H), 3.99(t, J=4.4 Hz, 2H), 4.32(t, J=4.2 Hz, 2H), 6.90(t, J== 7.9 Hz, 1H), 7.02(t, J=9.4 Hz, 1H), 7.15(dt, J=10.1, 4.5 Hz, 2H), 7.40(dt, J=12.3, 4.5 Hz, 2H), 7.52(dd, J=8.4, 2.6 Hz, 1H), 7.65(dd, J=15.0, 2.2 Hz, 1H), 8.15(d, J=2.6 Hz, 1H), 10.12(s, 1H). |
| 71 | 1-071 | | (300 MHz, DMSO-d6) δ : 1.31-1.36(m, 2H), 1.70-1.73(m, 2H), 2.23(s, 3H), 2.60-2.63(m, 2H), 3.23-3.24(m, 5H), 3.98 (t, J=4.4 Hz, 2H), 4.32(t, J=4.2 Hz, 2H), 6.90(t, J=7.9 Hz, 1H), 7.01(t, J=9.2 Hz, 1H), 7.14(t, J=9.2 Hz, 2H), 7.40(dd, J=13.4, 5.0 Hz, 2H), 7.52(dd, J=8.6, 2.4 Hz, 1H), 7.64(dd, J=15.0, 2.2 Hz, 1H), 8.14(s, 1H), 10.11(s, 1H). |

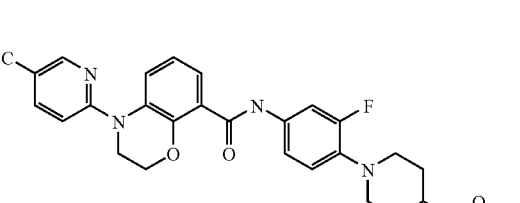

TABLE 10-continued

| Ex. No. | | Chemical Compounds | NMR |
|---|---|---|---|
| 72 | 1-072 | | (400 MHz, DMSO-d6) δ : 1.93-2.04(m, 2H), 2.24(s, 3H), 3.24-3.31(m, 5H), 3.51(dq, J=10.8, 2.6 Hz; 1H), 4.02(dd, J=7.7, 4.9 Hz, 2H), 4.36(t, J=4.4 Hz, 2H), 6.73(t, J=9.7 Hz, 1H), 6.93(t, J=7.9 Hz, 1H), 7.26-7.31(m, 3H), 7.42 (dd, J=8.1, 1.6 Hz, 1H), 7.60-7.62(m, 1H), 7.74-7.75(m, 1H), 8.17(s, 1H), 10.03(s, 1H). |
| 73 | 1-073 | | (400 MHz, DMSO-d6) 1.00(d, J=7.0 Hz, 6H), 1.95-2.08 (m, 1H), 2.23(s, 3H), 3.77-3.82(m, 5H), 3.97-4.02(m, 2H), 4.30-4.35(m, 2H), 6.91(t, J=7.9 Hz, 1H), 7.09-7.20(m, 3H), 7.42(d, J=7.9 Hz, 1H), 7.53(d, J=8.8 Hz, 1H), 7.80-7.8.4(m, 1H), 8.07-8.10(m, 1H), 8.15(brs, 1H), 10.13(s, 1H). |
| 74 | 1-074 | | (400 MHz, DMSO-d6) 0.98(t, J=8.1 Hz, 6H), 1.98-2.05(m, 1H), 2.23(s, 3H), 3.79(d, J=6.5 Hz, 2H), 3.99(t, J=4.4 Hz, 2H), 4.33(t, J=4.4 Hz, 2H), 6.91(t, J=7.9 Hz, 1H), 7.08(d, J=9.3 Hz, 1H), 7.14(d, J=8.3 Hz, 1H), 7.19(dd, J= 7.9, 1.4 Hz, 1H), 7.42(dd, J=7.9, 1.4 Hz, 1H), 7.53(dd, J= 8.3, 2.3 Hz, 1H), 7.81(dd, J=8.8, 2.8 Hz, 1H), 8.02(d, J= 2.8 Hz, 1H), 8.15(brs, 1H), 10.09(s, 1H), 12.59(s, 1H). |
| 75 | 1-075 | | (400 MHz, DMSO-d6) 1.01(d, J=6.6 Hz, 6H), 2.06-2.15 (m, 1H), 2.23(s, 3H), 3.90(d, J=6.6 Hz, 2H), 3.99(t, J== 4.4 Hz, 2H), 4.33(t, J=4.2 Hz, 2H), 6.91(t, J=7.9 Hz, 1H), 7.12-7.13(m, 2H), 7.19(dd, J=7.7, 3.9 Hz, 1H), 7.41(dd, J= 8.3, 1.7 Hz, 1H), 7.52(dd, J=5.8, 2.2 Hz, 1H), 7.58(bm, s, 1H), 7.60(brs, 1H), 7.85(dd, J=9.0, 2.8 Hz, 1H), 8.13(d, J= 2.9 Hz, 1H), 8.15(brs, 1H), 10.08(s, 1H). |
| 76 | 1-076 | | (300 MHz, DMSO-d6) 1.00(d, J=6.6 Hz, 6H), 2.06-2.14 (m, 1H), 2.23(s, 3H), 2.82(d, J=4.8 Hz, 3H), 3.87(d, J== 6.6 Hz, 2H), 3.99(t, J=4.2 Hz, 2H), 4.32(t,J=4.2 Hz, 2H), 6.90(t, J=7.9 Hz, 1H), 7.09-7.20(m, 3H), 7.41(d, J==4.0 Hz, 1H), 7.52(dd, J=8.4, 2.6 Hz, 1H), 7.83(dd, J=9.0, 2.8 Hz, 1H), 8.00-8.07(m, 2H), 8.15(brs, 1H), 10.08(s, 1H). |
| 77 | 1-077 | | (300 MHz, DMSO-d6) 0.95(d,.9 6.6 Hz, 6H), 1.90-2.04 (m, 1H), 2.23(5, 3H), 2.79(s, 3H), 2.98(s, 3H), 3.76(d, J= 6.2 Hz, 2H), 3.99(t, J=4.2 Hz, 2H), 4.33(t, J=4.4 Hz, 2H), 6.90(t, J=7.7 Hz, 1H), 7.03(d, J=8.8 Hz, 1H), 7.13(d, J= 8.8 Hz, 1H), 7.18(dd, J=7.3, 1.5 Hz, 1H), 7.41(dd, J=8.1, 1.5 Hz, 1H), 7.52(dd, J=8.6, 2.0 Hz, 1H), 7.57(d, J=2.6 Hz, 1H), 7.69(dd, J=9.0, 2.8 Hz, 1H), 8.15(d, J=2.6 Hz, 1H), 10.06(s, 1H). |

TABLE 11

| Ex. No. | | Chemical Compounds |
|---|---|---|
| 78 | 1-078 |  |

TABLE 11-continued
| | | |
|---|---|---|
| 79 | 1-079 | 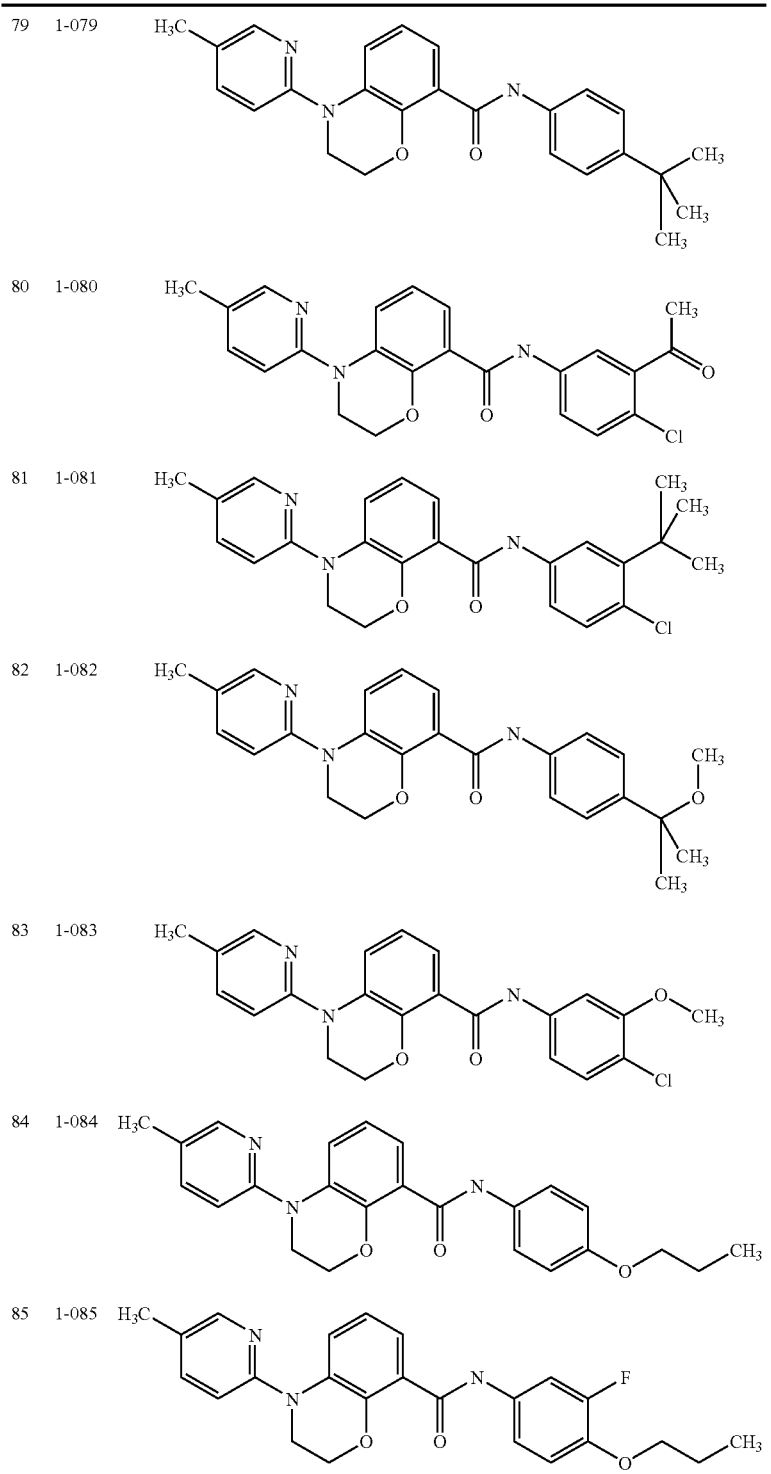 |
| 80 | 1-080 | |
| 81 | 1-081 | |
| 82 | 1-082 | |
| 83 | 1-083 | |
| 84 | 1-084 | |
| 85 | 1-085 | |
| NMR |
|---|
| 78 (400 MHZ. DMSO-d6) 2.23 (s, 3H), 2.55 (s, 3H), 3.99 (t, J = 4.4 Hz, 2H), 4.33 (t, J = 4.4 Hz, 2H), 6.92 (t, J = 7.9 Hz, 1H), 7.14 (d, J = 8.8 Hz, 1H), 7.18 (dd, J = 7.9, 1.4 Hz, 1H), 7.44 (dd, J = 8.1, 1.6 Hz, 1H), 7.53 (dd, J = 8.6, 2.6 Hz, 1H), 7.87 (d, J = 8.8 Hz, 2H), 7.96 (d, J = 8.8 Hz. 2H), 8.15 (s, 1H), 10.48 (s, 1H). |
| 79 (300 MHz, DMSO-d6) 1.42 (s, 6H), 2.23 (s, 3H), 4.00 (t, J = 4.4 Hz, 2H), 4.33 (t, J 4.4 Hz, 2H), 4.93 (s, 1H), 6.91 (t, J = |

TABLE 11-continued

| | |
|---|---|
| | 7.9 Hz, 1H), 7.13 (d, J = 8.4 Hz, 1H), 7.19 (dd, J = 7.7, 1.5 Hz, 1H). 7.39-7.43 (m, 3H), 7.52 (dd, J = 9.0, 2.4 Hz, 1H), 7.64 (d, J = 8.4 Hz, 2H), 8.15 (s, 1H), 10.04 (s, 1H). |
| 80 | (400 MHz, DMSO-d6) 2.23 (s, 3H), 2.59 (s, 3H), 3.99 (t, J = 4.4 Hz, 2H), 4.32 (t, J = 4.4 Hz, 2H), 6.92 (t, J = 7.9 Hz, 1H), 7.14 (d, J = 8.3 Hz, 1H), 7.18 (dd, J = 7.7, 1.6 Hz, 1H), 7.44 (dd, J = 8.1, 1.6 Hz, 1H), 7.50-7.55 (m, 2H), 7.87 (dd, J = 8.8, 2.3 Hz, 1H), 8.07 (d, J = 2.3 Hz, 1H). 8.15 (s, 1H), 10.42 (s, 1H). |
| 81 | (400 MHz, DMSO-d6) 1.59 (s, 6H), 2.23 (s, 3H), 3.99 (t, J = 4.4 Hz, 2H), 4.31 (t, J = 4.4 Hz, 2H), 5.28 (s, 1H), 6.91 (t, J = 7.9 Hz, 1H), 7.11-7.17 (m, 2H), 7.32 (d, J = 8.3 Hz, 1H), 7.42 (dd, J = 8.3, 1.4 Hz, 1H), 7.53 (dd, J = 8.6. 2.6 Hz, 1H), 7.70 (dd, J = 8.8, 2.8 Hz, 1H), 8.13-8.18 (m, 2H), 10.24 (s, 1H). |
| 82 | (300 MHz, DMSO-d6) 1.44 (s, 6H), 2.23 (s, 3H), 2.96 (s, 3H), 3.99 (t, J = 4.4 Hz, 2H), 4.32 (t, J = 4.4 Hz, 2H), 6.91 (t, J = 7.9 Hz, 1H). 7.14 (d, J = 8.4 Hz, 1H), 7.18 (dd, J = 7.7, 1.5 Hz, 1H), 7.33 (d, J = 8.8 Hz, 2H), 7.42 (dd, J = 8.3, 1.7 Hz, 1H), 7.52 (dd, J = 8.8, 2.2 Hz, 1H), 7.70 (d, J = 8.8 Hz, 2H), 8.15 (d, J = 2.6 Hz, 1H), 10.11 (s, 1H). |
| 83 | (300 MHz, CHLOROFORM-d) 2.28 (s, 3H), 3.97 (s, 3H), 4.17 (t, J = 4.4 Hz, 2H). 4.52 (t, J = 4.6 Hz, 2H), 6.84 (dd, J = 8.6, 2.4 Hz, 1H), 6.99 (t, J = 8.1 Hz, 1H), 7.10 (d, J = 8.4 Hz, 1H), 7.29 (d, J = 8.8 Hz, 1H), 7.38 (dd, J = 8.4, 2.2 Hz, 1H), 7.44 (dd, J = 8.1, 1.5 Hz, 1H), 7.88 (dd, J = 5.9. 2.2 Hz, 2H), 8.17 (d, J = 1.8 Hz, 1H), 9.71 (s, 1H). |
| 84 | (400 MHz, CHLOROFORM-d) 1.04 (t, J = 7.4 Hz, 3H), 1.79-1.83 (m, 2H), 2.27 (s, 3H), 3.92 (t, J = 6.7 Hz, 2H), 4.17 (t, J = 4.4 Hz, 2H), 4.49 (t, J = 4.4 Hz, 2H). 6.90 (d, J = 9.3 Hz, 2H), 6.97 (t, J = 8.1 Hz, 1H), 7.10 (d, J = 8.3 Hz, 1H), 7.37 (dd, J = 8.3, 2.3 Hz, 1H), 7.42 (dd, J = 8.1, 1.2 Hz, 1H), 7.57 (d, J = 8.8 Hz, 2H), 7.90 (dd, J = 7.9, 1.4 Hz, 1H). 8.16 (s, 1H), 9.52 (s, 1H). |
| 85 | (400 MHz, CHLOROFORM-d) 1.04-1.06 (m, 3H), 1.82-1.86 (m, 2H). 2.28 (s, 3H), 3.99-4.00 (d, 2H), 4.16-4.17 (m, 2H), 4.50-4.51 (m, 2H), 6.92-7.00 (m, 2H), 7.10 (dd, J = 8.3, 2.3 Hz, 1H), 7.27-7.30 (m, 1H), 7.36-7.45 (m, 2H), 7.57-7.60 (m, 1H), 7.87-7.91 (m, 1H), 8.17 (s, 1H), 9.57 (s. 1H). |

TABLE 12

| Ex. No. | | Chemical Compounds |
|---|---|---|
| 86 | 1-086 | |
| 87 | 1-087 | |
| 88 | 1-088 | |

TABLE 12-continued
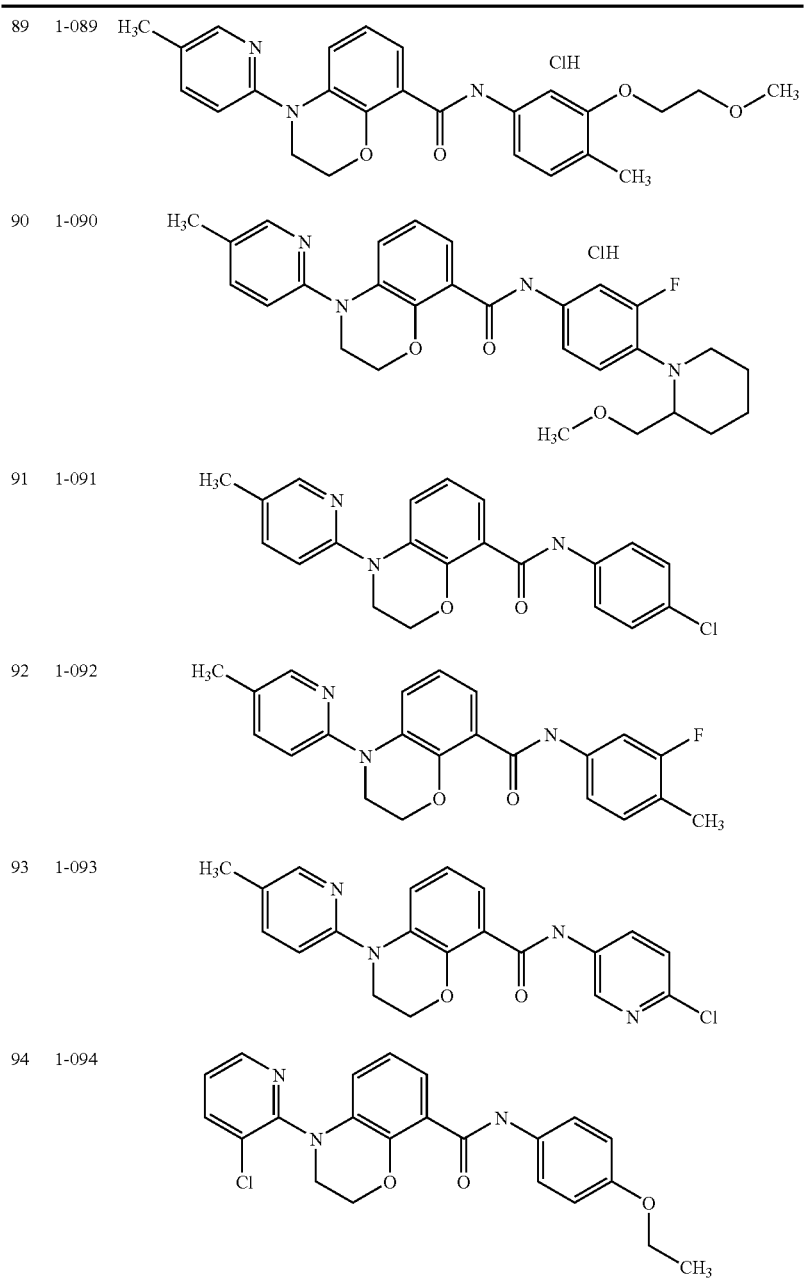
| | NMR |
|---|---|
| 86 | (400 MHz, CHLOROFORM-d) 1.44-1.45 (m, 3H), 2.28 (d, J = 3.2 Hz, 3H), 4.10-4.17 (m, 4H), 4.50-4.51 (m, 2H), 6.93-6.98 (m, 2H), 7.09-7.11 (m, 1H), 7.27-7.29 (m, 1H), 7.36-7.45 (m, 2H), 7.57-7.60 (m, 1H), 7.88-7.90 (m, 1H), 8.17 (s, 1H), 9.57 (s, 1H). |
| 87 | (400 MHz, CHLOROFORM-d) 1.44 (t, J = 7.0 Hz, 3H), 2.20 (s, 3H), 2.28 (s, 3H), 4.11 (q, J = 7.0 Hz. 2H), 4.17 (1, J = 4.4 Hz, 2H), 4.50 (t, J = 4.4 Hz, 2H), 6.82 (dd, J = 7.9, 1.9 Hz, 1H), 6.97 (t, J = 8.1 Hz, 1H), 7.09 (dd, J = 12.6, 8.1 Hz, 2H), 7.37 (dd, J = 8.3. 2.3 Hz, 2H), 7.42 (dd, J = 8.1, 1.6 Hz, 2H), 7.62 (d, J = 2.3 Hz, 1H), 7.89 (dd, J = 7.9, 1.4 Hz, 1H), 8.17 (s, 1H), 9.60 (s, 1H). |
| 88 | (400 MHz, DMSO-d6) 2.19 (S. 3H), 2.23 (s, 3H), 3.99 (t, J = 3.9 Hz, 2H), 4.32 (t, J = 4.6 Hz, 2H), 4.40 (s, 2H), 6.90 (t, J = 7.9 Hz, 1H), 7.08-7.17 (m, 3H), 7.24 (d, J = 7.9 Hz, 1H), 7.38-7.41 (m, 4H), 7.53 (dd, J = 8.8, 2.3 Hz, 1H), 8.15 (s, 1H), 10.07 (s, 1H). |

TABLE 12-continued

| | |
|---|---|
| 89 | (400 MHz, DMSO-d6) 2.12 (s, 3H), 2.28 (s, 3H), 3.70 (t, J = 4.6 Hz, 2H), 4.03-4.08 (m, 4H), 4.38 (t, J = 4.2 Hz, 2H), 6.95 (t, J = 7.9 Hz, 1H), 7.08 (d, J = 7.9 Hz, 1H), 7.20 (dd, J = 8.1, 1.6 Hz, 1H), 7.29 (dd, J = 14.8, 8.3 Hz, 2H), 7.44 (d J = 11.1 Hz, 2H), 7.76 (d, J = 8.8 Hz, 1H), 8.19 (s, 1H), 10.06 (s, 1H). |
| 90 | (400 MHz, DMSO-d6) 1.64 (br s, 1H), 1.79 (t, J = 10.0 Hz, 2H), 1.91 (s, 3H), 2.30 (s, 3H), 3.27 (d, J = 7.4 Hz, 1H), 3.45 (d, J = 10.0 Hz, 3H), 3.81-3.84 (m, 1H), 4.02-4.06 (m, 3H), 4.39 (br s, 2H), 6.98 (t, J = 7.7 Hz, 1H), 7.26-7.36 (m, 2H), 7.48 (d, J = 7.9 Hz, 1H), 7.58 (d, J = 7.4 Hz, 1H), 7.88-7.92 (m, 3H), 8.21 (s, 1H), 10.63 (s, 1H). |
| 91 | (300 MHz, DMSO-d6) 2.22 (s, 3H), 3.96 (q, J = 6.8 Hz, 2H), 4.29 (q, J = 6.6 Hz, 2H), 6.90 (t, J = 7.9 Hz, 1H), 7.12-7.15 (m, 2H), 7.35-7.43 (m, 3H), 7.52 (dd, J = 9.3, 2.3 Hz, 1H), 7.77 (d, J = 19.0 Hz, 2H), 8.14 (d, J = 2.3 Hz, 1H), 10.27 (s, 1H). |
| 92 | (300 MHz, DMSO-d6) 2.20 (d, J = 1.1 Hz, 3H), 2.23 (s, 3H), 3.99 (t, J = 4.2 Hz, 2H), 4.32 (t, J = 4.4 Hz, 2H), 6.91 (t, J = 7.7 Hz, 1H), 7.17-7.20 (m, 3H), 7.38-7.42 (m, 2H), 7.53 (dd, J = 8.4, 2.2 Hz, 1H), 7.67 (dd, J = 12.1, 1.8 Hz, 1H). 8.15 (d, J = 2.2 Hz, 1H), 10.23 (s, 1H). |
| 93 | (300 MHz, DMSO-d6) 2.23 (s, 3H), 3.99 (t, J = 4.4 Hz, 2H), 4.33 (t, J = 4.4 Hz, 2H), 6.92 (t, J = 7.9 Hz, 1H), 7.14-7.19 (m, 2H), 7.44-7.55 (m, 3H). 8.15 (q, J = 0.7 Hz, 1H), 8.23 (dd, J = 8.8, 2.6 Hz, 1H), 8.75 (d, J = 2.6 Hz, 1H), 10.48 (s, 1H). |
| 94 | (400 MHz, DMSO-d6) 1.31 (t, J = 7.2 Hz, 3H), 3.79 (t, J = 4.4 Hz, 2H), 3.99 J = 7.0 Hz, 2H), 4.42 (t, J = 4.4 Hz, 2H), 6.48 (dd, J = 8.1, 1.6 Hz, 1H), 6.78 (t, J = 7.9 Hz, 1H), 6.88 (d, J = 9.3 Hz, 2H), 7.07 (dd, J = 7.9, 1.4 Hz. 1H), 7.30 (dd, J = 7.6, 4.4 Hz, 1H), 7.64 (d, J = 8.8 Hz, 2H), 8.03 (dd, J = 7.9, 1.9 Hz, 1H), 8.41 (dd, J = 4.4, 1.6 Hz, 1H), 9.99 (s, 1H). |

TABLE 13

| Ex. No. | | Chemical Compounds |
|---|---|---|
| 95 | 1-095 | 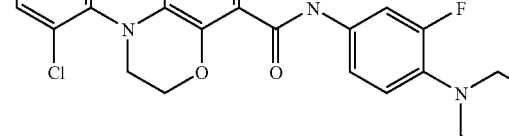 |
| 96 | 1-096 | 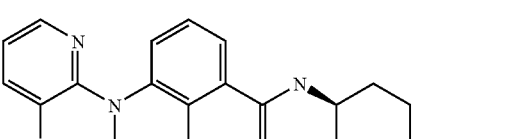 |
| 97 | 1-097 | 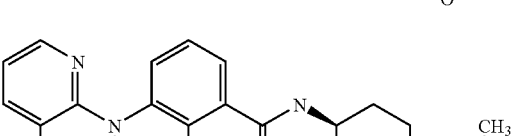 |
| 98 | 1-098 | 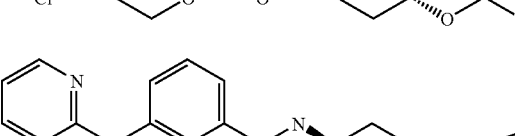 |

TABLE 13-continued

| | | |
|---|---|---|
| 99 | 1-099 | 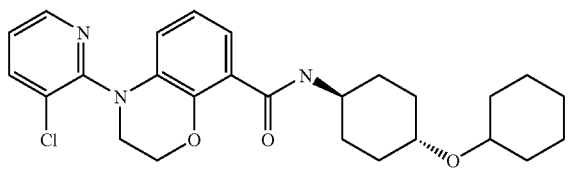 |
| 100 | 1-100 | 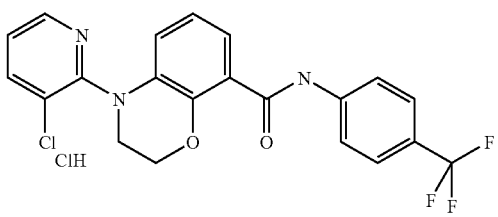 |
| 101 | 1-101 | 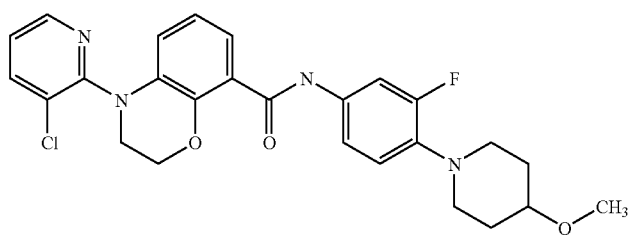 |
| 102 | 1-102 | 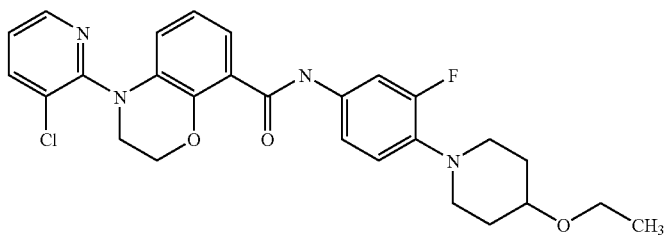 |

| | NMR |
|---|---|
| 95 | (400 MHz, DMSO-d6) 1.49-1.54 (m, 2H), 1.61-1.67 (m, 4H), 2.91 (t, J = 5.1 Hz, 4H), 3.79 (t, J = 4.4 Hz, 2H), 4.42 (t, J = 4.4 Hz, 2H), 6.49 (dd, J = 8.1, 1.6 Hz, 1H), 6.79 (t, J = 7.9 Hz, 1H), 6.99 (t, J = 9.3 Hz, 1H), 7.05 (dd, J = 7.4, 1.4 Hz, 1H), 7.30 (dd, J = 8.0, 4.4 Hz, 1H), 7.39 (dd, J = 8.6, 2.1 Hz, 1H), 7.64 (dd. J = 14.8, 2.3 Hz, 1H), 8.03 (dd, J = 7.9, 1.9 Hz, 1H), 8.42 (dd, J = 4.6, 1.4 Hz, 1H), 10.13 (s, 1H). |
| 96 | (400 MHz, DMSO-d6) 1.08 (t, J = 7.0 Hz, 3H), 1.18-1.37 (m, 4H), 1.85-1.98 (m, 4H), 3.17-3.24 (m, 1H), 3.43 (q, J = 7.0 Hz, 2H), 3.67-3.73 (m, 1 H), 3.76 (t, J = 4.4 Hz, 2H), 4.38 (t, J = 4.4 Hz, 2H), 6.44 (dd, J = 7.9, 1.4 Hz, 1H), 6.73 (t, J = 7.9 Hz. 1H), 7.07 (dd, J = 7.7, 1.6 Hz, 1H), 7.27 (dd, J = 8.0, 4.8 Hz, 1H), 7.92 (d, J = 7.4 Hz, 1H), 8.01 (dd, J = 7.9, 1.9 Hz, 1H), 8.39 (dd, J = 4.8, 2.0 Hz, 1H). |
| 97 | (400 MHz, DMSO-d6) 1.05 (d, J = 6.0 Hz, 6H), 1.15-1.38 (m, 4H), 1.85-1.90 (m, 4H), 3.27-3.31 (m, 1H), 3.63-3.73 (m, 2H), 3.76 (t, J = 4.6 Hz, 2H), 4.38 (t, J = 4.6 Hz, 2H), 6.44 (dd, J = 7.9, 1.4 Hz, 1H), 6.73 (t, J = 7.9 Hz, 1H), 7.07 (dd, J = 7.7. 1.6 Hz, 1H), 7.27 (dd, J = 8.0, 4.8 Hz, 1H), 7.91 (d, J = 7.9 Hz, 1H), 8.01 (dd, J = 7.9, 1.9 Hz, 1H), 8.39 (dd, J = 4.6, 1.4 Hz, 1H). |
| 98 | (400 MHz, DMSO-d6) 1.17-1.70 (m, 12H), 1.84-1.94 (m, 4H), 3.20-3.25 (m, 1H), 3.66-3.72 (m, 1H), 3.76 (t, J = 4.4 Hz, 2H), 3.98-4.01 (m, 1H), 4.38 (t, J = 4.4 Hz, 2H), 6.44 (dd, J = 8.1, 1.6 Hz, 1H), 6.72 (t, J = 7.9 Hz, 1H), 7.07 (dd, J = 1.4 Hz, 1H), 7.27 (dd, J = 8.1. 4.9 Hz, 1H), 7.91 (d, J = 7.9 Hz, 1H), 8.01 (dd, J = 7.9, 1.4 Hz, 1H), 8.39 (dd, J = 4.9, 1.6 Hz, 1H). |
| 99 | (400 MHz, DMSO-d6) 1.12-1.47 (m, 10H), 1.62-1.66 (m, 2H), 1.74-1.78 (m, 2H), 1.85-1.91 (m, 4H), 3.32-3.36 (m, 2H), 3.66-3.72 (m, 1H), 3.76 (t, J = 4.6 Hz, 2H), 4.38 (t, J = 4.4 Hz, 2H), 6.43 (dd, J = 8.1, 1.6 Hz, 1H), 6.72 (t, J = 7.9 Hz, 1H), 7.91 (d, J = 7.9 Hz, 1H), 8.01 (dd, J = 7.9, 1.9 Hz, 1H), 8.39 (dd, J = 4.8, 2.0 Hz, 1H). |

TABLE 13-continued
| | |
|---|---|
| 100 | (300 MHz, DMSO-d6) δ: 3.81 (t, J = 4.4 Hz, 2H), 4.43 (t, J = 4.4 Hz, 2H), 6.53 (dd, J = 8.1, 1.5 Hz, 1H), 6.82 (t, J = 7.9 Hz, 1H), 7.07 (dd, J = 7.5, 1.7 Hz, 1H), 7.32 (dd, J = 7.9, 4.6 Hz, 1H), 7.71 (d, J = 8.8 Hz, 2H), 7.97 (d, J = 8.8 Hz, 2H), 8.05 (dd, J = 8.1, 1.5 Hz, 1H), 8.43 (dd, J = 2.1, 1.0 Hz, 1H), 10.52 (s, 1H). |
| 101 | (300 MHz, DMSO-d6) δ: 1.56-1.61 (m, 2H), 1.95-1.99 (m, 2H), 2.74-2.79 (m, 2H), 3.17-3.19 (m, 2H), 3.29-3.33 (m, 4H), 3.80 (t, J = 4.4 Hz, 2H), 4.43 (t, J = 4.4 Hz, 2H), 6.50 (dd, J = 8.1, 1.5 Hz, 1H), 6.80(t, J = 7.9 Hz, 1H), 7.01-7.06 (m, 2H), 7.31 (dd, J = 7.7, 4.8 Hz, 1H), 7.40 (dd, J = 5.3, 2.7 Hz, 1H), 7.66 (dd, J = 15.0, 2.2 Hz, 1H) 5.04 (dd, J = 7.9, 1.7 Hz, 1H), 8.43 (dd, J = 2.1, 1.0 Hz, 1H), 10.13 (s, 1H). |
| 102 | (300 MHz, DMSO-d6) δ: 1.13 (t, J = 7.0 Hz, 3H), 1.52-1.63 (m, 2H), 1.95-1.97 (m, 2H), 2.74-2.77 (m, 2H), 3.18-3.20 (m, 2H), 3.42-3.49 (m, 3H), 3.80 (t, J = 4.4 Hz, 2H), 4.43 (t, J = 4.4 Hz, 2H), 6.50 (dd, J = 8.1, 1.5 Hz, 1H). 6.80 (t, J = 7.9 Hz, 1H), 7.01-7.06 (m, 2H), 7.31 (dd, J = 7.9, 4.6 Hz, 1H), 7.40 (dd, J = 8.8, 1.5 Hz, 1H), 7.66 (dd, J = 14.9, 2.4 Hz, 1H), 8.04 (dd, J = 7.9, 1.7 Hz, 1H), 8.43 (dd, J = 2.2, 1.1 Hz, 1H), 10.13 (s, 1H). |
TABLE 14
| Ex. No. | | Chemical Compounds |
|---|---|---|
| 103 | 1-103 | 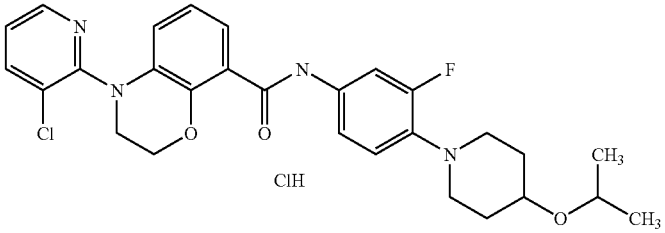 |
| 104 | 1-104 | 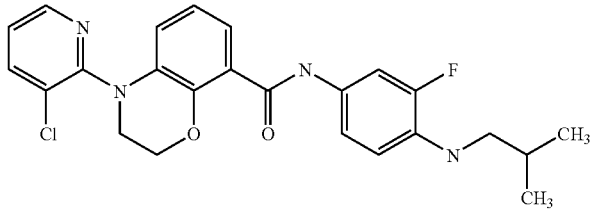 |
| 105 | 1-105 | 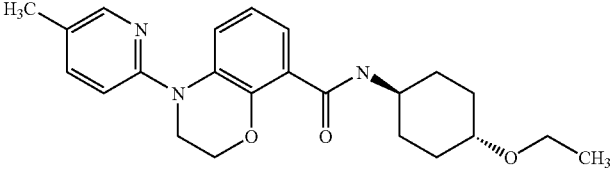 |
| 106 | 1-106 | 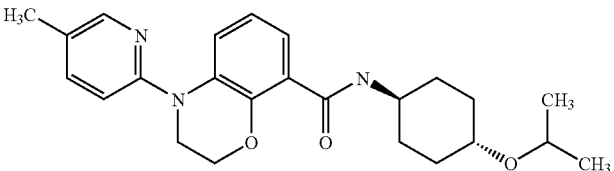 |
| 107 | 1-107 | 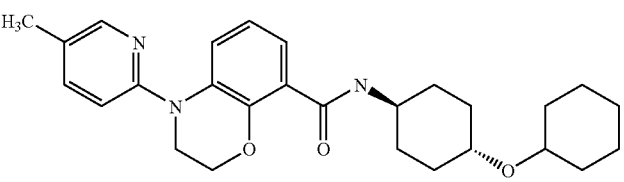 |

TABLE 14-continued

| | | |
|---|---|---|
| 108 | 1-108 | 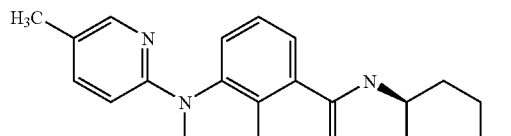 |
| 109 | 1-109 | 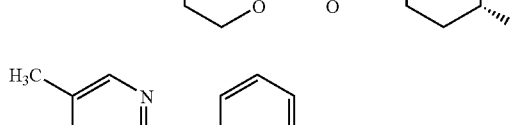 |
| 110 | 1-110 | 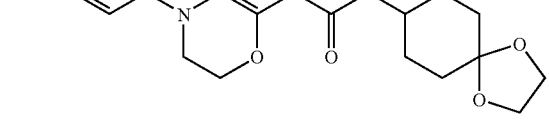 |

| | NMR |
|---|---|
| 103 | (300 MHz, DMSO-d6) δ: 1.10 (d, J = 5.9 Hz, 6H), 1.64-1.67 (m, 2H), 1.95-2.04 (m, 2H), 2.92-2.95 (m, 2H), 3.26-3.30 (m, 2H), 3.55-3.59 (m, 1 H), 3.72-3.79 (m, 3H), 4.43 (t, J = 4.4 Hz, 2H), 6.51 (dd, J = 8.1, 1.8 Hz, 1H), 6.80 (t, J = 7.7 Hz, 1H) 7.06 (dd, J = 7.7, 1.5 Hz, 1H), 7.30-7.33 (m, 2H), 7.45 (d, J = 8.4 Hz, 1H), 7.73 (d, J = 14.7 Hz, 1H), 8.04 (dd, J = 8.1, 1.8 Hz, 1H), 8.43 (dd, J = 4.8, 1.5 Hz, 1H), 10.24 (s, 1H). |
| 104 | (400 MHz. CHLOROFORM-d) 1.03 (s, 3H), 1.05 (s, 3H), 2.09-2.15 (m, 1H), 3.79 (d, J = 7.0 Hz, 2H), 3.95 (t, J = 4.4 Hz, 2H), 4.63 (t, J = 4.6 Hz, 2H), 6.67 (dd, J = 8.1, 1.6 Hz, 1H), 6.90-6.94 (m, 2H), 7.12 (q, J =4.2 Hz, 1H), 7.30 (t, J = 5.3 Hz, 1H), 7.58 (dd, J = 13.0, 2.8 Hz, 1H), 7.79-7.80 (m, 2H), 8.38 (dd, J = 4.6, 1.4 Hz, 1H), 9.58 (s, 1H). |
| 105 | (400 MHz, DMSO-d6) 1.08 (t, J = 6.8 Hz, 3H), 1.20-1.33 (m, 4H), 1.85-1.97 (m, 4H), 2.20 (s, 3H), 3.14-3.24 (m, 1H), 3.43 (q, J = 6.8 Hz, 2H), 3.66-3.78 (m, 1H), 3.95 (t, J = 4.4 Hz, 2H), 4.27 (t, J = 4.4 Hz, 2H), 6.84 (dd, J = 8.0, 7.6 Hz, 1H), 7.17 (d, J = 8.8 Hz, 1H), 7.17 (dd, J = 8.0, 2.0 Hz, 1H), 7.33 (dd, J = 8.0, 1.2 Hz, 1H), 7.48 (dd, J = 8.4, 2.4 Hz, 1H), 7.90 (d, J = 8.0 Hz, 1H), 8.11 (d, J = 2.4 Hz, 1H). |
| 106 | (400 MHz, DMSO-d6) 1.04 (d, J = 6.0 Hz, 6H), 1.16-1.37 (m, 4H), 1.81-1.91 (m, 4H), 2.20 (s, 3H), 3.23-3.33 (m, 1H), 3.62-3.73 (m, 1H), 3.95 (t, J = 4.4 Hz, 2H), 4.27 (t, J = 4.4 Hz, 2H), 6.84 (dd, J = 8.4, 7.2 Hz, 1H), 7.07 (d, J = 8.4 Hz, 1H), 7.18 (dd, J = 8.0, 2.0 Hz, 1H), 7.33 (dd, J = 8.0, 2.0 Hz, 1H), 7.48 (dd, J = 8.0, 2.0 Hz, 1H), 7.89 (d, J = 8.0 Hz, 1H), 8.11 (d, J = 1.6 Hz, 1H). |
| 107 | (400 MHz, DMSO-d6) 1.05-1.36 (m, 9H), 1.40-1.92 (m, 9H), 2.20 (s, 3H), 3.26-3.36 (m, 1H), 3.64-3.74 (m, 1H), 3.95 (t, J = 4.4 Hz, 2H), 4.27 (t, J = 4.4 Hz, 2H), 6.84 (dd, J = 8.0, 8.0 Hz, 1H), 7.07 (d, J = 8.5 Hz, 1H), 7.17 (dd, J = 7.4, 1.4 Hz, 1H), 7.33 (dd, J = 8.0, 1.4 Hz, 1H), 7.48 (dd, J = 8.5, 2.6 Hz, 1H), 7.90 (d, J = 8.0 Hz, 1H), 8.12 (d, J = 1.2 Hz, 1H). |
| 108 | (400 MHz, DMSO-d6) 1.04-1.34 (m, 4H), 1.72-1.87 (m, 4H), 2.20 (s, 3H), 2.48-2.58 (m, 1H), 3.30 (brs, 3H), 3.59-3.71 (m, 1H), 3.95 (t, J = 4.4 Hz, 2H), 4.27 (t, J = 4.4 Hz, 2H), 6.84 (dd, J = 8.0, 8.0 Hz, 1H), 7.07 (d, J = 8.5 Hz, 1H), 7.19 (dd, J = 8.0, 1.5 Hz, 1H), 7.33 (dd, J = 8.0. 1.5 Hz, 1H), 7.48 (dd, J = 8.5, 2.6 Hz, 1H). 7.86 (d, J = 8.0 Hz, 1H), 8.12 (d, J = 2.0 Hz, 1H). |
| 109 | (400 MHz, DMSO-d6) 1.48-1.84 (m, 8H), 2.20 (s, 3H), 3.78-3.88 (m, 5H), 3.95 (t, J = 4.4 Hz, 2H), 4.28 (t, J = 4.4 Hz, 2H), 6.84 (dd, J = 8.0, 8.0 Hz, 1H), 7.08 (d, J = 8.5 Hz, 1H), 7.18 (dd, J = 8.0, 1.5 Hz, 1H), 7.34 (dd, J = 8.0, 1.5 Hz, 1H), 7.48 (dd, J = 8.5, 2.5 Hz, 1H), 7.97 (d, J = 8.0 Hz, 1H), 8.12 (d, J = 2.5 Hz, 1H). |

TABLE 14-continued 110 (400 MHz, DMSO-d6) 1.74-1.84 (m, 2H), 2.05-2.09 (m, 2H), 2.20 (s, 3H), 2.26-2.33 (m, 2H), 2.41-2.46 (m, 2H), 3.95 (t, J = 4.4 Hz, 2H), 4.21-4.28 (m, 3H), 6.85 (t, J = 7.9 Hz, 1H), 7.08 (d, J = 8.8 Hz, 1H), 7.18 (dd, J = 7.7, 1.6 Hz, 1H), 7.35 (dd, J = 8.1, 1.6 Hz, 1H), 7.49 (dd, J = 8.8, 2.3 Hz, 1H), 8.11-8.13 (m, 2H).

TABLE 15

| Ex. No. | | Chemical Compounds |
|---|---|---|
| 111 | 1-111 | |
| 112 | 1-112 | |
| 113 | 1-113 | |
| 114 | 1-114 | |
| 115 | 1-115 | |

TABLE 15-continued

| | | | |
|---|---|---|---|
| 116 | 1-116 | 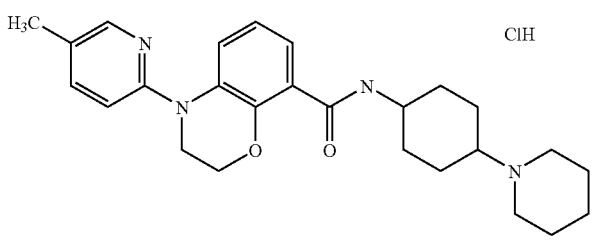 | ClH ClH |
| 117 | 1-117 | 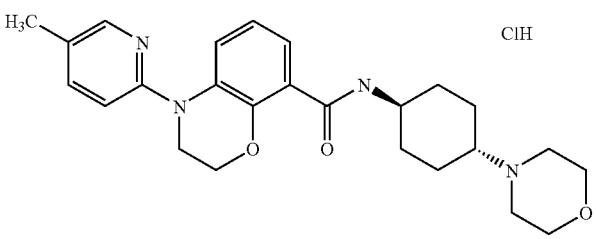 | ClH ClH |
| 118 | 1-118 | 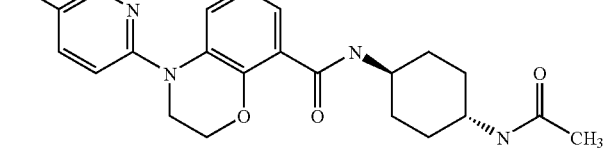 | |

| | NMR |
|---|---|
| 111 | (400 MHz, DMSO-d6) 149-1.78 (m, 8H), 2.16-2.20 (m, 4H), 2.43-2.45 (m, 4H), 3.55 (t, J = 4.6 Hz, 4H), 3.98 (t, J = 4.4 Hz, 3H), 4.31 (t, J = 4.6 Hz, 2H), 6.86 (t, J = 7.9 Hz, 1H), 7.08 (d, J = 8.3 Hz, 1H), 7.25 (dd, J = 7.7, 1.6 Hz, 1H), 7.35 (dd, J = 8.1. 1.6 Hz. 1H), 7.49 (dd, J = 8.3, 2.3 Hz, 1H), 8.02 (d, J = 7.4 Hz, 1H), 8.12 (s, 1H). |
| 112 | (400 MHz, DMSO-d6) 1.20-1.32 (m, 4H), 1.80 (bra, 2H), 1.90 (bra, 2H) 2.06-2.16 (m, 7H), 2.20 (s, 3H), 3.63-3.68 (m, 1H), 3.95 (brs, 2H), 4.27 (bra, 2H), 6.83 (t, J = 7.9 Hz, 1H), 7.07 (d, J = 8.8 Hz, 1H), 7.18 (d, J = 7.9 Hz, 1H), 7.33 (dd, J = 8.1, 1.6 Hz, 1H), 7.48 (dd, J = 8.6, 1.6 Hz, 1H), 7.68 (d, J = 7.9 Hz, 1H), 8.12 (s, 1H). |
| 113 | (400 MHz, DMSO-d6) 0.94 (t, J = 7.0 Hz, 6H), 1.26-1.32 (m, 4H), 1.70 (brs, 2H), 1.91 (brs, 2H), 2.20 (s, 3H), 2.43-2.46 (m, 5H), 3.63-3.68 (m, 1H), 3.95 (t, J = 4.4 Hz, 2H), 4.27 (t, J = 4.4 Hz, 2H), 6.84 (t, J = 7.9 Hz, 1H), 7.07 (d, J = 8.3 Hz, 1H), 7.19 (dd, J = 7.7, 1.6 Hz, 1H), 7.33 (dd, J = 8.1, 1.6 Hz, 1H), 7.48 (dd, J = 8.3, 2.3 Hz, 1H), 7.87 (d, J = 7.9 Hz, 1H), 8.12 (d, J = 2.3 Hz, 1H). |
| 114 | (400 MHz, DMSO-d6) 1.55-1.69 (m, 12H), 2.17-2.24 (m, 4H), 2.45-2.53 (m, 4H), 3.88-3.90 (m, 1H), 3.97 (t, J = 4.4 Hz, 2H), 4.31 (t, J = 4.2 Hz, 2H), 6.85 (t, J = 7.9 Hz, 1H), 7.08 (d, J = 8.8 Hz, 1H), 7.24 (dd, J = 7.9, 1.4 Hz, 1H), 7.34 (d, J = 7.9 Hz, 1H), 7.48 (dd, J = 6.6, 2.1 Hz, 1H), 7.97 (d, J = 7.0 Hz, 1H), 8.12 (brs, 1H). |
| 115 | (400 MHz, DMSO-d6) 1.18-1.34 (m, 4H), 1.64 (brs, 4H), 1.86-1.95 (m, 5H), 2.20 (s, 3H), 3.65-3.70 (m, 1H), 3.95 (t, J = 4.4 Hz, 2H), 4.27 (t, J = 4.4 Hz, 2H), 6.84 (t, J = 7.9 Hz, 1H), 7.07 (d, J = 8.8 Hz, 1H), 7.18 (dd, J = 7.9, 1.4 Hz, 1H), 7.33 (dd, J = 7.9, 1.4 Hz, 1H), 7.48 (dd, J = 8.8, 2.3 Hz, 1H), 7.89 (d, J = 7.9 Hz, 1H). 8.11 (s, 1H). |
| 116 | (400 MHz, DMSO-d6) 1.33-2.16 (m, 14H), 2.27 (s, 3H), 2.86-2.94 (m, 2H), 3.03-3.17 (m, 1H), 3.30-3.33 (m, 2H), 3.68-4.11 (m, 3H), 4.32-4.45 (m, 2H), 6.87-6.94 (m, 1H), 7.24-7.41 (m, 3H), 7.79 (d, J = 8.3 Hz, 1H), 7.99-8.12 (m, 1H), 8.17 (s, 1H), 10.43-10.53 (m, 1H). |
| 117 | (400 MHz, DMSO-d6) 1.29-1.40 (m, 2H), 1.56-1.65 (m, 2H), 1.94-2.01 (m, 2H), 2.16-2.19 (m, 2H), 2.24 (s, 3H), 3.01-3.15 (m, 3H), 3.33-3.38 (m, 2H), 3.44-4.01 (m, 7H), 4.31 (t, J = 4.4 Hz, 2H), 6.88 (t, J = 7.9 Hz, 1H), 7.21 (d, J = 7.9 Hz, 2H), 7.36 (dd, J = 8.3, 1.4 Hz, 1H), 7.67 (d, J = 8.3 Hz, 1H), 8.00 (d, J = 7.9 Hz, 1H), 8.15 (s, 1H), 11.13 (s, 1H). |

TABLE 15-continued

| | |
|---|---|
| 118 | (400 MHz, DMSO-d6) 1.21-1.38 (m, 4H), 1.76-1.88 (m, 7H), 2.20 (s, 3H), 3.44-3.49 (m, 1H), 3.66-3.72 (m, 1H), 3.95 (t, J = 4.2 Hz, 2H), 4.27 (t, J = 4.4 Hz, 2H), 6.84 (t, J = 7.9 Hz, 1H), 7.08 (d, J = 8.3 Hz, 1H), 7.18 (dd, J = 7.9, 1.4 Hz, 1H), 7.33 (dd, J = 6.3, 1.4H z, 1H), 7.48 (dd, J = 8.8, 2.3 Hz, 1H), 7.72 (d, J = 7.9 Hz, 1H), 7.92 (d, J = 7.9 Hz, 1H), 8.12 (d, J = 1.9 Hz, 1H). |

TABLE 16

| Ex. No. | | Chemical Compounds |
|---|---|---|
| 119 | 1-119 | |
| 120 | 1-120 | |
| 121 | 1-121 | |
| 122 | 1-122 | |
| 123 | 1-123 | |
| 124 | 1-124 | |

TABLE 16-continued

| | | |
|---|---|---|
| 125 | 1-125 | 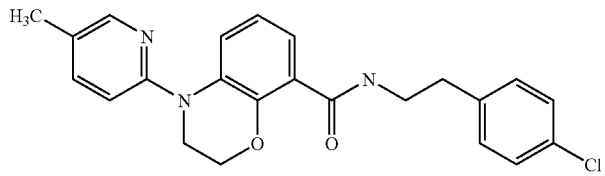 |
| 126 | 1-126 | 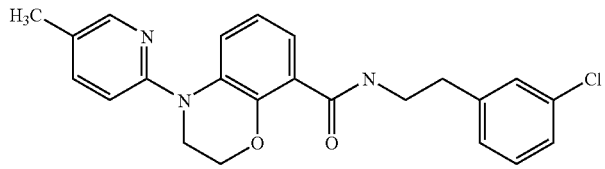 |

| NMR | |
|---|---|
| 119 | (400 MHz, DMSO-d6) 0.83-0.92 (m, 2H), 1.09-1.47 (m, 8H), 1.59-1.69 (m, 5H), 1.84-1.95 (m, 4H), 2.20 (s, 3H), 3.13-3.33 (m, 3H), 3.69-3.74 (m, 1H), 3.95 (t, J = 4.4 Hz, 2H), 4.27 (t, J = 4.4 Hz, 2H), 6.84 (d, J = 7.9 Hz, 1H), 7.07 (d, J = 8.3 Hz, 1H), 7.18 (dd, J = 7.7, 1.6 Hz, 1H), 7.33 (dd, J = 7.9, 1.4 Hz, 1H), 7.48 (dd, J = 8.3, 2.3 Hz, 1H), 7.90 (d, J = 7.9 Hz, 1H), 8.12 (d, J = 2.3 Hz, 1H). |
| 120 | (400 MHz, DMSO-d6) 1.30 (t, J = 7.0 Hz, 3H), 3.97 (q, J = 7.0 Hz, 2H), 4.02 (t, J = 4.6 Hz, 2H), 4.33 (t, J = 4.6 Hz, 2H), 6.88 (d, J = 9.3 Hz, 2H), 6.93 (t, J = 7.9 Hz, 1H), 7.21-7.24 (m, 2H), 7.47 (dd, J = 8.1, 1.6 Hz, 1H), 7.61 (d, J = 9.3 Hz, 2H), 7.74 (dd, J = 9.0, 2.6 Hz, 1H), 8.30 (d, J = 2.8 Hz, 1H), 9.98 (s, 1H). |
| 121 | (400 MHz, DMSO-d6) 4.02 (t, J = 4.5 Hz, 3H), 4.32 (t, J = 4.5 Hz, 2H), 6.94 (t, J = 7.9 Hz, 1H), 7.21-7.23 (m, 2H), 7.38 (d, J = 8.8 Hz, 2H), 7.49 (dd, J = 7.9, 1.4 Hz, 1H), 7.73-7.77 (m, 4H), 8.30 (d, J = 2.8 Hz, 1H), 10.27 (s, 1H). |
| 122 | (300 MHz, DMSO-d6) δ: 1.54-1.63 (m, 2H), 1.96-2.01 (m, 2H), 2.74-2.77 (m, 2H), 3.16-3.18 (m, 2H), 3.29-3.33 (m, 4H), 4.03 (t, J = 4.2 Hz, 2H), 4.34 (t, J = 4.4 Hz, 2H), 6.95-7.02 (m, 2H), 7.23 (d, J = 9.2 Hz, 2H), 7.38 (d, J = 8.4 Hz, 1H), 7.50 (dd, J = 8.1, 0.7 Hz, 1H), 7.64 (dd, J = 15.0, 2.2 Hz 1H), 7.76 (dd, J = 9.0, 2.8 Hz, 1H), 8.32 (d, J = 2.6 Hz, 1H), 10.12 (s, 1H). |
| 123 | (300 MHz, DMSO-d6) δ: 4.04 (t, J = 4.4 Hz, 2H), 4.35 (t, J = 4.4 Hz, 2H), 6.96 (t, J = 7.9 Hz, 1H), 7.23-7.26 (m, 2H), 7.53 (dd, J = 8.3, 1.7 Hz, 1H), 7.71 (d, J = 8.8 Hz, 2H), 7.77 (dd, J = 9.0, 2.8 Hz, 1H), 7.95 (d, J = 8.4 Hz, 2H), 8.32 (d, J = 2.6 Hz, 1H), 10.49 (s, 1H). |
| 124 | (400 MHz, DMSO-d6) 2.25 (s, 3H), 2.84 (t, J = 7.2 Hz, 2H), 3.50 (q, J = 6.6 Hz, 2H), 3.98 (t, J = 4.4 Hz, 2H), 4.28 (t, J = 4.6 Hz, 2H), 6.89 (t, J = 7.9 Hz, 1H), 7.24-7.35 (m, 8H), 7.65 (d, J = 8.8 Hz, 1H), 8.15-8.20 (m, 2H). |
| 125 | (400 MHz, CHLOROFORM-d) 2.26 (s, 3H), 2.91 (t, J = 7.0 Hz, 2H), 3.73 (q, J = 6.5 Hz, 2H), 4.07 (t, J = 4.6 Hz, 2H), 4.21 (t, J = 4.4 Hz, 2H), 6.92 (t, J = 7.9 Hz. 1H), 7.06 (d, J = 8.3 Hz, 1H), 7.20-7.21 (m, 2H), 7.27-7.30 (m, 2H), 7.36 (dd, J = 7.9, 1.9 Hz, 2H), 7.74 (s, 1H), 7.82 (dd, J = 7.9, 1.4 Hz, 1H), 8.14 (s, 1H). |
| 126 | (400 MHz, CHLOROFORM-d) 2.26 (s, 3H), 2.91 (t, J = 6.7 Hz, 2H), 3.74 (q, J = 6.5 Hz, 2H), 4.08 (s, 2H), 4.24 (t, J = 4.4 Hz, 2H), 7.76 (s, 1H), 7.83 (d, J = 6.5 Hz, 1H), 8.14 (s, 1H). |

TABLE 17

| Ex. No. | Chemical Compounds |
|---|---|
| 127  1-127 | 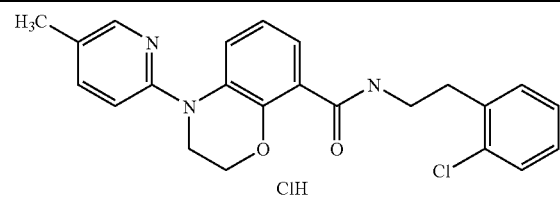 |

TABLE 17-continued
| | | |
|---|---|---|
| 128 | 1-128 | 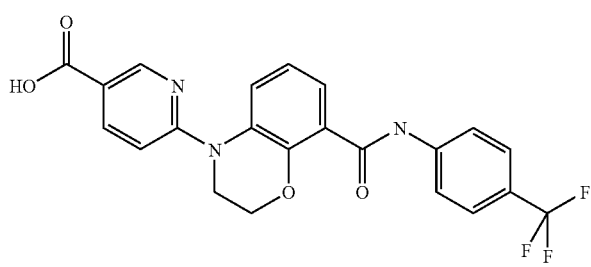 |
| 129 | 1-129 | 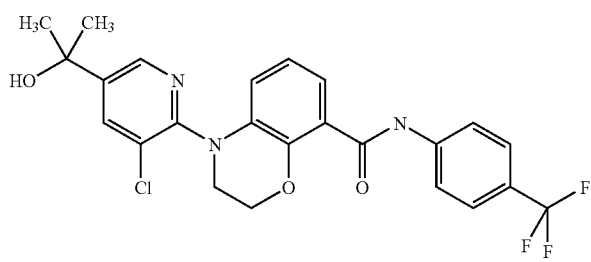 |
| 130 | 1-130 | 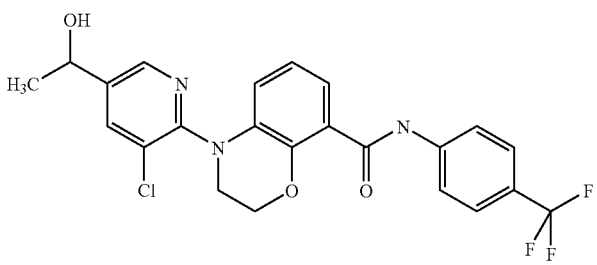 |
| 131 | 1-131 | 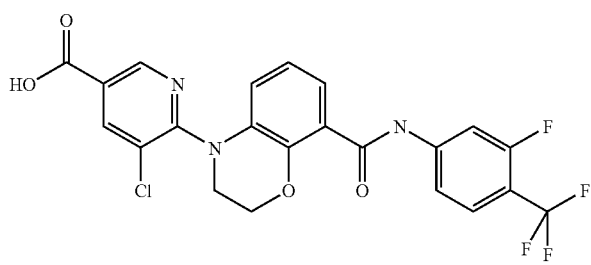 |
| 132 | 1-132 | 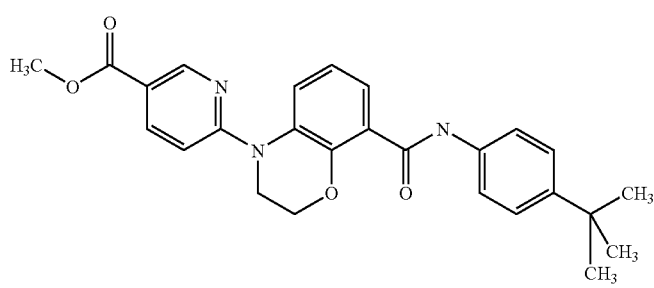 |

TABLE 17-continued

| 133 | 1-133 | 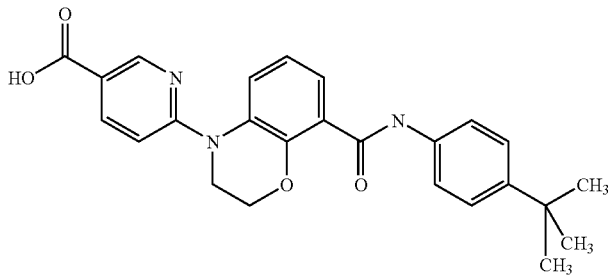 |
|---|---|---|

| | NMR |
|---|---|
| 127 | (400 MHz, DMSO-d6) 2.26 (s, 3H), 298 (t, J = 7.2 Hz, 2H), 3.53 (q, J = 6.6 Hz, 2H), 3.99 (t, J = 4.4 Hz, 2H), 6.90 (t, J = 7.9 Hz, 1H), 7.23-7.33 (m, 4H), 7.38-7.40 (m, 2H), 7.44 (dd, J = 7.7, 1.6 Hz, 1H), 7.69 (d, J = 8.8 Hz, 1H), 8.16 (s, 1H), 8.23 (t, J = 5.3 Hz, 1H). |
| 128 | (300 MHz, DMSO-d6) δ: 4.16 (t, J = 4.4 Hz, 2H), 4.37 (t, J = 4.2 Hz, 2H), 6.99 (t, J = 7.9 Hz, 1H), 7.24-7.28 (m, 2H), 7.60 (dd, J = 8.3, 1.7 Hz, 1H), 7.71 (d, J = 8.8 Hz, 2H), 7.95 (d, J = 8.4 Hz, 2H), 8.08 (dd, J = 8.8, 2.2 Hz, 1H), 8.77 (d, J = 2.6 Hz, 1H), 10.51 (s, 1H). |
| 129 | (300 MHz, DMSO-d6) δ: 1.51 (s, 6H), 3.78 (t, J = 4.2 Hz, 2H), 4.43 (t, J = 4.2 Hz, 2H), 5.33 (s, 1H), 6.46-6.52 (m, 1H), 6.83 (t, J = 16.7 Hz, 1H), 7.05 (dd, J = 7.7, 1.5 Hz, 1H), 7.68-7.71 (m, 2H), 7.94-7.97 (m, 2H), 8.04 (d, J = 2.2 Hz, 1H), 8.51 (d, J = 2.2 Hz, 1H), 10.50 (s, 1H). |
| 130 | (300 MHz, DMSO-d6) δ: 1.40 (d, J = 6.6 Hz, 3H), 3.76-3.80 (m, 2H), 4.41-4.44 (m, 2H), 4.62-4.84 (m, 1H), 5.43 (d, J = 4.8 Hz, 1H), 6.47 (dd, J = 8.1, 1.5 Hz, 1H), 6.81 (t, J = 7.9 Hz, 1H), 7.05 (d, J = 3.9 Hz, 1H), 7.70 (d, J = 8.8 Hz, 2H), 7.95-7.96 (m, 4H), 8.40-8.40 (m, 1H), 10.50 (s, 1H). |
| 131 | (300 MHz, DMSO-d6) δ: 3.90-3.92 (m, 2H), 4.42-4.43 (m, 2H), 6.77 (d, J = 4.0 Hz, 1H), 6.87 (d, J = 7.7 Hz, 1H), 7.16-7.17 (m, 1H), 7.73 (d, J = 9.2 Hz, 2H), 7.96 (d, J = 14.3 Hz, 1H), 8.30 (d, J = 1.8 Hz, 1H), 8.83 (d, J = 1.8 Hz, 1H), 10.72 (s, 1H). |
| 132 | (400 MHz, CHLOROFORM-d) 1.33 (s, 9H), 3.92 (s, 3H), 4.36 (t, J = 4.6 Hz, 2H), 4.55 (t, J = 4.6 Hz, 2H), 7.06 (t, J = 7.9 Hz, 1H), 7.21 (d, J = 8.8 Hz, 1H), 7.38 (t, J = 4.4 Hz, 2H), 7.52 (dd, J = 8.1, 1.6 Hz, 3H), 7.58 (dd, J = 6.7, 4.9 Hz, 3H), 8.02 (dd, J = 7.9. 1.4 Hz, 2H), 6.08 (dd, J = 8.8, 2.3 Hz, 2H), 8.93 (d, J = 2.3 Hz, 1H), 9.48 (s, 1H). |
| 133 | (400 MHz, CHLOROFORM-d) 1.28 (s, 9H), 4.16 (t, J = 4.2 Hz, 2H), 4.37 (t, J = 4.2 Hz, 2H), 6.98 (t, J = 7.9 Hz, 1H), 7.26 (dd, J = 20.4, 8.3 Hz, 2H), 7.35 (d, J = 8.8 Hz, 2H), 7.57 (d, J = 8.3 Hz, 1H), 7.64 (d, J = 8.8 Hz, 2H), 8.07 (dd, J = 8.8, 1.9 Hz, 1H), 8.77 (d, J = 2.3 Hz, 1H), 10.07 (s, 1H). |

TABLE 18

| Ex. No. | Chemical Compounds |
|---|---|
| 134 | 1-134 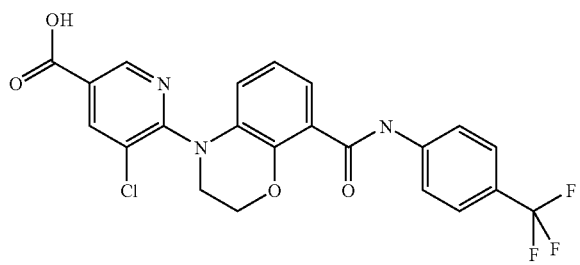 |

TABLE 18-continued
| 135 | 1-135 | 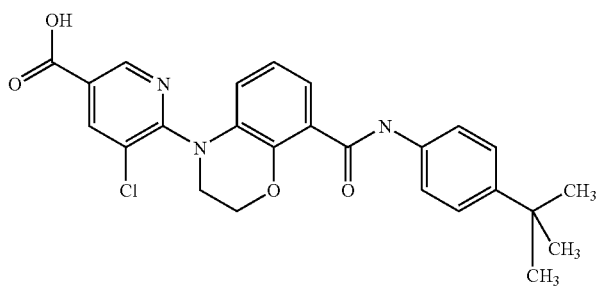 |
| 136 | 1-136 | 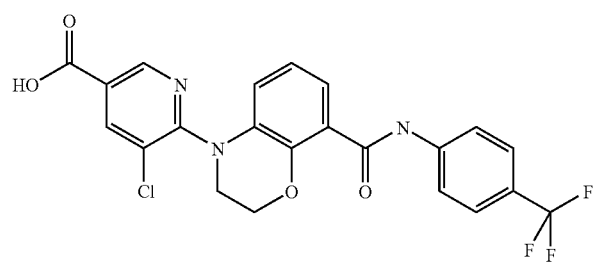 |
| 137 | 1-137 | 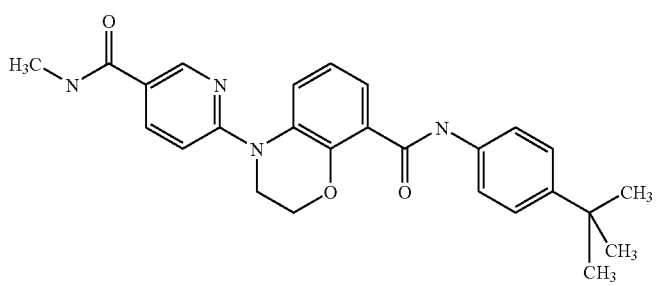 |
| 138 | 1-138 | 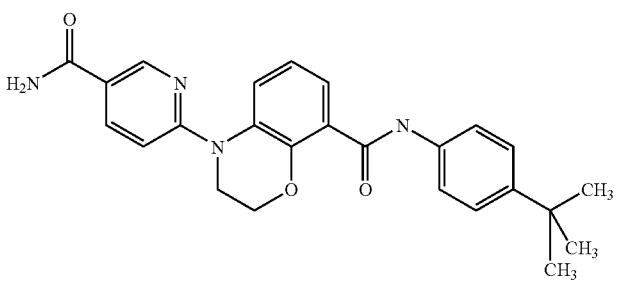 |
| 139 | 1-139 | 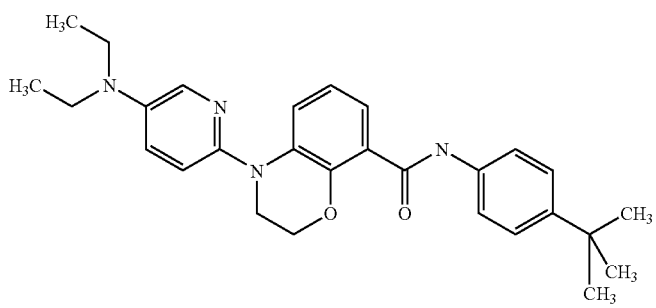 |

TABLE 18-continued

| 140 | 1-140 | 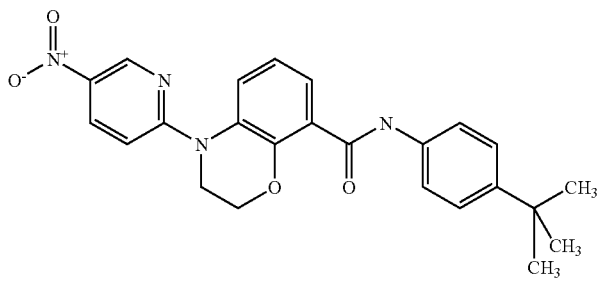 |

| | NMR |
|---|---|
| 134 | (300 MHz, DMSO-d6) 3.92 (t, J = 4.2 Hz, 2H), 4.43 (t, J = 4.4 Hz, 2H), 6.76 (dd, J = 8.1, 1.5 Hz, 1H), 6.86 (t, J = 7.9 Hz. 1H), 7.17 (dd, J = 7.5, 1.7 Hz, 1H), 7.71 (d, J = 8.8 Hz, 2H), 7.97 (d, J = 8.4 Hz, 2H), 8.31 (d, J = 2.2 Hz, 1H), 8.83 (d, J = 2.2 Hz, 1H), 10.53 (s, 1H). |
| 135 | (300 MHz, DMSO-d6) 1.28 (s, 9H), 3.92 (t, J = 4.2 Hz, 2H), 4.44 (t, J = 4.2 Hz, 2H), 6.73 (dd, J = 8.1, 1.5 Hz, 1H), 6.84 (t, J = 7.9 Hz, 1H), 7.18 (dd, J = 7.5, 1.7 Hz, 1H), 7.35 (d, J = 8.8 Hz, 2H), 7.65 (d, J = 8.8 Hz, 2H), 8.30 (d, J = 2.2 Hz, 1H), 8.83 (d, J = 2.2 Hz, 1H), 10.07 (s, 1H). |
| 136 | (300 MHz, DMSO-d6) δ: 2.62 (s, 3H), 3.94 (t, J = 4.6 Hz, 2H), 4.44 (t, J = 4.4 Hz, 2H), 6.76 (dd, J = 8.1, 1.8 Hz, 1H), 6.87 (t, J = 7.9 Hz, 1H), 7.19 (dd, J = 7.3, 1.5 Hz, 1H), 7.71 (d, J = 8.4 Hz, 3H), 7.97 (d, J = 8.4 Hz, 3H), 8.38 (d, J = 2.2 Hz, 1H), 8.91 (d, J = 1.8 Hz, 1H), 10.52 (s, 1H). |
| 137 | (400 MHz, DMSO-d6) 1.27 (s, 9H), 2.78 (d, J = 4.6 Hz, 3H), 4.14 (t, J = 4.2 Hz, 2H), 4.36 (t, J = 4.6 Hz, 2H), 6.98 (t, J = 7.9 Hz, 1H), 7.26 (q, J = 7.4 Hz, 2H), 7.35 (d, J = 8.8 Hz, 2H), 7.56 (d, J = 8.3 Hz, 1H), 7.64 (d, J = 8.8 Hz, 2H), 8.05 (dd, J = 8.8, 2.3 Hz, 1H), 8.39 (d, J = 5.6 Hz, 1H), 8.73 (d, J = 2.3 Hz, 1H), 10.06 (s, 1H). |
| 138 | (400 MHz, DMSO-d6) 1.28 (s, 9H), 4.15 (t, J = 4.4 Hz, 2H), 4.36 (t, J = 4.4 Hz, 2H), 6.98 (t, J = 7.9 Hz, 1H), 7.25-7.33 (m, 5H), 7.56 (d, J = 8.3 Hz, 1H), 7.64 (d, J = 8.8 Hz, 2H), 7.93 (s, 1H), 8.09 (dd, J = 8.8, 2.8 Hz, 1H), 8.78 (d, J = 2.3 Hz, 1H), 10.07 (s, 1H). |
| 139 | (400 MHz, DMSO-d6) 1.08 (t, J = 7.0 Hz, 6H), 1.27 (s, 9H), 3.31-3.40 (m, 4H), 3.82 (t, J = 4.4 Hz, 2H), 4.34 (t, J = 4.4 Hz, 2H), 6.81 (t, J = 7.9 Hz, 1H), 7.02-7.16 (m, 4H), 7.34 (d, J = 8.8 Hz, 2H), 7.64 (d, J = 8.3 Hz, 2H), 7.85 (d, J = 3.2 Hz, 1H), 10.02 (s, 1H). |
| 140 | (400 MHz, CHLOROFORM-d) 1.33 (s, 9H), 4.44 (dd, J = 6.0, 3.2 Hz, 2H), 4.59 (t, J = 4.9 Hz, 2H), 7.10-7.12 (m, 1H), 7.25-7.26 (m, 1H), 7.39 (dd, J = 8.6, 1.6 Hz, 2H), 7.52-7.54 (m, 1H), 7.58 (dd, J = 8.6, 1.6 Hz, 2H), 8.09-8.11 (m, 1H), 8.26-8.28 (m, 1H), 9.17 (t, J = 1.9 Hz, 1H), 9.40 (s, 1H). |

TABLE 19

| Ex. No. | Chemical Compounds |
|---|---|
| 141 | 1-141 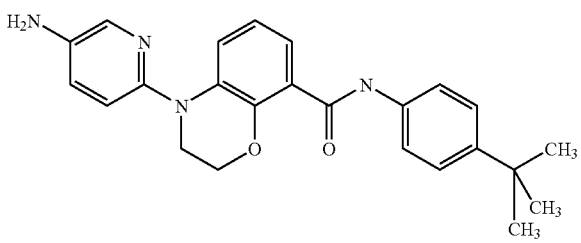 |

TABLE 19-continued
| 142 | 1-142 | 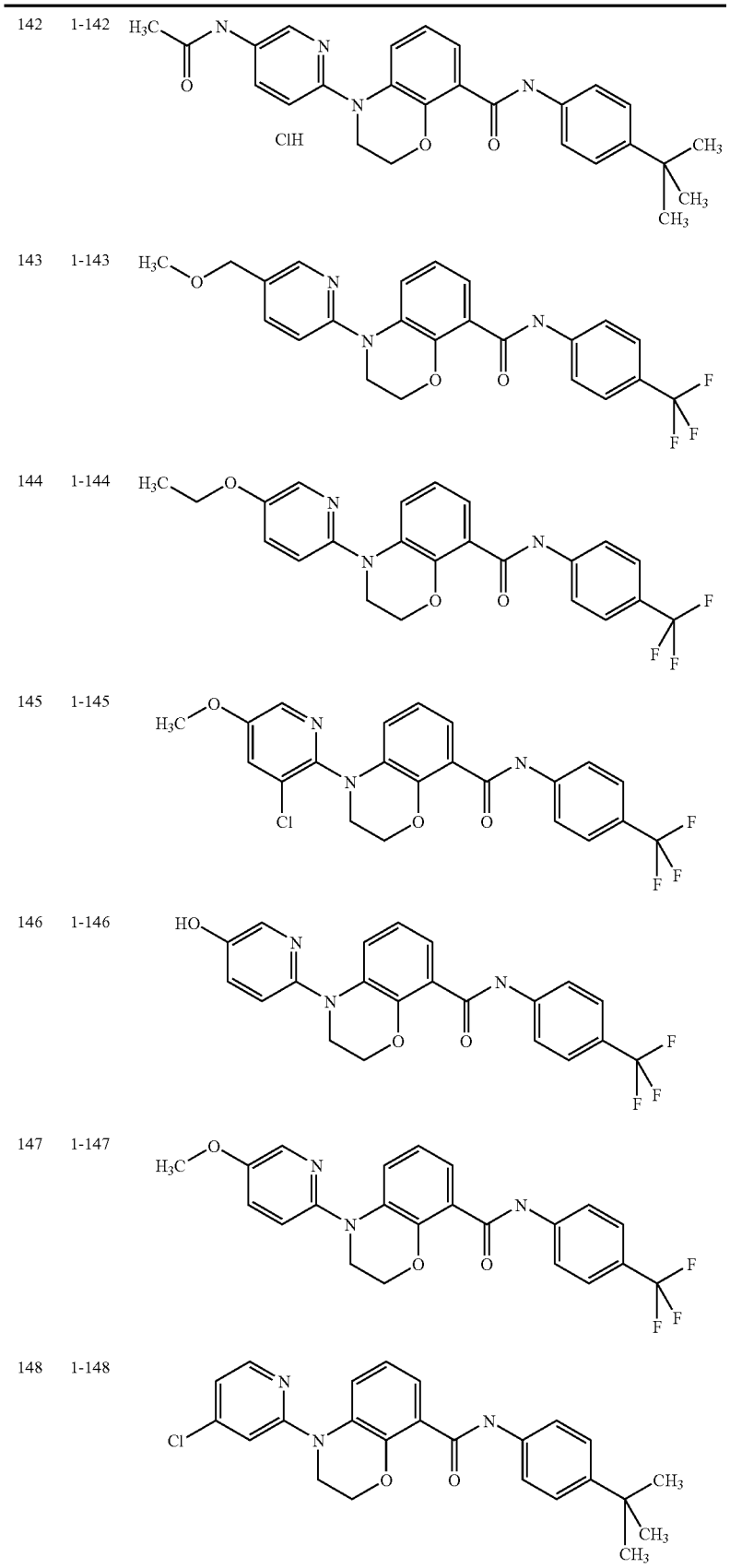 |
| 143 | 1-143 | |
| 144 | 1-144 | |
| 145 | 1-145 | |
| 146 | 1-146 | |
| 147 | 1-147 | |
| 148 | 1-148 | |

TABLE 19-continued

| | NMR |
|---|---|
| 141 | (400 MHz, CHLOROFORM-d) 132 (s, 9H), 3.54 (s, 2H), 4.02 (t, J = 4.4 Hz, 2H), 4.49 J = 4.4 Hz, 2H), 5.92 (t, J = 8.1 Hz, 1H), 7.00-7.03 (m, 2H). 7.22-7.26 (m, 1H), 7.37 (t, J = 4.4 Hz, 2H), 7.59 (d, J =8.3 Hz, 2H), 7.80 (dd, J = 7.9, 1.4 Hz, 1H), 7.91 (d, J = 2.8 Hz, 1H), 9.59 (s, 1 H). |
| 142 | (400 MHz, DMSO-d6) 1.28 (s, 9H), 2.05 (s, 3H), 3.98 (t, J = 4.2 Hz, 2H), 4.33 (t, J = 4.2 Hz, 2H), 6.91 (t, J = 7.9 1H), 7.19 (dd, J = 13.0, 8.3 Hz,2H), 7.33 (dd, J = 12.3, 6.7 Hz, 2H), 7.40 (d, J = 8.3 Hz, 1H), 7.64 (d, J = 8.3 Hz, 2H), 7.92 (t, J = 5.8 Hz, 1H), 8.49 (s, 1H), 10.05 (s, 2H). |
| 143 | (400 MHz, DMSO-d6) 3.29 (s, 3H), 4.06 (t, J = 4.4 Hz, 2H), 4.34 (t, J = 4.6 Hz, 2H), 4.36 (s, 2H), 6.95 (t, J = 7.9 Hz, 1H), 7.22 (d, J = 8.3 Hz, 2H), 7.52 (dd, J = 8.1, 1.6 Hz, 1H), 7.65 (dd, J = 8.6, 2.6 Hz, 1H), 7.71 (d, J = 8.8 Hz, 2H), 7.95 (d, J = 8.8 Hz, 2H), 8.26 (d, J = 1.9 Hz, 1H), 10.50 (s, 1H). |
| 144 | (300 MHz, DMSO-d6) δ: 1.34 (t, J = 7.0 Hz, 3H), 3.91 (t, J = 4.4 Hz, 2H), 4.08 (q, J = 7.1 Hz, 2H), 4.33 (t, J = 4.2 Hz, 2H), 6.88 (t, J = 7.9 Hz, 1H), 7.12-7.17 (m, 2H), 7.28-7.41 (m, 4H), 7.85 (d, J = 9.2 Hz, 2H), 8.06 (d, J = 3.3 Hz, 1H), 10.31 (s, 1H). |
| 145 | (400 MHz, DMSO-d6) 3.71 (t, J = 4.4 Hz, 2H), 3.90 (s, 3H), 4.44 (t, J = 4.4 Hz, 2H), 6.36 (dd, J = 7.9, 1.4 Hz, 1H), 6.78 (t, J = 7.9 Hz, 1H), 6.99 (dd, J = 7.9, 1.4 Hz, 1H), 7.71 (d, J = 8.3 Hz, 2H), 7.77 (d, J = 2.8 Hz, 1H), 7.97 (d, J = 8.3 Hz, 2H), 8.22 (d, J = 2.8 Hz, 1H), 10.50 (s, 1H). |
| 146 | (400 MHz, DMSO-d6) 3.86 (t, J = 4.4 Hz, 2H), 4.33 (t, J = 4.4 Hz, 2H), 6.86 (t, J = 7.9 Hz, 1H), 7.07-7.10 (m, 2H), 7.18-7.23 (m, 2H), 7.70 (d, J = 8.3 Hz, 2H), 7.94-7.95 (m, 3H), 9.72 (brs, 1H), 10.48 (s, 1H). |
| 147 | (400 MHz, DMSO-d6) 3.81 (s, 3H), 3.92 (t, J = 4.4 Hz, 2H), 4.34 (t, J = 4.4 Hz, 2H), 6.89 (t, J = 7.9 Hz, 1H), 7.12 (dd, J = 7.9, 1.6 Hz, 1H), 7.20 (d, J = 9.3 Hz, 1H), 7.31 (dd, J = 7.9, 1.6 Hz, 1H), 7.41 (dd, J = 9.3, 3.2 Hz, 1H), 7.71 (d, J = 8.8 Hz, 2H), 7.96 (d, J = 8.8 Hz, 2H), 8.08 (d, J = 3.2 Hz, 1H), 10.50 (s, 1H). |
| 148 | (300 MHz, DMSO-d6) 1.28 (s, 9H), 4.08 (t, J = 4.4 Hz, 2H), 4.34 (t, J = 4.4 Hz, 2H), 6.97 (t, J = 7.9 Hz, 1H), 7.02 (dd, J = 5.3, 1.7 Hz, 1H), 7.20 (d, J = 1.5 Hz, 1H), 7.28 (dd, J = 7.7, 1.5 Hz, 1H), 7.35 (d, J = 8.8 Hz, 2H), 7.56 (dd, J = 8.4, 1.5 Hz, 1H), 7.64 (d, J = 8.8 Hz, 2H), 8.27 (d, J = 5.1 Hz, 1H), 10.04 (s, 1H). |

TABLE 20

| Ex. No. | | Chemical Compounds |
|---|---|---|
| 149 | 1-149 | 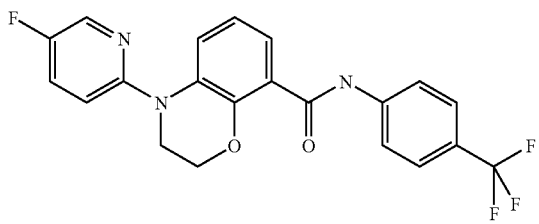 |
| 150 | 1-150 | 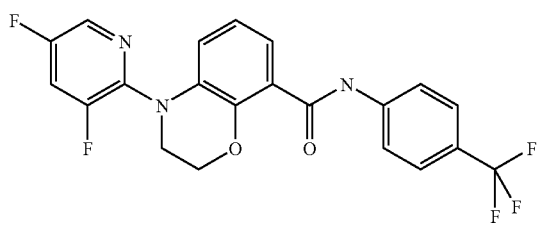 |

TABLE 20-continued
| 151 | 1-151 | 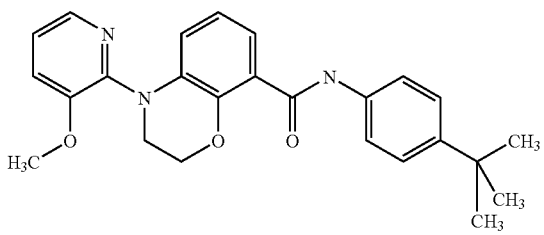 |
| 152 | 1-152 | 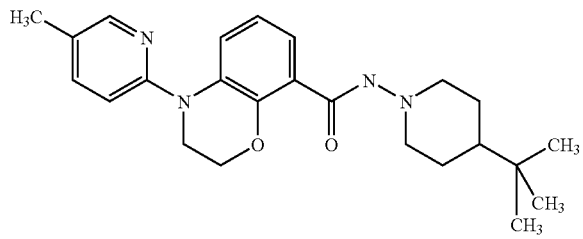 |
| 153 | 1-153 | 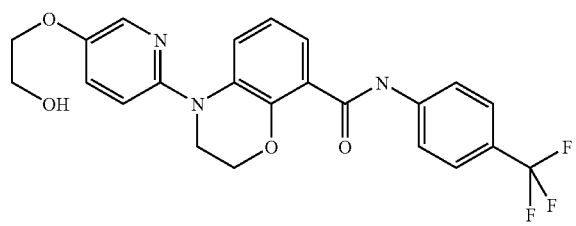 |
| 154 | 1-154 | 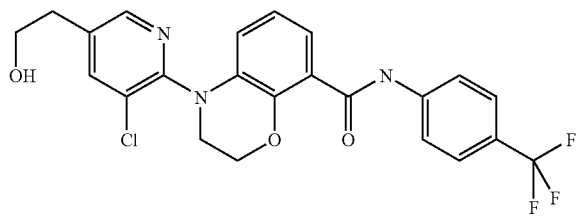 |
| 155 | 1-155 | 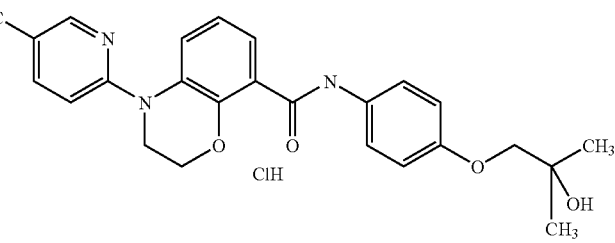 |
| 156 | 1-156 | 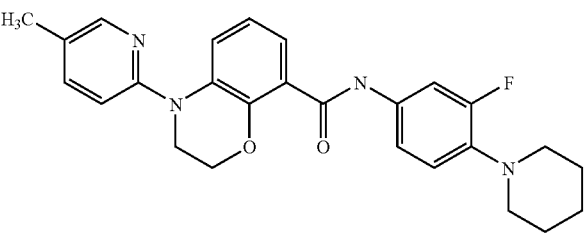 |
| | NMR |
|---|---|
| 149 | (300 MHz, DMSO-d6) 3.99 (t, J = 4.4 Hz, 2H), 4.35 (t, J = 4.2 Hz, 2H), 6.94 (t, J = 7.7 Hz, 1H), 7.19-7.28 (m, 2H), 7.22 (s, 2H), 7.45 (d, J = 4.0 Hz, 1H), 7.65 (dd, J = 8.6, 3.1 Hz, 1H), 7.71 (d, J = 8.8 Hz, 2H), 7.96 (d, J = 8.8 Hz, 2H), 8.31 (d, J = 2.9 Hz, 1H), 10.49 (s, 1H). |
| 150 | (300 MHz, DMSO-d6) 3.83 (t, J = 4.2 Hz, 2H), 4.43 (t, J = 4.4 Hz, 2H), 6.74-6.77 (m, 1H), 6.85 (t, J = 7.9 Hz, 1H), 7.09 (dd, J = 7.3, 1.5 Hz, 1H), 7.71 (d, J = 8.8 Hz, 2H), 7.96 (d, J = |

TABLE 20-continued

| | |
|---|---|
| | 8.4 Hz, 2H), 8.00-8.07 (m, 1H), 8.35 (d, J = 2.2 Hz, 1H), 10.51 (s, 1H). |
| 151 | (300 MHz, CHLOROFORM-d) 1.32 (s, 9H), 3.82 (s, 3H), 3.93 (t, J = 4.4 Hz, 2H), 4.58 (t, J = 4.4 Hz, 2H), 6.68 (dd, J = 8.1, 1.5 Hz, 1H), 6.85 (t, J = 7.9 Hz, 1H), 7.10 (dd, J = 8.1, 4.8 Hz, 1H), 7.24 (dd, J = 8.1, 1.1 Hz, 1H), 7.37 (6, J = 8.8 Hz, 2H), 7.80 (d, J = 8.4 Hz, 2H), 7.75 (dd, J = 7.9, 1.7 Hz, 1H), 8.03 (dd, J = 4.6, 1.3 Hz, 1H), 9.63 (s, 1H). |
| 152 | (300 MHz, DMSO-d6) δ: 0.86 (s, 9H), 0.96-1.00 (m, 1H), 1.27-1.39 (Tn, 2H), 1.64 (d, J = 13.2 Hz, 2H), 2.22 (s, 3H), 2.58 (d, J = 10.6 Hz, 2H), 3.07 (d, J = 10.3 Hz, 2H), 3.96 (t, J = 4.2 Hz, 2H), 4.27 (t, J = 4.4 Hz, 2H), 6.84 (t, J = 7.7 Hz, 1H), 7.05-7.10 (m, 2H), 7.34 (dd, J = 8.1, 1.5 Hz, 1H), 7.50 (dd, J = 8.6, 2.0 Hz, 1H), 8.13 (6, J = 2.2 Hz, 1H), 8.88 (s, 1H). |
| 153 | (400 MHz, DMSO-d6) 3.72 (q, J = 5.1 Hz, 2H), 3.92 (t, J = 4.2 Hz, 2H), 4.04 (t, J = 5.1 Hz, 2H), 4.34 (t, J = 4.2 Hz, 2H), 4.89 (t, J = 5.1 Hz, 1H), 6.89 (t, J = 7.9 Hz, 1H), 7.12-7.13 (m, 1H), 7.19 (d, J = 8.8Hz, 1H), 7.31-7.32 (m, 1H), 7.42 (dd, J = 8.8, 3.2 Hz, 1H), 7.71 (d, J = 8.3 Hz, 2H), 7.96 (d, J = 8.3 Hz, 2H), 8.08 (d, J = 2.8 Hz, 1H), 10.49 (s, 1H). |
| 154 | (300 MHz, DMSO-d6) 2.77 (t, J = 6.4 Hz, 2H), 3.67 (q, J = 5.9 Hz, 2H), 3.77 (t, J = 4.4 Hz, 2H), 4.43 (t, J = 4.2 Hz, 2H), 4.72 (t, J = 5.1 Hz, 1H), 6.47 (dd, J = 8.1, 1.8 Hz, 1H), 6.80 (t, J = 7.9 Hz, 1H), 7.04 (dd, J = 7.7, 1.5 Hz, 1H), 7.69-7.72 (m, 3H), 7.96 (dd, J = 9.9, 5.1 Hz, 3H), 6.30 (6, J = 1.8 Hz, 1H), 10.50 (s, 1H). |
| 155 | (400 MHz, DMSO-d6) δ: 1.20 (s, 6H), 2.318s, 3H), 3.65 (s, 2H), 4.04 (t, J = 4.4 Hz, 2H). 4.37 (t, J = 4.4 Hz, 2H), 6.72 (m, 3H), 7.28 (m, 2H), 7.30 (dd, J = 8.1, 1.8 Hz, 1H), 7.63 (dd, J = 9.0, 2.4 Hz, 1H), 7.72 (dd, J = 9, 2.4 Hz, 2H), 8.18 (d, J = 2.6 Hz, 1H), 10.00 (s, 1H). |
| 156 | (400 MHz, DMSO-d6) δ: 1.50-1.51 (m, 2H), 1.60-1.66 (m, 4H), 2.21 (s, 3H), 2.89-2.90 (m, 4H), 3.97 (t, J = 4.4 Hz, 2H), 4.30 (t, J = 4.4 Hz, 2H), 6.89 (t, J = 7.9 Hz, 1H), 6.99 (t, J = 9.5 Hz, 1H), 7.12-7.14 (m, 2H), 7.38 (ddd, J = 13.6, 8.2, 1.7 Hz, 2H), 7.51 (dd, J = 8.8, 2.3 Hz, 1H), 7.63 (dd, J = 14.8, 2.3 Hz, 1H), 8.13-8.14 (m, 1H), 10.11 (s, 1H). |

TABLE 21

| Ex. No. | | Chemical Compounds |
|---|---|---|
| 157 | 1-157 | |
| 158 | 1-158 | |
| 159 | 1-159 | |

TABLE 21-continued
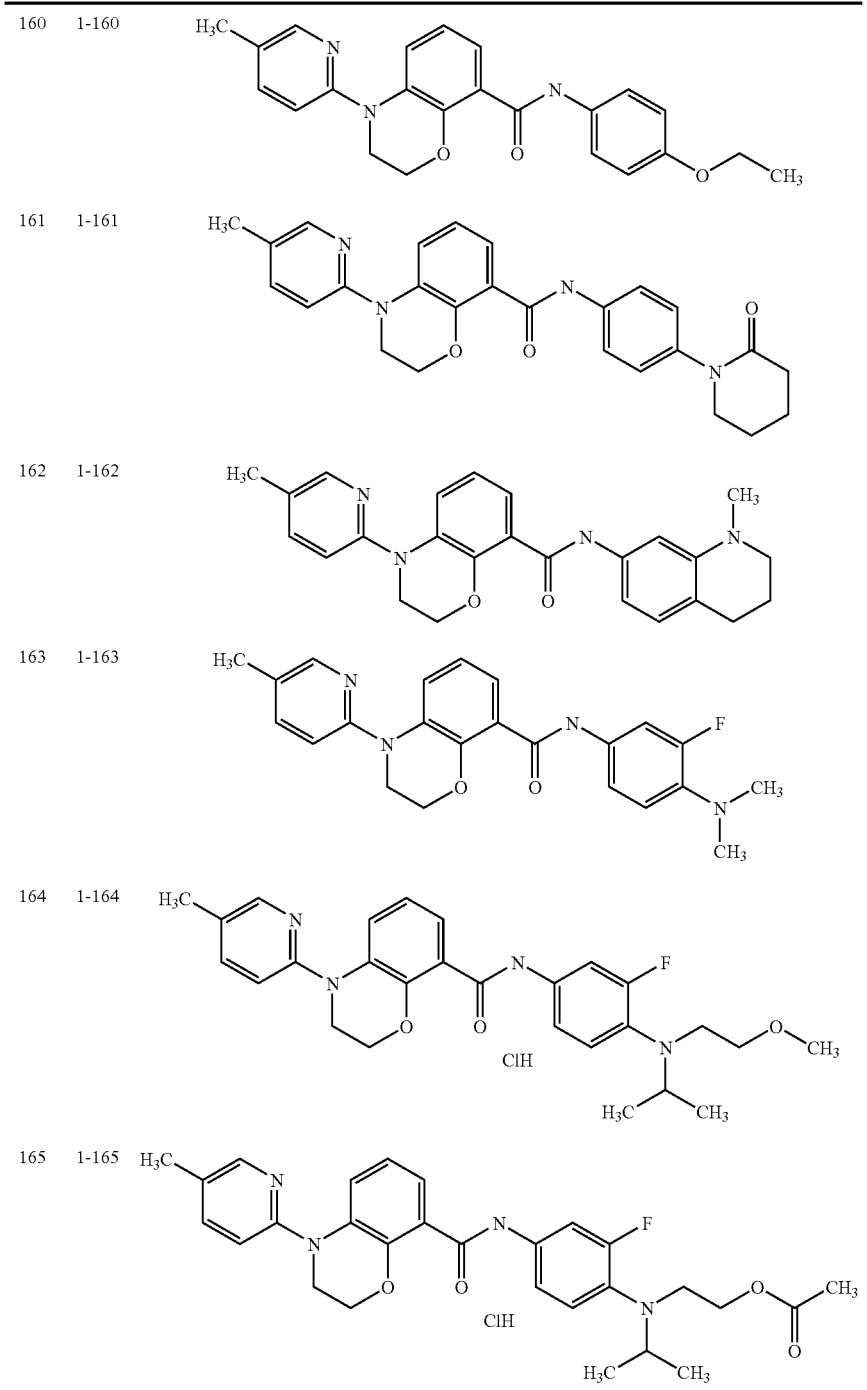
| | | |
|---|---|---|
| 160 | 1-160 | |
| 161 | 1-161 | |
| 162 | 1-162 | |
| 163 | 1-163 | |
| 164 | 1-164 | |
| 165 | 1-165 | |
| NMR | |
|---|---|
| 157 | (400 MHz, DMSO-d6) δ: 2.21 (s, 3H), 2.90-2.96 (m, 4H), 3.71-3.72 (m, 4H), 3.96 (t, J = 20.4 Hz, 2H), 4.30 (t, J = 4.2 Hz, 2H), 6.89 (dd. J = 5.3, 2.6 Hz, 1H), 7.00 (t, J = 9.5 Hz, 1H), 7.11-7.14 (m, 2H), 7.39-7.41 (m, 2H), 7.51 (td, J = 4.2, 2.0 Hz, 1H), 7.66 (dd, J = 15.1, 2.1 Hz, 1H), 8.13-8.14 (m, 1H), 10.15 (S, 1H). |
| 158 | (400 MHz, DMSO-d6) δ: 2.21 (s, 3H), 3.97 (t, J = 4.4 Hz, 2H), 4.30 (t, J = 4.4 Hz, 2H), 6.90 (dd, J = 11.1, 4.6 Hz, 1H), 7.13 (td, J = 6.0, 4.3 Hz, 2H), 7.36-7.53 (m, 4H), 7.89-7.92 (m, 1H), 8.13-8.14 (m, 1H), 10.35 (s, 1H). |
| 159 | (400 MHz, DMSO-d6) δ: 2.21 (s, 3H), 3.80 (s, 3H), 3.97 (t, J = 4.4 Hz, 2H), 4.30 (t, J = 4.4 Hz, 2H), 6.89 (t, J = 7.9 Hz, |

TABLE 21-continued

| | |
|---|---|
| | 1H), 7.11-7.16 (m, 3H), 7.41 (q, J = 4.6 Hz, 2H), 7.51 (dd, J = 8.3, 2.3 Hz. 1H), 7.70 (dd, J = 13.7, 2.6 Hz, 1H), 8.13 (s, 1H), 10.14 (s, 1H). |
| 160 | (400 MHz, DMSO-d6) δ: 1.32 (t, J = 7.0 Hz, 3H), 2.25 (d, J = 10.6 Hz, 3H), 3.96-4.03 (m, 4H), 4.32 (t, J = 4.4 Hz, 2H), 6.88-6.93 (m, 3H), 7.16 (td, J = 9.4, 3.8 Hz, 2H), 7.41 (dd, J = 8.1, 1.8 Hz, 1H), 7.52 (dd, J = 9.0, 2.4 Hz, 1H), 7.63 (dt, J = 9.9, 2.8 Hz, 2H), 8.15 (d, J = 2.6 Hz, 1H), 9.98 (s, 1H). |
| 161 | (300 MHz, DMSO-d6) δ: 1.83-1.86 (m, 4H), 2.23 (s, 3H), 2.36-2.39 (m, 1H), 3.56-3.60 (m, 2H), 3.98-4.01 (m, 2H), 4.31-4.34 (m, 2H), 6.91-6.94 (m, 1H), 7.12-7.23 (m, 4H), 7.47 (dd, J = 31.2, 7.7 Hz, 2H), 7.72 (d, J = 8.1 Hz, 2H), 8.15 (s, 1H), 10.16 (s, 1H). |
| 162 | (300 MHz, DMSO-d6) δ: 1.83-1.91 (m, 2H), 2.23 (s, 3H), 2.63-2.65 (m, 2H), 2.60 (s, 3H), 3.16-3.18 (m, 2H), 3.99 (t, J = 4.4 Hz, 2H), 4.32 (t, J = 4.2 Hz, 2H), 6.81 (d, J = 8.1 Hz, 1H), 6.90 (dd, J = 9.2, 6.6 Hz, 2H), 7.02-7.06 (m, 1H), 7.14-7.17 (m, 2H), 7.40 (d, J = 8.4 Hz, 1H), 7.52 (d, J = 8.4 Hz, 1H), 8.14-8.15 (m, 1H), 9.83 (s, 1H). |
| 163 | (300 MHz, DMSO-d6) δ: 2.23 (s, 3H), 2.73 (a, 6H), 3.99 (t, J = 4.2 Hz, 2H), 4.32 (t, J = 4.4 Hz, 2H), 6.90-6.95 (m, 2H), 7.13-7.17 (m, 2H), 7.36-7.43 (m, 2H), 7.52 (dd, J = 8.4, 2.2 Hz, 1H), 7.63 (dd, J = 15.4, 2.2 Hz, 1H), 8.15 (d, J = 1.8 Hz, 1H), 10.08 (s, 1H). |
| 164 | (300 MHz, DMSO-d6) δ: 1.09-1.18 (m, 7H), 2.28 (s, 3H), 3.11 (s, 3H). 3.38-3.41 (m, 2H), 3.56-3.59 (m, 1H), 4.01-4.05 (m, 2H), 4.37-4.38 (m, 2H), 6.96 (t, J = 7.9 Hz, 1H), 7.27 (dd, J = 18.5, 7.9 Hz, 2H), 7.46 (d, J = 8.1 Hz, 1H), 7.54-7.58 (m, 1H), 7.75 (d, J = 8.8 Hz, 1H), 7.88 (d, J = 13.2 Hz, 1H), 8.17-8.21 (m, 1H), 10.52 (s, 1H). |
| 165 | (300 MHz, DMSO-d6) δ: 1.05-1.07 (m, 6H), 2.26 (s, 3H), 2.26 (s, 3H), 3.31 (s, 1H), 3.95-4.00 (m, 3H), 4.27-4.42 (m, 2H), 6.93 (t, J = 7.9 Hz, 1H), 7.19-7.23 (m, 2H), 7.39-7.44 (m, 2H), 7.63-7.69 (m, 2H), 8.17-8.19 (m, 1H), 10.21 (s, 1H). |

TABLE 22

| Ex. No. | | Chemical Compounds |
|---|---|---|
| 166 | 1-166 | 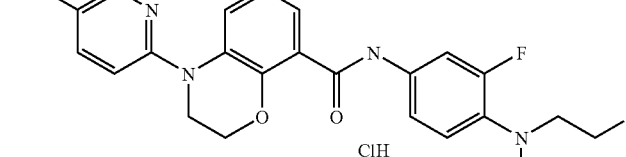 |
| 167 | 1-167 |  |

US 8,008,292 B2
TABLE 22-continued
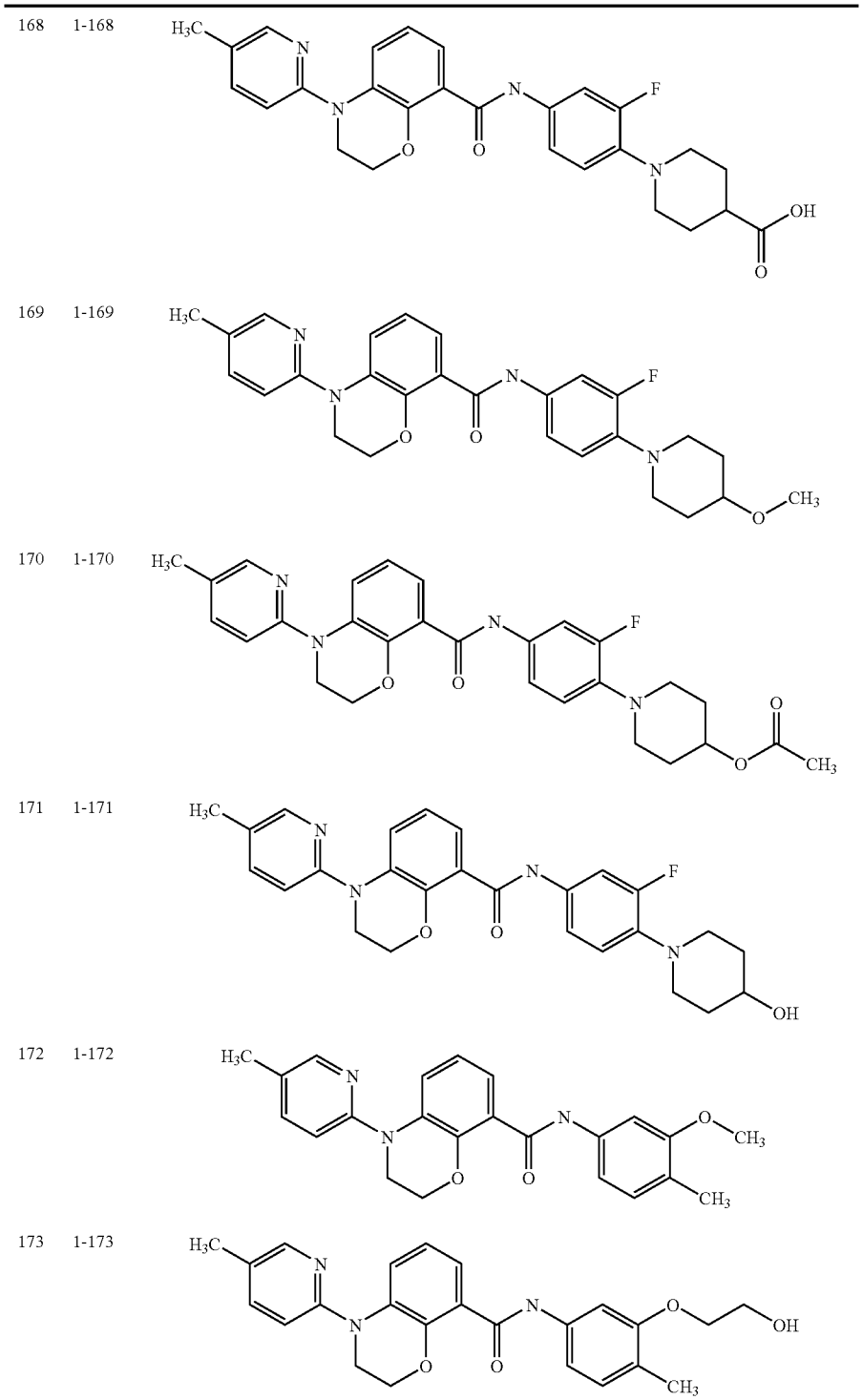
| | NMR |
|---|---|
| 166 | (300 MHz, DMSO-d6) δ: 1.17-1.20 (m, 6H), 2.26 (s, 3H), 3.45-3.50 (m, 4H), 3.77-3.80 (m, 1H), 3.99-4.04 (m, 2H), 4.35 (t, J = 4.4 Hz, 2H), 6.95 (t, J = 7.9 Hz, 1H), 7.22 (dt, J = 10.5, 4.7 Hz, 2H), 7.46 (dd, J = 8.1, 1.5 Hz, 1H), 7.57-7.66 (m, 3H), 7.89 (d, J = 13.9 Hz, 1H), 8.18 (d, J = 1.1 Hz, 1H), 10.52 (s, 1H). |
| 167 | (400 MHz, DMSO-d6) δ: 1.20 (t, J = 5.1 Hz, 3H), 1.66-1.79 (m, 2H), 1.91-1.99 (m, 2H), 2.25 (s, 3H), 2.69-2.72 (m, 2H), 3.24-3.33 (m, 1H), 3.99 (t, J = 4.8 Hz, 2H), 4.09 (q, J = 26.4 |

TABLE 22-continued

| | |
|---|---|
| | Hz, 2H), 4.32 (t, J = 4.4 Hz, 2H), 6.90 (t, J = 7.9 Hz, 1H), 7.01 (t, J = 9.4 Hz, 1H), 7.13-7.16 (m, 2H), 7.40 (td, J = 8.1, 4.0 Hz, 2H), 7.52 (dt, J = 8.4, 1.3 Hz, 1H), 7.65 (dd, J = 14.9, 2.4 Hz, 1H), 8.15 (t, J = 1.3 Hz. 1H), 10.12 (s, 1H). |
| 168 | (300 MHz, DMSO-d6) δ: 1.67-1.75 (m, 2H), 1.91-1.94 (m, 2H), 2.23 (s, 3H), 2.33-2.38 (m, 1H), 2.67-2.71 (m, 2H), 3.19-3.25 (m, 2H), 3.99 (t, J = 4.2 Hz, 2H), 4.32 (t, J = 4.4 Hz, 2H), 6.90 (t, J = 7.9 Hz, 1H), 7.01 (t, J = 9.5 Hz, 1H), 7.13-7.17 (m, 2H), 7.40 (td, J = 8.4, 1.7 Hz, 2H), 7.52 (dt, J = 9.5, 1.3 Hz, 1H), 7.65 (dd, J = 14.9, 2.4 Hz, 1H), 8.15 (t, J = 1.3 Hz. 1H), 10.12 (s, 1H). |
| 169 | (400 MHz, DMSO-d6) δ: 1.55-1.58 (m, 2H), 1.93-1.95 (m, 1H), 2.20 (s, 3H), 2.74 (dt, J = 15.0, 5.4 Hz, 2H), 3.13-3.18 (m, 2H), 3.31 (s, 3H), 3.97 (t, J = 4.4 Hz, 2H), 4.30 (t, J = 4.4 Hz, 2H), 6.89 (t, J = 7.9 Hz, 1H), 7.00 (t, J = 9.5 Hz, 1H), 7.13 (dt, J = 11.3, 5.0 Hz, 2H), 7.38 (ddd, J = 13.9, 8.3, 1.9 Hz, 2H), 7.51 (dd, J = 8.3, 2.3 Hz, 1H), 7.63 (d, J = 14.8, 2.3 Hz, 1H), 8.14 (d, J = 2.3 Hz, 1H), 10.12 (s, 1H). |
| 170 | (400 MHz, DMSO-d6) δ: 1.69-1.73 (m, 2H), 1.93-1.98 (m, 2H), 2.02 (s, 3H), 2.22 (s, 3H), 2.82-2.88 (m, 2H), 3.13-3.19 (m, 2H), 3.97 (t, J = 4.4 Hz, 2H), 4.30 (t, J = 4.4 Hz, 2H), 4.77-4.81 (m, 1H), 6.89 (t, J = 7.9 Hz, 1H), 7.03 (t, J = 9.3 Hz 1H), 7.13 (dt, J = 11.1, 4.9 Hz, 2H), 7.39 (dt, J = 13.0, 4.9 Hz, 2H), 7.51 (dd, J = 8.3, 2.3 Hz, 1H), 7.65 (dd, J = 14.8, 2.3 Hz, 1H), 8.14 (d, J = 1.2 Hz, 1H), 10.13 (s, 1H). |
| 171 | (300 MHz, DMSO-d6) δ: 1.50-1.57 (m, 2H), 1.84-1.85 (m, 2H), 2.25 (s, 3H), 2.70-2.74 (m, 2H), 3.16-3.20 (m, 2H), 3.59-3.62 (m, 1H), 3.99 (t, J = 4.2 Hz, 2H), 4.32 (t, J = 4.4 Hz, 2H), 4.66 (d, J = 4.4 Hz, 1H), 6.90 (t, J = 7.9 Hz, 1H), 7.01 (t, J = 9.4 Hz, 1H), 7.13-7.16 (m, 2H), 7.36-7.43 (m, 2H), 7.52 (dd, J = 8.4, 2.6 Hz, 1H), 7.64 (dd, J = 15.0, 2.2 Hz, 1H), 8.15 (d, J = 2.6 Hz, 1H), 10.11 (s, 1H). |
| 172 | (400 MHz, DMSO-d6) 2.11 (s, 3H), 2.23 (s, 3H), 3.99 (t, J = 4.2 Hz, 2H), 4.32 (t, J = 4.2 Hz, 2H), 6.91 (t, J = 7.9 Hz, 1H), 7.06 (d, J = 7.9 Hz, 1H), 7.14 (d, J = 8.3 Hz, 1H), 7.17-7.20 (m, 3H), 7.41 (d, J = 7.9 Hz, 1H), 7.48 (s, 1H), 7.53 (dd, J = 2.3 Hz, 1H), 8.15 (s, 1H), 10.06 (s, 1H). |
| 173 | (400 MHz, DMSO-d6) 2.13 (s, 3H), 2.23 (s, 3H), 3.75 (q, J = 5.3 Hz, 2H), 3.97 (dt, J = 15.3, 4.6 Hz, 4H), 4.33 (t, J = 4.4 Hz 2H), 4.83 (t, J = 5.6 Hz, 1H), 6.91 (t, J = 7.9 Hz, 1H), 7.06 (d, J = 8.3 Hz, 1H), 7.16 (dd, J = 18.6, 7.9 Hz, 3H), 7.43 (t, J = 9.0 Hz, 2H), 7.53 (dd, J = 8.8, 1.9 Hz, 1H), 8.15 (s, 1H), 10.03 (s, 1H). |

TABLE 23

| Ex. No. | | Chemical Compounds |
|---|---|---|
| 174 | 1-174 | [chemical structure] |
| 175 | 1-175 | [chemical structure] |
| 176 | 1-176 | [chemical structure] |

TABLE 23-continued

| 177 | 1-177 | (structure) |
| 178 | 1-178 | (structure) |
| 179 | 1-179 | (structure) |
| 180 | 1-180 | (structure) |
| 181 | 1-181 | (structure) |

| | NMR |
|---|---|
| 174 | (400 MHz, DMSO-d6) 1.55 (br s, 2H), 1.87-190 (m, 2H), 2.23 (s, 3H), 2.54 (s, 6H), 3.17-3.19 (m, 2H), 3.63 (br s, 2H), 3.99 (t, J = 4.4 Hz, 2H), 4.31 (t, J = 4.4 Hz, 2H), 4.47 (s, 1H), 6.91 (t, J = 7.9 Hz, 1H), 7.15-7.21 (m, 3H), 7.40-7.43 (m, 2H), 7.51-7.54 (m, 1H), 7.73 (dd, J = 13.2, 2.1 Hz, 1H), 8.15 (d, J = 1.9 Hz, 1H), 10.18 (s, 1H). |
| 175 | (400 MHz, DMSO-d6) 1.86-1.91 (m, 3H), 2.08-2.13 (m, 2H), 2.29 (s, 3H), 3.06 (br s, 2H), 3.20 (br s, 2H), 4.06 (t, J = 4.2 Hz, 2H), 4.38 (t, J = 4.2 Hz, 2H), 4.55-4.59 (m, 1H), 6.96 (t, J = 7.9 Hz, 1H), 7.25 (dd, J = 12.3, 5.8 Hz, 2H), 7.33 (d, J = 8.8 Hz, 1H), 7.45 (dd, J = 10.7, 3.7 Hz, 2H), 7.75-7.80 (m, 2H), 8.20 (s, 1H), 9.12 (d, J = 32.5 Hz, 2H), 10.25 (s, 1H). |
| 176 | (400 MHz, DMSO-d6) 1.19 (t, J = 7.2 Hz, 3H), 1.25-1.31 (m, 4H), 1.85-1.99 (m, 4H), 2.20 (s, 3H), 3.28-3.34 (m, 1H), 3.70-3.73 (m, 1H), 3.95 (t, J = 4.4 Hz, 2H), 4.07.4.13 (m, 4H), 4.27 (t, J = 4.4 Hz, 2H), 6.84 (t, J = 7.9 Hz, 1H), 7.07 (d, J = 8.3 Hz, 1H), 7.17 (dd, J = 7.9, 1.4 Hz, 1H), 7.33 (dd, J = 8.1, 1.6 Hz, 1H), 7.48 (dd, J = 8.3, 1.9 Hz, 1H), 7.90 (d, J = 7.9 Hz, 1H), 8.12 (d, J = 2.3 Hz, 1H). |
| 177 | (400 MHz, DMSO-d6) 1.21-1.35 (m, 4H), 1.85-1.99 (m, 4H), 2.20 (s, 3H), 3.22-3.35 (m, 1H), 3.69-3.74 (m, 1H), 3.95 (t, J = 4.2 Hz, 2H), 4.00 (a, 2H), 4.27 (t, J = 4.2 Hz, 2H), 6.84 (t, J = 7.9 Hz, 1H), 7.07 (d, J = 8.3 Hz, 1H), 7.18 (d, J = 7.4 Hz, |

TABLE 23-continued

| | |
|---|---|
| | 1H), 7.33 (dd, J = 8.1, 1.6 Hz, 1H), 7.48 (d, J = 8.8 Hz, 1H), 7.90 (d, J = 7.4 Hz, 1H), 8.12 (s, 1H), 12.46 (brs, 1H). |
| 178 | (400 MHz, DMSO-d6) 1.26-1.36 (m, 4H), 1.88 (brs, 2H), 1.99 (brs, 2H), 2.20 (s, 3H), 3.26-3.30 (m, 1H), 3.70-3.74 (m, 1H), 3.79 (s, 2H), 3.95 (brs, 2H), 4.27 (brs, 2H), 6.84 (t, 7.17 (d, J = 7.4 Hz, 1H), 7.22 (brs, 1H), 7.33 (d, J = 8.3 Hz, J = 7.9 Hz, 1H), 7.04 (brs, 1H), 7.07 (d, J = 8.3 Hz, 1H), 7.48 (d, J = 8.3 Hz, 1H), 7.91 (d, J = 7.9 Hz, 1H), 8.12 1H). |
| 179 | (400 MHz, DMSO-d6) 1.28-1.33 (m, 4H), 1.88 (brs, 2H), 1.99 (brs, 2H), 2.20 (s, 3H), 2.61 (d, J = 4.6 Hz, 3H), 3.26-3.29 (m, 1H), 3.71-3.74 (m, 1H), 3.84 (s, 2H), 3.95 (t, J = 4.4 Hz, 2H), 4.27 (t, J = 4.4 Hz, 2H), 6.84 (t, J = 7.9 Hz, 1H), 7.07 (d, J = 8.8 Hz, 1H), 7.17 (dd, J = 7.7, 1.6 Hz, 1H), 7.33 (dd, J = 8.1, 1.6 Hz, 1H), 7.46 (dd, J = 6.3, 2.3 Hz, 1H), 7.53 (brs, 1H), 7.92 (d, J = 7.9 Hz, 1H), 8.12 (d, J = 2.3 Hz, 1H). |
| 180 | (400 MHz, DMSO-d6) 1.25-1.31 (m, 4H), 1.86-2.00 (m, 4H), 2.20 (s, 3H), 2.79 (s, 3H), 2.92 (s, 3H), 3.26-3.29 (m, 1H), 3.70-3.74 (m, 1H), 3.95 (t, J = 4.4 Hz, 2H), 4.10 (s, 2H), 4.27 (t, J = 4.4 Hz, 2H). 6.84 (t, J = 7.9 Hz, 1H), 7.07 (d, J = 6.3 Hz, 1H), 7.17 (dd, J = 7.4, 1.4 Hz, 1H), 7.33 (dd, J = 8.3, 1.4 Hz, 1H), 7.48 (dd, J = 8.8. 2.3 Hz, 1H), 7.91 (d, J = 7.4 Hz, 1H), 8.11 (s, 1H). |
| 181 | (400 MHz, DMSO-d6) 1.14-1.31 (m, 4H), 1.81-1.93 (m, 4H), 2.16 (s, 3H), 3.16-3.21 (m, 1H), 3.35-3.42 (m, 4H), 3.65-3.68 (m, 1H), 3.91 (t, J = 4.0 Hz, 2H), 4.23 (t, J = 4.0 Hz, 2H), 4.47 (t, J = 5.3 Hz, 1H), 6.79 (t, J = 7.9 Hz, 1H), 7.03 (d, J = 8.8 Hz, 1H), 7.13 (d, J = 7.9 Hz, 1H), 7.29 (d, J = 7.9 Hz, 1H), 7.44 (d, J = 8.3 Hz, 1H), 7.86 (d, J = 7.9 Hz, 1H), 8.07 (s, 1H). |

TABLE 24

| Ex. No. | | Chemical Compounds |
|---|---|---|
| 182 | 1-182 |  |
| 183 | 1-183 |  |
| 184 | 1-184 |  (ClH) |
| 185 | 1-185 |  (ClH) |

TABLE 24-continued

| | | |
|---|---|---|
| 186 | 1-186 | 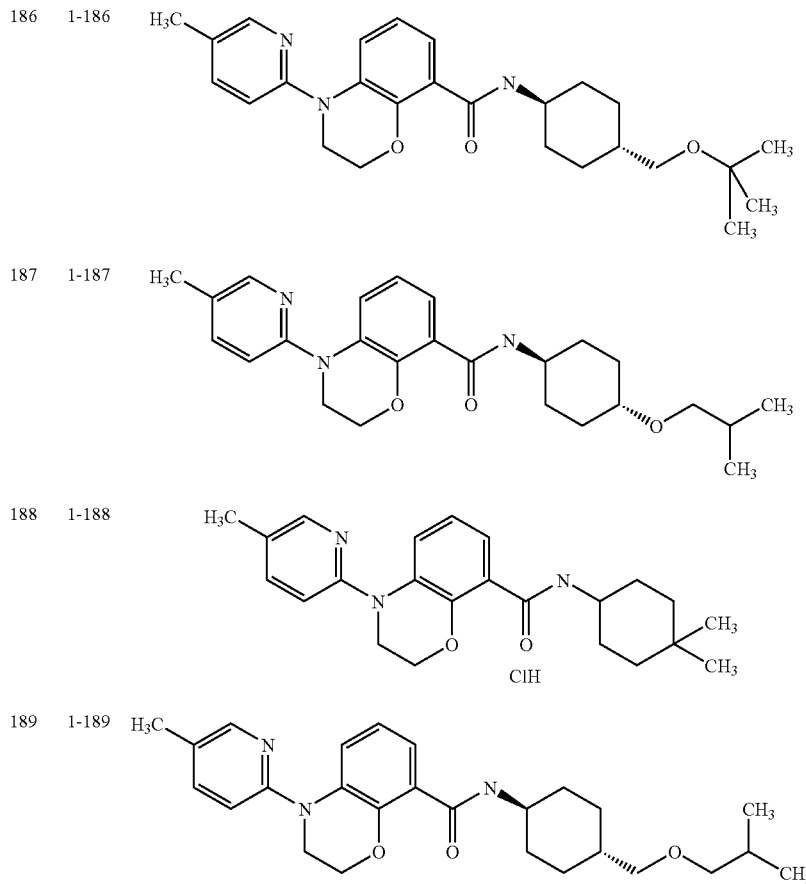 |
| 187 | 1-187 | |
| 188 | 1-188 | |
| 189 | 1-189 | |

| NMR | |
|---|---|
| 182 | (400 MHz, DMSO-d6) 0.96-1.06 (m, 2H), 1.20-1.30 (m, 2H), 1.45-152 (m, 1H), 1.72-1.75 (m, 2H), 1.86-1.91 (m, 2H), 2.21 (s, 3H), 3.14 (d, J = 6.5 Hz, 2H), 3.21 (s, 3H), 3.63-3.71 (m, 1H), 3.96 (t, J = 4.4 Hz, 2H), 4.28 (t, J = 4.4 Hz, 2H), 6.84 (t, J = 7.9 Hz, 1H), 7.08 (d, J = 8.8 Hz, 1H), 7.19 (dd, J = 7.7, 1.6 Hz, 1H), 7.34 (dd, J = 7.9, 1.4 Hz, 1H), 7.49 (dd, J = 8.8, 2.3 Hz, 1H), 7.90 (d, J = 7.9 Hz, 1H), 8.12 (d, J = 1.9 Hz, 1H). |
| 183 | (400 MHz, DMSO-d6) 0.94-1.03 (m, 2H), 1.06 (d, J = 6.5 Hz, 6H), 1.19-1.30 (m, 2H), 1.38-1.43 (m, 1H), 1.75-1.78 (m, 2H), 1.86-1.91 (m, 2H), 2.21 (s, 3H), 3.16 (d, J = 6.5 Hz, 2H), 3.44-3.50 (m, 1H), 3.63-3.72 (m, 1H), 3.96 (t, J = 4.4 Hz, 2H), 4.28 (t, J = 4.4 Hz, 2H), 6.84 (t, J = 7.9 Hz, 1H), 7.08 (d, J = 8.3 Hz, 1H), 7.20 (dd, J = 7.7, 1.6 Hz, 1H), 7.34 (dd, J = 8.1, 1.6 Hz, 1H), 7.49 (dd, J = 8.3, 2.3 Hz, 1H), 7.88 (d, J = 7.9 Hz, 1H), 8.12 (d, J = 2.3 Hz, 1H). |
| 184 | (400 MHz, DMSO-d6) 1.27-1.36 (m, 2H), 1.50-1.70 (m, 7H), 2.23 (s, 3H), 3.20 (d, J = 6.5 Hz, 2H), 3.22 (s, 3H), 3.99-4.04 (m, 3H), 4.35 (t, J = 4.4 Hz, 2H), 6.88 (t, J = 7.9 Hz, 1H), 7.16 (d, J = 8.8 Hz, 1H), 7.32 (dd, J = 7.7, 1.6 Hz, 1H), 7.37 (dd, J = 8.1, 1.6 Hz, 1H), 7.59 (d, J = 7.4 Hz, 1H), 8.01 (d, J = 7.9 Hz, 1H), 8.14 (s, 1H). |
| 185 | (400 MHz, DMSO-d6) 1.06 (d, J = 6.0 Hz, 6H), 1.29-1.35 (m, 2H), 1.50-1.70 (m, 7H), 2.24 (s, 3H), 3.23 (d, J = 6.5 Hz, 2H), 3.45-3.51 (m, 1H), 4.01 (t, J = 4.2 Hz, 3H), 4.36 (t, J = 4.4 Hz, 2H), 6.89 (t, J = 7.9 Hz, 1H), 7.21 (d, J = 8.3 Hz, 1H), 7.34 (d, J = 7.4 Hz, 1H), 7.38 (d, J = 8.3 Hz, 1H), 7.65 (d, J = 8.3 Hz, 1H), 8.01 (d, J = 7.4 Hz, 1H), 8.14 (s, 1H). |
| 186 | (400 MHz, DMSO-d6) 0.94-1.37 (m, 14H), 1.75-1.91 (m, 4H), 2.21 (s, 3H), 3.11 (d, J = 6.5 Hz, 2H), 3.63-3.72 (m, 1H), 3.96 (t, J = 4.4 Hz, 2H), 4.28 (t, J = 4.4 Hz, 2H), 6.84 (t, J = 7.9 Hz, 1H), 7.08 (d, J = 8.3 Hz, 1H), 7.20 (dd, J = 7.7, 1.6 Hz, 1H), 7.34 (dd, J = 8.1, 1.6 Hz, 1H), 7.49 (dd, J = 8.3, 2.3 Hz, 1H), 7.88 (d, J = 7.9 Hz, 1H), 8.12 (d, J = 2.3 Hz, 1H). |

TABLE 24-continued

| | |
|---|---|
| 187 | (400 MHz, DMSO-d6) 0.86 (d, J=8.4 Hz, 6H), 1.23-1.34(m, 4H), 1.86-1.97(m, 4H), 2.22(s, 3H), 3.16(m, 3H), 3.96(t, J=4.4 Hz, 2H), 4.29(t, J=4.4 Hz, 2H), 6.85(t, J=8 Hz, 1H), 7.09(d, J=8.4 Hz, 1H), 7.19(d, J=8 Hz, 1H), 7.49(d, J=8.4 Hz, 1H), 7.91(d, J=8 Hz, 1H), 8.12(s, 1H) |
| 188 | (400 MHz, DMSO-d6) 0.92(s, 6H), 1.17-1.47(m, 6H), 1.62-1.72(m, 2H), 2.27(s, 3H), 3.73(m, 3H), 4.02(t, J=4.4 Hz, 2H), 4.37(t, J=4.4Hz, 2H), 6.91(t, J=8 Hz, 1H), 7.28(m, 2H), 7.38(d, J=8 Hz, 1H), 7.76(d, J=8 Hz, 1H), 7.94(d, J=8 Hz, 1H), |
| 189 | (400 MHz, DMSO-d6) 0.83(d, J=8.4 Hz, 6H), 1.2-1.4(m, 6H), 1.8-2.0(m, 4H), 2.20(s, 3H), 3.20(m, 1H), 3.41(d, J=8 Hz, 2H), 6.85(t, J=8 Hz, 1H), 7.09(d, J=8 Hz, 1H), 7.19(d, J=8 Hz, 1H), 7.34(d, J=8 Hz, 1H), 7.49(d, J=8 Hz, 1H), 7.91(d, J=8 Hz, 1H), 8.12(s, 1H) |

TABLE 25

| Ex. No. | | Chemical Compounds |
|---|---|---|
| 190 | 1-190 | |
| 191 | 1-191 | |
| 192 | 1-192 | |
| 193 | 1-193 | |
| 194 | 1-194 | |

TABLE 25-continued

| 195 | 1-195 | 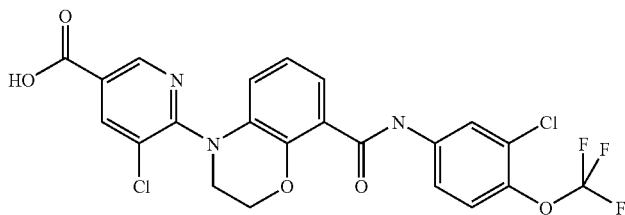 |
| 196 | 1-196 | 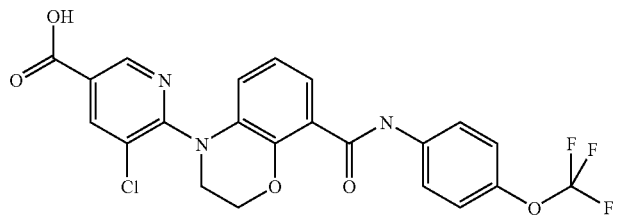 |
| 197 | 1-197 | 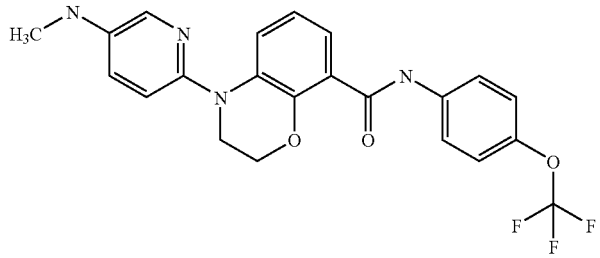 |

| | NMR |
|---|---|
| 190 | (400 MHz, DMSO-d6) 1.3-1.4(m, 4H), 1.85-1.95(m, 2H), 2.0-2.1(m, 2H), 2.22(s, 3H), 3.34(m, 1H), 3.76(m, 1H), 3.96(t, J=4.6 Hz, 2H), 4.29(t, J=4.6 Hz, 2H), 4.55(s, 2H), 6.85(t, J=8 Hz, 1H), 7.10(d, J=8 Hz, 1H), 7.19(d, J=8 Hz, 1H), 7.22-7.4(m, 6H), 7.50(d, J=8 Hz, 1H), 7.94(d, J=8 Hz, 1H) |
| 191 | (400 MHz, DMSO-d6) 0.85(d, J=6.4 Hz, 6H), 1.0-1.15(m, 3H), 1.2-1.35(m, 2H), 1.35-1.5(m, 1H), 1.6-1.75(m, 2H), 1.85-1.95(m, 2H), 2.22(s, 3H), 3.66(m, 1H), 3.97(t, J=4 Hz, 2H), 4.29(t, J=4 Hz, 2H), 6.85(t, J=8 Hz, 1H), 7.09(d, J=8 Hz, 1H), 7.20(d, J=8 Hz, 1H), 7.34(d, J=8 Hz, 1H), 7.49(d, J=8 Hz, 1H), 7.88(d, J=8 Hz, 1H), 8.13(s, 1H) |
| 192 | (400 MHz, DMSO-d6) 0.86(t, J=7.2 Hz, 3H), 0.8-1.0(m, 2H), 1.1-1.35(m, 6H), 1.7-1.8(m, 2H), 1.8-1.9(m, 2H), 2.22(s, 6.85(t, J=8 Hz, 1H), 7.08(d, J=8 Hz, 1H), 7.33(d, J=8 Hz, 1H), 7.48(d, J=8 Hz, 1H), 7.88(d, J=8 Hz, 1H), 8.13(s, 1H) |
| 193 | (400 MHz, DMSO-d6) 0.86(s, 9H), 1.2-1.4(m, 4H), 1.8-2.0(m, 4H), 2.22(s, 3H), 3.07(s, 2H), 3.17(m, 1H). 3.73(m, 1H), 3.96(t, J=4 Hz, 2H), 4.29(t, J=4 Hz, 2H), 6.85(t, J=8 Hz, 1H), 7.09(d, J=8 Hz, 1H), 7.18(d, J=8 Hz, 1H), 7.36(dd, J=8, 2.4Hz, 1H), 7.50(dd, J=8, 2.4 Hz), 7.92(d, J=8 Hz, 1H), 8.13(s, 1H) |
| 194 | (300 MHz, DMSO-d6) 1.28 (s, 9H), 3.29 (s, 3H), 4.06 (t, J = 4.4 Hz, 2H), 4.31-4.36 (m, 4H), 6.93 (t, J = 7.9 Hz, 1H), 7.18-725 (m, 2H), 7.34 (d, J = 8.8 Hz, 2H), 7.48 (dd, J = 8.1, 1.5 Hz, 1H), 7.60-7.68 (m, 3H), 8.25 (d, J = 2.2 Hz, 1H), 10.05 (s, 1H). |
| 195 | (400 MHz, DMSO-d6) 3.92 (t, J = 4.2 Hz, 2H), 4.43 (t, J = 4.4 Hz, 2H), 6.76 (dd, J = 8.3, 1.4 Hz, 1H), 6.86 (t, J = 7.9 Hz, 1H), 7.17 (dd, J = 7.4, 1.4 Hz, 1H), 7.56 (d, J = 7.9 Hz, 1H), 7.78 (dd, J = 9.0, 2.6 Hz, 1H), 8.14 (d, J = 2.8 Hz, 1H), 8.30 (d, J = 1.9 Hz, 1H), 8.83 (d, J = 1.9 Hz, 1H), 10.51 (s, |
| 196 | (300 MHz, DMSO-d6) 3.92 (t, J = 4.2 Hz, 2H), 4.43 (t, J = 4.0 Hz, 2H), 6.74 (dd, J = 8.1, 1.5 Hz, 1H), 6.85 (t, J = 7.9 Hz, 1H), 7.17 (dd, J = 7.7, 1.5 Hz, 1H), 7.35 (d, J = 8.8 Hz, 2H), 7.86 (d, J = 8.8 Hz, 2H), 8.30 (d, J = 2.2 Hz, 1H), 8.83 (d, J = 2.2 Hz, 1H), 10.35 (s, 1H), 13.46 (brs, 1H). |
| 197 | (400 MHz, DMSO-d6) 2.70 (d, J = 5.1 Hz, 3H), 3.78 (t, J = 4.2 Hz, 2H), 4.33 (t, J = 4.4 Hz, 2H), 5.69 (q, J = 5.1 Hz, 1H), 6.80 (t, J = 7.9 Hz, 1H), 6.97-7.06 (m, 4H), 7.34 (d, J = 8.8 Hz, 2H), 7.75 (d, J = 2.8 Hz, 1H), 7.84 (d, J = 8.8 Hz, 2H), 10.30 (s, 1H). |

TABLE 26

| Ex. No. | | Chemical Compounds |
|---|---|---|
| 198 | 1-198 | |
| 199 | 1-199 | |
| 200 | 1-200 | |
| 201 | 1-201 | |
| 202 | 1-202 | |
| 203 | 1-203 | |
| 204 | 1-204 | |

TABLE 26-continued

| 205 | 1-205 | 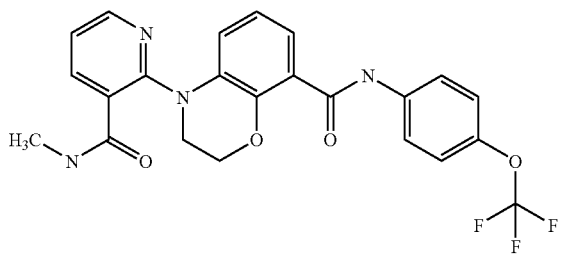 |

| | NMR |
|---|---|
| 198 | (300 MHz, DMSO-d6) δ: 1.34 (t, J = 7.0 Hz, 3H), 3.91 (t, J = 4.4 Hz, 2H), 4.08 (q, J = 7.1 Hz, 2H), 4.33 (t, J = 4.2 Hz, 2H), 6.88 (t, J = 7.9 Hz, 1H), 7.12-7.17 (m, 2H), 7.28-7.41 (m, 4H), 7.85 (d, J = 9.2 Hz, 2H), 8.06 (d, J = 3.3 Hz, 1H), 10.31 (s, 1H). |
| 199 | (400 MHz, DMSO-d6) 3.71 (t, J = 4.4 Hz, 2H), 3.89 (s, 3H), 4.43 (t, J = 4.4 Hz, 2H), 6.35 (dd, J = 7.9, 1.4 Hz, 1H), 6.77 (t, J = 7.9 Hz, 1H), 6.98 (dd, J = 7.7, 1.6 Hz, 1H), 7.35 (d, J = 8.8 Hz, 2H), 7.77 (d, J = 3.2 Hz, 1H), 7.86 (d, J = 8.8 Hz, 2H), 8.22 (d, J = 2.8 Hz, 1H), 10.33 (s, 1H). |
| 200 | (400 MHz, DMSO-d6) 3.72 (q, J = 5.1 Hz, 2H), 3.91 (t, J = 4.4 Hz, 2H), 4.04 (t, J = 5.1 Hz, 2H), 4.33 (t, J = 4.4 Hz, 2H), 4.89 (t, J = 5.1 Hz, 1H), 6.88 (t, J = 7.9 Hz, 1H), 7.11 (dd, J = 7.9, 1.6 Hz, 1H), 7.18 (d, J = 6.8 Hz, 1H), 7.31 (dd, J = 7.9, 1.6 Hz, 1H), 7.35 (d, J = 8.8 Hz, 2H), 7.41 (dd, J = 8.8, 3.0 Hz, 1H), 7.85 (d, J = 8.8 Hz, 2H), 8.08 (d, J = 3.0 Hz, 1H), 10.32 (s, 1H). |
| 201 | (300 MHz, DMSO-d6) 3.86 (t, J = 4.2 Hz, 2H), 4.33 (t, J = 4.2 Hz, 2H), 6.85 (t, J = 7.9 Hz, 1H), 7.07-7.10 (m, 2H), 7.20-7.21 (m, 2H), 7.34 (d, J = 8.8 Hz, 2H), 7.85 (d, J = 9.2 Hz, 2H), 7.93 (d, J = 2.9 Hz, 1H), 10.30 (s, 1H). |
| 202 | (300 MHz, DMSO-d6) 3.81 (s, 3H), 3.91 (t, J = 4.0 Hz, 2H), 4.33 (t, J = 4.2 Hz, 2H), 6.88 (t, J = 7.9 Hz, 1H), 7.12 (dd, J = 7.7, 1.5 Hz, 1H), 7.19 (d, J = 8.8 Hz, 1H), 7.28-7.43 (m, 4H), 7.85 (d, J = 9.2 Hz, 2H), 8.08 (d, J = 3.3 Hz, 1H), 10.31 (s, 1H). |
| 203 | (400 MHz, DMSO-d6) 3.95 (t, J = 4.2 Hz, 2H), 4.39 (t, J = 4.4 Hz, 2H), 6.86 (t, J = 7.9 Hz, 1H), 7.05 (dd, J = 7.9, 1.4 Hz, 1H), 7.18 (dd, J = 7.7, 1.6 Hz, 1H), 7.27 (dd, J = 7.9, 5.1 Hz, 1H), 7.34 (d, J = 8.8 Hz. 2H), 7.84 (d, J = 8.8 Hz, 2H). 8.29 (dd, J = 7.9, 1.9 Hz, 1H), 8.59 (dd, J = 4.4, 2.0 Hz, 1H), 10.34 (s, 1H). |
| 204 | (400 MHz, DMSO-d6) 3.78 (t, J = 4.2 Hz, 2H), 4.43 (t, J = 4.2 Hz, 2H), 6.74 (t, J = 7.9 Hz, 1H), 6.81 (dd, J = 8.1, 1.6 Hz, 1H), 7.05 (dd, J = 7.4, 1.9 Hz, 1H), 7.24 (dd, J = 7.7, 4.9 Hz, 1H), 7.34 (d, J = 8.8 Hz. 2H), 7.43 (s, 1H), 7.84 (t, J = 8.1 Hz, 3H), 7.92 (dd, J = 7.4, 1.9 Hz, 1H), 8.45 (dd, J = 4.4, 2.0 Hz, 1H), 10.30 (s, 1H). |
| 205 | (400 MHz, DMSO-d6) 2.55 (d, J = 4.6 Hz, 3H), 3.78 (t, J = 4.2 Hz, 2H), 4.41 (t, J = 4.2 Hz, 2H), 6.74 (t, J = 7.9 Hz, 1H), 6.83 (dd, J = 8.1, 1.6 Hz, 1H), 7.09 (dd, J = 7.7, 1.6 Hz, 1H), 7.20 (dd, J = 7.4, 4.6 Hz, 1H), 7.34 (d, J = 8.8 Hz, 2H), 7.83-7.87 (m, 3H), 8.27-8.30 (m, 1H), 8.43 (dd, J = 4.8, 2.0 Hz, 1H), 10.27 (s, 1H). |

TABLE 27

| Ex. No. | Chemical Compounds |
|---|---|
| 206 | 1-206 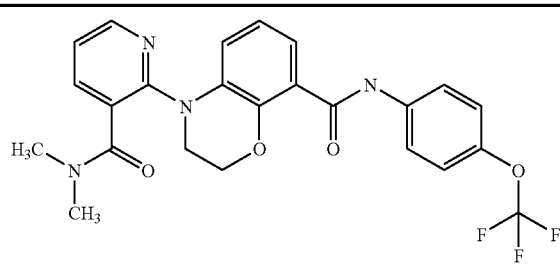 |

TABLE 27-continued
| 207 | 1-207 | 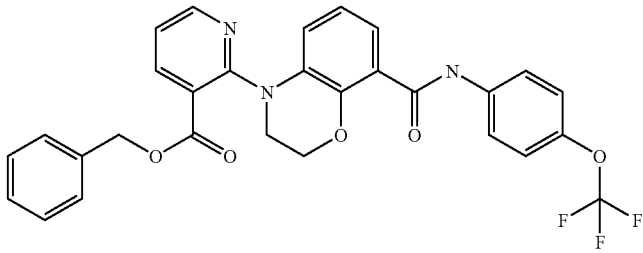 |
| 208 | 1-208 | 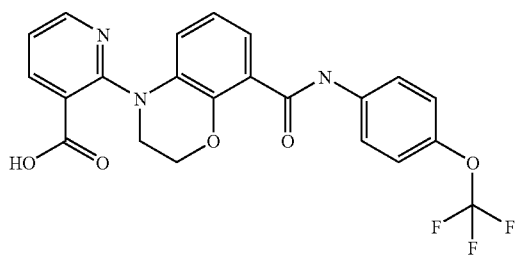 |
| 209 | 1-209 | 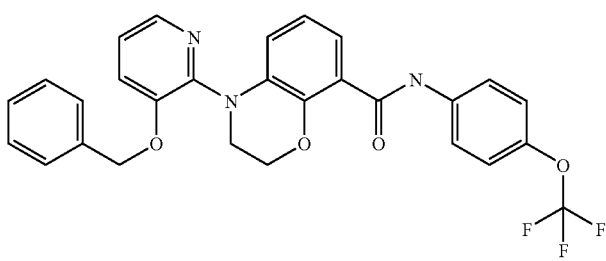 |
| 210 | 1-210 | 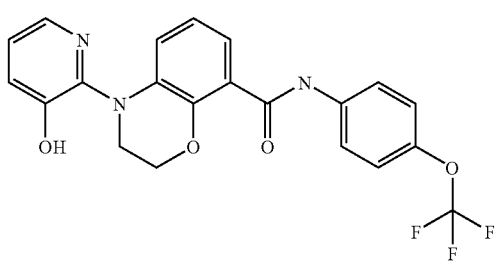 |
| 211 | 1-211 | 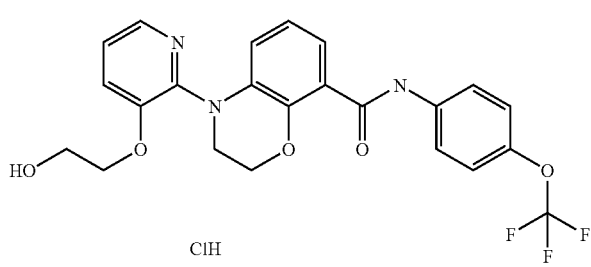<br>ClH |
| 212 | 1-212 | 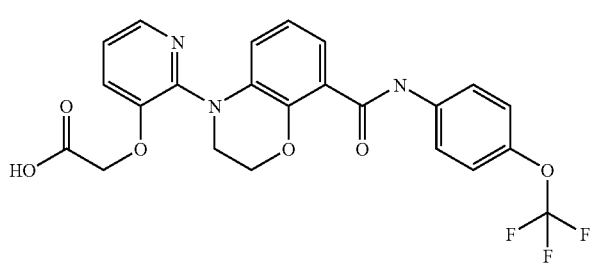 |

TABLE 27-continued

| | NMR |
|---|---|
| 206 | (400 MHz, DMSO-d6) 2.81 (s, 3H), 2.86 (s, 3H), 3.71 (s, 2H), 4.34 (s, 2H), 6.80 (t, J = 7.9 Hz, 1H), 6.91 (dd, J = 8.1, 1.6 Hz, 1H), 7.11 (dd, J = 7.4, 1.4 Hz, 1H), 7.21 (dd, J = 7.4, 4.6 Hz, 1H), 7.34 (d, J = 8.3 Hz, 2H), 7.76 (dd, J = 7.4, 1.9 Hz, 1H), 7.85 (d, J = 9.3 Hz, 2H), 8.41 (dd, J = 5.2, 2.0 Hz, 1H), 10.28 (s, 1H). |
| 207 | (400 MHz, DMSO-d6) 3.84 (t, J = 4.2 Hz, 2H), 4.25 (t, J = 4.2 Hz, 2H), 4.93 (s, 2H), 6.77 (t, J = 7.9 Hz, 1H), 6.87 (dd, J = 8.1, 1.6 Hz, 1H), 7.16 (dd, J = 7.4, 1.4 Hz, 1H), 7.21 (dd, J = 8.0, 4.8 Hz, 1H), 7.28-7.37 (m, 7H), 7.86 (d, J = 8.8 Hz, 2H) 8.12 (dd, J = 7.9, 1.9 Hz, 1H), 8.53 (dd, J = 5.2, 2.4 Hz, 1H), 10.26 (s, 1H). |
| 208 | (400 MHz, DMSO-d6) 3.82 (t, J = 4.2 Hz, 2H), 4.39 (t, J = 4.2 Hz, 2H), 6.77 (t, J = 7.9 Hz, 1H), 6.87 (dd, J = 8.3, 1.4 Hz, 1H), 7.08 (dd, J = 7.7, 1.6 Hz, 1H), 7.20 (dd, J = 7.4, 4.6 Hz, 1H), 7.34 (d, J = 8.3 Hz, 2H), 7.86 (d, J = 9.3 Hz, 2H), 8.10 (dd, J = 7.9, 1.9 Hz, 1H), 8.49 (dd, J = 4.4, 2.0 Hz, 1H), 10.29 (s, 1H), 13.28 (d, J = 155.4 Hz, 1H). |
| 209 | (400 MHz, DMSO-d6) 3.79 (t, J = 4.2 Hz, 2H), 4.38 (t, J = 4.4 Hz, 2H), 5.18 (s, 2H), 6.61 (dd, J = 8.3, 1.4 Hz, 1H), 6.78 (t, J = 7.9 Hz, 1H), 7.03 (dd, J = 7.4, 1.4 Hz, 1H), 7.21 (dd, J = 8.0,4.8 Hz, 1H), 7.27-7.35 (m, 7H), 7.61 (dd, J = 7.9, 1.4 Hz, 1H), 7.85 (d, J = 8.8 Hz, 2H), 8.00 (dd, J = 4.9, 1.6 Hz, 1H), 10.29 (s, 1H), 10.29 (s, 1H). |
| 210 | (400 MHz, DMSO-d6) 3.75 (t, J = 4.4 Hz, 2H), 4.41 (t, J = 4.2 Hz, 2H), 6.50 (t, J = 3.9 Hz, 1H), 6.76 (t, J = 7.9 Hz, 1H), 6.97 (d, J = 6.5 Hz, 1H), 7.10 (dd, J = 8.0, 4.8 Hz, 1H), 7.29 (dd, J = 7.9, 1.4 Hz, 1H), 7.34 (d, J = 8.8 Hz, 2H), 7.85 (d, J = 8.8 Hz, 2H), 7.90 (dd, J = 4.4, 1.2 Hz 1H), 9.97 (s, 1H), 10.31 (s, 1H). |
| 211 | (400 MHz, CHLOROFORM-d) 3.70 (brs, 2H), 4.15 (brs, 2H), 4.33 (brs, 2H), 4.65 (brs, 2H), 6.73 (d, J = 7.4 Hz, 1H), 6.94 (t, J = 7.4 Hz, 1H), 7.22 (d, J = 8.3 Hz, 2H), 7.34 (brs, 1H), 7.64 (d, J = 6.0 Hz, 1H), 7.73 (d, J = 8.8 Hz, 2H), 7.87 (d, J = 7.4 Hz, 1H), 8.12 (brs, 1H), 9.56 (s, 1H). |
| 212 | (400 MHz, DMSO-d6) 3.81 (t, J = 4.4 Hz, 2H), 4.39 (t, J = 4.2 Hz, 2H), 4.79 (s, 2H), 6.70-6.77 (m, 2H), 7.09 (dd, J = 7.2, 2.1 Hz, 1H), 7.18 (dd, J = 8.0, 4.8 Hz. 1H), 7.34 (d, J = 8.3 Hz, 2H), 7.42 (dd, J = 8.3, 1.4 Hz, 1H), 7.85 (d, J = 9.3 Hz, 2H), 7.99 (dd, J = 4.6, 1.4 Hz, 1H), 10.32 (s, 1H), 13.12 (s, 1H). |

TABLE 28

| Ex. No. | | Chemical Compounds |
|---|---|---|
| 213 | 1-213 | 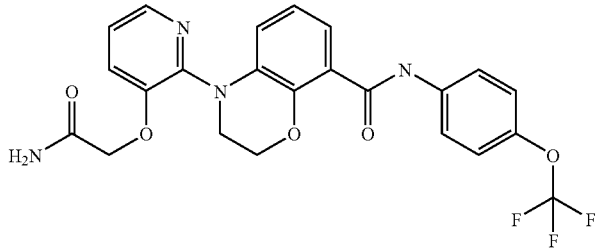 |
| 214 | 1-214 | 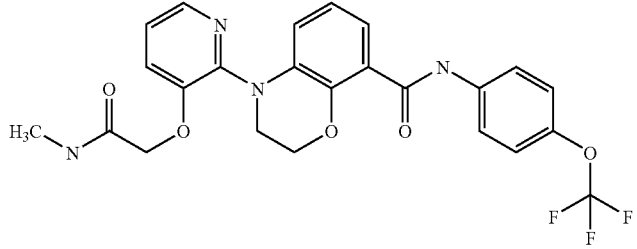 |

TABLE 28-continued
| 215 | 1-215 | 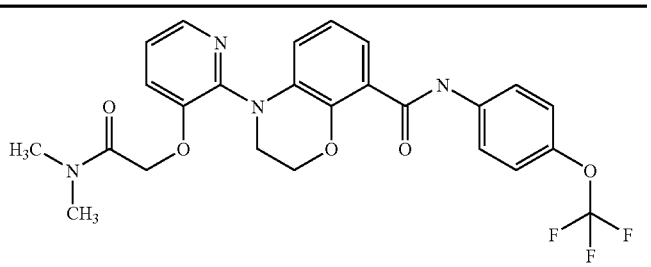 |
| 216 | 1-216 | 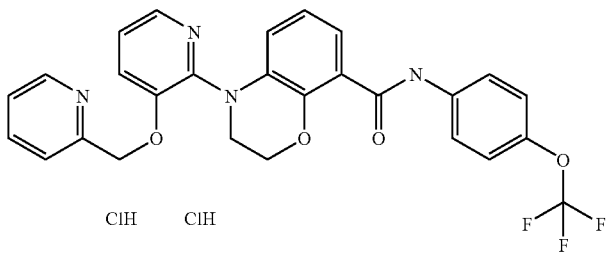 |
| 217 | 1-217 | 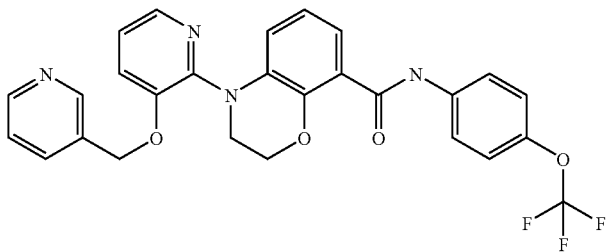 |
| 218 | 1-218 | 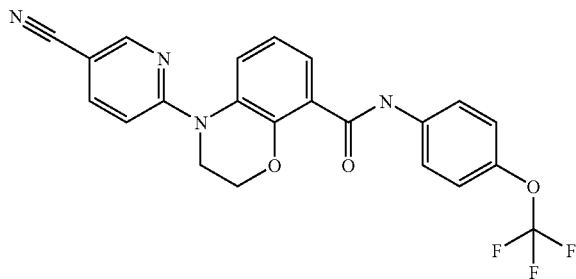 |
| 219 | 1-219 | 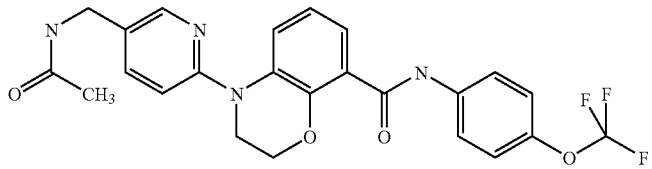 |
| | NMR |
|---|---|
| 213 | (400 MHz, DMSO-d6) 3.82 (t, J = 4.2 Hz, 2H), 4.39 (t, J = 4.2 Hz, 2H), 4.54 (s, 2H), 6.68 (dd, J = 8.1, 1.6 Hz, 1H), 6.76 (t, J = 7.9 Hz, 1H), 7.02 (dd, J = 7.4, 1.4 Hz, 1H), 7.09 (s, 1H), 7.18 (dd, J = 8.0, 4.8 Hz, 1H), 7.32-7.42 (m, 4H), 7.85 (d, J = 9.3 Hz, 2H), 7.99 (dd, J = 4.6. 1.4 Hz, 1H), 10.29 (s, 1H). |
| 214 | (400 MHz, DMSO-d6) 2.58 (d, J = 4.6 Hz, 3H), 3.83 (t, J = 4.2 Hz, 2H), 4.39 (t, J = 4.2 Hz, 2H), 4.56 (s, 2H), 6.69 (dd, J = 8.1, 1.6 Hz, 1H), 6.77 (t, J = 7.9 Hz, 1H), 7.03 (dd, J = 7.4, 1.4 Hz, 1H), 7.17 (dd, J = 8.4, 4.8 Hz, 1H), 7.33 (d, J = 8.8 Hz, 2H), 7.40-7.46 (m, 2H), 7.85 (d, J = 9.3 Hz, 2H), 8.00 (dd, J = 4.6, 1.4 Hz, 1H), 10.31 (s, 1H). |
| 215 | (400 MHz, DMSO-d6) 2.82 (s, 3H), 2.95 (s, 3H), 3.83 (s, 2H), 4.36 (s, 2H), 4.96 (s, 2H), 6.71-6.79 (m, 2H), 6.97-7.00 (m, 1H), 7.12-7.16 (m, 1H), 7.32-7.37 (m, 3H), 7.84 (d, J = 8.8 Hz, 2H), 7.93-7.95 (m, 1H), 10.30 (s, 1H). |

TABLE 28-continued

| | |
|---|---|
| 216 | (400 MHz, DMSO-d6) 3.84 (t, J = 4.1 Hz, 2H), 4.40 (t, J = 4.1 Hz, 2H), 5.31 (s, 2H), 6.65 (dd, J = 8.1, 1.5 Hz, 1H), 6.75 (t, J = 7.7 Hz. 1H), 7.02 (dd, J = 7.4, 1.5 Hz, 1H), 7.22 (dd, J = 8.0, 4.8 Hz, 1H), 7.33 (t, J = 8.3 Hz, 2H), 7.42-7.46 (m, 1H), 7.64 (dd. J = 8.0, 1.5 Hz, 1H), 7.84-7.91 (m, 3H), 8.03 (dd, J = 4.6, 1.4 Hz, 1H), 8.60 (d, J = 5.1 Hz, 1H), 10.31 (s, 1H). |
| 217 | (400 MHz, DMSO-d6) 3.78 (t, J = 4.3 Hz, 2H), 4.37 (t, J = 4.3 Hz, 2H), 5.23 (s, 2H), 6.60 (dd, J = 8.3, 1.5 Hz, 1H), 6.77 (t, J = 7.9 Hz, 1H), 7.02 (dd, J = 7.7, 1.5 Hz, 1H), 7.23 (dd, J = 8.0, 4.8 Hz, 1H), 7.32-7.36 (m, 3H), 7.84-7.69 (m, 2H), 7.85 (d, J = 9.3 Hz, 2H), 8.02 (dd, J = 4.8, 1.2 Hz, 1H), 8.50 (dd, J = 4.8, 2.0 Hz, 1H), 8.54 (d, J = 2.0 Hz, 1H), 10.28 (s, 1H). |
| 218 | (400 MHz, DMSO-d6) H1-NMR (DMSO-d6) δ: 4.16 (t, J = 4.5 Hz, 2H), 4.37 (t, J = 4.5 Hz, 2H), 6.99 (t, J = 8.0 Hz, 1H), 7.28-7.35 (m, 4H), 7.61 (dd, J = 8.0, 1.6 Hz, 1H), 7.82 (d, J = 9.3 Hz, 2H), 8.02 (dd, J = 8.8, 2.3 Hz, 1H), 8.69 (d, J = 2.3 Hz, 1H), 10.33 (s, 1H). |
| 219 | (300 MHz, DMSO-d6) δ: 1.85 (s, 3H), 4.02 (t, J = 4.4 Hz, 2H), 4.19 (d, J = 5.9 Hz, 2H), 4.32 (t, J = 4.6 Hz, 2H), 6.93 (t, J = 7.9 Hz, 1H), 7.17-7.21 (m, 2H), 7.34 (d, J = 8.4 Hz, 2H), 7.46 (dd, J = 8.3, 1.7 Hz, 1H), 7.58 (dd, J = 8.6, 2.4 Hz, 1H), 7.84 (d, J = 9.2 Hz, 2H), 8.20 (d, J = 2.2 Hz, 1H), 8.30 (t, J = 6.1 Hz, 1H), 10.32 (s, 1H). |

TABLE 29

| | Ex. No. | Chemical Compounds |
|---|---|---|
| 220 | 1-220 | |
| 221 | 1-221 | |
| 222 | 1-222 | |
| 223 | 1-223 | |

TABLE 29-continued

| | | |
|---|---|---|
| 224 | 1-224 | 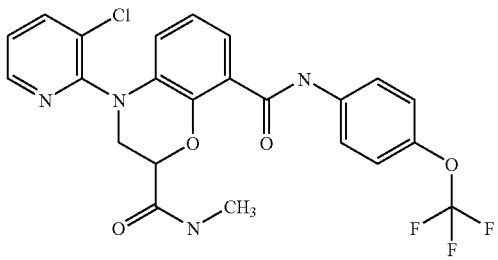 |
| 225 | 1-225 | 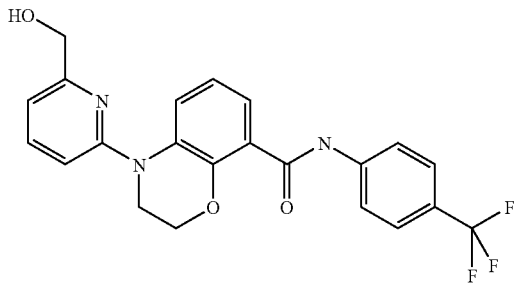 |
| 226 | 1-226 | 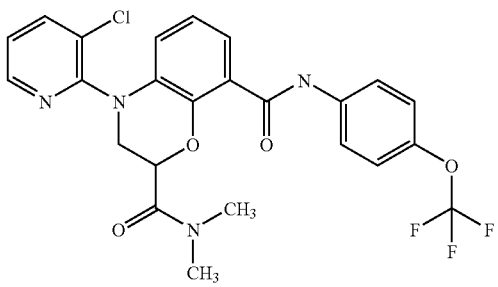 |
| 227 | 1-227 | 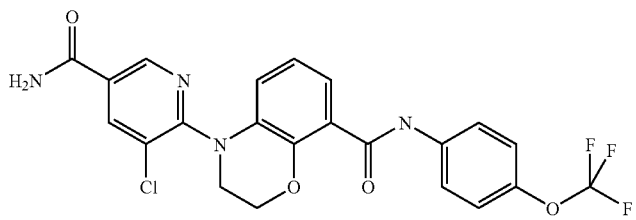 |

| NMR | |
|---|---|
| 220 | (300 MHz, DMSO-d6) δ: 3.34 (s, 3H), 3.80 (t, J = 4.2 Hz, 2H), 4.42 (t, J = 4.2 Hz, 2H), 4.47 (s, 2H), 6.51 (dd, J = 8.1, 1.5 Hz, 1H), 6.80 (t, J = 7.7 Hz, 1H), 7.06 (dd, J = 7.7, 1.5 Hz, 1H), 7.35 (d, J = 8.4 Hz, 2H), 7.86 (d, J = 8.8 Hz, 2H), 7.98 (d, J = 1.8 Hz, 1H), 8.38 (d, J = 1.8 Hz, 1H), 10.33 (s, 1H). |
| 221 | (300 MHz, DMSO-d6) δ: 2.05 (s, 2H, keto), 2.10 (s, 1H, enol), 2.78 (s, 1H, enol), 2.94 (s, 2H, keto), 4.03-4.04 (m, 2H), 4.32-4.35 (m, 2H), 4.43 (s, 1.3H, keto), 4.50 (e. 0.6H, enol), 6.91-8.94 (m, 1H), 7.18-7.25 (m, 2H), 7.34 (d, J = 8.8 Hz 2H), 7.50-7.55 (m, 2H), 7.85 (d, J = 9.2 Hz, 2H), 8.18-8.22 (m, 1H), 10.32 (s, 1H). |
| 222 | (400 MHz, DMSO-d6) δ: 3.66 (s, 2H), 4.01 (t, J = 4.2 Hz, 2H), 4.32 (t, J = 4.4 Hz, 2H). 6.92 (t, J = 7.9 Hz, 1H), 7.17 (d, J = 8.8 Hz, 2H), 7.34 (d, J = 8.3 Hz, 2H), 7.44 (dd, J = 8.3, 1.4 Hz, 1H), 7.66 (dd, J = 8.3, 2.3 Hz, 1H), 7.84 (d, J = 9.3 Hz, 2H), 8.23 (d, J = 1.9 Hz, 1H), 10.33 (s, 1H). |
| 223 | (300 MHz, DMSO-d6) δ: 2.13 (s, 6H), 3.33 (s, 2H), 4.03 (t, J = 4.4 Hz, 2H), 4.34 (t, J = 4.4 Hz, 2H), 6.91 (q, J = 8.7 Hz, 1H), 7.19 (d, J = 3.9 Hz, 2H), 7.35 (d, J = 8.4 Hz, 2H), 7.49 (dd, J = 8.1, 1.5 Hz, 1H), 7.60 (dd, J = 8.4, 2.2 Hz, 1H), 7.85 (d, J = 9.2 Hz, 2H), 8.18 (d, J = 1.8 Hz, 1H), 10.32 (s, 1H). |
| 224 | (400 MHz, DMSO-d6) 2.65 (d, J = 4.6 Hz, 3H), 3.91-4.00 (m, 2H), 5.12 (t, J = 4.6 Hz, 1H), 6.54 (dd, J = 8.1, 1.5 Hz, 1H), 6.89 (t, J = 7.9 Hz, 1H), 7.24 (dd, J = 7.7, 1.5 Hz, 1H), |

TABLE 29-continued 7.30 (dd, J = 7.7, 4.6 Hz, 1H), 7.38 (d, J = 8.5 Hz, 2H), 7.88 (d, J = 8.5 Hz, 2H), 8.01 (dd, J = 7.9, 1.5 Hz, 1H), 8.15 (q, J = 4.6 Hz, 1H), 8.43 (dd, J = 4.6, 2.0 Hz, 1H), 10.66 (s, 1H).

225 (400 MHz, DMSO-d6) 4.05 (t, J = 4.4 Hz, 2H), 4.33 (t, J = 4.4 Hz, 2H), 4.48 (d, J = 5.6 Hz, 2H), 5.33 (t, J = 5.6 Hz, 1H), 6.94 (t, J = 7.9 Hz, 1H), 7.02 (d, J = 7.9 Hz, 1H), 7.07 (d, J = 7.9 Hz, 1H), 7.21 (dd, J = 7.7, 1.6 Hz, 1H), 7.51 (dd, J = 7.7, 1.6 Hz, 1H), 7.67 (d, J = 7.7 Hz, 1H), 7.71 (d, J = 8.3 Hz, 2H), 7.95 (d, J = 8.3 Hz, 2H), 10.51 (s, 1H).

226 (400 MHz, DMSO-d6) 2.88 (s, 3H), 3.05 (s, 3H), 3.58 (dd, J = 13.0, 8.8 Hz, 1H), 4.20 (dd, J = 13.0, 4.0 Hz, 1H), 5.54 (t, J = 7.9 Hz, 1H), 7.24 (dd, J = 7.9, 1.4 Hz, 1H), 7.31 (dd, J = 8.8, 4.0 Hz, 1H), 6.56 (dd, J = 8.0, 1.4 Hz, 1H), 6.89 8.0, 4.8 Hz, 1H), 7.37 (d, J = 8.3 Hz, 2H), 7.88 (d, J = 8.3 Hz, 2H), 8.03 (dd, J = 8.0, 1.4 Hz, 1H), 8.44 (dd, J = 4.8, 1.4 Hz, 1H), 10.80 (s, 1H).

227 (400 MHz, DMSO-d6) 3.88 (t, J = 4.2 Hz, 2H), 4.42 (t, J = 4.2 Hz, 2H), 6.68 (dd, J = 7.9, 1.6 Hz, 1H), 6.84 (t, J = 7.9 Hz, 1H), 7.13 (dd, J = 7.9, 1.6 Hz, 1H), 7.36 (d, J = 8.3 Hz, 2H), 7.66 (s, 1H), 7.87 (d, J = 8.3 Hz, 2H), 8.17 (s, 1H), 8.38 (d, J = 2.3 Hz, 1H), 8.82 (d, J = 2.3 Hz, 1H), 10.38 (s, 1H)

TABLE 30

| Ex. No. | | Chemical Compounds | NMR |
|---|---|---|---|
| 228 | 1-228 | | (400 MHz, DMSO-d6) 1.80 (s, 3H), 3.23-3.29 (m, 1H), 3.45-3.51 (m, 1H), 4.06-4.09 (m, 1H), 4.17 (d, J = 10.5 Hz, 1H), 4.47 (d, J = 10.5 Hz, 1H), 6.48 (dd, J = 8.0, 1.2 Hz, 1H), 6.84 (t, J = 7.7 Hz, 1H), 7.07 (dd, J = 7.7, 1.2 Hz, 1H), 7.36 (dd, J = 8.0, 4.8 Hz, 1H), 7.72 (d, J = 8.3 Hz, 2H), 8.00 (d, J = 8.3 Hz, 2H), 8.08 (dd, J = 8.0, 1.2 Hz, 1H), 8.16 (t, J = 5.6 Hz, 1H), 8.46 (dd, J = 4.8, 1.2 Hz, 1H), 10.46 (s, 1H). |
| 229 | 1-229 | | (400 MHz, DMSO-d6) 4.41 (dd, J = 10.7, 2.8 Hz, 1H), 4.68-4.75 (m, 2H), 6.58 (d, J = 7.9 Hz, 1H), 6.84 (t, J = 7.9 Hz, 1H), 7.05 (dd, J = 7.9, 1.5 Hz, 1H), 7.26 (dd, J = 8.0, 4.5 Hz, 1H), 7.69 (d, J = 8.0 Hz, 2H), 7.95-8.00 (m, 3H), 8.38 (dd, J = 4.5, 1.5 Hz, 1H), 10.53 (s, 1H), 13.04 (s, 1H). |
| 230 | 1-230 | | (400 MHz, DMSO-d6) 3.63 (s, 3H), 4.01 (d, J = 3.7 Hz, 2H), 5.45 (t, J = 3.7 Hz, 1H), 6.50 (dd, J = 7.9, 1.4 Hz, 1H), 6.87 (t, J = 7.9 Hz, 1H), 7.23 (dd, J = 7.9, 1.4 Hz, 1H), 7.33 (dd, J = 8.0, 4.8 Hz, 1H), 7.38 (d, J = 8.5 Hz, 2H), 7.88 (d, J = 8.5 Hz, 2H), 8.04 (dd, J = 7.9, 1.4 Hz, 1H), 8.44 (dd, J = 4.6, 1.4 Hz, 1H), 10.33 (s, 1H). |

TABLE 30-continued

| Ex. No. | | Chemical Compounds | NMR |
|---|---|---|---|
| 231 | 1-231 | | (400 MHz, DMSO-d6) 3.67 (dd, J = 13.0, 7.4 Hz, 1H), 3.74 (t, J = 5.5 Hz, 2H), 3.92 (dd, J = 13.0, 2.8 Hz, 1H), 4.48-4.54 (m, 1H), 5.22 (t, J = 5.5 Hz, 1H), 6.56 (dd, J = 7.9, 1.5 Hz, 1H), 6.85 (t, J = 7.9 Hz, 1H), 7.27 (dd, J = 7.9, 1.5 Hz, 1H), 7.32 (dd, J = 7.9, 4.5 Hz, 1H), 7.38 (d, J = 8.8 Hz, 2H), 7.89 (d, J = 8.8 Hz, 2H), 8.05 (dd, J = 7.9, 1.9 Hz, 1H), 8.44 (dd, J = 4.5, 1.4 Hz, 1H), 10.40 (s, 1H). |
| 232 | 1-232 | | (400 MHz, DMSO-d6) 3.93-4.08 (m, 2H), 5.31 (t, J = 4.2 Hz, 1H), 6.53 (dd, J = 7.9, 1.4 Hz, 1H), 6.87 (t, J = 7.9 Hz, 1H), 7.27-7.34 (m, 2H), 7.38 (d, J = 8.3 Hz, 2H), 7.88 (d, J = 9.3 Hz, 2H), 8.03 (dd, J = 8.3, 1.4 Hz, 1H), 8.44 (dd, J = 4.8, 2.0 Hz, 1H), 10.45 (s, 1H), 13.59 (s, 1H). |
| 233 | 1-233 | | (400 MHz, DMSO-d6) 4.27 (dd, J = 10.7, 2.5 Hz, 1H), 4.58-4.60 (m, 1H), 4.74 (dd, J = 10.7, 2.5 Hz, 1H), 6.58 (dd, J = 7.9, 1.4 Hz, 1H), 6.85 (t, J = 7.9 Hz, 1H), 7.07 (dd, J = 7.4, 1.4 Hz, 1H), 7.33-7.37 (m, 2H). 7.52 (s, 1H), 7.70 (d, J = 8.8 Hz, 2H), 7.96 (d, J = 8.3 Hz, 2H), 8.06 (dd, J = 7.9, 1.4 Hz, 1H), 8.42 (dd, J = 4.6, 1.4 Hz, 1H), 10.53 (s, 1H). |
| 234 | 1-234 | | (400 MHz, DMSO-d6) 2.60 (d, J = 4.6 Hz, 3H), 4.26 (d, J = 8.5 Hz, 1H), 4.60 (s, 1H), 4.74 (d, J = 8.5 Hz, 1H), 6.60 (d, J = 7.9 Hz, 1H), 6.86 (t, J = 7.9 Hz, 1H), 7.08 (d, J = 6.5 Hz, 1H), 7.33 (q, J = 4.2 Hz, 1H), 7.70 (d, J = 8.8 Hz, 2H), 7.95-8.06 (m, 4H), 8.42 (dd, J = 4.6. 1.4 Hz, 1H), 10.52 (s, 1H). |

TABLE 31

| Ex. No. | | Chemical Compounds |
|---|---|---|
| 235 | 1-235 | |
| 236 | 1-236 | |

TABLE 31-continued
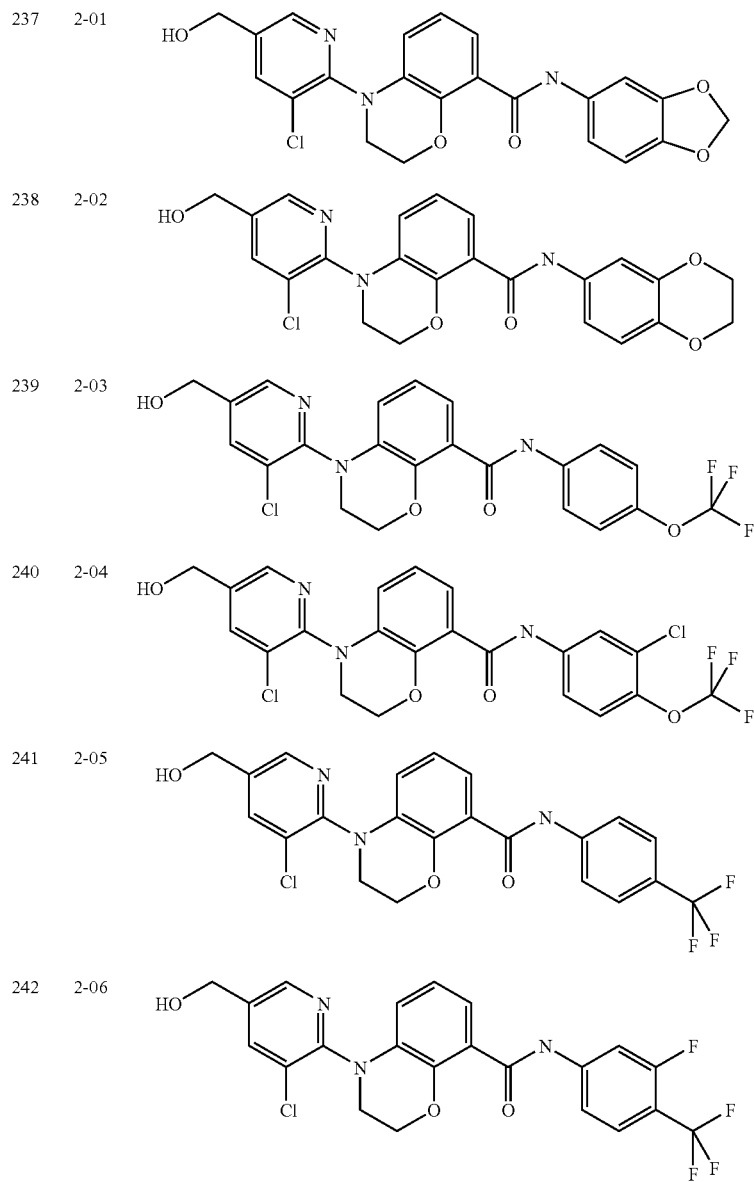
| | NMR |
|---|---|
| 235 | (400 MHz, DMSO-d6) 3.83 (dd, J = 13, 6.5 Hz, 1H), 4.10 (dd, J = 13, 4.0 Hz, 1H), 5.07 (dd, J = 6.5, 4.0 Hz, 1H), 6.56 (dd, J = 8.0, 1.5 Hz, 1H), 6.89 (t, J = 8.0 Hz, 1H), 7.26 (dd, J = 7.7, 1.5 Hz, 1H), 7.31 (dd, J = 7.7, 4.0 Hz, 1H), 7.37 (d, J = 8.3 Hz, 2H), 7.71 (d, J =6.5 Hz, 2H), 7.90 (d, J =8.3 Hz, 2H), 8.03 (dd, J =8.0, 1.5 Hz, 1H), 8.44 (dd, J = 4.0, 1.5 Hz, 1H), 10.77 (s, 1H). |
| 236 | (400 MHz, DMSO-d6) 2.27 (s, 3H), 3.34 (s, 3H), 4.10 (brs, 4H), 6.78 (t, J = 7.0 Hz, 1H), 6.96 (d, J = 6.5 Hz, 1H), 7.18-7.29 (m, 6H), 7.79 (d, J = 7.9 Hz, 1H), 8.16 (s, 1H), |
| 237 | (400 MHz, DMSO-d6) 3.75 (t, J=4.4 Hz, 2H), 4.40(t, J=4.4 Hz, 2H), 4.53(d, J=5.6 Hz, 2H), 5.39(t, J=5.6 Hz, 1H), 5.97(s, 2H), 6.42(dd, J=8.1, 1.6 Hz, 1H). 6.75(dd, J=8.1, 7.6 Hz, 1H), 6.85(d, J=8.4 Hz, 1H), 7.02(dd, J=7.6, 1.6Hz, 1H), 7.13(dd, J=8.4, 2.1 Hz, 1H), 7.42(d, J=2.1 Hz, 1H), 7.92(d, J=2.0 Hz, 1H), 8.34(d, J=2.0 Hz, 1H), 10.01(s, 1H) |
| 238 | (400 MHz, DMSO-d6) 3.77(t, J=4.4 Hz, 2H), 4.21-4.24(m, 4H), 4.42(t, J=4.4 Hz, 2H), 4.56(d, J=5.6 Hz, 2H), 5.43(t, J=5.6 Hz, 1H), 6.45(dd, J=8.1, 1.6 Hz, 1H), 6.78(dd, J=8.1, 7.9Hz, 1H),6.80(d, J=8.8 Hz, 1H), 7.04(dd, J=7.9, 1.6 Hz, |

TABLE 31-continued

| | |
|---|---|
| | 1H), 7.15(dd, J=8.8, 2.6 Hz, 1H), 7.38(d, J=2.6 Hz, 1H), 7.95(d, J=2.1 Hz, 1H), 8.37(d, J=2.1 Hz, 1H), 9.96(s, 1H) |
| 239 | (400 MHz, DMSO-d6) 3.78 (t, J = 4.2 Hz, 2H), 4.42 (t, J = 4.4 Hz, 2H), 4.56 (d, J = 4.6 Hz, 2H), 5.44 (t, J = 5.1 Hz, 1H), 6.47 (dd, J = 8.3. 1.4 Hz, 1H), 6.80 (1, J = 7.9 Hz, 1H), (dd, J = 7.4, 1.4 Hz, 1H), 7.35 (d, J = 8.8 Hz, 2H), 7.86 (d, J = 8.8 Hz, 2H), 7.95 (d, J = 2.3 Hz, 1H), 8.37 (d, J = 1.9 Hz, 1H), 10.35 (s, 1H). |
| 240 | (400 MHz, DMSO-d6) 3.78 (t, J = 4.2 Hz, 2H), 4.43 (t, J = 4.2 Hz, 2H), 4.56 (d, J = 5.6 Hz, 2H), 5.44 (t, J = 5.6 Hz, 1H), 6.49 (dd, J = 7.9, 1.4 Hz, 1H), 6.81 (t, J = 7.7 Hz, 1H), J = 7.7, 1.2 Hz, 1H), 7.56 (dd, J = 9.0, 1.2 Hz, 1H), 7.78 (dd, J = 8.8, 2.3 Hz, 1H), 7.95 (d, J = 1.9 Hz, 1H), 8.14 (d, J = 2.3 Hz, 1H), 8.37 (d, J = 1.4 Hz, 1H), 10.49 (s, 1H). |
| 241 | (400 MHz, DMSO-d6) 3.79 (t, J = 4.4 Hz, 2H), 4.43 (t, J = 4.2 Hz, 2H), 4.56 (d, J = 4.2 Hz, 2H), 5.44 (br s, 1H), 6.49 (dd, J = 7.9, 1.4 Hz, 1H), 6.81 (t, J = 7.9 Hz, 1H), 7.05 (dd, J = 7.7, 1.6 Hz, 1H), 7.71 (d, J = 8.8 Hz, 2H), 7.97 (t, J = 4.6 Hz, 3H), 8.37 (d, J = 2.3 Hz, 1H), 10.52 (s, 1H). |
| 242 | (300 MHz, DMSO-d6) 3.79 (t, J = 4.2 Hz, 2H), 4.43 (t, J = 4.2 Hz, 2H), 4.56 (d, J = 5.1 Hz, 2H), 5.42 (t, J = 5.3 Hz, 1H), 6.50 (dd, J = 8.1, 1.5 Hz, 1H), 6.62 (t, J = 7.7 Hz, 1H), 7.05 (dd, J = 7.3, 1.5 Hz, 1H), 7.66-7.78 (m, 2H), 7.96-7.97 (m, 2H), 8.37 (d, J = 1.8 Hz, 1H), 10.69 (s, 1H). |

TABLE 32

| | Ex. No. | Chemical Compounds |
|---|---|---|
| 243 | 2-07 | |
| 244 | 2-08 | |
| 245 | 2-09 | |
| 246 | 2-10 | |

TABLE 32-continued

| 247 | 2-11 | 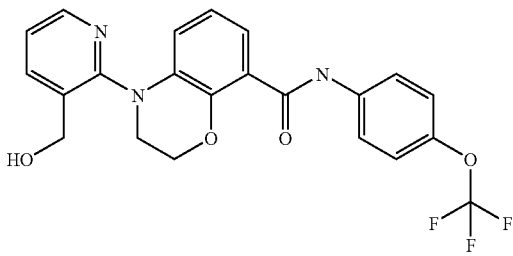 |
| 248 | 2-12 | 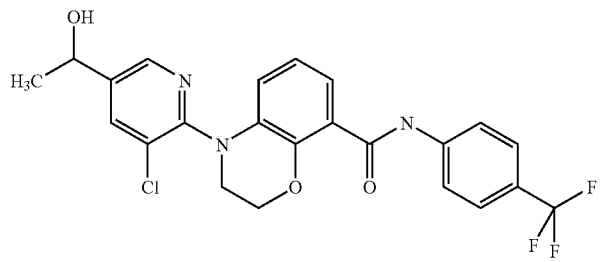 |
| 249 | 2-13 | 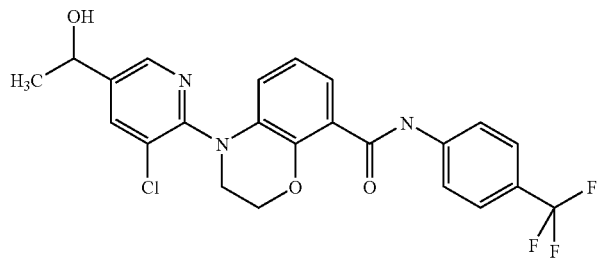 |

| | NMR |
|---|---|
| 243 | (300 MHz, DMSO-d6) 4.08 (t, J = 4.4 Hz, 2H), 4.39 (t, J = 4.2 Hz, 2H), 4.50 (t, J = 13.2 Hz, 2H), 6.98 (t, J = 7.9 Hz, 1H), 7.28 (dd, J = 7.7, 1.5 Hz, 1H), 7.36 (d, J = 8.8 Hz, 1H), 7.50 (dt, J = 8.1, 1.5 Hz, 1H), 7.71 (d, J = 8.8 Hz, 2H), 7.85 (dd, J = 8.8, 2.2 Hz, 1H), 7.96 (d, J = 8.4 Hz, 2H), 8.25 (d, J = 1.8 Hz, 1H), 10.53 (s, 1H). |
| 244 | (300 MHz, DMSO-d6) 0.98 (d, J = 6.6 Hz, 6H), 1.91-2.08 (m, 1H), 3.72 (d, J = 6.6 Hz, 2H), 4.03 (t, J = 2.9 Hz, 2H), 4.33 (t, J = 4.4 Hz, 2H), 4.45 (s, 2H), 6.87-6.95 (m, 3H), 7.18-7.23 (m, 2H), 7.44 (dd, J = 8.1, 1.5 Hz, 1H), 7.63 (m, 3H), 8.24 (d, J = 1.8 Hz, 1H), 9.97 (s, 1H). |
| 245 | (300 MHz, DMSO-d6) δ: 3.34 (s, 3H), 3.80 (t, J = 4.2 Hz, 2H), 4.43 (t, J = 4.0 Hz, 2H), 4.48 (s, 2H), 6.50-6.54 (m, 1H), 6.81 (t, J = 7.7 Hz, 1H), 7.07 (dd, J = 7.5, 1.3 Hz, 1H), 7.71 (d, J = 8.8 Hz, 2H), 7.97 (d, J = 8.4 Hz, 3H), 8.38 (d, J = 1.5 Hz, 1H), 10.51 (s, 1H). |
| 246 | (400 MHz, DMSO-d6) 4.06 (t, J = 4.4 Hz, 2H), 4.33 (t, J = 4.4 Hz, 2H), 4.49 (d, J = 5.1 Hz, 2H), 5.37 (t, J = 5.6 Hz, 1H), 6.86 (d, J = 5.1 Hz, 1H), 6.96 (t, J = 7.9 Hz, 1H), 7.21-7.23 (m, 2H), 7.50 (dd, J = 8.1, 1.6 Hz, 1H), 7.71 (d, J = 8.8 Hz, 2H), 7.96 (d, J = 8.8 Hz, 2H), 6.23 (d, J = 5.1 Hz, 1H). |
| 247 | (400 MHz, DMSO-d6) 3.71 (t, J = 4.4 Hz, 2H), 4.44-4.46 (m, 2H), 5.33 (t, J = 5.3 Hz, 1H), 6.26 (dd, J = 8.0, 1.8 Hz, 1H), 6.74 (t, J = 8.0 Hz, 1H), 6.98 (dd, J = 8.0, 1.6 Hz, 1H), 7.32-7.36 (m, 3H), 7.85 (d, J = 9.0 Hz, 2H), 8.00 (dd, J = 8.0, 2.0 Hz, 1H), 8.38 (dd, J = 4.8, 2.2 Hz, 1H), 10.3 (s, 1H). |
| 248 | (300 MHz, DMSO-d6) δ: 1.40 (d, J = 6.6 Hz, 3H), 3.77-3.78 (m, 2H), 4.41-4.44 (m, 2H), 4.82-4.84 (m, 1H), 5.43-5.46 (m, 1H), 6.47 (dd, J = 8.1, 1.5 Hz, 1H), 6.81 (t, J = 7.9 Hz, 1H), 7.05 (dd, J = 7.3, 1.5 Hz, 1H), 7.71 (d, J = 8.4 Hz, 2H), 7.96 (t, J = 3.1 Hz, 3H), 8.40 (d, J = 2.2 Hz, 1H), 10.51 (s, 1H). |
| 249 | (300 MHz, DMSO-d6) δ: 1.40 (d, J = 6.6 Hz, 3H), 3.76-3.80 (m, 2H), 4.41-4.44 (m, 2H), 4.80-4.84 (m, 1H), 5.43-5.47 (m, 1H), 6.47 (d, J = 8.4 Hz, 1H), 6.81 (t, J = 7.9 Hz, 1H), 7.05 (t, J = 3.9 Hz, 1H), 7.71 (d, J = 8.8 Hz, 2H), 7.96 (t, J = 2.9 Hz, 4H), 8.40 (d, J = 1.8 Hz, 1H), 10.51 (s, 1H). |

TABLE 33
| Ex. No. | | Chemical Compounds |
|---|---|---|
| 250 | 2-14 | 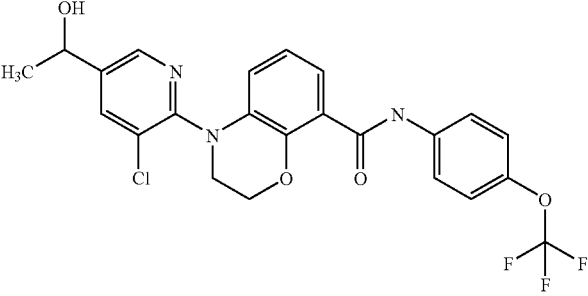 |
| 251 | 2-15 | 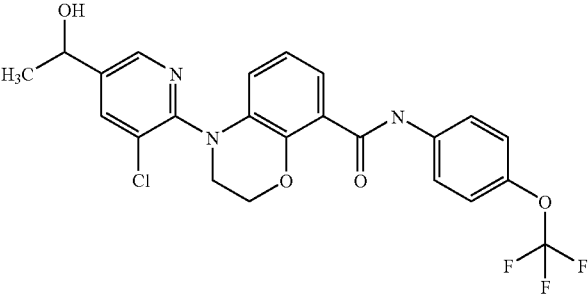 |
| 252 | 2-16 | 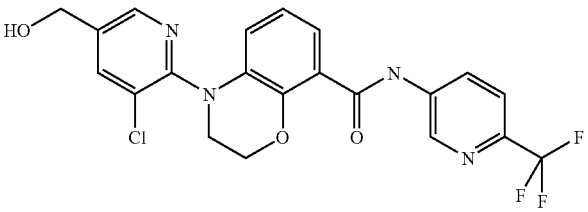 |
| 253 | 2-17 | 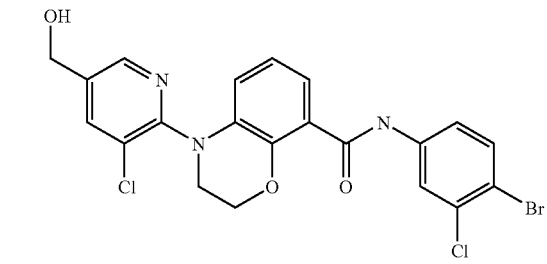 |
| 254 | 2-18 | 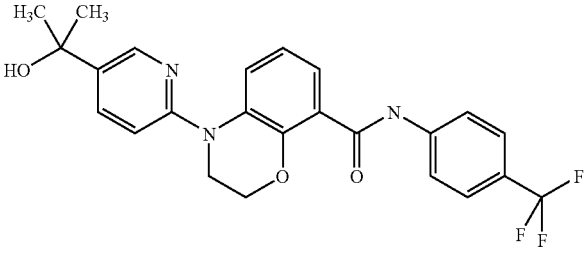 |
| 255 | 2-19 | 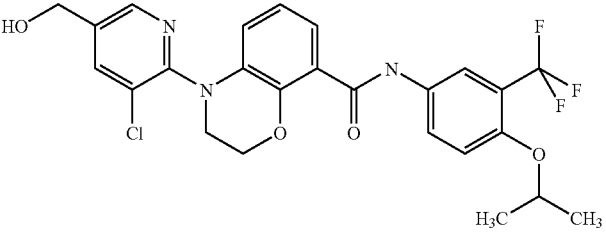 |

TABLE 33-continued

| 256 | 2-20 | 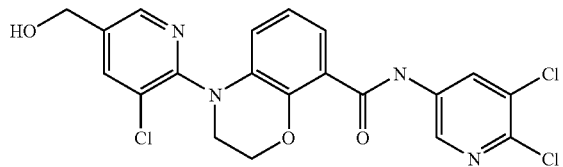 |

| NMR |
|---|
| 250 (400 MHz, DMSO-d6) 1.39 (d, J = 6.5 Hz, 3H), 3.77 (t, J = 4.4 Hz, 2H), 4.41 (t, J = 4.4 Hz, 2H), 4.79-4.85 (m, 1H), 5.44 (d, J = 4.4 Hz, 1H), 6.46 (dd, J =8.0, 1.4 Hz, 1H), 6.79 (t, J = 8.0 Hz, 1H), 7.03 (dd, J = 8.0, 1.4 Hz, 1H), 7.34 (d, J = 8.8 Hz, 2H), 7.85 (d, J = 8.8 Hz, 2H), 7.96 (d, J = 1.9 Hz, 1H), 8.39 (d, J = 1.9 Hz, 1H), 10.3 (s, 1H). |
| 251 (400 MHz, DMSO-d6) 1.39 (d, J = 6.5 Hz, 3H), 3.77 (t, J = 4.4 Hz, 2H), 4.41 (t, J = 4.4 Hz, 2H), 4.79-4.86 (m, 1H), 5.44 (d, J = 4.4 Hz, 1H), 6.46 (dd, J = 6.0, 1.5 Hz, 1H), 6.79 (t, J = 8.0 Hz, 1H), 7.03 (dd, J = 8.0, 1.5 Hz, 1H), 7.34 (d, J = 9.0 Hz, 2H), 7.85 (d, J = 9.0 Hz, 2H), 7.96 (d, J = 1.9 Hz, 1H), 8.39 (d, J = 1.9 Hz, 1H), 10.3 (s, 1H). |
| 252 (300 MHz, DMSO-d6) δ: 3.80 (t, J = 4.4 Hz, 2H), 4.45 (t, J = 4.4 Hz, 2H), 4.57 (d, J = 4.8 Hz, 2H). 5.43 (t, J = 5.3 Hz, 1H), 6.51 (dd, J = 8.1, 1.5 Hz, 1H), 6.83 (t, J = 7.9 Hz, 1H), 7.09 (dd, J = 7.3, 1.5 Hz, 1H), 7.93 (dd, J = 14.3, 7.2 Hz, 2H), 8.38 (d, J = 1.8 Hz, 1H), 8.47 (d, J = 8.8 Hz, 1H), 9.04 (d, J = 2.2 Hz, 1H), 10.73 (s, 1H). |
| 253 (400 MHz, DMSO-d6) 3.78(t, J=4.3 Hz, 2H), 4.43(t, J=4.3Hz, 2H), 4.57(d, J=5.1 Hz, 2H), 5.43(t, J=5.1 Hz, 1H), 6.48(dd, J=8.2, 1.5 Hz, 1H), 6.80(dd, J=8.2, 7.6 Hz, 1H), 7.05(dd, J=7.6, 1.5 Hz, 1H), 7.63(dd, J=8.6, 2.4 Hz, 1H), 7.73(d, J=8.6 Hz, 1H), 7.95(d, J=2.0 Hz, 1H), 8.14(d, J=2.4 Hz, 1H), 6.37(d, J=2.0 Hz, 1H), 10.43(s, 1H) |
| 254 (300 MHz, DMSO-d6) δ: 1.37 (s, 6H), 4.02 (t, J = 4.2 Hz, 2H), 4.33 (t, J = 4.2 Hz, 2H), 5.07 (s, 1H), 6.93 (t, J = 7.9 Hz, 1H), 7.15-7.20 (m, 2H), 7.48 (dd, J = 8.3, 1.7 Hz, 1H), 7.71-7.76 (m, 3H), 7.95 (d, J = 8.4 Hz, 2H), 8.40 (d, J = 1.8 Hz, 1H), 10.48 (s, 1H). |
| 255 (400 MHz, DMSO-d6) δ: 1.27 (d, J = 6.0 Hz, 6H), 3.77 (t, J = 3.9 Hz, 2H), 4.42 (t, J = 4.2 Hz, 2H), 4.55 (d, J = 4.6 Hz, 2H), 4.71-4.77 (m, 1H), 5.41-5.44 (s, 1H), 6.46 (dd, J = 7.9, 1.4 Hz, 1H), 6.79 (t, J = 7.9 Hz, 1H), 7.05 (dd, J = 7.4, 1.4 Hz, 1H), 7.29 (d, J = 9.3 Hz, 1H), 7.89 (d, J = 9.3 Hz, 1H), (s, 1H), 8.08 (s, 1H), 8.36 (s, 1H), 10.22 (s, 1H). |
| 256 (400 MHz, DMSO-d6) 3.79 (t, J = 4.4 Hz, 2H), 4.44 (t, J = 4.4 Hz, 2H), 4.56 (d, J = 5.1 Hz, 2H), 5.44 (t, J = 5.1 Hz, 1H), 6.51 (dd, J = 7.9, 1.6 Hz, 1H), 6.82 (t, J = 7.9 Hz, 1H), 7.09 (dd, J = 7.9, 1.6 Hz, 1H), 7.95 (d, J = 2.3 Hz, 1H), 8.37 (d, J = 1.9 Hz, 1H), 8.54 (d, J = 2.3 Hz, 1H), 8.73 (d, J = 2.3 Hz, 1H), 10.65 (s, 1H). |

TABLE 34

| Ex. No. | | Chemical Compounds |
|---|---|---|
| 257 | 2-21 | 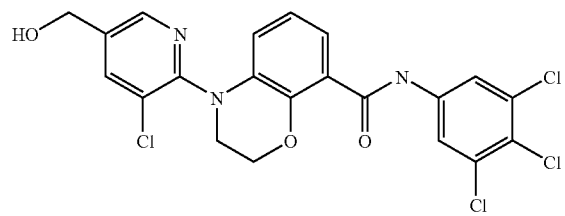 |
| 258 | 2-22 | 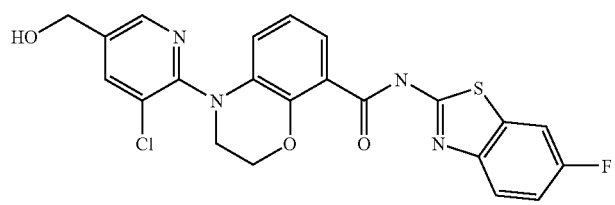 |

TABLE 34-continued
| 259 | 2-23 | 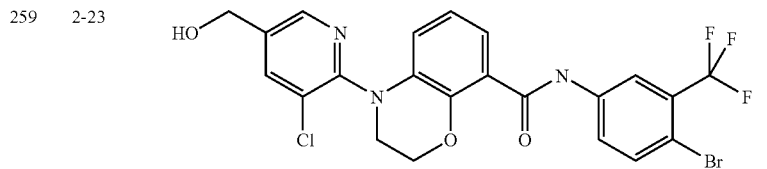 |
| 260 | 2-24 | 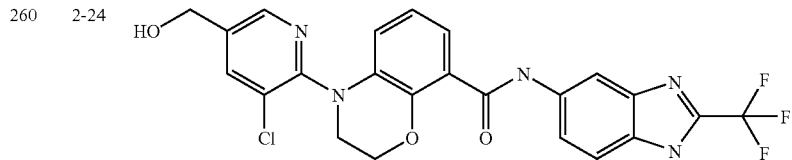 |
| 261 | 2-25 | 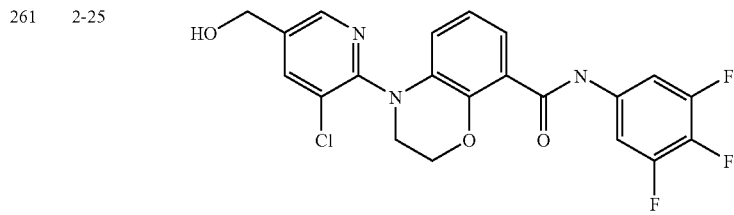 |
| 262 | 2-26 | 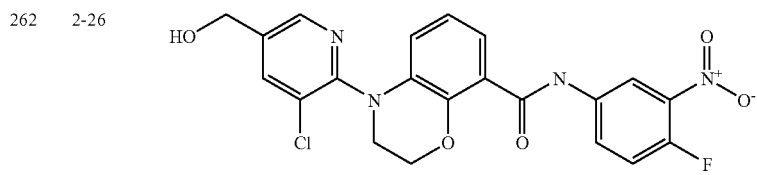 |
| 263 | 2-27 | 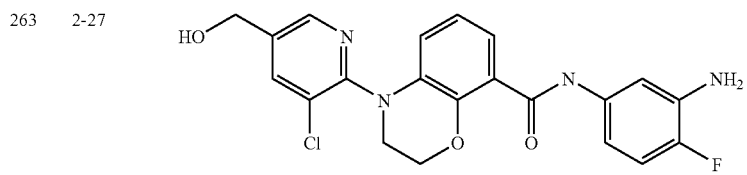 |
| 264 | 2-28 | 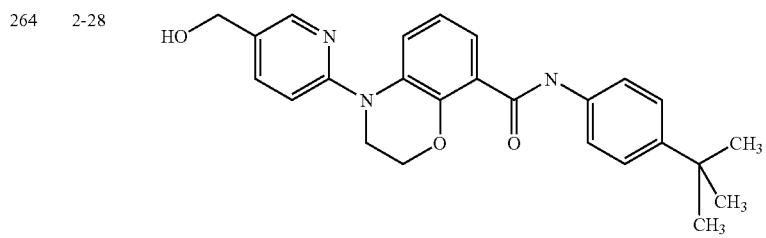 |
NMR
257 (400 MHz, DMSO-d6) 3.79 (t, J = 4.2 Hz, 2H), 4.44 (t, J = 4.2 Hz, 2H), 4.56 (d, J = 5.1 Hz, 2H), 5.43 (t, J = 5.1 Hz, 1H), 6.50 (dd, J = 7.9, 1.4 Hz, 1H), 6.82 (t, J = 7.9 Hz, 1H), 7.06 (dd, J = 7.9, 1.4 Hz, 1H), 7.95 (d, J = 1.9 Hz, 1H), 8.07 (s, 2H), 8.37 (d, J = 1.9 Hz, 1H), 10.53 (s, 1H).
258 (400 MHz, DMSO-d6) 3.81 (t, J = 3.7 Hz, 2H), 4.49 (t, J = 3.7 Hz, 2H), 4.57 (d, J = 5.6 Hz, 2H), 5.44 (t, J = 5.6 Hz, 1H), 6.56 (d, J = 7.9 Hz, 1H), 6.85 (t, J = 7.9 Hz, 1H), 7.19 (d, J = 7.9 Hz, 1H), 7.31 (t, J = 9.3 Hz, 1H), 7.77-7.79 (m, 1H), 7.93-7.96 (m, 2H), 8.38 (s, 1H), 12.18 (s, 1H).
259 (400 MHz, DMSO-d6) 3.79 (t, J = 3.9 Hz, 2H), 4.43 (t, J = 3.9 Hz, 2H), 4.57 (d, J = 5.6 Hz, 2H). 5.44 (t, J = 5.6 Hz, 1H), 6.49 (dd, J = 7.9, 1.4 Hz, 1H), 6.81 (t, J = 7.9 Hz, 1H), 7.06 (dd, J = 7.4, 1.4 Hz, 1H), 7.85 (d, J = 8.3 Hz, 1H), 7.95 (d, J = 7.4 Hz, 2H), 8.36 (d, J = 7.9 Hz, 2H), 10.57 (s, 1H).
260 (400 MHz, DMSO-d6) 3.80 (t, J = 4.2 Hz, 2H), 4.46 (t, J = 4.2 Hz, 2H), 4.58 (s, 2H), 5.45 (br s, 1H), 6.49 (dd, J = 7.9, 1.4 Hz, 1H), 6.82 (t, J = 7.9 Hz, 1H), 7.10 (dd, J = 7.4, 1.4 Hz, 1H), 7.59 (br s, 1H), 7.71 (d, J = 8.3 Hz, 1H), 7.96 (d, J =

TABLE 34-continued

|   | |
|---|---|
|   | 1.9 Hz, 1H), 8.38 (d, J = 1.9 Hz, 1H), 8.40 (br s, 1H), 10.35 (s, 1H), 13.82 (br s, 1 H). |
| 261 | (400 MHz, DMSO-d6) 3.78 (t, J = 4.4 Hz, 2H), 4.43 (t, J = 4.4 Hz, 2H), 4.56 (s, 2H), 5.43 (s, 1H). 6.49 (dd, J = 8.1, 1.6 H), 6.81 (t, J = 7.9 Hz, 1H), 7.04 (dd, J = 7.9, 1.4 Hz, 1H), 7.69 (dd, J = 10.7, 6.5 Hz, 2H), 7.95 (d, J = 1.4 Hz, 1H), 8.37 (d, J = 1.4 Hz, 1H), 10.49 (s, 1H). |
| 262 | (400 MHz, DMSO-d6) 3.79 (t, J = 4.2 Hz, 2H), 4.44 (t, J = 4.2 Hz, 2H), 4.57 (d, J = 4.2 Hz, 2H), 5.44 (t, J = 4.9 Hz, 1H), 6.50 (dd, J = 8.1, 1.2 Hz, 1H), 6.82 (t, J = 7.9 Hz, 1H), 7.07 (d, J = 6.5 Hz, 1H), 7.59 (dd, J = 11.1, 9.3 Hz, 1H), 7.96 (d, J = 1.9 Hz, 1H), 8.05-8.06 (m, 1H). 8.37 (d, J = 1.9 Hz, 1H), 8.70-8.71 (m, 1H), 10.61 (s, 1H). |
| 263 | (400 MHz, DMSO-d6) 3.78 (t, J = 4.4 Hz, 2H), 4.42 (t, J = 4.4 Hz, 2H), 4.56 (d, J = 5.6 Hz, 2H), 5.14 (s, 2H), 5.43 (t, J = 5.8 Hz, 1H), 6.45 (dd, J = 7.9, 1.4 Hz, 1H), 6.76-6.82 (m, 2H), 6.87-6.94 (m, 1H), 7.03 (dd, J = 7.4, 1.4 Hz, 1H), 7.31 (dd, J = 8.3, 2.8 Hz, 1H), 7.95 (d, J = 1.9 Hz, 1H), 8.36 (d, J = 1.9 Hz, 1H), 9.91 (s, 1H). |
| 264 | (300 MHz, DMSO-d6) 1.28 (s, 9H), 4.04 (t, J = 4.4 Hz, 2H), 4.33 (t, J = 4.4 Hz, 2H), 4.45 (d, J = 5.5 Hz, 2H), 5.16 (t, J = 5.7 Hz, 1H), 6.93 (t, J = 7.9 Hz, 1H), 7.16-7.22 (m, 2H), 7.34 (d, J = 8.4 Hz, 2H), 7.45 (dd, J = 8.1, 1.5 Hz, 1H), 7.64 (t, J = 4.4 Hz, 3H), 8.24 (d, J = 1.8 Hz, 1H), 10.05 (s, 1H). |

TABLE 35

| | Ex. No. | Chemical Compounds |
|---|---|---|
| 265 | 2-29 | |
| 266 | 2-30 | |
| 267 | 2-31 | |

TABLE 35-continued

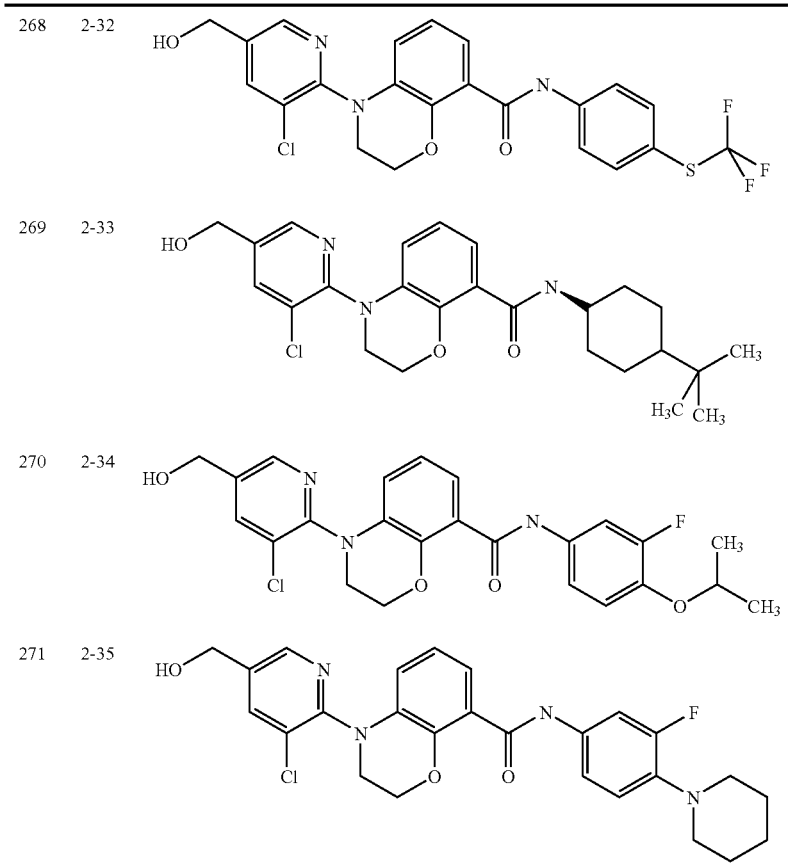

| | | |
|---|---|---|
| 268 | 2-32 | |
| 269 | 2-33 | |
| 270 | 2-34 | |
| 271 | 2-35 | |

| | NMR |
|---|---|
| 265 | (400 MHz, DMSO-d6) 3.78(t, J=4.4 Hz, 2H), 4.44(t, J=4.4 Hz, 2H), 4.56(d, J=5.6 Hz, 2H), 5.43(t, J=5.6 Hz, 1H), 6.50(dd, J=8.2, 1.4 Hz, 1H), 6.82(dd, J=8.2, 7.6 Hz, 1H), 7.09(dd, J=7.6, 1.4 Hz, 1H), 7.79(s, 1H), 7.95(d, J=2.1 Hz, 1H), 8.37(d, J=2.1 Hz, 1H)8.46(s, 2H), 10.78(s, 1H) |
| 266 | (400 MHz, DMSO-d6) 3.75(t, J=4.6 Hz, 2H), 4.40(t, J=4.6 Hz, 2H), 4.53(d, J=5.1 Hz, 2H), 4.80(q, J=8.8 Hz, 2H), 5.40(t, J=5.1 Hz, 1H), 6.44(dd, J =8.1, 1.4 Hz, 1H), 6.76(dd, J=8.1, 7.7 Hz, 1H), 7.03(dd, J=7.7, 1.4 Hz, 1H), 7.25(d, J=9.0 Hz, 1H), 7.63(dd, J=9.0, 2.6 Hz, 1H), 7.91-7.94(m, 2H), 8.34(d, J=2.1 Hz, 1H), 10.19(s, 1H) |
| 267 | (400 MHz,CHLOROFORM-d) 3.93(t, J=4.4 Hz, 2H), 4.80(q, J=8.8 Hz, 2H), 4.62(t, J=4.4 Hz, 2H), 4.75(s, 2H), 6.65(dd, J=8.1, 1.6 Hz, 1H), 6.89(dd, J=8.1, 7.9 Hz, 1H), 6.96(d, J=8.8 Hz, 2H), 7.64, (d, J=8.8 Hz, 2H), 7.80(dd, J=7.9, 1.6 Hz, 1H), 7.85(d, J=1.9 Hz, 1H), 9.34(d, J=1.9 Hz, 1H), 9.59(s, 1H) |
| 268 | (400 MHz, DMSO-d6) 3.75(t, J=4.4 Hz, 2H), 4.39(t, J=4.4 Hz, 2H), 4.52(d, J=4.6 Hz, 2H), 5.40(t, J=4.6 Hz, 1H), 6.45(dd, J=8.1, 1.7 Hz, 1H), 6.77(dd, J=8.1, 7.7 Hz, 1H), 7.01(dd, J=7.7, 1.7 Hz, 1H). 7.66(d, J=8.5 Hz, 1H), 7.88(d, J=8.5 Hz, 2H), 7.92(d, J=2.1 Hz, 1H), 8.34(d, J=2.1 Hz, 1H), 10.45(s, 1H) |
| 269 | (300 MHz, DMSO-d6) δ: 0.85 (s, 9H), 0.99-1.08 (m, 1H), 1.19-1.36 (m, 1H), 1.75-1.78 (m, 2H), 1.93-1.97 (m, 2H), 3.60-3.68 (m, 1H), 3.73-3.75 (m, 2H), 4.40 (t, J = 4.4 Hz, 2H), 4.55 (d, J = 5.5 Hz, 2H), 5.41 (t, J = 5.7 Hz, 1H), 6.40 (dd, J = 8.1, 1.5 Hz, 1H), 6.73 (t, J = 7.7 Hz, 1H), 7.08 (d, J = 7.7. 1.5 Hz, 1H), 7.88 (d, J = 8.1 Hz, 1H), 7.92 (d, J = 1.5 Hz, 1H), 8.34 (d, J = 1.5 Hz, 1H). |
| 270 | (300 MHz, DMSO-d6) δ: 1.27 (d, J = 5.9 Hz, 6H), 3.78 (t, J = 4.2 Hz, 2H), 4.43 (t, J = 4.2 Hz, 2H), 4.50-4.57 (m, 3H), 5.43 5.7 Hz, 1H), 6.46 (dd, J = 8.1. 1.5 Hz, 1H), 6.62-6.87 (m, 1H), 7.04 (dd, J = 7.5, 1.3 Hz, 1H), 7.14 (t, J = 9.2 Hz, 1H), 7.41 (d, J = 9.5 Hz, 1H), 7.73 (dd, J = 13.6, 2.2 Hz, 1H), 7.95 (d, J = 1.8 Hz, 1H), 8.37 (d, J = 1.8 Hz, 1H), 10.16 (s, 1H). |

TABLE 35-continued 271 (300 MHz, DMSO-d6) δ: 1.53-1.64 (m, 6H), 2.92 (t, J = 5.1 3.78 (t, J = 4.2 Hz, 4H), 4.43 (t, J = 4.4 Hz, 2H), 4.58 (d, J = 5.9 Hz, 2H), 5.42 (t, J = 5.7 Hz, 1H), 6.46 (dd, J = 8.1, 1.5 Hz, 1H), 6.79 (t, J = 7.9 Hz, 1H), 6.99-7.04 (m, 2H), 7.40 (dd, J = 8.6, 1.7 Hz, 1H), 7.65 (dd, J = 14.9, 2.4 Hz, 1H), 7.95 (d, J = 1.8 Hz, 1H), 8.38 (d J = 1.8 Hz, 1H), 10.12 (s, 1H).

TABLE 36

| Ex. No. | | Chemical Compounds |
|---|---|---|
| 272 | 2-36 | |
| 273 | 2-37 | |
| 274 | 2-38 | |
| 275 | 2-39 | |
| 276 | 2-40 | |
| 277 | 2-41 | |

TABLE 36-continued

| 278 | 2-42 | 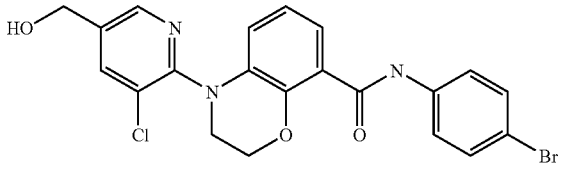 |
| 279 | 2-43 | 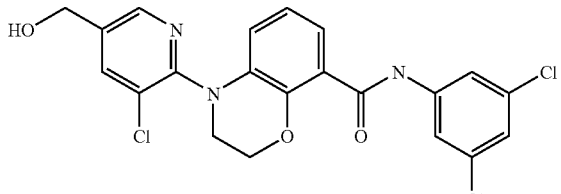 |

| | NMR |
|---|---|
| 272 | (300 MHz, DMSO-d6) 1.28 (s, 9H), 3.78 (t, J = 4.4 Hz, 2H), 4.43 (t, J = 4.4 Hz, 2H), 4.58 (d, J = 5.1 Hz, 2H), 5.42 (t, J = 5.7 Hz. 1H), 6.46 (dd, J = 8.1, 1.5 Hz, 1H), 6.79 (t, J = 7.9 Hz, 1H), 7.06 (dd, J = 7.7, 1.5 Hz, 1H), 7.35 (d, J = 8.8 Hz, 2H), 7.65 (d, J =8.4 Hz, 2H), 7.95 (d, J = 1.8 Hz, 1H), 8.37 (d, J = 1.8 Hz, 1H), 10.05 (s. 1H). |
| 273 | (400 MHz, DMSO-d6) 3.79 (t, J = 4.2 Hz, 2H), 4.43 (t, J = 4.2 Hz, 2H), 4.56 (d, J = 5.6 Hz, 2H), 5.43 (t, J = 5.6 Hz, 1H), 6.48 (dd, J = 7.9, 1.4 Hz, 1H), 6.81 (t, J = 7.9 Hz, 1H), 7.05 (dd, J = 7.9, 1.4 Hz, 1H), 7.64 (d, J = 8.8 Hz, 2H), 7.87 (d, J = 8.8 Hz, 2H), 7.95 (d, J = 1.9 Hz, 1H), 8.37 (d, J = 1.9 Hz, 1H), 8.62 (s, 1H), 10.37 (s, 1H). |
| 274 | (400 MHz, DMSO-d6) 3.78 (t, J = 4.4 Hz, 2H), 4.43 (t, J = 4.4 Hz, 2H), 4.56 (d, J = 5.6 Hz, 2H), 5.44 (t, J = 5.6 Hz, 1H), 6.48 (dd, J = 7.9, 1.4 Hz, 1H), 6.81 (t, J = 7.9 Hz, 1H), 7.05 (dd, J = 7.9, 1.4 Hz, 1H), 7.46 (d, J = 8.8 Hz, 1H), 7.61 (dd, J = 8.8, 2.3 Hz, 1H), 7.95-7.96 (m, 2H), 8.37 (d, J = 1.9 Hz, 1H), 10.47 (s, 1H). |
| 275 | (400 MHz, DMSO-d6) 0.98 (d, J = 7.0 Hz, 6H), 1.97-2.04 (m, 1H), 3.72 (d, J = 6.5 Hz, 2H), 3.78 (t, J = 4.4 Hz, 2H), 4.43 (t, J = 4.4 Hz, 2H), 4.56 (s, 2H), 6.45 (dd, J = 8.1, 1.6 Hz 1H), 6.78 (t, J = 7.9 Hz, 1H), 6.90 (d, J = 9.3 Hz, 2H), 7.06 (dd, J = 7.7, 1.6 Hz, 1H), 7.64 (d, J = 8.8 Hz, 2H), 7.95 (d, J = 2.3 Hz, 1H), 8.37 (d, J = 1.9 Hz, 1H), 9.99 (s, 1H). |
| 276 | (400 MHz, DMSO-d6) 3.78 (t, J = 4.2 Hz, 2H), 4.43 (t, J = 4.2 Hz, 2H), 4.56 (d, J = 5.1 Hz, 2H), 5.43 (t, J = 5.8 Hz, 1H), 6.48 (dd, J = 7.9, 1.4 Hz, 1H), 6.81 (t, J = 7.9 Hz, 1H), 7.05 (dd, J = 7.4, 1.4 Hz, 1H), 7.60 (d, J = 8.8 Hz, 1H), 7.70 (dd, J = 9.0, 2.6 Hz, 1H), 7.95 (d, J = 1.9 Hz, 1H), 8.14 (d, J = 2.3 Hz, 1H), 8.37 (d, J = 1.9 Hz, 1H), 10.43 (s, 1H). |
| 277 | (400 MHz, DMSO-d6) 3.78 (t, J = 4.2 Hz, 2H), 4.43 (t, J = 4.4 Hz, 2H), 4.56 (d, J = 5.1 Hz, 2H), 5.43 (t, J = 5.8 Hz, 1H), 6.48 (dd, J = 7.9, 1.4 Hz, 1H), 6.80 (t, J = 7.9 Hz, 1H), 7.04 (dd, J = 7.7, 1.6 Hz, 1H), 7.49 (dd, J = 8.8, 1.9 Hz, 1H), 7.66 (t, J = 8.3 Hz, 1H), 7.90 (dd, J = 11.8, 2.3 Hz, 1H), 7.95 (d, J = 1.9 Hz, 1H), 8.37 (d, J = 1.9 Hz, 1H), 10.47 (s, 1H). |
| 278 | (400 MHz, DMSO-d6) 3.78 (t, J = 4.4 Hz, 2H), 4.42 (t, J = 4.2 Hz, 2H), 4.56 (s, 2H), 5.42 (s, 1H), 6.47 (dd, J = 8.3, 1.4 Hz, 1H), 6.79 (t, J = 7.9 Hz, 1H), 7.04 (dd, J = 7.7, 1.6 Hz, 1H), 7.52 (dd, J = 7.0, 1.9 Hz, 2H), 7.73 (d, J = 8.8 Hz, 2H), 7.95 (d, J = 1.9 Hz, 1H), 8.37 (d, J = 1.9 Hz, 1H), 10.28 (s, 1H). |
| 279 | (400 MHz, DMSO-d6) 3.78 (t, J = 4.4 Hz, 2H), 4.43 (d, J = 4.2 Hz, 2H), 4.56 (d, J = 5.6 Hz, 2H), 5.43 (t, J = 5.8 Hz, 1H), 6.49 (dd, J = 8.3, 1.4 Hz, 1H), 6.81 (t, J = 7.7 Hz, 1H), 7.05 (dd, J = 7.9, 1.4 Hz, 1H), 7.31 (t, J = 1.9 Hz, 1H), 7.86 (d, J = 1.4 Hz, 2H), 7.97 (t, J = 5.8 Hz, 1H), 8.37 (d, J = 1.9 Hz, 1H), 10.47 (s, 1H). |

TABLE 37

| Ex. No. | | Chemical Compounds |
|---|---|---|
| 280 | 2-44 | |
| 281 | 2-45 | |
| 282 | 2-46 | |
| 283 | 2-47 | |
| 284 | 2-48 | |
| 285 | 3 | |
| 286 | 4-01 | |

TABLE 37-continued

| 287 | 4-02 | 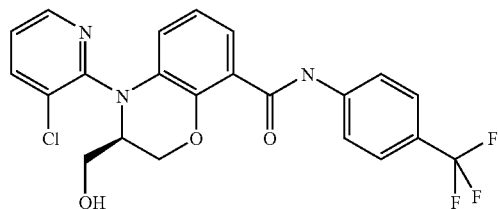 |
|---|---|---|

| NMR |
|---|
| 280 (400 MHz, DMSO-d6) 3.78 (t, J = 4.4 Hz, 2H), 4.43 (t, J = 4.4 Hz, 2H), 4.56 (d, J = 5.6 Hz, 2H), 5.43 (t, J = 5.6 Hz, 1H), 6.47 (dd, J = 8.1, 1.6 Hz, 1H), 6.80 (t, J = 7.9 Hz, 1H), (dd, J = 7.9, 1.4 Hz, 1H), 7.16 (t, J = 74.4 Hz, 1H), 7.17 (d, J = 8.8 Hz, 2H), 7.79 (d, J = 8.8 Hz, 2H), 7.95 (d, J = 1.9 Hz, 1H), 8.37 (d, J = 2.3 Hz, 1H), 10.22 (s, 1H). |
| 281 (300 MHz, DMSO-d6) 3.78 (t, J = 4.2 Hz, 2H), 4.43 (t, J = 4.2 Hz, 2H), 4.56 (d, J = 5.1 Hz, 2H), 5.42 (t, J = 5.7 Hz, 1H), 6.47 (dd, J = 8.1, 1.5 Hz, 1H), 6.80 (t, J = 7.9 Hz, 1H), 7.05 (dd, J = 7.7, 1.5 Hz, 1H), 7.39 (dt, J = 9.5, 2.6 Hz, 2H), 7.79 (d, J = 9.2 Hz, 2H), 7.95 (d, J = 2.2 Hz, 1H), 8.37 (d, J = 1.8 Hz, 1H), 10.28 (s, 1H). |
| 282 (300 MHz, DMSO-d6) 1.20 (d, J = 7.0 Hz, 6H), 2.82-2.91 (m, 1H), 3.78 (t, J = 4.2 Hz, 2H), 4.43 (t, J = 4.2 Hz, 2H), 4.56 (d, J = 5.1 Hz, 2H), 5.42 (t, J = 5.5 Hz, 1H), 6.46 (d, J = 8.1 Hz, 1H), 6.79 (t, J = 7.9 Hz, 1H), 7.06 (d, J = 7.7 Hz, 1H), 7.20 (d, J = 8.4 Hz, 2H), 7.65 (d, J = 8.4 Hz, 2H), 7.95 (d, J = 1.5 Hz, 1H), 8.37 (d, J = 1.1 Hz, 1H), 10.04 (s, 1H). |
| 283 (300 MHz, DMSO-d6) 3.78 (t, J = 4.0 Hz, 2H), 4.43 (t, J = 4.2 Hz, 2H), 4.56 (d, J = 5.1 Hz, 2H), 5.42 (t, J = 5.5 Hz, 1H), (dd, J = 8.1, 1.5 Hz, 1H), 6.80 (t, J = 7.9 Hz, 1H), 7.05-7.06 (m, 2H), 7.47 (t, J = 8.3 Hz, 1H), 7.67 (d, J = 7.3 Hz, 1H), 7.95 (d, J = 1.8 Hz, 2H), 8.37 (d, J = 1.8 Hz, 1H), 10.42 (s, 1H). |
| 284 (300 MHz, DMSO-d6) δ: 1.39 (d, J = 7.9 Hz, 3H), 3.78 (s, 2H), 4.41-4.42 (m, 2H), 4.82-4.84 (m, 1H), 6.46 (dd, J = 8.1, 1.5 Hz, 1H), 6.80 (t, J = 7.9 Hz, 1H), 7.04-7.05 (m, 1H), 7.35 (d, J = 8.8 Hz, 2H), 7.86 (d, J = 9.2 Hz, 2H), 7.97 (d, J = 1.5 Hz, 1H), 8.40 (d, J = 1.8 Hz, 1H), 10.33 (s, 1H). |
| 285 (400 MHz, DMSO-d6) δ: 5.04 (2H, s), 6.40-6.42 (1H, m), 7.04 (1H, dd, J = 7.9, 3.9 Hz), 7.32 (1H, dd, J = 7.9. 1.4 Hz), 7.38 (2H, d, J = 8.3 Hz), 7.71 (1H, q, J = 4.2 Hz), 7.86 (2H, dd, J = 12.3, 3.0 Hz), 8.32 (1H, dd, J = 7.9, 1.4 Hz), 8.69 (1H, dd, J = 4.6, 1.4 Hz), 10.51 (1H, s). |
| 286 (400 MHz, DMSO-d6) 3.50-3.55 (m, 1H), 3.69-3.77 (m, 1H), 3.96-4.00 (m, 1H), 4.17-4.19 (m, 1H), 4.60-4.67 (m, 1H), 5.08 (t, J = 5.3 Hz, 1H), 6.43 (dd, J = 8.9, 1.4 Hz, 1H), 6.81 (t, J = 7.9 Hz, 1H), 7.03 (dd, J = 7.9, 1.4 Hz, 1H), 7.33-7.40 (m, 3H), 7.88 (d, J = 8.8 Hz, 2H), 8.07 (dd, J = 7.9, 1.9 Hz, 1H), 8.47 (dd, J = 4.6, 1.4 Hz, 1H), 10.39 (s, 1H). |
| 287 (400 MHz, DMSO-d6) 3.50-3.55 (s, 1H), 3.70-3.77 (m, 1H), 3.95-4.01 (m, 1H), 4.16-4.20 (s, 1H), 4.60-4.66 (s, 1H), 5.08 (t, J = 5.3 Hz, 1H), 6.44 (dd, J = 7.9, 1.6 Hz, 1H), 6.82 (t, J = 7.9 Hz, 1H), 7.04 (dd, J = 7.9, 1.6 Hz, 1H), 7.37 (dd, J = 7.9, 4.6 Hz, 1H), 7.72 (d, J = 8.8 Hz, 2H), 7.98 (d, J = 8.8 Hz, 2H), 8.08 (dd, J = 7.9, 1.4 Hz, 1H), 8.47 (dd, J = 4.6, 1.4 Hz, 1H), 10.56 (s, 1H). |

TABLE 38

| Ex. No. | | Chemical Compounds |
|---|---|---|
| 288 | 4-03 | 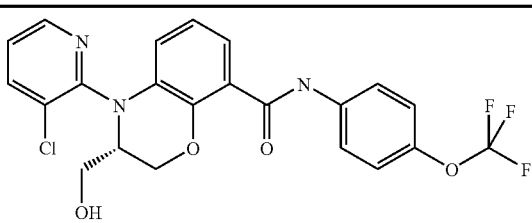 |

TABLE 38-continued
| 289 | 4-04 | 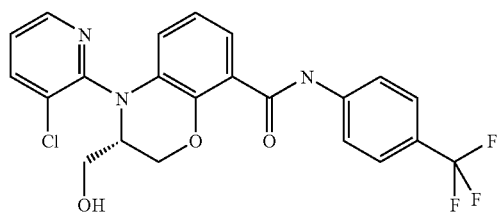 |
| 290 | 4-05 | 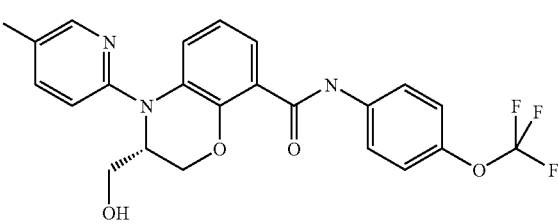 |
| 291 | 4-06 | 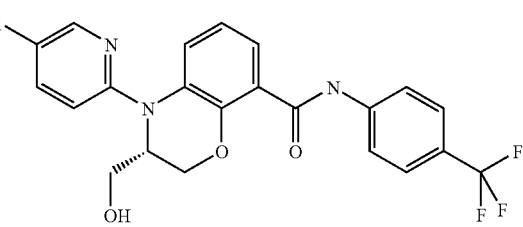 |
| 292 | 4-07 | 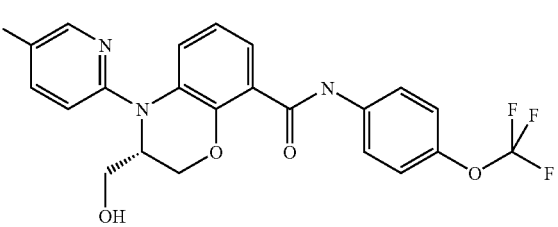 |
| 293 | 4-08 | 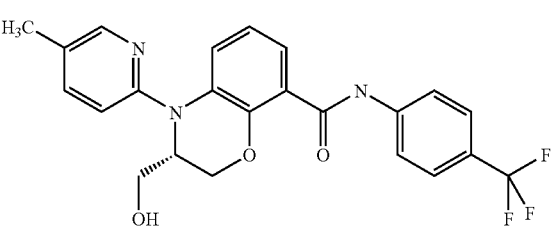 |
| 294 | 4-09 | 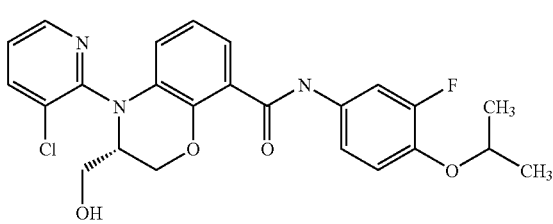 |
| | NMR |
|---|---|
| 288 | (400 MHz, DMSO-d6) 3.47-3.56 (m, 1H), 3.69-3.75 (m, 1H), 3.95-4.02 (m, 1H), 4.16-4.19 (m, 1H), 4.61-4.64 (m, 1H), 5.07 (t, J = 5.5 Hz, 1H), 6.42 (dd, J = 8.1, 1.5 Hz, 1H), 6.81 (t, J = 7.7 Hz, 1H), 7.03 (dd, J = 7.3, 1.5 Hz, 1H), 7.34-7.38 (m, 3H), 7.87 (d, J = 9.2 Hz, 2H), 8.07 (dd, J = 7.9, 1.7 Hz, 1H), 6.46 (dd, J = 4.6, 1.0 Hz, 1H), 10.37 (s, 1H). |
| 289 | (300 MHz, DMSO-d6) 3.49-3.54 (m, 1H), 3.71-3.75 (m, 1H), 3.95-4.00 (m, 1H), 4.17-4.20 (m, 1H), 4.60-4.64 (m, 1H), 5.07 (t, J = 5.3 Hz, 1H), 6.43 (dd, J = 6.1, 1.5 Hz, 1H), 6.82 (t, J = 7.9 Hz, 1H), 7.04 (dd, J = 7.5, 1.7 Hz, 1H), 7.36 (dd, J = |

TABLE 38-continued

| | |
|---|---|
| | 8.1, 4.8 Hz, 1H), 7.72 (d, J = 8.8 Hz, 2H), 7.97 (d, J = 8.1 Hz, 2H), 8.07 (dd, J = 7.9, 1.7 Hz, 1H), 8.46 (dd, J = 4.6, 1.7 Hz, 1H), 10.54 (s, 1H). |
| 290 | (400 MHz, DMSO-d6) 3.43-3.49 (m, 1H), 3.59-3.64 (m, 1H), 4.11 (dd, J = 11.1, 2.3 Hz, 1H), 4.48 (t, J = 7.0 Hz, 1H), 4.58 (d, J = 10.2 Hz, 1H), 5.14 (t, J = 5.6 Hz, 1H), 6.93 (I, J = 7.9 Hz 1H), 7.17 (dd, J = 7.4, 1.4 Hz, 1H), 7.31 (d, J = 8.8 Hz, 1H), 7.36 (d, J = 8.3 Hz, 2H), 7.44 (dd, J = 8.3, 1.4 Hz, 1H), 7.79 (dd, J = 9.0, 2.6 Hz, 1H), 7.65 (d, J = 9.3 Hz, 2H), 8.32 (d, J = 2.8 Hz, 1H), 10.38 (s, 1H). |
| 291 | (400 MHz, DMSO-d6) 3.42-3.50 (m, 1H), 3.59-3.65 (m, 1H), 4.12 (dd, J = 10.9, 2.6 Hz, 1H), 4.48 (t, J = 7.0 Hz, 1H), 4.58 (d, J = 10.7 Hz, 1H). 5.15 (t, J = 5.6 Hz, 1H), 6.93(t, J = 7.9 Hz, 1H), 7.18 (dd, J = 7.7, 1.6 Hz, 1H), 7.31 (d, J = 9.3 Hz, 1H), 7.45 (dd, J = 8.1, 1.6 Hz, 1H), 7.71 (d, J = 8.8 Hz, 2H), 7.79 (dd, J = 8.8, 2.8 Hz, 1H), 7.95 (d, J = 8.3 Hz, 2H), 8.33 (d, J = 2.8 Hz, 1H), 10.54 (s, 1H). |
| 292 | (400 MHz, DMSO-d6) 3.42-3.49 (m, 1H), 3.62-3.67 (m, 1H), 4.08 (dd, J = 11.1, 2.3 Hz, 1H), 4.40 (t, J = 7.2 Hz, 1H), 4.59 (d, J = 10.2 Hz, 1H), 5.14 (t, J = 5.6 Hz, 1H), 6.89 (t, J = 7.9 Hz 1H), 7.10 (dd, J = 7.9, 1.4 Hz, 1H), 7.21 (d, J = 8.3 Hz, 1H) 7.32-7.37 (m, 3H), 7.55 (dd, J = 8.8, 2.3 Hz, 1H), 7.86 (d, J = 9.3 Hz, 2H), 8.16 (d, J = 2.3 Hz, 1H), 10.37 (s, 1H). |
| 293 | (400 MHz, DMSO-d6) 3.42-3.49 (m, 1H), 3.62-3.67 (m, 1H), 4.09 (dd, J = 10.7, 2.3 Hz, 1H), 4.40 (t, J = 7.2 Hz, 1H), 4.58 (d, J = 10.7 Hz, 1H), 5.15 (t, J = 5.6 Hz, 1H), 6.90 (t, J = 7.9 Hz, 1H), 7.11 (dd, J = 7.4, 1.4 Hz, 1H), 7.21 (d, J = 8.3 Hz, 1H), 7.35 (dd, J = 8.3, 1.4 Hz, 1H), 7.56 (dd, J = 8.6, 2.6 Hz, 1H), 7.71 (d, J = 8.3 Hz, 2H), 7.96 (d, J = 8.3 Hz, 2H), 8.16 (d, J = 2.3 Hz, 1H), 10.54 (s, 1H). |
| 294 | (400 MHz, DMSO-d6) 1.27 (d, J = 6.0 Hz, 6H), 3.48-3.55 (m, 1H), 3.70-3.75 (m, 1H), 3.96-3.99 (m, 1H), 4.17 (dd, J = 10.7, 2.3 Hz, 1H), 4.50-4.59 (m, 1H), 4.63 (dd, J = 11.1, 1.9 Hz, 1H), 5.09 (t, J = 5.6 Hz, 1H), 6.41 (dd, J = 8.1, 1.6 Hz, 1H), 6.80 (t, J = 7.9 Hz, 1H), 7.02 (dd, J = 7.7, 1.6 Hz, 1H), 7.15 (t, J = 9.3 Hz, 1H), 7.36 (q, J = 4.2 Hz, 1H), 7.41-7.44 (m, 1H), 7.74 (dd, J = 13.7, 2.6 Hz, 1H), 8.07 (dd, J = 8.1, 1.6 Hz, 1H), 8.46 (dd, J = 4.6, 1.4 Hz, 1H), 10.21 (s, 1H). |

TABLE 39

| | Ex. No. | Chemical Compounds |
|---|---|---|
| 295 | 4-10 | |
| 296 | 4-11 | |
| 297 | 4-12 | |

TABLE 39-continued

| | | |
|---|---|---|
| 298 | 4-13 | 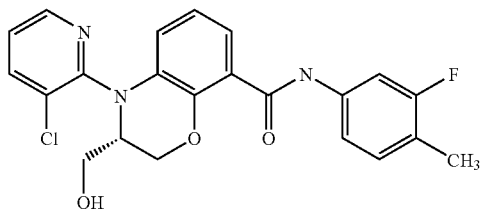 |
| 299 | 4-14 | 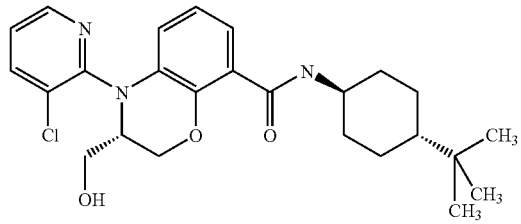 |
| 300 | 4-15 | 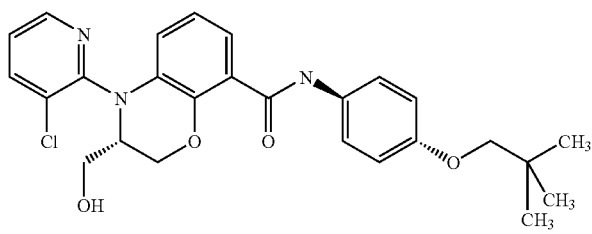 |
| 301 | 4-16 | 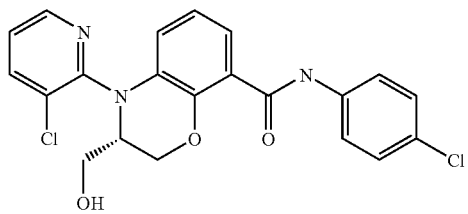 |

| | NMR |
|---|---|
| 295 | (400 MHz, DMSO-d6) 1.52-1.68 (m, 6H), 2.92 (t, J = 5.1 Hz, 4H), 3.51 (td, J = 10.3, 6.2 Hz, 1H), 3.70-3.75 (m, 1H), 3.95-3.99 (m, 1H), 4.17 (dd, J = 10.7, 2.3 Hz, 1H), 4.62 (dd, J = 10.7, 1.9 Hz, 1H), 5.09 (t, J = 5.6 Hz, 1H), 6.41 (dd, J = 7.9, 1.4 Hz, 1H), 6.80 (t, J = 7.9 Hz, 1H), 7.01 (dt, J = 11.3, 3.1 Hz, 2H), 7.36 (q, J = 4.2 Hz, 1H), 7.41 (dd, J = 8.6, 1.6 Hz, 1H), 7.66 (dd, J = 14.8, 2.8 Hz, 1H), 8.07 (dd, J = 8.1, 1.6 Hz, 1H), 8.45-8.47 (m, 1H), 10.15 (s, 1H). |
| 296 | (400 MHz, DMSO-d6) 3.47-3.55 (m, 1H), 3.70-3.76 (m, 1H), 3.96-4.00 (m, 1H), 4.15-4.20 (m, 1H), 4.63 (dd, J = 10.9, 1.6 Hz, 1H), 5.09 (t, J = 5.3 Hz, 1H), 6.44 (dd, J = 8.1, 1.6 Hz, 1H), 6.82 (t, J = 7.9 Hz, 1H), 7.03 (dd, J = 7.4, 1.4 Hz, 1H), 7.36 (q, J = 4.2 Hz, 1H), 7.58 (dd, J = 9.0, 1.2 Hz, 1H), 7.79 (dd, J = 8.8, 2.3 Hz, 1H), 8.08 (dd, J = 7.9, 1.9 Hz, 1H), 8.16 (d, J = 2.8 Hz, 1H), 8.46 (q, J = 2.2 Hz, 1H), 10.54 (s, 1H). |
| 297 | (400 MHz, DMSO-d6) 2.74 (s, 6H), 3.47-3.55 (m, 1H), 3.70-3.75 (m, 1H), 3.96-3.99 (m, 1H), 4.17 (dd, J = 10.9, 2.1 Hz, 1H), 4.63 (dd, J = 11.1, 1.9 Hz, 1H), 5.09 (t, J = 5.6 Hz, 1H), 6.41 (dd, J = 8.1, 1.6 Hz, 1H), 6.80 (t, J = 7.7 Hz, 1H), 6.96 (dd, J = 10.0, 9.0 Hz, 1H), 7.02 (dd, J = 7.4, 1.4 Hz, 1H), 7.36 (q, J = 4.2 Hz, 1H), 7.40 (dd, J = 8.8, 1.9 Hz, 1H), 7.66 (dd, J = 15.5, 2.6 Hz, 1H), 8.07 (dd, J = 8.1, 1.6 Hz, 1H), 8.46 (dd, J = 4.9, 1.6 Hz, 1H), 10.15 (s, 1H). |
| 298 | (400 MHz, DMSO-d6) 2.20 (s, 3H), 3.48-3.54 (m, 1H), 3.70-3.74 (m, 1H), 3.95-3.99 (m, 1H), 4.17 (dd, J = 10.7, 2.3 Hz, 1H), 4.62 (dd, J = 11.1, 1.9 Hz, 1H), 5.09 (t, J = 5.3 Hz, 1H), 6.42 (dd, J = 8.1, 1.6 Hz, 1H), 6.80 (t, J = 7.9 Hz, 1H), 7.02 (dd, J = 7.7, 1.6 Hz, 1H), 7.24 (t, J = 8.8 Hz, 1H), 7.36 (q, J = 4.2 Hz, 2H), 7.40 (dd, J = 8.1, 2.1 Hz, 2H), 7.70 (dd, J = 12.3, 2.1 Hz, 1H), 8.07 (dd, J = 7.9, 1.9 Hz, 1H), 8.46 (q, J = 2.2 Hz, 1H), 10.29 (s, 1H). |
| 299 | (400 MHz, DMSO-d6) 0.85 (a, 9H), 0.95-1.12 (m, 3H), 1.26 (q, J = 12.2 Hz, 2H), 1.77 (d, J = 10.7 Hz, 2H), 1.96 (dd, J = |

TABLE 39-continued

|  |  |
|---|---|
|  | 12.8, 3.0 Hz, 2H), 3.41-3.49 (m, 1H), 3.61-3.72 (m, 2H), 3.95-3.99 (m, 1H), 4.12 (dd, J = 10.9, 2.6 Hz, 1H), 4.61 (dd, J = 10.9, 1.6 Hz, 1H), 5.09 (dd, J = 6.0, 5.1 Hz, 1H), 6.34 (dd, J = 8.1, 1.6 Hz, 1H), 6.74 (t, J = 7.9 Hz, 1H), 7.04 (dd, J = 7.7, 1.6 Hz, 1H), 7.34 (q, J = 4.2 Hz, 1H), 7.93 (d, J = 7.9 Hz, 1H), 8.05 (dd, J = 7.9, 1.9 Hz, 1H), 8.44 (dd, J = 4.6, 1.4 Hz, 1H). |
| 300 | (400 MHz, DMSO-d6) 0.87 (s, 8H), 1.23-1.40 (m, 4H), 1.89-1.99 (m, 4H), 3.08 (s, 2H), 3.16-3.21 (m, 1H), 3.43-3.49 (m, 1H), 3.65-3.77 (m, 2H), 3.95-3.99 (m, 1H), 4.12 (dd, J = 11.1, 2.3 Hz. 1H), 4.61 (dd, J = 11.1, 1.9 Hz, 1H), 5.09 (t, J = 5.6 Hz, 1H), 6.35 (dd, J = 8.1, 1.6 Hz, 1H), 6.74 (t, J = 7.9 Hz, 1H), 7.04 (dd, J = 7.7, 1.6 Hz, 1H), 7.34 (td, J = 5.1, 2.6 Hz, 1H), 7.97 (d, J = 7.9 Hz, 1H), 8.05 (dd, J = 8.1, 1.6 Hz, 1H), 8.44 (dd, J = 4.6, 1.4 Hz, 1H). |
| 301 | (400 MHz, DMSO-d6) 3.48-3.55 (m, 1H), 3.70-3.75 (m, 1H), 3.96-3.99 (m, 1H), 4.17 (dd, J = 10.9, 2.1 Hz, 1H), 4.62 (dd, J = 10.9, 1.6 Hz, 1H), 5.09 (t, J = 5.6 Hz, 1H), 6.42 (dd, J = 8.3, 1.4 Hz, 1H), 6.81 (t, J = 7.9 Hz, 1H), 7.02 (dd, J = 7.4, 1.4 Hz, 1H), 7.36 (q, J = 4.2 Hz, 1H), 7.41 (dt, J = 9.6, 2.6 Hz, 2H), 7.80 (dd, J = 7.0, 1.9 Hz, 2H), 8.07 (dd, J = 7.9, 1.9 Hz, 1H), 8.46 (q, J = 2.2 Hz, 1H), 10.33 (s, 1H). |

TABLE 40

| Ex. No. | | Chemical Compounds | NMR |
|---|---|---|---|
| 302 | 4-17 |  | (400 MHz, DMSO-d6) 1.20 (d, J = 7.0 Hz, 6H), 2.83-2.90 1H), 3.48-3.55 (m, 1H), 3.70-3.75 (m, 1H), 3.95-4.00 (m, 1H), 4.18 (dd, J = 10.7, 2.3 Hz, 1H), 4.63 (dd, J = 10.7, 1.9 Hz, 1H), 5.09 (t, J = 5.6 Hz, 1H), 6.41 (dd, J = 8.1, 1.6 Hz, 1H), 6.80 (t, J = 7.9 Hz, 1H), 7.03 (dd, J = 7.7, 1.6 Hz, 1H), 7.21 (d, J = 8.8 Hz, 2H), 7.36 (q, J = 4.2 Hz, 1 H), 7.66 (d, J = 8.8 Hz, 2H), 8.07 (dd, J = 7.9, 1.4 Hz, 1H), 8.46 (dd, J = 4.6, 1.4 Hz, 1H), 10.10 (s, 1H). |
| 303 | 4-18 |  | (400 MHz, DMSO-d6) 3.48-3.54 (m, 1H), 3.70-3.76 (m, 1H), 3.96-4.00 (m, 1H), 4.17 (dd, J = 10.7. 2.3 Hz, 1H), 4.63 (dd, J = 10.9, 1.6 Hz, 1H), 5.09 (t, J = 5.6 Hz, 1H), 6.44 (dd, J = 8.1, 1.6 Hz, 1H), 6.82 (t, J = 7.9 Hz, 1H), 7.04 (dd, J = 7.4, 1.4 Hz, 1H), 7.36 (q, J = 4.2 Hz, 1H), 7.53 (t, J = 9.7 Hz, 1H), 8.01-8.05 (m, 1H), 8.07 (dd, J = 8.1, 1.6 Hz, 1H), 8.28 (dd, J = 6.5, 2.3 Hz, 1H), 8.46 (dd, J = 4.6, 1.4 Hz, 1H), 10.54 (s, 1H). |
| 304 | 4-19 |  | (400 MHz, DMSO-d6) 3.47-3.54 (m, 1H), 3.70-3.75 (m, 1H), 3.96-3.99 (m, 1H), 4.17 (dd, J = 10.7, 2.3 Hz, 1H), 4.63 (dd, J = 10.9, 1.6 Hz, 1H), 5.09 (dd, J = 6.0, 5.1 Hz, 1H), 6.43 (dd, J = 8.1, 1.6 Hz, 1H), 6.82 (t, J = 7.9 Hz, 1H), 7.03 (dd, J = 7.7, 1.6 Hz, 1H), 7.36 (q, J = 4.2 Hz, 1H), 7.64 (dd, J = 8.8, 2.3 Hz, 1H), 7.74 (d, J = 8.8 Hz, 1H), 8.07 (dd, J = 7.9, 1.4 Hz, 1H), 8.14 (d, J = 2.3 Hz, 1H), 8.46 (dd, J = 4.6, 1.4 Hz, 1H), 10.47 (s, 1H). |
| 305 | 4-20 |  | (400 MHz, DMSO-d6) 2.63 (s, 6H), 3.48-3.54 (m, 1H), 3.70-3.75 (m, 1H), 3.95-4.00 (m, 1H), 4.17 (dd, J = 10.9, 2.1 Hz, 1H), 4.62 (dd, J = 10.7, 1.9 Hz, 1H), 5.08 (t, J = 5.6 Hz, 1H), 6.42 (dd, J = 7.9, 1.4 Hz, 1H), 6.81 (t, J = 7.9 Hz, 1H), 7.03 (dd, J = 7.7, 1.6 Hz, 1H), 7.36 (q, J = 4.2 Hz, 1H), 7.57 (d, J = 8.8 Hz, 1H), 7.95 (dd, J = 8.8, 2.3 Hz, 1H), 8.07 (dd, J = 7.9, 1.4 Hz, 1H), 8.14 (d, J = 2.3 Hz, 1H), 8.46 (q, J = 2.2 Hz, 1H), 10.38 (s, 1H). |

TABLE 40-continued

| Ex. No. | | Chemical Compounds | NMR |
|---|---|---|---|
| 306 | 4-21 | | (400 MHz, DMSO-d6) 1.28 (d, J = 6.0 Hz, 6H), 3.48-3.55 (m, 1H), 3.70-3.75 (m, 1H), 3.96-4.00 (m, 1H), 4.17 (dd, J = 10.7, 2.3 Hz, 1H), 4.63 (dd, J = 11.1, 1.9 Hz, 1H), 4.72-4.78 (m, 1H), 5.09 (t, J = 5.6 Hz, 1H), 6.42 (dd, J = 7,9, 1.4 Hz, 1H), 6.81 (t, J = 7.9 Hz, 1H), 7.03 (dd, J = 7.7, 1.6 Hz, 1H), 7.31 (d, J = 8.8 Hz, 1H), 7.36 (q, J = 4.2 Hz, 1H), 7.90 (dd, J = 9.0, 2.6 Hz, 1H), 8.07 (dd, J = 7.9, 1.9 Hz, 1H), 8.10 (d, J = 2.3 Hz, 1H), 8.46 (q, J = 2.2 Hz, 1H), 10.25 (s, 1H). |
| 307 | 4-22 | | (400 MHz, DMSO-d6) 1.50-1.55 (m, 2H), 1.59-1.66 (m, 4H), 2.79 (t, J = 5.1 Hz, 4H), 3.48-3.55 (m, 1H), 3.70-3.75 (m, 1H), 3.95-4.00 (m, 1H), 4.17 (dd, J = 10.9, 2.1 Hz, 1H), 4.62 (dd, J = 10.9, 1.6 Hz, 1H), 5.08 (t, J = 5.3 Hz, 1H), 6.42 (dd, J = 8.1, 1.6 Hz, 1H), 6.81 (t, J = 7.7 Hz, 1H), 7.02 (dd, J = 7.9, 1.4 Hz, 1H), 7.36 (q, J = 4.2 Hz, 1H), 7.52 (d, J = 8.8 Hz, 1H), 7.95 (dd, J = 8.8, 2.3 Hz, 1H), 8.07 (dd, J = 7.9, 1.4 Hz, 1H), 8.14 (d, J = 2.3 Hz, 1H), 8.46 (dd, J = 4.6, 1.4 Hz, 1H), 10.38 (s, 1H). |
| 308 | 4-23 | | (400 MHz, DMSO-d6) 1.34 (t, J = 7.0 Hz, 3H), 3.48-3.54 (m, 1H), 3.70-3.75 (m, 1H), 3.96-3.99 (m, 1H), 4.08 (q, J = 7.0 Hz, 2H). 4.17 (dd, J = 10.7, 2.3 Hz, 1H), 4.63 (dd, J = 10.7, 1.9 Hz, 1H), 5.09 (t, J = 5.8 Hz, 1H), 6.41 (dd, J = 8.1, 1.6 Hz, 1H), 6.80 (t, J = 7.9 Hz, 1H), 7.02 (dd, J = 7.4, 1.4 Hz, 1H), 7.14 (t, J = 9.5 Hz, 1H), 7.36 (q, J = 4.2 Hz, 1H), 7.42-7.45 (m, 1H), 7.74 (dd, J = 13.7, 2.6 Hz, 1H), 8.07 (dd, J = 7.9, 1.4 Hz, 1H), 8.46 (q, J = 2.2 Hz, 1H), 10.20 (s, 1H). |

TABLE 41

| Ex. No. | | Chemical Compounds |
|---|---|---|
| 309 | 4-24 | |
| 310 | 4-25 | |
| 311 | 4-26 | |

TABLE 41-continued

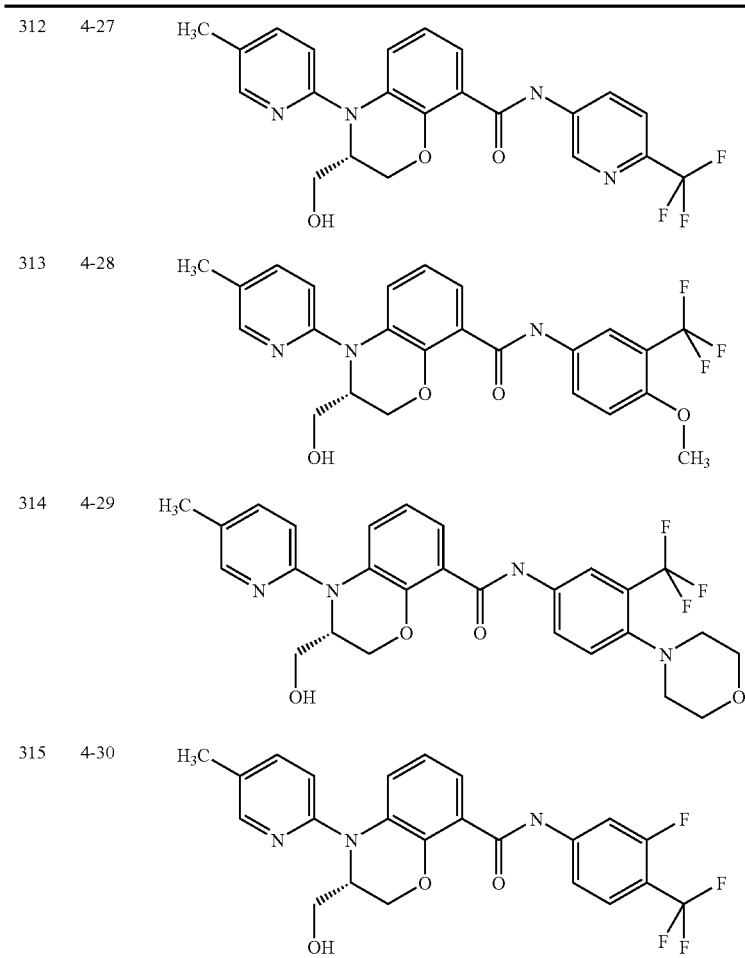

| | | NMR |
|---|---|---|
| | 309 | (400 MHz, DMSO-d6) 3.48-3.55 (m, 1H), 3.70-3.75 (m, 1H), 3.88 (s, 3H), 3.96-4.00 (m, 1H), 4.17 (dd, J = 10.7, 2.3 Hz. 1H), 4.63 (dd, J = 10.9, 1.6 Hz, 1H), 5.09 (t, J = 5.6 Hz, 1H), 6.42 (dd, J = 8.1, 1.6 Hz, 1H), 6.81 (t, J = 7.9 Hz, 1H), 7.04 (dd, J = 7.4, 1.4 Hz, 1H), 7.28 (d, J = 9.3 Hz, 1H), 7.36 (q, J = 4.2 Hz, 1H), 7.95 (dd, J = 9.0, 2.6 Hz, 1H), 8.07 (dd, J = 7.9, 1.4 Hz, 1H), 8.12 (d, J = 2.8 Hz, 1H), 8.46 (dd, J = 4.9, 1.6 Hz, 1H), 10.29 (s, 1H). |
| | 310 | (400 MHz, DMSO-d6) δ: 3.49-3.52 (m, 1H), 3.57-3.59 (m, 1H), 3.80.3.85 (m, 1H), 3.89 (s, 3H), 4.17 (d, J = 9.3 Hz, 1H), 4.56 (d, J = 8.8 Hz, 1H), 4.98 (t, J = 5.6 Hz, 1H), 6.24 (dd,J = 8.1, 1.6 Hz, 1H), 6.77 (t, J = 7.9 Hz, 1H), 6.93 (dd, J = 1.4 Hz, 1H), 7.70 (d, J = 8.8 Hz, 2H), 7.79 (d, J = 2.8 Hz, 1H), 7.96 (d, J = 8.3 Hz, 2H), 8.24 (d, J = 2.8 Hz, 1H), 10.53 (s, 1H). |
| | 311 | (400 MHz, DMSO-d6) δ: 3.48-3.50 (m, 1H), 3.58-3.59 (m, 1H), 3.78.3.81 (m, 1H), 3.89 (s, 3H), 4.16 (d, J = 8.8 Hz, 1H), 4.56 (d, J = 8.3 Hz, 1H), 4.97 (t, J = 5.6 Hz, 1H), 6.23 (dd, J = 8.1, 1.6 Hz, 1H), 6.76 (t, J = 7.9 Hz, 1H), 6.91 (dd, J = 7.7, 1.6 Hz, 1H), 7.34 (d, J = 8.8 Hz, 2H), 7.79 (d, J = 2.8 Hz, 1H). 7.85 (d, J = 9.3 Hz, 2H), 8.24 (d, J = 2.8 Hz, 1H), 10.36 (s, 1H). |
| | 312 | (400 MHz, DMSO-d6) δ: 2.24 (s, 3H), 3.43-3.45 (m, 1H), 3.57-3.78 (m, 1H), 4.08 (dd, J = 10.9, 2.6 Hz, 1H), 4.38 (t, J = 7.4 Hz, 1H), 4.58 (d, J = 10.2 Hz, 1H), 5.14 (t, J = 5.6 Hz, 1H), 6.90 (t, J = 7.9 Hz, 1H), 7.13 (dd, J = 7.7, 1.6 Hz, 1H), 7.21 (d, J = 8.3 Hz, 1H), 7.36 (dd, J = 8.1, 1.6 Hz, 1H), 7.55 (dd, J = 6.3, 1.9 Hz, 1H), 7.91 (d, J = 8.8 Hz, 1H), 8.15 (t, J = 1.2 Hz, 1H). 8.45 (d, J = 6.5 Hz, 1H), 9.02 (d, J = 2.3 Hz, 1H), 10.77 (s, 1H). |
| | 313 | (400 MHz, DMSO-d6) δ: 2.23 (s, 3H), 3.42-3.45 (m, 1H), 3.61-3.67 (m, 1H), 3.87 (s, 3H), 4.06 (dd, J = 10.9, 2.6 Hz, |

TABLE 41-continued

| | |
|---|---|
| | 1H), 4.39 (t, J = 7.4 Hz, 1H), 4.58 (d, J = 9.7 Hz, 1H), 5.14 (s, 1H), 6.88 (t, J = 7.9 Hz, 1H), 7.10 (dd, J = 7.7, 1.6 Hz, 1H), 7.20 (d, J = 8.3 Hz, 1H), 7.26 (d, J = 9.3 Hz, 1H), 7.32 (dd, J = 8.3, 1.4 Hz, 1H), 7.54 (dd, J = 9.0, 2.6 Hz, 1H), 7.92 (dd, J = 9.3, 2.3 Hz, 1H), 8.12 (dd, J = 21.6, 2.6 Hz, 2H), 10.29 (s, 1H). |
| 314 | (400 MHz. DMSO-d6) δ: 2.23 (s, 3H), 2.62 (t, J = 4.4 Hz, 4H), 3.41-3.45 (m, 1H), 3.59-3.65 (m, 1H), 3.69 (t, J = 4.4 Hz, 4H), 3.99-4.07 (m, 1H), 4.38 (t, J = 7.4 Hz, 1H), 4.56 (d, J = 10.2 Hz, 1H), 5.13 (t, J = 5.3 Hz, 1H), 6.88 (t, J = 7.9 Hz, 1H), 7.08 (dd, J = 7.7, 1.6 Hz, 1H), 7.20 (d, J = 8.3 Hz, 1H), 7.32 (dd, J = 8.1, 1.6 Hz. 1H), 7.55-7.58 (m, 2H), 7.94 (dd, J = 8.6, 2.6 Hz, 1H). 8.15 (d, J = 2.3 Hz, 2N), 10.40 (s, 1H). |
| 315 | (300 MHz, DMSO-d6) δ: 2.24 (s, 3H), 3.42-3.47 (m, 1H), 3.60-3.67 (m, 1H), 3.99-4.10 (m, 1H), 4.36-4.38 (m, 1H), 4.58 (d, J = 9.9 Hz, 1H), 5.13(t, J = 5.5 Hz, 1H), 6.90 (t, J = 7.9 Hz, 1H), 7.10 (dd, J = 7.7, 1.5 Hz, 1H), 7.21 (d, J = 8.4 Hz, 1H), 7.36 (dd, J = 8.3, 1.7 Hz, 1H), 7.56 (dd, J = 8.6, 2.4 Hz, 1H), 7.66 (d, J = 9.5 Hz, 1H), 7.76 (t, J = 8.4 Hz, 1H), 7.96 (d, J = 13.9 Hz, 1H), 8.16 (d, J = 2.2 Hz, 1H), 10.73 (s, 1H). |

TABLE 42

| | Ex. No. | Chemical Compounds |
|---|---|---|
| 316 | 4-31 |  |
| 317 | 4-32 |  |
| 318 | 4-33 |  |
| 319 | 4-34 |  |

TABLE 42-continued

| 320 | 4-35 | 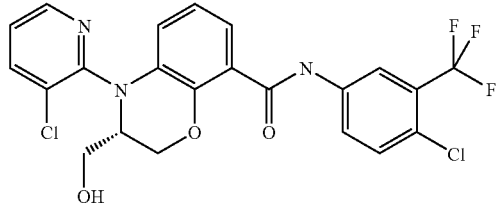 |
| 321 | 4-36 | 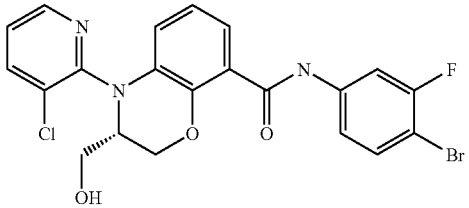 |
| 322 | 4-37 | 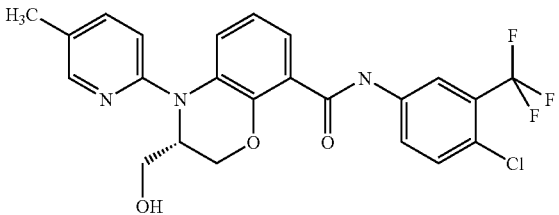 |

| | NMR |
|---|---|
| 316 | (300 MHz, DMSO-d6) δ: 2.25 (s, 3H), 3.44 (t, J = 9.9 Hz, 1H), 3.62-3.65 (m, 1H), 4.07409 (m, 1H), 4.39441 (m, 1H), 4.58 (d, J = 9.9 Hz, 1H), 6.90 (t, J = 7.9 Hz, 1H), 7.10 (dd, J = 7.3, 1.5 Hz, 1H), 7.21 (d, J = 8.4 Hz, 1H), 7.35 (dd, J = 8.1, 1.5 Hz, 1H), 7.56 (dd, J = 9.0, 1.3 Hz, 2H), 7.77 (dd, J = 9.0, 2.4 Hz, 1H), 8.15 (dd, J = 8.3, 2.4 Hz, 2H), 10.51 (s, 1H). |
| 317 | (300 MHz, DMSO-d6) δ: 2.24 (s, 3H), 3.44 (t, J = 9.9 Hz, 1H), 3.61-3.65 (m, 1H), 4.07 (d, J = 5.3 Hz, 1H), 4.39 (t, J = 6.8 Hz, 1H), 4.59 (d, J = 9.9 Hz, 1H), 6.89 (t, J = 7.9 Hz. 1H), 7.10 (dd, J = 7.7, 1.5 Hz, 1H), 7.21 (d, J = 8.4 Hz, 1H), 7.34 (dd, J = 8.1, 1.5 Hz, 1H), 7.54-7.71 (m, 3H), 8.14 (dd, J = 10.3, 2.2 Hz, 2H), 10.45 (s, 1H). |
| 318 | (400 MHz, DMSO-d6) 1.00 (d, J = 6.5 Hz, 6H), 2.00-2.09 (m, 1H), 3.48-3.55 (m, 1H), 3.70-3.75 (m, 1H), 3.87 (d, J = 6.0 Hz, 2H), 3.96-4.00 (m, 1H), 4.17 (dd, J = 10.7, 2.3 Hz, 1H), 4.63 (dd, J = 11.1, 1.9 Hz, 1H), 5.09 (t, J = 5.3 Hz, 1H), 6.42 (dd, J = 6.1, 1.6 Hz, 1H), 6.81 (t, J = 7.9 Hz, 1H), 7.04 (dd, J = 7.7, 1.6 Hz, 1H), 7.24 (d, J = 8.8 Hz, 1H), 7.36 (q, J = 4.2 Hz, 1H), 7.92 (dd, J = 8.8, 2.3 Hz, 1H), 8.07 (dd, J = 8.1, 1.6 Hz, 1H), 8.12 (d, J = 2.8 Hz, 1H), 8.46 (dd, J = 4.9, 1.6 Hz, 1H), 10.28 (s, 1H). |
| 319 | (400 MHz, DMSO-d6) 3.48-3.54 (m, 1H), 3.70-3.75 (m, 1H), 3.95-4.00 (m, 1H), 4.17 (dd, J = 10.7, 2.3 Hz, 1H), 4.63 (dd, 10.9, 1.6 Hz, 1H), 5.09 (t, J = 5.6 Hz, 1H), 6.43 (dd, J = 7.9, 1.4 Hz, 1H), 6.82 (t, J = 7.9 Hz, 1H), 7.03 (dd, J = 7.7, 1.6 Hz, 1H), 7.36 (q, J = 4.3 Hz, 1H), 7.61 (d, J = 8.8 Hz, 1H), 7.71 (dd, J = 8.8, 2.3 Hz, 1H), 8.07 (dd, J = 7.9, 1.4 Hz, 1H), 8.15 (d, J = 2.3 Hz, 1H), 8.46 (q, J = 2.2 Hz, 1H), 10.48 (s, 1H). |
| 320 | (400 MHz, DMSO-d6) 3.47-3.55 (m, 1H), 3.70-3.76 (m, 1H), 3.96-4.00 (m, 1H), 4.17 (dd, J = 10.7, 2.3 Hz, 1H), 4.62 (dd, J = 11.1, 1.9 Hz, 1H), 5.09 (t, J = 5.6 Hz, 1H), 6.44 (dd, J = 7.9, 1.4 Hz, 1H), 6.82 (t, J = 7.7 Hz, 1H), 7.03 (dd, J = 7.4, 1.4 Hz, 1H), 7.36 (q, J = 4.2 Hz, 1H). 7.71 (d, J = 8.8 Hz, 1H), 8.03 (dd, J = 8.8, 2.3 Hz, 1H), 8.08 (dd, J = 7.9, 1.9 Hz, 1H), 8.37 (d, J = 2.3 Hz, 1H), 8.46 (dd, J = 4.6, 1.4 Hz, 1H), 10.62 (s, 1H). |
| 321 | (400 MHz, DMSO-d6) 3.47-3.55 (m, 1H), 3.70-3.75 (m, 1H), 3.96-3.99 (m, 1H), 4.17 (dd, J = 10.7, 2.3 Hz, 1H), 4.62 (dd, J = 10.9, 1.6 Hz, 1H), 5.09 (t, J = 5.6 Hz, 1H), 6.43 (dd, J = 8.1, 1.6 Hz, 1H), 6.82 (t, J = 7.9 Hz, 1H), 7.02 (dd, J = 7.4, Hz, 1H), 7.36 (q, J = 4.2 Hz, 1H), 7.50 (dd, J = 8.8, 1.9 |

TABLE 42-continued

Hz, 1H), 7.67 (t, J = 8.3 Hz, 1H), 7.92 (dd, J = 11.6, 2.3 Hz, 1H), 8.07 (dd, J = 8.1, 1.6 Hz, 1H), 8.46 (dd, J = 4.6, 1.4 Hz, 1H), 10.52 (s, 1H).

322 (300 MHz, DMSO-d6) δ: 2.24 (s, 3H), 3.40-3.49 (m, 1H), 3.60-3.67 (m, 1H), 4.05-4.09 (m, 1H), 4.39 (t, J = 7.2 Hz, 1H), 4.58 (d, J = 10.3 Hz, 1H), 5.13 (t, J = 5.5 Hz, 1H), 6.90 (t, J = 7.9 Hz, 1H), 7.11 (dd, J = 7.7, 1.5 Hz, 1H), 7.21 (d, J = 8.4 Hz, 1H), 7.35 (dd, J = 8.1, 1.5 Hz. 1H), 7.56 (dd, J = 8.4, 2.2 Hz, 1H), 7.71 (d, J = 8.8 Hz, 1H), 8.00 (dd, J = 8.6, 2.4 Hz, 1H), 8.16 (d, J = 2.2 Hz, 1H), 8.35 (d, J = 2.6 Hz, 1H), 10.60 (s, 1H).

TABLE 43

| Ex No. | | Chemical Compounds |
|---|---|---|
| 323 | 4-38 | |
| 324 | 4-39 | |
| 325 | 4-40 | |
| 326 | 4-41 | |
| 327 | 4-42 | |

TABLE 43-continued

| 328 | 4-43 | 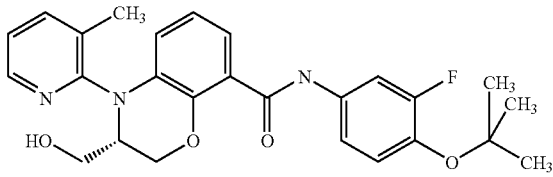 |
|---|---|---|
| 329 | 4-44 | 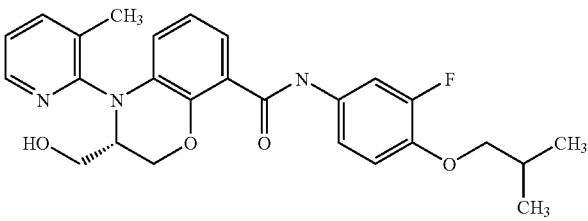 |

| | NMR |
|---|---|
| 323 | (300 MHz, DMSO-d6) δ: 1.28 (d, J = 3.1 Hz, 6H), 2.24 (s, 3H), 3.45 (t, J = 10.3 Hz, 1H), 3.62-3.65 (m, 1H), 4.07 (d, J = 10.3 Hz, 1H), 4.38-4.41 (m, 1H), 4.59 (d, J = 10.6 Hz, 1H), 4.74-4.76 (m, 1H), 6.88 (t, J = 7.3 Hz, 1H), 7.11 (d, J = 7.7 Hz, 1H), 7.21 (d, J = 8.1 Hz, 1H), 7.31 (t, J = 8.4 Hz, 2H), 7.55 (d, J = 8.4 Hz, 1H), 7.88 (d, J = 9.2 Hz, 1H), 8.12 (d, J = Hz, 2H), 10.25 (s, 1H). |
| 324 | (400 MHz, DMSO-d6) 2.84 (t, J = 4.4 Hz, 4H), 3.48-3.54 (m, 1H), 3.68-3.75 (m, 5H), 3.95-4.00 (m, 1H), 4.17 (dd, J = 10.9. 2.1 Hz, 1H), 4.62 (dd, J = 10.7, 1.9 Hz, 1H), 5.08 (t, J = 5.3 Hz, 1H), 6.43 (dd, J = 8.1, 1.6 Hz, 1H), 6.81 (t, J = 7.9 Hz, 1H), 7.02 (dd, J = 7.4. 1.4 Hz, 1H), 7.36 (q, J = 4.2 Hz, 1H), 7.60 (d, J = 8.8 Hz, 1H), 7.98 (dd, J = 8.8, 2.3 Hz, 1H), 8.07 (dd, J = 7.9, 1.4 Hz, 1H), 8.18 (d, J = 2.8 Hz, 1H), 8.46 (dd, J = 4.6, 1.4 Hz, 1H), 10.42 (s, 1H). |
| 325 | (300 MHz, DMSO-d6) δ: 2.25 (s, 3H), 3.44-3.49 (m, 1H), 3.65-3.67 (m, 1H), 4.29-4.31 (m, 1H), 4.45-4.48 (m, 1H), 4.82 (d, J = 10.3 Hz, 1H), 5.19 (t, J = 5.3 Hz, 1H), 6.99 (t, J = 7.9 Hz, 1H), 7.22 (d, J = 8.4 Hz, 1H), 7.44 (dd, J = 8.1, 1.5 Hz, 1H), 7.55-7.62 (m, 2H), 7.80 (d, J = 8.8 Hz, 1H), 8.01 (d, J = 18 Hz, 1H), 8.17 (d, J = 2.2 Hz, 1H), 8.72 (d, J = 8.8 Hz, 1H), 10.77 (s, 1H). |
| 326 | (300 MHz,DMSO-d6) 2.16 (s, 3H), 3.37 (br s, 1H), 3.50 (t, J = 9.7 Hz, 1H), 3.65 (br s, 1H), 3.96 (d, J = 2.9 Hz, 1H), 4.24 (dd, J = 10.6, 2.2 Hz, 1H), 4.60 (dd, J = 11.0, 2.2 Hz, 1H), 6.18 (dd, J = 8.1, 1.5 Hz, 1H), 6.78 (t, J = 7.9 Hz, 1H), 6.95 (dd, J = 7.7, 1.5 Hz, 1H), 7.29 (dd, J = 7.7, 4.8 Hz, 1H), 7.36 (d, J = 8.4 Hz, 2H), 7.79 (dd, J = 7.7, 1.1 Hz, 1H), 7.87 (d, J = 8.8 Hz, 2H), 8.38 (dd, J = 4.6, 1.7 Hz, 1H), 10.35 (s, 1H). |
| 327 | (300 MHz, DMSO-d6) 2.16 (s, 3H), 3.50 (t, J = 9.7 Hz, 1H), 3.65 (s, 1H), 3.96 (d, J = 2.9 Hz, 1H), 4.24 (dd, J = 10.6, 2.2 Hz, 1H), 4.60 (dd, J = 11.0, 2.2 Hz, 1H), 6.18 (dd, J = 8.1, 1.5 Hz, 1H), 6.78 (t, J = 7.9 Hz, 1H), 6.95 (dd, J = 7.7, 1.5 Hz 1H), 7.29 (dd, J = 7.7, 4.8 Hz, 1H), 7.36 (d, J = 8.4 Hz, 2H), 7.79 (dd, J = 7.7, 1.1 Hz, 1H), 7.57 (d, J = 8.8 Hz, 2H), 8.38 (dd, J = 4.6, 1.7 Hz, 1H), 10.35 (s, 1H). |
| 328 | (400 MHz, DMSO-d6) 1.30 (s, 9H), 3.47-3.55 (m, 1H), 3.69-3.75 (m, 1H), 3.95-4.00 (m, 1H), 4.16 (dd, J = 10.7, 2.3 Hz, 1H), 4.62 (dd, J = 10.7, 1.9 Hz, 1H), 5.08 (t, J = 5.3 Hz, 1H), 6.42 (dd, J = 8.3, 1.4 Hz, 1H), 6.80 (t, J = 7.9 Hz, 1H), 7.01 (dd, J = 7.7, 1.6 Hz, 1H), 7.12 (t, J = 9.0 Hz, 1H), 7.36 (q, J = 4.2 Hz, 1H), 7.41 (dt, J = 8.8, 1.2 Hz, 1H), 7.77 (dd, J = 13.0, 2.8 Hz, 1H), 8.07 (dd, J = 7.9, 1.9 Hz, 1H), 8.46 (dd, J = 4.6, 1.4 Hz, 1H), 10.30 (s, 1H). |
| 329 | (400 MHz, DMSO-d6) 0.99 (d, J = 6.5 Hz, 6H), 1.98-2.08 (m, 1H), 3.47-3.55 (m, 1H), 3.70-3.75 (m, 1H), 3.80 (d, J = 6.5 Hz, 2H), 3.98-3.99 (m, 1H), 4.17 (dd, J = 10.7, 2.3 Hz, 1H), 4.63 (dd, J = 10.7, 1.9 Hz, 1H), 5.09 (t, J = 5.6 Hz, 1H), 6.41 (dd, J = 7.9, 1.4 Hz, 1H), 6.80 (t, J = 7.9 Hz, 1H), 7.02 J = 7.7, 1.6 Hz, 1H), 7.14 (t, J = 9.3 Hz, 1H), 7.36 (q, J = 4.2 Hz, 1H), 7.44 (dd, J = 8.8, 1.4 Hz, 1H), 7.74 (dd, J = 13.7, 2.6 Hz, 1H), 8.07 (dd, J = 7.9, 1.4 Hz, 1H), 8.46 (dd, J = 4.6, 1.4 Hz, 1H), 10.20 (s, 1H). |

TABLE 44
| Ex. No. | | Chemical Compounds |
|---|---|---|
| 330 | 4-45 | 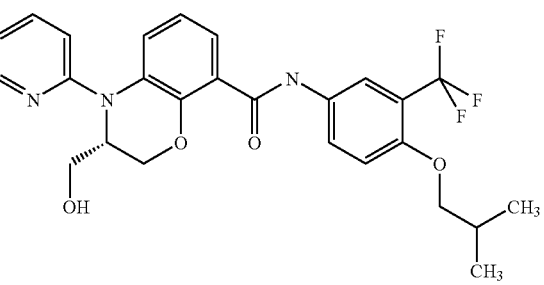 |
| 331 | 4-46 | 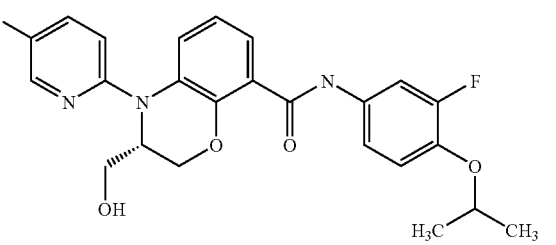 |
| 332 | 4-47 | 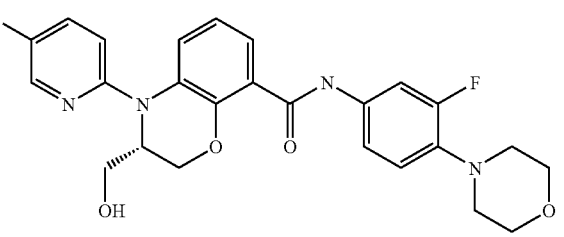 |
| 333 | 4-48 | 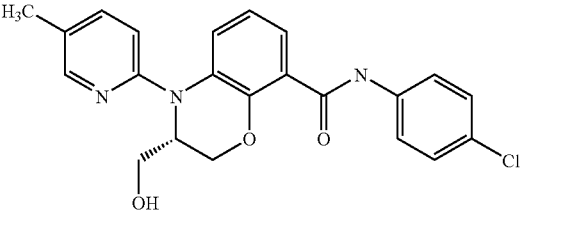 |
| 334 | 4-49 | 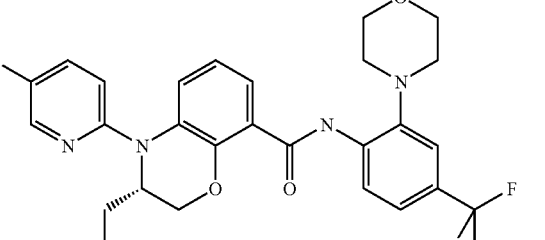 |
| 335 | 4-50 | 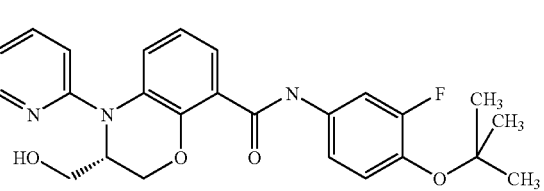 |

TABLE 44-continued

| 336 | 4-51 | 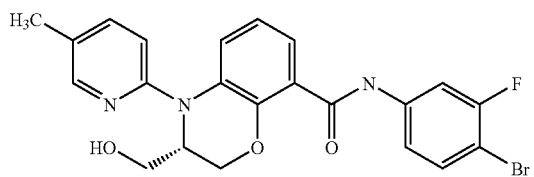 |

| NMR |
|---|

330 (300 MHz, DMSO-d6) δ: 1.00 (d, J = 7.0 Hz, 6H), 2.00-2.09 (m, 1H), 2.24 (s, 3H), 3.45 (t, J = 9.9 Hz, 1H), 361-3.65 (m, 1H), 3.87 (d, J = 6.2 Hz, 2H), 4.07 (dd, J = 11.0, 2.2 Hz, 1H), 4.40 (t, J = 7.2 Hz, 1H), 4.59 (d, J = 10.6 Hz, 1H), 6.88 (t, J = 7.9 Hz, 1H), 7.12 (dd, J = 7.3, 1.5 Hz, 1H), 7.22 (t, J = 8.1 Hz, 2H), 7.33 (dd, J = 8.4, 1.5 Hz, 1H), 7.56 (dd, J = 8.4, 2.2 Hz, 1H), 7.89 (dd, J = 9.0, 2.4 Hz, 1H), 8.13 (dd, J = 19.4, 2.2 Hz, 2H), 10.25 (s, 1H).

331 (300 MHz, DMSO-d6) δ: 1.27 (d, J = 5.9 Hz, 6H), 2.24 (s, 3H), 3.42-3.46 (m, 1H), 3.60-3.64 (m, 1H), 4.06 (d, J = 8.4 Hz, 1H), 4.38-4.41 (m, 1H), 4.53-4.58 (m, 2H), 5.11-5.14 (m, 1H), 6.88 (t, J = 7.9 Hz, 1H), 7.12-7.17 (m, 4H), 7.32-7.38 (m, 2H), 7.55 (dd, J = 8.4, 2.2 Hz, 1H), 7.72 (dd, J = 13.8, 2.4 Hz, 1H), 8.16 (s, 1H), 10.18 (s, 1H).

332 (300 MHz, DMSO-d6) δ: 2.24 (s, 3H), 2.96 (t, J = 4.8 Hz, 4H), 3.43-3.47 (m, 1H), 3.63 (s, 1H), 3.74 (t, J = 4.6 Hz, 4H), 4.06 (dd, J = 10.5, 2.4 Hz, 1H), 4.37-4.39 (m, 1H), 4.58 (d, J = 9.9 Hz, 1H), 5.11-5.15 (m, 1H), 6.88 (t, J = 7.7 Hz, 1H), 6.99-7.11 (m, 2H), 7.20 (d, J = 8.4 Hz, 1H), 7.32 (dd, J = 8.11, 1.5 Hz, 1H). 7.41 (dd, J = 8.6, 1.7 Hz, 1H), 7.55 (dd J = 8.4, 2.2 Hz, 1H), 7.68 (dd, J = 15.0, 2.6 Hz, 1H), 8.16 (d, J = 2.2 Hz, 1H), 10.18 (s, 1H).

333 (300 MHz, DMSO-d6) δ: 2.24 (s, 3H), 3.45-3.47 (m, 1H), 3.63-3.64 (m, 1H), 4.06 (d, J = 8.4 Hz, 1H), 4.37-4.41 (m, 1H), 4.58 (d, J = 10.6 Hz, 1H), 5.13 (t, J = 5.5 Hz, 1H), 6.88 (t, J = 7.9 Hz, 1H), 7.09 (dd, J = 7.7, 1.5 Hz, 1H), 7.20 (d, J = 8.4 Hz, 1H), 7.34-7.38 (m, 3H), 7.55 (dd, J = 9.0, 2.4 Hz, 1H), 7.77 (d, J = 8.8 Hz, 2H), 8.16 (d, J = 2.2 Hz, 1H), 10.30 (s, 1H).

334 (300 MHz, DMSO-d6) δ: 2.25 (s, 3H), 2.90-2.91 (m, 4H), 3.42-3.51 (m, 1H), 3.67-3.74 (m, 1H), 3.81 (t, J = 4.4 Hz, 4H), 4.29 (t, J = 5.3 Hz, 1H), 4.50-4.52 (m, 1H), 4.87 (d J = 10.3 Hz, 1H), 5.18 (t, J = 5.1 Hz, 1H), 6.98 (t, J = 8.1 Hz, 1H), 7.23 (d, J = 8.4 Hz, 1H), 7.41 (dd, J = 8.1, 1.5 Hz, 1H), 7.55-7.62 (m, 4H), 8.18 (d, J = 1.8 Hz, 1H), 8.64 (d, J = 8.4 Hz, 1H), 10.57 (s, 1H).

335 (400 MHz, DMSO-d6) 1.29 (s, 9H), 2.24 (s, 3H), 3.41-3.47 (m, 1H), 3.60-3.65 (m, 1H), 4.06 (dd, J = 10.9, 2.6 Hz, 1H), 4.39 (t, J = 7.0 Hz, 1H), 4.58 (dd, J = 10.9, 1.2 Hz, 1H), 5.14 (t, J = 5.3 Hz, 1H), 6.88 (t, J = 7.9 Hz, 1H), 7.06-7.14 (m, 2H), 7.21 (d, J = 8.3 Hz, 1H), 7.32 (dd, J = 8.1, 1.6 Hz, 1H), 7.38 (dd, J = 8.8, 1.4 Hz, 1H), 7.55 (dd, J = 8.8, 2.3 Hz, 1H), 7.75 (dd, J = 13.2, 2.6 Hz, 1H), 8.16 (d, J = 2.3 Hz, 1H), 10.28 (s, 1H).

336 (400 MHz, DMSO-d6) 2.24 (s, 3H), 3.40-3.47 (m, 1H), 3.60-3.65 (m, 1H), 4.06 (dd, J = 10.9, 2.6 Hz, 1H), 4.38 (t, J = 7.0 Hz, 1H), 4.58 (dd, J = 11.1, 0.9 Hz, 1H), 5.15 (t, J = 5.6 Hz, 1H), 6.89 (t, J = 7.9 Hz, 1H), 7.09 (dd, J = 7.4, 1.4 Hz, 1H), 7.20 (d, J = 8.3 Hz, 1H), 7.34 (dd, J = 8.1, 1.6 Hz, 1H), 7.47 (dd, J = 8.8, 1.9 Hz, 1H), 7.55 (dd, J = 8.3, 1.9 Hz, 1H), 7.66 (t, J = 8.3 Hz, 1H), 7.90 (dd, J = 11.1, 2.3 Hz, 1H), 8.16 (d, J = 2.3 Hz, 1H), 10.50 (s, 1H).

TABLE 45
| Ex. No. | | Chemical Compounds |
|---|---|---|
| 337 | 4-52 | 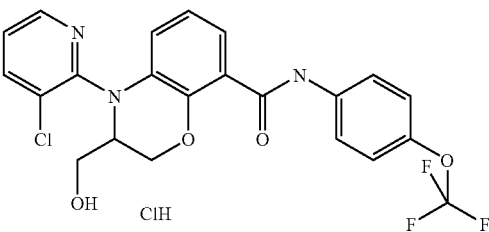 |
| 338 | 4-53 | 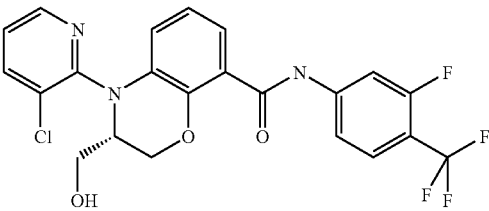 |
| 339 | 4-54 | 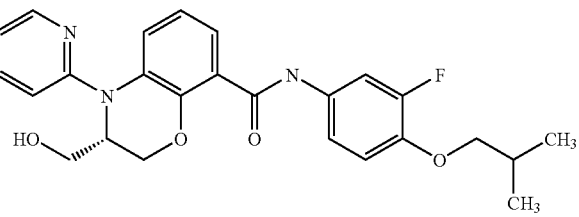 |
| 340 | 4-55 | 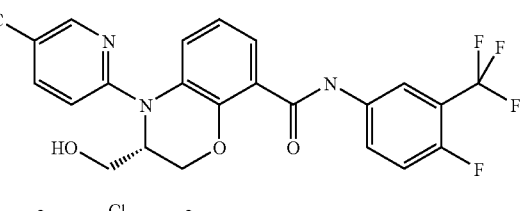 |
| 341 | 4-56 | 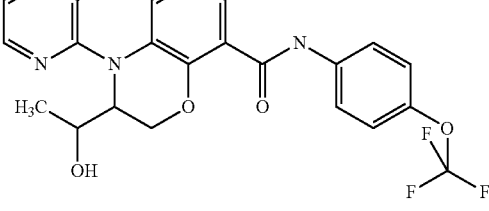 |
| 342 | 4-57 | 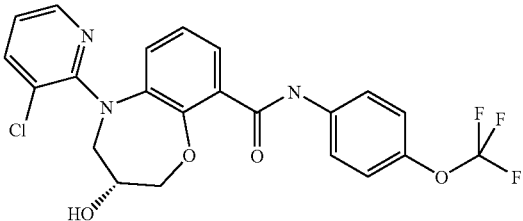 |
| 343 | 4-58 | 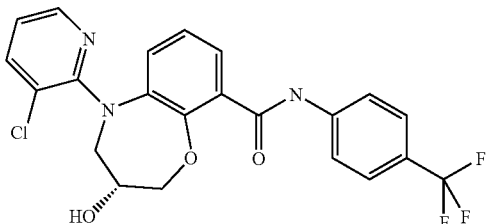 |

TABLE 45-continued

| | NMR |
|---|---|
| 337 | (300 MHz, DMSO-d6) δ: 348-3.52 (m, 1H), 3.71-3.73 (m, 1H), 4.01-4.03 (m, 1H), 4.18 (d, J = 10.3 Hz, 1H), 4.63 (d, J = 10.6 Hz, 1H), 6.42 (dd, J = 8.1, 1.5 Hz, 1H), 6.81 (t, J = 7.9 Hz, 1H), 7.03 (d, J = 7.7 Hz, 1H), 7.35-7.37 (m, 3H), 7.88 (d, J = 9.2 Hz, 2H), 8.07 (dd, J = 7.9, 1.7 Hz, 1H), 8.48-8.47 (m, 1H), 10.36 (s, 1H). |
| 338 | (300 MHz, DMSO-d6) δ: 3.48-3.53 (m, 1H), 3.72-3.74 (m, 1H), 3.95-3.98 (m, 1H), 4.18 (d, J = 9.5 Hz, 1H), 4.62 (d, J = 9.9 Hz, 1H), 5.05-5.07 (m, 1H), 6.44 (d, J = 7.0 Hz, 1H), 6.83 (t, J = 7.7 Hz, 1H), 7.03 (d, J = 7.3 Hz, 1H), 7.36 (dd, J = 7.9, 4.6 Hz, 1H), 7.67-7.79 (m, 2H), 7.98 (d, J = 14.7 Hz, 1H), 8.07 (d, J = 6.6 Hz, 1H), 8.46 (d, J = 3.3 Hz, 1H), 10.74 (s, 1H). |
| 339 | (400 MHz, DMSO-d6) 0.98 (d, J = 7.0 Hz, 6H), 1.97-2.07 (m, 1H), 2.24 (s, 3H), 3.41-3.47 (m, 1H), 3.60-3.65 (m, 1H), 3.80 (d, J = 6.5 Hz, 2H), 4.06 (dd, J = 10.9, 2.6 Hz, 1H), 4.39 (t, J = 7.0 Hz, 1H), 4.59 (d, J = 10.2 Hz, 1H), 5.14 (t, J = 5.6 Hz, 1H), 6.88 (t, J = 7.7 Hz, 1H) 7.08-7.11 (m, 1H), 7.15 (d, J = 9.3 Hz, 1H), 7.20 (d, J = 8.3 Hz, 1H), 7.32 (dd, J = 8.3, 1.4 Hz, 1H), 7.41 (dd, J = 9.3, 1.4 Hz, 1H), 7.55 (dd, J = 8.8, 2.3 Hz, 1H), 7.72 (dd, J = 13.7, 2.6 Hz, 1H), 8.16 (d, J = 2.3 Hz, 1H), 10.18 (s, 1H). |
| 340 | (300 MHz, DMSO-d6) 2.25 (s, 3H), 3.43-3.46 (m, 1H), 3.60-3.67 (m, 1H), 4.07 (dd, J = 11.0, 2.6 Hz, 1H), 4.40 (t, J = 7.2 Hz, 1H), 4.59 (d, J = 10.3 Hz, 1H), 5.13 (t, J = 5.5 Hz, 1H), 6.90 (t, J = 7.9 Hz, 1H), 7.11 (dd, J = 7.3, 1.5 Hz, 1H), 7.21 (d, J = 8.4 Hz, 1H), 7.34 (dd, J = 8.1, 1.5 Hz, 1H), 7.51-7.55 (m, 2H), 7.97-8.03 (m, 1H), 8.16 (d, J = 2.2 Hz, 1H), 8.26 (dd, J = 6.8, 2.6 Hz, 1H), 10.52 (s, 1H). |
| 341 | (300 MHz, DMSO-d6) δ: 1.14 (d, J = 6.2 Hz, 3H), 3.93-3.96 (m, 1H), 4.08-4.12 (m, 1H), 4.77 (d, J = 9.2 Hz, 1H), 4.95 (d, J = 5.5 Hz, 1H), 6.53 (t, J = 3.9 Hz, 1H), 6.82 (t, J = 7.9 Hz, 1H), 7.05 (d, J = 7.7 Hz, 1H), 7.32-7.37 (m, 4H), 7.87 (d, J = 9.2 Hz, 3H), 8.04 (dd, J = 7.9, 1.7 Hz, 1H), 8.48-8.48 (m, 1H), 10.33 (s, 1H). |
| 342 | (300 MHz, DMSO-d6) 3.87 (br s, 1H), 4.24-4.35 (m, 3H), 4.51 (q, J = 5.3 Hz, 1H), 6.36 (d, J = 2.2 Hz, 1H), 6.79-6.83 (m, 3H), 7.06 (dd, J = 7.7, 4.8 Hz, 1H), 7.33 (d, J = 8.8 Hz, 2H), 7.84 (d, J = 9.2 Hz, 2H), 7.92 (dd, J = 7.7, 1.1 Hz, 1H), 8.13 (dd, J = 4.6, 1.3 Hz, 1H), 10.22 (s, 1H). |
| 343 | (300 MHz, DMSO-dS) 3.83-3.92 (m, 1H), 4.24-4.35 (m, 3H), 4.51 (dd, J = 10.8, 5.4 Hz, 1H), 6.38 (d, J = 2.6 Hz, 1H), 6.77-6.86 (m, 3H), 7.06 (dd, J = 7.7, 4.8 Hz, 1H), 7.69 (d, J = 8.4 Hz, 2H), 7.90-7.96 (m, 3H), 8.13 (dd, J = 5.0, 1.7 Hz, 1H), 10.38 (s, 1H). |

TABLE 46

| Ex. No. | | Chemical Compounds |
|---|---|---|
| 344 | 4-59 | |
| 345 | 5-01 | |

TABLE 46-continued
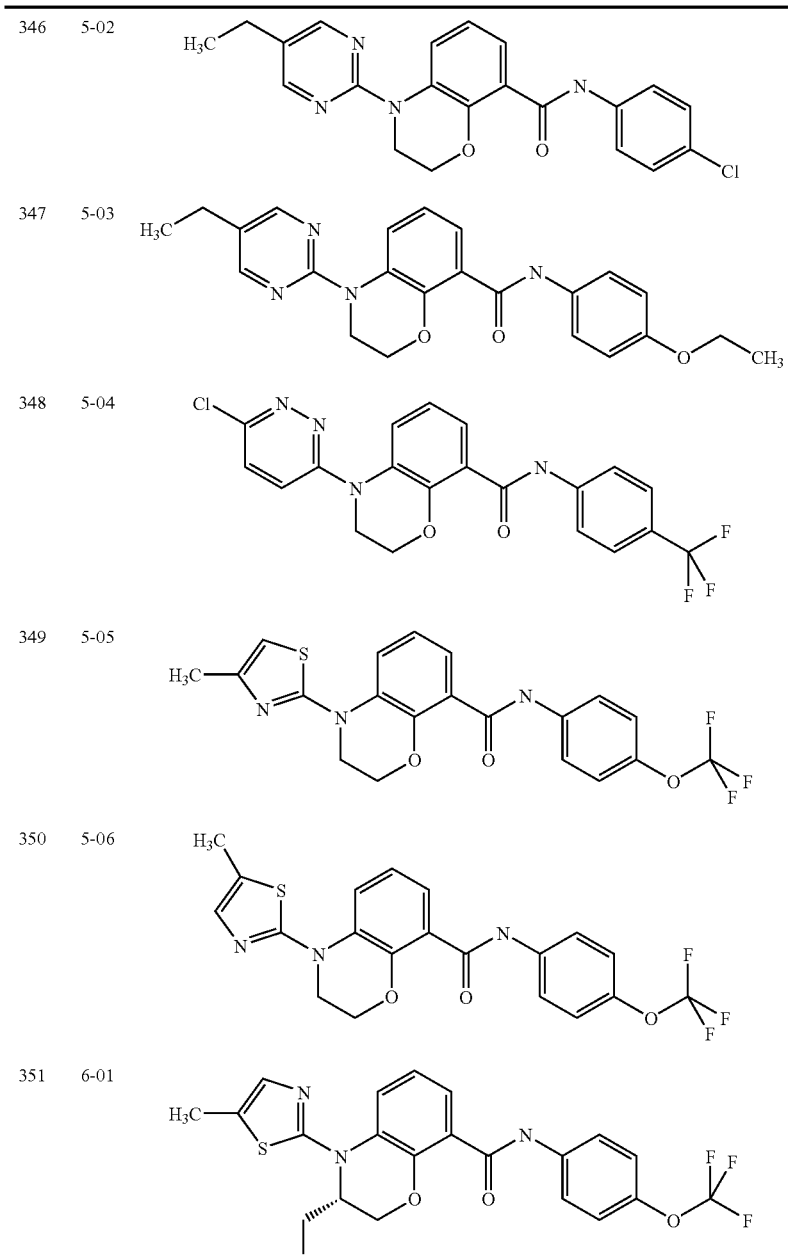
| | | NMR |
|---|---|---|
| | 344 | (400 MHz, DMSO-d6) 3.87 (m, 1H), 4.26-4.4 (m, 3H), 4.51 (m, 1H), 6.37 (d, J = 2.4 Hz, 1H), 6.7-6.86 (m, 3H), 7.06 (m, 1H), 7.33 (d, J = 8.4 Hz, 2H), 7.83 (dd, J = 6.8, 1.6 Hz), 7.92 (dd, J = 7.2, 1.2 Hz), 8.13 (dd, J = 4.4, 1.6 Hz, 1H), 10.23 (s, 1H). |
| | 345 | (300 MHz, DMSO-d6) δ: 1.25 (s, 9H), 4.06 (t, J = 4.2 Hz, 2H), 4.38 (t, J = 4.4 Hz. 2H), 6.96 (t, J = 7.9 Hz, 1H), 7.27 (dd, J = 7.7, 1.5 Hz, 1H), 7.35 (d, J = 8.8 Hz, 2H), 7.59-7.65 (m, 3H), 8.12 (d, J = 2.6 Hz, 1H), 8.30 (dd, J = 1.3, 0.7 Hz, 1H), 8.60 (d, J = 1.5 Hz, 1H), 10.06 (s, 1H). |
| | 346 | (400 MHz, DMSO-d6) 1.18 (t, J = 7.4 Hz, 3H), 2.54 (q, J = 7.4 Hz, 2H), 4.22 (t, J = 4.2 Hz, 2H), 4.36 (t, J = 4.4 Hz, 2H), 6.96 (t, J = 7.9 Hz, 1H), 7.24 (dd, J = 7.4, 1.4 Hz, 1H), 7.39 (t, J = 4.4 Hz, 2H), 7.77 (d, J = 8.8 Hz, 2H), 8.04 (dd, J = 8.3, 1.4 Hz, 1H), 8.45 (s, 2H), 10.27 (s, 1H). |
| | 347 | (400 MHz, DMSO-d6) 1.18 (t, J = 7.7 Hz, 3H), 1.32 (t, J = 7.0 Hz, 3H), 2.54 (q, J = 7.7 Hz, 1H), 4.00 (q, J = 7.0 Hz, 2H), 4.22 (t, J = 4.4 Hz, 2H), 4.37 (t, J = 4.4 Hz, 2H), 6.89 |

TABLE 46-continued

| | |
|---|---|
| | (d, J = 8.8 Hz, 2H), 6.95 (t, J = 7.9 Hz, 1H), 7.25 (d, J = 7.4 Hz, 1H), 7.63 (d, J = 8.8 Hz, 2H), 8.01 (d, J = 8.3 Hz, 1H), 8.45 (s, 2H), 9.97 (s, 1H). |
| 348 | (400 MHz, DMSO-d6) 4.12 (d, J=4.6 Hz, 2H), 4.38(d, 2H), 6.95(dd, J=8.1, 7.6 Hz, 1H), 7.27(dd, J=7.6, 1.5 Hz, 1H), 7.48(dd, J=8.1, 1.5 Hz, 1H), 7.61(d, J=9.3 Hz, 1H), 7.67(d, J=9.3 Hz, 1H), 7.68(d, 8.8 HZ, 2H), 7.92(d, 8.8 Hz, 2H), 10.50(s, 1H) |
| 349 | (400 MHz, DMSO-d6) 2.26 (s, 3H), 4.03 (t, J=4.4 Hz, 2H), 4.37(t, J=4.4 Hz, 2H), 6.65(d, J=1.6 Hz, 1H), 7.04 (t, J = 8 Hz, 1H), 7.25 (d, J = 8 Hz, 1H), 7.26 (d, J = 9.2 Hz, 2H), 7.83 (d, J = 9.2 Hz, 2H), 8.19 (d, J = 8 Hz, 1H), 10.36 (s, 1H). |
| 350 | (300 MHz, DMSO-d6) 2.33 (s, 3H), 3.40 (t, J=4.4 Hz, 2H), 4.36(t, J=4.4 Hz, 2H), 6.9-7.1 (m, 2H), 7.23 (d, J = 1.8 Hz, 1H), 7.34 (d, J = 9.2 Hz, 2H), 7.84(d, J = 9.2 Hz, 2H), 8.10 (d, J = 8 Hz, 1H), 10.34 (s, 1H). |
| 351 | (400 MHz, DMSO-d6) 2.34 (d, J = 1.4 Hz, 3H), 3.46-3.60 (m, 2H), 4.14 (dd, J = 11.1, 2.8 Hz, 1H), 4.35-4.41 (m, 1H), 4.56 (d, J = 11.1 Hz, 1H), 5.19 (t, J = 5.8 Hz, 1H), 7.00 (t, J = 7.9 Hz, 1H), 7.07 (d, J = 1.4 Hz, 1H), 7.19(dd, J = 7.9, 1.6 Hz, 1H), 7.36 (d, J = 8.3 Hz, 2H), 7.84 (d, J = 8.3 Hz, 2H), 8.00 (dd, J = 7.9, 1.6 Hz, 1H), 10.39 (s, 1H). |

TABLE 47

| Ex. No. | | Chemical Compounds |
|---|---|---|
| 352 | 6-02 | 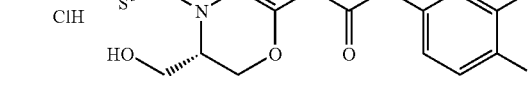 |
| 353 | 6-03 | |
| 354 | 6-04 | |
| 355 | 6-05 | 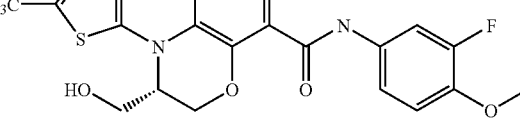 |
| 356 | 6-06 |  |

TABLE 47-continued

| | | |
|---|---|---|
| 357 | 6-07 | 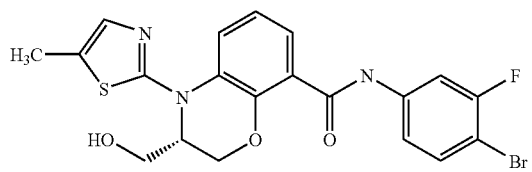 |
| 358 | 6-08 | 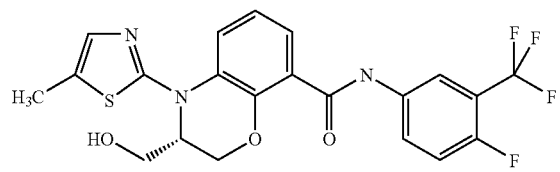 |
| 359 | 6-09 | 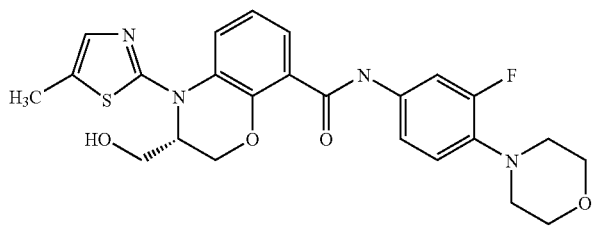 |

| | NMR |
|---|---|
| 352 | (400 MHz, DMSO-d6) 2.34 (d, J = 1.4 Hz, 3H), 3.47-3.60 (m, 2H), 4.15 (dd, J = 11.1, 2.3 Hz, 1H), 4.34-4.42 (m, 1H), 4.57 (d, J = 11.1 Hz, 1H), 5.20 (t, J = 5.8 Hz, 1H), 7.01 (t, J = 7.9 Hz, 1H), 7.07 (d, J = 1.4 Hz, 1H), 7.20 (dd, J = 7.9, 1.4 Hz, 1H), 7.72 (d, J = 8.3 Hz, 2H), 7.94 (d, J = 8.3 Hz, 2H), 8.02 (dd, J = 7.9, 1.4 Hz, 1H), 10.56 (s, 1H). |
| 353 | (400 MHz, DMSO-d6) 2.34 (d, J = 1.4 Hz, 3H), 3.48-3.59 (m, 2H), 4.16 (dd, J = 11.1, 2.3 Hz, 1H), 4.37-4.43 (m, 1H), 4.58 (d, J = 11.1 Hz, 1H), 6.51 (br, 2H), 7.01 (t, J = 7.9 Hz, 1H), 7.09 (d, J = 1.4 Hz, 1H), 7.21 (dd, J = 7.9, 1.4 Hz, 1H), 7.61 (d, J = 8.8 Hz, 1H), 7.68 (dd, J = 8.8, 2.3 Hz, 1H), 8.01 (dd, J = 7.9, 1.4 Hz, 1H), 8.12 (d, J = 2.3 Hz, 1H), 10.51 (s, 1H). |
| 354 | (400 MHz, DMSO-d6) 1.27 (d, J = 6.0 Hz, 7H), 2.34 (d, J = 1.4 Hz, 3H), 3.46-3.59 (m, 2H), 4.13 (dd, J = 11.1, 2.3 Hz, 1H), 4.35-4.41 (m, 1H), 4.49-4.60 (m, 2H), 5.19 (t, J = 5.6 Hz, 1H), 6.99 (t, J = 8.1 Hz, 1H), 7.07 (d, J = 1.4 Hz, 1H), 7.12-7.20 (m, 2H), 7.36-7.40 (m, 1H), 7.71 (dd, J = 13.7, 2.6 Hz, 1H), 7.99 (dd, J = 8.1, 1.4 Hz, 1H), 10.21 (s, 1H). |
| 355 | (400 MHz, DMSO-d6) 1.29 (s, 9H), 2.34 (d, J = 1.4 Hz, 3H), 3.45-3.60 (m, 2H), 4.13 (dd, J = 11.1, 2.8 Hz, 1H), 4.34-4.41 (m, 1H), 4.57 (d, J = 11.1 Hz, 1H), 5.19 (t, J = 5.8 Hz, 1H), 7.00 (t, J = 8.1 Hz, 1H), 7.07 (d, J = 1.4 Hz, 1H), 7.11 (t, J = 9.0 Hz, 1H), 7.17 (dd, J = 8.1, 1.6 Hz, 1H), 7.33-7.39 (m, 1H), 7.73 (dd, J = 13.0, 2.3 Hz, 1H), 8.00 (dd, J = 8.1, 1.6 Hz, 1H), 10.30 (s, 1H). |
| 356 | (400 MHz, DMSO-d6) 0.98 (d, J = 6.5 Hz, 6H), 1.99-2.05 (m, 1H), 2.34 (d, J = 1.4 Hz, 3H), 3.46-3.59 (m, 2H), 3.80 (d, J = 6.5 Hz, 2H), 4.13 (dd, J = 11.1, 2.8 Hz, 1H), 4.35-4.41 (m, 1H), 4.57 (d, J = 11.1 Hz, 1H), 5.20 (t, J = 5.6 Hz, 1H), 6.99 (t, J = 7.9 Hz, 1H), 7.07 (d, J = 1.4 Hz, 1H), 7.13 (t, J = 9.3 Hz, 1H), 7.18 (dd, J = 7.9, 1.4 Hz, 1H), 7.37-7.41 (m, 1H), 7.70 (dd, J = 13.7, 2.6 Hz, 1H), 7.99 (dd, J = 8.9, 1.4 Hz, 1H), 10.19 (s, 1H). |
| 357 | (400 MHz,DMSO-d6) 2.35 (d, J = 0.9 Hz, 3H), 3.49-3.61 (m, 2H), 4.15 (dd, J = 11.1, 2.8 Hz, 1H), 4.37 (t, J = 5.1 Hz, 1H), 4.58 (dd, J = 11.1, 0.9 Hz, 1H), 5.21 (t, J = 5.8 Hz, 1H), 7.02 (t, J = 7.9 Hz, 1H), 7.08 (d, J = 1.4 Hz, 1H), 7.20 (dd, J = 7.7, 1.6 Hz, 1H), 7.46 (dd, J = 8.8, 1.9 Hz, 1H), 7.68 (t, J = 8.3 Hz, 1H), 7.90 (dd, J = 11.6, 2.3 Hz, 1H), 8.03 (dd, J = 8.3, 1.4 Hz, 1H), 10.53 (s, 1H). |
| 358 | (400 MHz, DMSO-d6) 2.34 (d, J = 0.9 Hz, 3H), 3.46-3.60 (m, 2H), 4.14 (dd, J = 11.4, 2.6 Hz, 1H), 4.38 (t, J = 7.0 Hz, 1H), 4.58 (dd, J = 11.4, 1.2 Hz, 1H), 5.20 (t, J = 5.6 Hz, 1H), 7.01 (t, J = 8.1 Hz, 1H), 7.07 (d, J = 1.4 Hz, 1H), 7.21 (dd, J = 7.4, 1.4 Hz, 1H), 7.52 (t, J = 9.7 Hz, 1H), 7.96-8.03 (m, 2H), 8.25 (q, J = 3.1 Hz, 1H), 10.55 (s, 1H). |
| 359 | (400 MHz, DMSO-d6) 2.33 (d, J = 1.4 Hz, 3H), 2.96 (t, J = 4.6 Hz, 4H), 3.47-3.60 (m, 2H), 3.74 (t, J = 4.6 Hz, 4H), 4.13 |

TABLE 47-continued (dd, J = 10.9, 2.6 Hz, 1H), 4.38 (t, J = 6.7 Hz, 1H), 4.57 (dd, J = 1.4 Hz, 1H), 5.19 (t, J = 5.6 Hz, 1H), 6.97-7.05 (m, 2H), 7.07 (d, J = 1.4 Hz, 1H), 7.18 (dd, J = 7.7, 1.6 Hz, 1H), d, J = 8.8 Hz, 1H), 7.66 (dd, J = 14.8, 2.3 Hz, 1H), 7.99 (dd, J = 8.1, 1.6 Hz, 1H), 10.21 (s, 1H).

TABLE 48

| | Ex. No. | Chemical Compounds |
|---|---|---|
| 360 | 6-10 | |
| 361 | 6-11 | |
| 362 | 6-12 | |
| 363 | 6-13 | |
| 364 | 6-14 | |
| 365 | 6-15 | |

TABLE 48-continued

| | | |
|---|---|---|
| 366 | 6-16 | 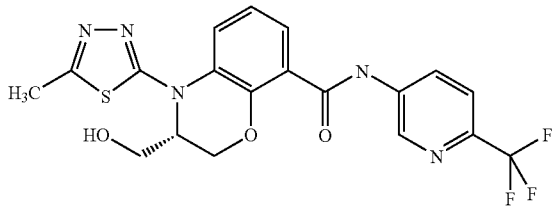 |
| 367 | 6-17 | 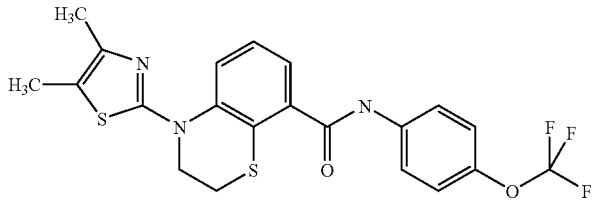 |

| | NMR |
|---|---|
| 360 | (400 MHz, DMSO-d6) 2.34 (d, J = 1.4 Hz, 3H), 3.47-3.53 (m, 1H), 3.55-3.60 (m, 1H), 4.15 (dd, J = 11.1, 2.3 Hz, 1H), 4.38 (t, J = 7.2 Hz, 1H), 4.58 (dd, J = 11.1, 0.9 Hz, 1H), 5.21 (t, J = 5.3 Hz, 1H), 7.03 (t, J = 7.9 Hz, 1H), 7.08 (d, J = 1.4 Hz, 1H), 7.23 (dd, J = 7.7, 1.6 Hz, 1H), 7.92 (d, J = 8.8 Hz, 1H), 8.05 (dd, J = 8.3, 1.4 Hz, 1H), 8.44 (dd, J = 8.8, 1.9 Hz, 1H), 9.01 (d, J = 2.3 Hz, 1H), 10.80 (s, 1H). |
| 361 | (300 MHz, DMSO-d6) 2.28 (d, J = 1.1 Hz, 3H), 3.51-3.57 (m, 2H), 4.16 (dd, J = 11.2, 2.4 Hz, 1H), 4.43 (t, J = 7.2 Hz, 1H), 4.59 (d, J = 10.3 Hz, 1H), 5.17 (t, J = 5.7 Hz, 1H), 6.69 (d, J = 1.5 Hz, 1H), 7.01 (t, J = 8.1 Hz, 1H), 7.15 (dd, J = 7.7, 1.5 Hz, 1H), 7.35 (d, J = 8.4 Hz, 2H), 7.84 (d, J = 9.2 Hz, 2H), 8.22 (dd, J = 8.3, 1.7 Hz, 1H), 10.36 (s, 1H). |
| 362 | (300 MHz, DMSO-d6) 2.28 (d, J = 1.5 Hz, 3H), 3.51-3.57 (m, 2H), 4.17 (dd, J = 11.2, 2.4 Hz, 1H), 4.44 (t, J = 7.2 Hz, 1H), 4.59 (d, J = 9.9 Hz, 1H), 5.18 (t, J = 5.7 Hz, 1H), 6.69 (d, J = 1.5 Hz, 1H), 7.02 (t, J = 7.9 Hz, 1H), 7.16 (dd, J = 7.7, 1.5 Hz, 1H), 7.71 (d, J = 8.8 Hz, 2H), 7.94 (d, J = 8.4 Hz, 2H), 8.23 (dd, J = 8.3, 1.7 Hz, 1H), 10.53 (s, 1H). |
| 363 | (400 MHz, DMSO-d6) 2.15 (s, 3H), 2.23 (s, 3H), 3.44-3.58 (m, 2H), 4.11 (dd, J = 11.1, 2.3 Hz, 1H), 4.37-4.43 (m, 1H), 4.56 (d, J = 11.1 Hz, 1H), 5.18 (t, J = 5.8 Hz, 1H), 7.00 (t, J = 7.9 Hz, 1H), 7.18 (dd, J = 7.9, 1.4 Hz, 1H), 7.36 (d, J = 8.3 Hz, 2H), 7.83 (d, J = 8.3 Hz, 2H), 7.98 (dd, J = 7.9, 1.4 Hz, 1H), 10.39 (s, 1H). |
| 364 | (400 MHz, DMSO-d6) 2.16 (s, 3H), 2.24 (s, 3H), 3.44-3.59 (m, 2H), 4.12 (dd, J = 11.1, 2.3 Hz, 1H), 4.37-4.43 (m, 1H), 4.56 (d, J = 11.1 Hz, 1H), 5.19 (t, J = 5.8 Hz, 1H), 7.01 (t, J = 8.1 Hz, 1H), 7.20 (dd, J = 8.1, 1.6 Hz, 1H), 7.71 (d, J = 8.8 Hz, 2H), 7.94 (d, J = 6.8 Hz, 2H), 7.99 (dd, J =8.1, 1.6 Hz, 1H), 10.56 (s, 1H). |
| 365 | (400 MHz, DMSO-d6) 2.60 (d, J = 4.2 Hz, 3H), 3.51-3.64 (m, 2H), 4.22 (dd, J = 11.1, 2.8 Hz, 1H), 4.42 (t, J = 7.4 Hz, 1H), 4.56 (d, J = 10.2 Hz, 1H), 5.24 (t, J = 5.8 Hz, 1H), 7.04 (t, J = 7.9 Hz, 1H), 7.24 (dd, J = 7.9, 1.4 Hz, 1H), 7.36 (d, J = 8.3 Hz, 2H), 7.83 (d, J = 8.8 Hz, 2H), 7.96 (dd, J = 8.3, 1.4 Hz, 1H), 10.41 (s, 1H). |
| 366 | (400 MHz, DMSO-d6) 2.60 (d, J = 2.8 Hz, 3H), 3.52-3.64 (m, 2H), 4.23 (dd, J = 11.1, 2.8 Hz, 1H), 4.42 (t, J = 7.0 Hz, 1H), 4.56 (d, J = 10.2 Hz, 1H), 5.24 (t, J = 5.8 Hz, 1H), 7.05 (t, J = 7.9 Hz, 1H), 7.25 (dd, J = 7.7, 1.6 Hz, 1H), 7.72 (d, J = 8.8 Hz, 2H), 7.92-7.98 (m, 3H), 10.58 (s, 1H). |
| 367 | (400 MHz, DMSO-d6) 2.11 (s, 3H), 2.17 (s, 3H), 3.08 (t, J = 5.6 Hz, 2H), 4.05 (t, J = 5.6 Hz, 2H), 7.23 (t, J = 7.9 Hz, 1H), 7.32-7.39 (m, 3H), 7.66 (dd, J = 7.9, 1.4 Hz, 1H), 7.83 (d, J = 9.3 Hz, 2H), 10.62 (s, 1H) |

TABLE 49

| Ex. No. | | Chemical Compounds |
|---|---|---|
| 368 | 6-18 | |
| 369 | 7-01 | |
| 370 | 7-02 | |
| 371 | 7-03 | |
| 372 | 7-04 | |
| 373 | 7-05 | |
| 374 | 7-06 | |

TABLE 49-continued

| 375 | 7-07 | 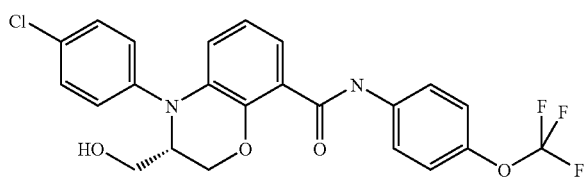 |
|---|---|---|

| | NMR |
|---|---|
| 368 | (400 MHz, DMSO-d6) 2.19 (s, 3H), 2.28 (s, 3H), 2.90-3.01 (m, 1H), 3.41-3.48 (m, 1H), 3.96-4.06 (m, 1H), 4.23-4.31 (m, 1H), 7.26 (d, J = 7.4 Hz, 1H), 7.39 (d, J = 8.8 Hz, 2H), 7.59 (t, J = 7.9 Hz, 1H), 7.84-7.90 (m, 3H), 10.81 (s, 1H) |
| 369 | (400 MHz, CHLOROFORM-d) 1.33 (s, 9H), 3.75 (t, J = 4.2 Hz, 2H), 3.83 (s, 3H), 4.54 (t, J = 4.4 Hz, 2H), 6.76 (dd, J = 8.1, 1.2 Hz, 1H), 6.82 (t, J = 8.1 Hz, 1H), 6.94 (d, J = 8.8 Hz, 2H), 7.17 (d, J = 8.8 Hz, 2H), 7.38 (d, J = 8.8 Hz, 2H), 7.60 (d, J = 8.3 Hz, 2H), 7.64 (dd, J = 8.1, 1.6 Hz, 1H), 9.61 (s, 1H). |
| 370 | (400 MHz, CHLOROFORM-d) 1.03 (d, J = 7.0 Hz, 6H), 2.05-2.12 (m, 1H), 3.73 (d, J = 6.5 Hz, 2H), 3.75 (t, J = 4.4 Hz, 2H), 3.83 (s, 3H), 4.54 (t, J = 4.4 Hz, 2H), 6.76 (dd, J = 7.9, 1.9 Hz, 1H), 6.82 (t, J = 7.9 Hz, 1H), 6.90 (d, J = 8.8 Hz, 2H), 6.94 (dd, J = 7.0, 2.3 Hz, 2H), 7.17 (dd, J = 6.5, 2.3 Hz, 2H), 7.58 (d, J = 8.8 Hz, 2H), 7.65 (dd, J = 7.7, 1.6 Hz, 1H), 9.57 (s, 1H). |
| 371 | (400 MHz, CHLOROFORM-d) 3.76 (br s, 2H), 3.84 (s, 3H), 4.56 (br s, 2H), 8.81 (d, J = 17.6 Hz, 2H), 6.96 (br s, 2H), 7.17 (br s, 2H), 7.33 (br s, 2H), 7.65 (br s, 3H), 9.73 (s, 1H). |
| 372 | (400 MHz, DMSO-d6) 3.46-3.79 (m, 3H), 4.23 (d, J = 10 Hz, 1H), 4.56 (d, J = 10 Hz, 1H), 4.96 (s, 1H), 6.10 (d, J = 7.0 Hz, 1H), 6.71-6.90 (m, 2H), 7.34-7.71 (m, 6H), 7.86 (d, J = 8.8 Hz, 2H), 10.36 (s, 1H). |
| 373 | (400 MHz, DMSO-d6) 3.46-3.79 (m, 3H), 4.23 (d, J = 10 Hz, 1H), 4.56 (d, J = 10 Hz, 1H), 4.97 (s, 1H), 6.11 (d, J = 7.0 Hz, 1H), 6.74-6.91 (m, 2H), 7.39-7.72 (m, 8H), 7.96 (d, J = 8.3 Hz, 2H), 10.53 (s, 1H). |
| 374 | (400 MHz, DMSO-d6) 3.45-3.80 (m, 3H), 4.23 (brd, J = 10 Hz, 1H), 4.56 (brd, J = 10 Hz, 1H), 4.97 (s, 1H), 6.12 (d, J = 7.9 Hz, 1H), 6.74-6.90 (m, 2H), 7.40-7.78 (m, 6H), 7.97 (d, J = 13.0 Hz, 1H), 10.73 (s, 1H). |
| 375 | (300 MHz, DMSO-d6) 3.46-3.60 (m, 2H), 3.79 (t, J = 7.0 Hz, 1H), 4.08 (dd, J = 10.8, 2.0 Hz, 1H), 4.49 (d, J = 10.3 Hz, 1H), 5.09 (t, J = 5.3 Hz, 1H), 6.80-6.91 (m, 2H), 7.01 (dd, J = 7.3, 1.5 Hz, 1H), 7.35-7.44 (m, 6H), 7.85 (d, J = 8.8 Hz, 2H), 10.33 (s, 1H). |

TABLE 50

| Ex. No. | Chemical Compounds |
|---|---|
| 376 | 7-08 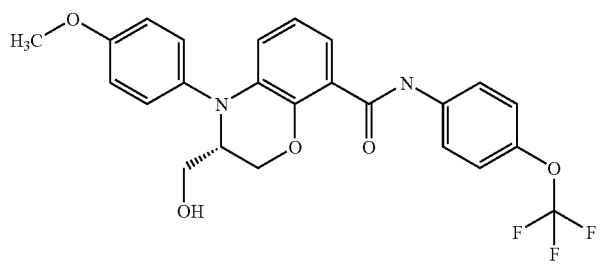 |

TABLE 50-continued

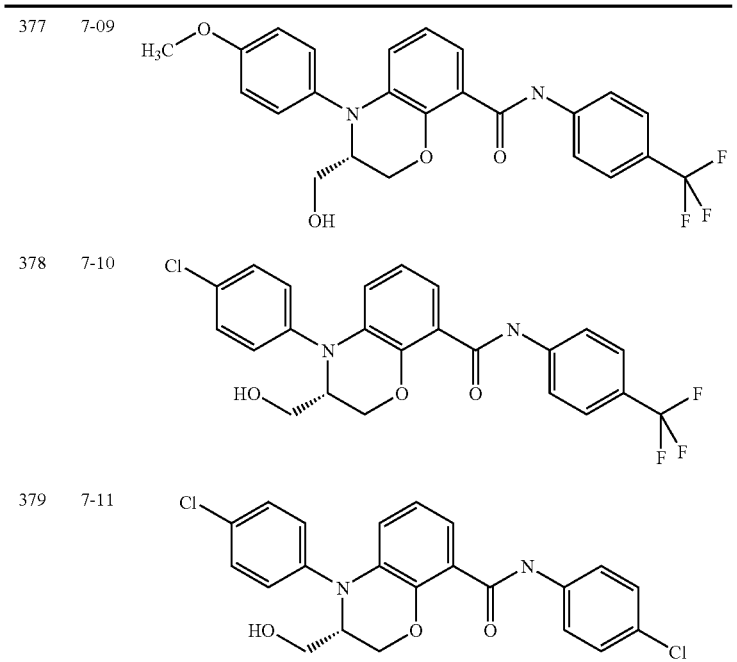

| | | NMR |
|---|---|---|
| | 376 | (400 MHz, DMSO-d6) 3.45-3.68 (m, 3H), 3.77 (s, 3H), 4.13 (dd, J = 10.9, 2.1 Hz, 1H), 4.49 (dd, J = 10.9, 2.1 Hz, 1H), 4.97 (t, J = 5.3 Hz, 1H), 6.51 (dd, J = 8.0, 1.5 Hz, 1H), 6.74 (t, J = 8.0 Hz, 1H), 6.86 (dd, J = 7.4, 1.5 Hz, 1H), 7.01 (d, J = 8.8 Hz, 2H), 7.24 (d, J = 8.8 Hz, 2H), 7.35 (d, J = 8.8 Hz, 2H), 7.85 (d, J = 8.8 Hz, 2H), 10.33 (s, 1H). |
| | 377 | (400 MHz, DMSO-d6) 3.43-3.66 (m, 3H), 3.77 (s, 3H), 4.14 (d, J = 8.6 Hz, 1H), 4.50 (t, J = 5.5 Hz, 1H), 4.98 (t, J = 5.5 Hz, 1H), 6.52 (dd, J = 7.9, 1.4 Hz, 1H), 6.75 (t, J = 7.9 Hz, 1H), 6.87 (dd, J = 7.9, 1.4 Hz, 1H), 7.01 (d, J = 8.8 Hz, 2H), 7.25 (d, J = 8.5 Hz, 2H), 7.71 (d, J = 8.3 Hz, 2H), 7.96 (d, J = 8.3 Hz, 2H), 10.50 (s, 1H). |
| | 378 | (300 MHz, DMSO-d6) 3.46-3.61 (m, 2H), 3.79 (t, J = 7.0 Hz. 1H), 4.09 (d, J = 8.8 Hz, 1H), 4.50 (d, J = 9.9 Hz, 1H), 5.10 (t, J = 5.5 Hz, 1H), 6.82-6.93 (m, 2H), 7.02 (dd, J = 7.3, 1.8 Hz, 1H), 7.40 (m, 4H), 7.71 (d, J = 8.8 Hz, 2H), 7.96 (d, J = 8.4 Hz, 2H), 10.50 (s, 1H). |
| | 379 | (300 MHz, DMSO-d6) 3.51-3.56 (m, 2H), 3.79 (t, J = 7.2 Hz, 1H), 4.08 (dd, J = 10.8, 2.4 Hz, 1H), 4.50 (d, J = 9.9 Hz, 1H), 5.10 (t, J = 5.3 Hz, 1H), 6.80-6.91 (m, 2H), 7.01 (dd, J = 7.2, 1.7 Hz, 1H), 7.33-7.46 (m, 6H), 7.78 (d, J = 8.8 Hz, 2H), 10.28 (s, 1H). |

Test Example

The assay for evaluation of VR1 inhibition by the inventive compounds will be described below. The assay was intended to evaluate in vitro inhibition of $Ca^{2+}$ entry in cells caused by proton, one of the VR1 agonists.

Test Example 1

Inhibition of $Ca^{2+}$ Entry in Cells

Rat glioma (C6BU1) cells stably expressing human VR1 were suspended in 20 mM MES buffer (at pH 6.8, contg. 20 mM 2-morpholinoethanesulfonate (referred to as MES hereinafter), 115 mM NaCl, 5 mM KCl, 1 mM $MgCl_2$ and 14 mM D-glucose) to make a cell density of $1 \times 10^6$ cells/mL. A fluorescent dye, Fura 2-AMsolution (DojindoCorporate, Cat. No. 343-05401) was added to the suspension to make a 5 µM concentration thereof. Further, Pluronic F-127 (Wako Pure Chemical Industries, Ltd., Cat. No. P6866) was added to make a 0.1% content thereof. Then, the suspension was incubated at 37° C. for 30 min. The cells were harvested and washed three times with 20 mM MES buffer. The cells were suspended again to make a cell density of $5 \times 10^5$ cells/mL. A 500-µL portion of the suspension was taken with a cuvette (MC MEDICAL, INC., Cat. No. SSR3121), to which 10 µL of 20 mM MES buffer containing 250 mM $CaCl_2$ was added to incorporate $Ca^{2+}$ into the cells. At the same time, 5 µL of a test compound solution (in a range of 100 µM to 10 nM in DMSO) was also added to provide a final concentration thereof in a range of 1 µM to 0.1 nM. Alternatively, 5 µL of DMSO was added as control to provide a final concentration of 1% DMSO. The suspension was set in an intracellular ionometer (CAF-110; JASCO) 10 min after those additions. The cells were stimulated with protons by addition of 60 µL of 20 mM MES buffer at pH 1.1 to the suspension to set its pH at 5.5. The activity of the test compound was determined as a difference between the minimum of fluorescence intensity before agonist stimulation and its maximum after the stimulation. The value of $IC_{50}$ was derived from percentage of inhibition by the test compound compared with the control. The results are shown in Tables 51 to 56 below.

In the tables, the symbol "++" indicates an $IC_{50}$ value less than 100 nM and the symbol "+" indicates an $IC_{50}$ value of 100 nM to 1,000 nM inclusive.

TABLE 51

| Ex. No. | IC50 | Ex. No. | IC50 | Ex. No. | IC50 | Ex. No. | IC50 |
|---|---|---|---|---|---|---|---|
| 1-001 | ++ | 1-003 | ++ | 1-004 | ++ | 1-005 | ++ |
| 1-006 | ++ | 1-007 | ++ | 1-009 | ++ | 1-011 | ++ |
| 1-016 | ++ | 1-017 | ++ | 1-018 | + | 1-019 | + |
| 1-020 | ++ | 1-021 | ++ | 1-022 | ++ | 1-023 | + |
| 1-024 | ++ | 1-025 | ++ | 1-026 | + | 1-027 | ++ |
| 1-029 | ++ | 1-030 | ++ | 1-031 | ++ | 1-032 | + |
| 1-033 | ++ | 1-034 | ++ | 1-039 | + | 1-040 | + |
| 1-041 | + | 1-043 | + | 1-044 | ++ | 1-045 | ++ |
| 1-047 | ++ | 1-048 | ++ | 1-049 | + | 1-050 | + |
| 1-051 | ++ | 1-052 | ++ | 1-053 | ++ | 1-054 | ++ |
| 1-055 | ++ | 1-056 | ++ | 1-057 | ++ | 1-058 | + |
| 1-059 | + | 1-060 | ++ | 1-061 | + | 1-062 | ++ |
| 1-063 | ++ | 1-068 | ++ | 1-069 | ++ | 1-070 | ++ |
| 1-071 | ++ | 1-072 | ++ | 1-073 | ++ | 1-075 | + |
| 1-076 | + | 1-077 | + | 1-078 | ++ | 1-079 | ++ |
| 1-080 | ++ | 1-081 | ++ | 1-082 | ++ | 1-083 | ++ |
| 1-084 | ++ | 1-085 | ++ | 1-086 | ++ | 1-087 | ++ |
| 1-089 | ++ | 1-090 | ++ | 1-091 | ++ | 1-092 | ++ |
| 1-093 | + | 1-094 | ++ | 1-095 | ++ | 1-098 | + |
| 1-099 | + | 1-100 | ++ | 1-101 | ++ | 1-102 | ++ |
| 1-103 | ++ | 1-104 | ++ | 1-106 | + | 1-107 | ++ |
| 1-119 | ++ | 1-120 | ++ | 1-121 | ++ | 1-122 | ++ |
| 1-123 | ++ | 1-124 | ++ | 1-125 | ++ | 1-126 | ++ |
| 1-127 | ++ | 1-128 | + | 1-129 | ++ | 1-130 | ++ |
| 1-131 | + | 1-132 | + | 1-133 | + | 1-136 | ++ |
| 1-140 | ++ | 1-143 | ++ | 1-144 | ++ | 1-141 | ++ |
| 1-145 | ++ | 1-146 | ++ | 1-147 | ++ | 1-148 | ++ |
| 1-149 | ++ | 1-150 | ++ | 1-151 | ++ | 1-152 | + |
| 1-153 | + | 1-154 | ++ | 1-155 | ++ | 1-156 | ++ |
| 1-157 | ++ | 1-158 | ++ | 1-159 | ++ | 1-160 | ++ |
| 1-162 | ++ | 1-163 | ++ | 1-164 | ++ | 1-165 | ++ |
| 1-166 | + | 1-167 | ++ | 1-169 | ++ | 1-170 | + |
| 1-171 | + | 1-172 | ++ | 1-173 | ++ | 1-174 | ++ |
| 1-176 | + | 1-183 | + | 1-186 | ++ | 1-187 | ++ |
| 1-189 | ++ | 1-190 | + | 1-191 | ++ | 1-192 | ++ |
| 1-193 | ++ | 1-194 | ++ | 1-195 | + | 1-196 | + |
| 1-197 | ++ | 1-198 | + | 1-199 | ++ | 1-200 | + |
| 1-201 | + | 1-202 | ++ | 1-203 | ++ | 1-207 | + |
| 1-209 | ++ | 1-210 | + | 1-216 | + | 1-217 | + |
| 1-218 | + | 1-220 | ++ | 1-227 | ++ | 1-228 | ++ |
| 1-229 | + | 1-231 | + | 1-233 | ++ | 1-234 | ++ |

TABLE 52

| Ex. No. | IC50 | Ex. No. | IC50 | Ex. No. | IC50 | Ex. No. | IC50 |
|---|---|---|---|---|---|---|---|
| 2-01 | + | 2-03 | ++ | 2-04 | ++ | 2-05 | ++ |
| 2-06 | ++ | 2-07 | ++ | 2-08 | ++ | 2-09 | ++ |
| 2-11 | + | 2-12 | ++ | 2-13 | ++ | 2-14 | ++ |
| 2-15 | ++ | 2-16 | ++ | 2-17 | ++ | 2-19 | ++ |
| 2-20 | ++ | 2-21 | ++ | 2-22 | ++ | 2-23 | ++ |
| 2-25 | ++ | 2-26 | + | 2-28 | ++ | 2-29 | ++ |
| 2-30 | ++ | 2-31 | ++ | 2-32 | ++ | 2-33 | ++ |
| 2-34 | ++ | 2-35 | ++ | 2-36 | ++ | 2-37 | ++ |
| 2-38 | ++ | 2-39 | ++ | 2-40 | ++ | 2-41 | ++ |
| 2-42 | ++ | 2-43 | ++ | 2-44 | ++ | 2-45 | ++ |
| 2-46 | ++ | 2-47 | ++ | 2-48 | ++ | | |

TABLE 53

| Ex. No. | IC50 | Ex. No. | IC50 | Ex. No. | IC50 | Ex. No. | IC50 |
|---|---|---|---|---|---|---|---|
| 4-01 | + | 4-03 | ++ | 4-04 | ++ | 4-05 | ++ |
| 4-06 | ++ | 4-07 | ++ | 4-08 | ++ | 4-09 | ++ |
| 4-10 | ++ | 4-11 | ++ | 4-12 | ++ | 4-13 | ++ |
| 4-14 | ++ | 4-15 | ++ | 4-16 | ++ | 4-17 | ++ |
| 4-18 | ++ | 4-19 | ++ | 4-20 | ++ | 4-21 | ++ |
| 4-22 | ++ | 4-23 | ++ | 4-24 | ++ | 4-25 | ++ |
| 4-26 | ++ | 4-27 | ++ | 4-28 | ++ | 4-29 | ++ |
| 4-30 | ++ | 4-31 | ++ | 4-32 | ++ | 4-33 | ++ |
| 4-34 | ++ | 4-35 | ++ | 4-36 | ++ | 4-37 | ++ |
| 4-38 | ++ | 4-39 | ++ | 4-40 | ++ | 4-41 | ++ |
| 4-42 | ++ | 4-43 | ++ | 4-44 | ++ | 4-45 | ++ |
| 4-46 | ++ | 4-47 | ++ | 4-48 | ++ | 4-50 | ++ |
| 4-51 | ++ | 4-52 | ++ | 4-53 | ++ | 4-54 | ++ |
| 4-55 | ++ | 4-56 | ++ | | | | |

TABLE 54

| Ex. No. | IC50 | Ex. No. | IC50 | Ex. No. | IC50 | Ex. No. | IC50 |
|---|---|---|---|---|---|---|---|
| 5-1 | + | 5-2 | + | 5-4 | ++ | 5-5 | + |
| 5-6 | ++ | | | | | | |

TABLE 55

| Ex. No. | IC50 | Ex. No. | IC50 | Ex. No. | IC50 | Ex. No. | IC50 |
|---|---|---|---|---|---|---|---|
| 6-1 | ++ | 6-2 | ++ | 6-3 | ++ | 6-4 | ++ |
| 6-5 | ++ | 6-6 | ++ | 6-7 | ++ | 6-8 | ++ |
| 6-9 | ++ | 6-10 | ++ | 6-11 | ++ | 6-12 | ++ |
| 6-13 | ++ | 6-14 | ++ | 6-15 | ++ | 6-16 | + |

TABLE 56

| Ex. No. | IC50 | Ex. No. | IC50 | Ex. No. | IC50 | Ex. No. | IC50 |
|---|---|---|---|---|---|---|---|
| 7-01 | ++ | 7-02 | ++ | 7-03 | ++ | 7-04 | ++ |
| 7-05 | ++ | 7-06 | ++ | 7-07 | ++ | 7-08 | ++ |
| 7-09 | ++ | 7-10 | ++ | 7-11 | ++ | | |

INDUSTRIAL APPLICABILITY

The condensed benzamide compound of the present invention effectively inhibits vanilloid receptor subtype 1 (VR1) activity, and therefore it is effective in the medical treatment and/or prevention of diseases such as pain, acute pain, chronic pain, neuropathic pain, rheumatoid arthritis pain, neuralgia, neuropathy, hyperalgesia, migraine, joint pain, acute herpetic pain, postherpetic neuralgia, chronic postherpetic neuralgia, postoperative pain, cancer pain, inflammatory pain, interstitial cystitis, posttraumatic neuralgia, diabetic neuropathy, neurodegenerative disease, cerebral apoplexy, ischemic symptom, nerve injury, neurogenic skin disorder, inflammatory disease, pruritus, allergic rhinitis, apoplexy, irritable bowel syndrome, asthma, chronic obstructive pulmonary disease, dermatitis, mucositis, stomach and duodenal ulcer and inflammatory bowel disease, bladder hypersensitivity, and overactive bladder type frequent urination and urinary incontinence.

The invention claimed is:

1. A condensed benzamide compound represented by the following formula [1] or a pharmaceutically acceptable salt thereof:

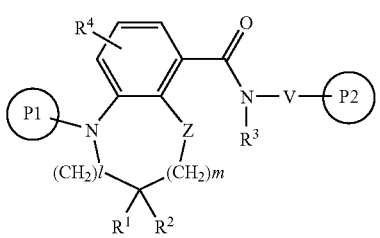

[wherein Z is
  (1) —O—,
  (2) —NR$^5$— (wherein R$^5$ is a hydrogen atom or a C1-6 alkyl group),
  (3) —S—,
  (4) —SO— or
  (5) —SO$_2$—;
l is 0, 1 or 2;
m is 0, 1 or 2;
R$^1$ is
  (1) a hydrogen atom or
  (2) a C1-6 alkyl group which may be substituted with 1 to 5 substituents selected from the following Group A:
Group A:
  (a) a halogen atom,
  (b) a hydroxyl group,
  (c) a C1-6 alkoxy group,
  (d) a carboxyl group,
  (e) a C1-6 alkoxycarbonyl group,
  (f) —CONR$^6$R$^7$ (wherein R$^6$ and R$^7$ are the same or different and each represents a hydrogen atom, a C1-6 alkyl group or an acyl group and said alkyl group may be substituted with a hydroxyl group or an acyloxy group),
  (g) —NR$^6$R$^7$ (wherein R$^6$ and R$^7$ are the same as above),
  (h) —NR$^6$COR$^7$ (wherein R$^6$ and R$^7$ are the same as above),
  (i) —NR$^8$CONR$^6$R$^7$ (wherein R$^6$ and R$^7$ are the same as above, and R$^8$ is a hydrogen atom or a C1-6 alkyl group); and
  (j) —NR$^6$SO$_2$R$^9$ (wherein R$^6$ is the same as above, and R$^9$ is a C1-6 alkyl group);
R$^2$ is
  (1) a hydrogen atom,
  (2) a hydroxyl group,
  (3) a C1-6 alkyl group which may be substituted with 1 to 5 substituents selected from the Group A (wherein the Group A is the same as above),
  (4) a carboxyl group,
  (5) a C1-6 alkoxycarbonyl group or
  (6) —CONR$^{10}$R$^{11}$ (wherein R$^{10}$ and R$^{11}$ are the same or different and each represents a hydrogen atom or a C1-6 alkyl group); or R$^2$ together with R$^1$ forms =O;
R$^3$ is
  (1) a hydrogen atom, or
  (2) a C1-6 alkyl group;
R$^4$ is
  (1) a hydrogen atom,
  (2) a halogen atom
  (3) a C1-6 alkyl group which may be substituted with 1 to 5 substituents selected from the following Group B,
  (4) a C1-6 alkoxy group which may be substituted with 1 to 5 substituents selected from the following Group B,
  (5) a cycloalkyl group which may be substituted with 1 to 5 substituents selected from the following Group B,
  (6) an aralkyl group which may be substituted with 1 to 5 substituents selected from the following Group B,
  (7) an aralkoxy group which may be substituted with 1 to 5 substituents selected from the following Group B, or
  (8) a cycloalkylalkoxy group which may be substituted with 1 to 5 substituents selected from the following Group B,
Group B:
  (a) a halogen atom,
  (b) a halo C1-6 alkyl group,
  (c) a hydroxyl group,
  (d) a halo C1-6 alkoxy group,
  (e) a C1-6 alkoxycarbonyl group,
  (f) a C1-6 alkoxy group,
  (g) a carboxyl group,
  (h) —CONR$^{12}$R$^{13}$ (wherein R$^{12}$ and R$^{13}$ are the same or different and each represents a hydrogen atom or a C1-6 alkyl group);
  (i) —NR$^{12}$R$^{13}$ (wherein R$^{12}$ and R$^{13}$ are the same as above),
  (j) —NR$^{12}$COR$^{13}$ (wherein R$^{12}$ and R$^{13}$ are the same as above),
  (k) —NR$^{14}$CONR$^{12}$R$^{13}$ (wherein R$^{12}$ and R$^{13}$ are the same as above, and R$^{14}$ is a hydrogen atom or a C1-6 alkyl group),
  (l) —SO$_2$R$^{15}$ (wherein R$^{15}$ is a C1-6 alkyl group), and
  (m) —NR$^{12}$SO$_2$R$^{15}$ (wherein R$^{12}$ and R$^{15}$ are the same as above);
  (9) a hydroxyl group,
  (10) —NR$^{16}$R$^{17}$ (wherein R$^{16}$ and R$^{17}$ are the same or different and each represents a hydrogen atom or a C1-6 alkyl group)
  (11) —COR$^{18}$ (wherein R$^{18}$ is a C1-6 alkyl group, a C1-6 alkoxy group, a cycloalkyl group, an aralkyl group, an aralkoxy group, a cycloalkylalkoxy group or a hydroxyl group),
  (12) —CONR$^{16}$R$^{17}$ (wherein R$^{16}$ and R$^{17}$ are the same as above),
  (13) —NR$^{19}$CONR$^{16}$R$^{17}$ (wherein R$^{16}$ and R$^{17}$ are the same as above, and R$^{19}$ is a hydrogen atom or a C1-6 alkyl group),
  (14) —NR$^{16}$COOR$^{20}$ (wherein R$^{16}$ is the same as above, and R$^{20}$ is a C1-6 alkyl group or a cycloalkyl group),
  (15) —SR$^{20}$ (wherein R$^{20}$ is the same as above),
  (16) —SOR$^{20}$ (wherein R$^{20}$ is the same as above),
  (17) —SO$_2$R$^{20}$ (wherein R$^{20}$ is the same as above),
  (18) —SO$_2$NR$^{16}$R$^{17}$ (wherein R$^{16}$ and R$^{17}$ are the same as above) or
  (19) —NR$^{16}$COR$^{18}$ (wherein R$^{16}$ and R$^{18}$ are the same as above);
V is
  (1) a single bond or
  (2) —(CR$^{21}$R$^{22}$)$_n$— (wherein R$^{21}$ and R$^{22}$ are the same or different and each represents a hydrogen atom or a C1-6 alkyl group, and n is 1 or 2);
P1 and P2 rings are the same or different and each represents
  (1) a carbocyclic group which may be substituted with 1 to 5 substituents selected from the following group C or
  (2) a heterocyclic group which may be substituted with 1 to 5 substituents selected from the following group
Group C:
  (a) a halogen atom,
  (b) a hydroxyl group,
  (c) a C1-6 alkoxy group which may be substituted with 1 to 5 substituents selected from the Group A,
  (d) an C1-6 alkylthio group, (e) a C1-6 alkyl group which may be substituted with 1 to 5 substituents selected from the Group A,
(f) —CONR$^{23}$R$^{24}$ (wherein R$^{23}$ and R$^{24}$ are the same or different and each represents a hydrogen atom or a C1-6 alkyl group which may be substituted with 1 to 5 substituents selected from the Group A),
(g) —NR$^{123}$R$^{124}$ (wherein R$^{123}$ and R$^{124}$ are the same or different and each represents a hydrogen atom or a C1-6 alkyl group which may be substituted with 1 to 5 substituents selected from the Group A),
(h) —NR$^{223}$COR$^{224}$ (wherein R$^{223}$ and R$^{224}$ are the same or different and each represents a hydrogen atom or a C1-6 alkyl group which may be substituted with 1 to 5 substituents selected from the Group A),
(i) —NR$^{25}$CONR$^{323}$R$^{324}$ (wherein R$^{323}$ and R$^{324}$ are the same or different and each represents a hydrogen atom or a C1-6 alkyl group which may be substituted with 1 to 5 substituents selected from the Group A),
(j) —SR$^{26}$ (wherein R$^{26}$ is a C1-6 alkyl group),
(k) —SOR$^{126}$ (wherein R$^{126}$ is a C1-6 alkyl group),
(l) —SO$_2$R$^{226}$ (wherein R$^{226}$ is a C1-6 alkyl group),
(m) —NR$^{423}$SO$_2$R$^{326}$ (wherein R$^{423}$ is a hydrogen atom or a C1-6 alkyl group which may be substituted with 1 to 5 substituents selected from the Group A, and R$^{326}$ is a C1-6 alkyl group),
(n) —SO$_2$NR$^{523}$R$^{524}$ (wherein R$^{523}$ and R$^{524}$ are the same or different and each represents a hydrogen atom or a C1-6 alkyl group which may be substituted with 1 to 5 substituents selected from the Group A),
(o) —COR$^{27}$ (wherein R$^{27}$ is a C1-6 alkyl group, C1-6 alkoxy group, a cycloalkyl group, an aralkyl group, an aralkoxy group, a cycloalkylalkoxy group or a hydroxyl group),
(p) a carbocyclic group which may be substituted with 1 to 5 substituents selected from (a) to (o) of the Group C,
(q) a heterocyclic group which may be substituted with 1 to 5 substituents selected from (a) to (o) of the Group C,
(r) —O—R$^{28}$ (wherein R$^{28}$ is an acyl group, a carbocyclic group which may be substituted with 1 to 5 substituents selected from (a) to (o) of the Group C or a heterocyclic group which may be substituted with 1 to 5 substituents selected from (a) to (o) of the Group C),
(s) —O—(CR$^{121}$R$^{122}$)$_n$—R$^{128}$ (wherein R$^{121}$ and R$^{122}$ are the same or different and each represents a hydrogen atom or a C1-6 alkyl group, n is 1 or 2, and R$^{128}$ is an acyl group, a carbocyclic group which may be substituted with 1 to 5 substituents selected from (a) to (i) of the Group C or a heterocyclic group which may be substituted with 1 to 5 substituents selected from (a) to (l) of the Group C),
(t) a nitro group, and
(u) a cyano group.

2. The condensed benzamide compound or pharmaceutically acceptable salt thereof according to claim 1 wherein Z is —O—, —NR$^5$—, —S— or —SO—.

3. The condensed benzamide compound or pharmaceutically acceptable salt thereof according to claim 1 wherein R$^3$ is a hydrogen atom or a C1-4 alkyl group.

4. The condensed benzamide compound or pharmaceutically acceptable salt thereof according to claim 1 wherein the P1 ring is a saturated or unsaturated 5-membered or 6-membered heterocyclic ring having 1 to 4 hetero atoms selected from a nitrogen atom, an oxygen atom and a sulfur atom, or a condensed ring of these heterocyclic rings, or a condensed heterocyclic ring of said heterocyclic ring and a carbocyclic ring selected from benzene, cyclopentane and cyclohexane, or a phenyl group (wherein said heterocyclic ring may be substituted with a halogen atom, a hydroxyl group, a C1-6 alkyl group which may be substituted with 1 to 5 substituents selected from the Group A, and a C1-6 alkoxy group which may be substituted with 1 to 5 substituents selected from the Group A).

5. The condensed benzamide compound or a pharmaceutically acceptable salt thereof according to claim 1 wherein the P2 ring is a carbocyclic group which may be substituted with a substituent group selected from the group consisting of
a halogen atom,
a hydroxyl group,
a C1-6 alkoxy group (wherein said alkoxy group may be substituted with a halogen atom, —CONR$^{623}$R$^{624}$ (wherein R$^{623}$ and R$^{624}$ are the same or different and each represents a hydrogen atom or a C1-6 alkyl group which may be substituted with 1 to 5 substituents selected from the Group A), a C3-8 cycloalkyl group, a C1-6 alkoxy group, a carboxyl group or a C1-6 alkoxycarbonyl group),
a C1-6 alkyl group (wherein said alkyl group may be substituted with a halogen atom, a hydroxyl group or a C1-6 alkoxy group),
—NR$^{123}$R$^{124}$ (wherein R$^{123}$ and R$^{124}$ are the same as above),
—NR$^{223}$COR$^{224}$ (wherein R$^{223}$ and R$^{224}$ are the same as above),
—COR$^{27}$ (wherein R$^{27}$ is a C1-6 alkyl group, C1-6 alkoxy group, a cycloalkyl group, an aralkyl group, an aralkoxy group, a cycloalkylalkoxy group or a hydroxyl group),
—CONR$^{23}$R$^{24}$ (wherein R$^{23}$ and R$^{24}$ are the same as above),
a heterocyclic group as a saturated or unsaturated substituent group which has 1 to 3 nitrogen atoms as hetero atoms (wherein said heterocyclic group may be substituted with a substituent group selected from a hydroxyl group, —CONR$^{723}$R$^{724}$ (wherein R$^{723}$ and R$^{724}$ are the same or different and each represents a hydrogen atom or a C1-6 alkyl group which may be substituted with 1 to 5 substituents selected from the Group A), a C1-6 alkoxy group, a carboxyl group, a C1-6 alkyl group which may be substituted with a C1-6 alkoxy group, a C1-6 alkoxycarbonyl group and an acyloxy group),
—O—R$^{28}$ (wherein R$^{28}$ is an acyl group, a carbocyclic group which may be substituted with 1 to 5 substituents selected from (a) to (i) of the Group C or a heterocyclic group which may be substituted with 1 to 5 substituents selected from (a) to (l) of the Group C),
—O—(CR$^{121}$R$^{122}$)$_n$—R$^{128}$ (wherein R$^{121}$ and R$^{122}$ are the same or different and each represents a hydrogen atom or a C1-6 alkyl group, n is 1 or 2, and R$^{128}$ is an acyl group, a carbocyclic group which may be substituted with 1 to 5 substituents selected from (a) to (i) of the Group C or a heterocyclic group which may be substituted with 1 to 5 substituents selected from (a) to (l) of the Group C),
a nitro group and
a cyano group, and
a heterocyclic group which may be substituted with a substituent as described for the carbocyclic group (wherein said heterocyclic group means a saturated or unsaturated 5-membered or 6-membered heterocyclic ring which has 1 to 4 hetero atoms selected from a nitrogen atom, an oxygen atom and a sulfur atom, or a condensed ring of these heterocyclic rings, or a condensed heterocyclic group of said heterocyclic ring and a carbocyclic ring selected from benzene, cyclopentane and cyclohexane).

6. A pharmaceutical composition comprising a condensed benzamide compound or a pharmaceutically acceptable salt thereof according to claim 1 and a pharmaceutically acceptable carrier.

* * * * *